(12) United States Patent
Imazaki et al.

(10) Patent No.: US 7,199,147 B2
(45) Date of Patent: Apr. 3, 2007

(54) RHO KINASE INHIBITORS

(75) Inventors: Naonori Imazaki, Suita (JP);
Masafumi Kitano, Takatsuki (JP);
Naohito Ohashi, Takatsuki (JP);
Kazuki Matsui, Sanda (JP)

(73) Assignee: Dainippon Sumitomo Pharma Co., Ltd., Osaka (JP)

(*) Notice: Subject to any disclaimer, the term of this patent is extended or adjusted under 35 U.S.C. 154(b) by 261 days.

(21) Appl. No.: 10/480,526

(22) PCT Filed: Jun. 6, 2002

(86) PCT No.: PCT/JP02/05609

§ 371 (c)(1),
(2), (4) Date: Dec. 12, 2003

(87) PCT Pub. No.: WO02/100833

PCT Pub. Date: Dec. 19, 2002

(65) Prior Publication Data

US 2004/0138286 A1    Jul. 15, 2004

(30) Foreign Application Priority Data

Jun. 12, 2001  (JP) ............................... 2001-176826
Dec. 28, 2001  (JP) ............................... 2001-398992

(51) Int. Cl.
*A61K 31/415* (2006.01)
*C07D 231/56* (2006.01)

(52) U.S. Cl. ............... 514/394; 514/405; 548/361.1; 548/362.5

(58) Field of Classification Search ............ 548/361.1, 548/362.5, 304.4, 304.7; 514/394, 405
See application file for complete search history.

(56) References Cited

U.S. PATENT DOCUMENTS

| | | | |
|---|---|---|---|
| 4,143,149 A * | 3/1979 | Wiedemann et al. | 514/406 |
| 4,778,511 A | 10/1988 | Heywang et al. | |
| 4,978,603 A * | 12/1990 | Inoue et al. | 430/265 |
| 5,444,038 A | 8/1995 | James et al. | |
| 5,880,151 A | 3/1999 | Medina et al. | |
| 2001/0034346 A1 | 10/2001 | Milton et al. | |
| 2003/0125344 A1* | 7/2003 | Nagarathnam et al. | 514/266.2 |
| 2004/0102437 A1* | 5/2004 | Takami et al. | 514/217.12 |

FOREIGN PATENT DOCUMENTS

| | | |
|---|---|---|
| DE | 2 619 164 A | 11/1977 |
| EP | 195238 A1 | 9/1986 |
| JP | 61-194076 A | 8/1986 |
| JP | 02-48670 A | 2/1990 |
| JP | 03-254698 A | 11/1991 |
| JP | 11-310568 A | 11/1999 |
| WO | WO 93/18008 A1 | 9/1993 |
| WO | WO 95/00509 A1 | 1/1995 |
| WO | WO 00/06173 A1 | 2/2000 |
| WO | WO 00/27819 A1 | 5/2000 |
| WO | WO 01/56988 A1 | 8/2001 |
| WO | WO 01/81303 A1 | 11/2001 |

OTHER PUBLICATIONS

Kwartler et al., 1944, CAS:38:455.*
Weidemann et al., 1978, CAS:88:50853.*
Honjo, et al., "Effects of Rho-Associated Protein Kinase Inhibitor Y-27632 on Intraocular Pressure and Outflow Facility," IOVS, vol. 42, No. 1, Jan. 2001, pp. 137-144.
Uehata et al., "Calcium sensitization of smooth muscle mediated by a Rho-associated protein kinase in hypertension," Nature, vol. 389, Oct. 30, 1997, pp. 990-994.
Satoh, et al., "Antiischemic Properties of Fasudil in Experimental Models of Vasopastic Angina," Jpn J. Pharmacol. 87, 34-40 (2001).
Sato, et al., "Involvement of Rho-Kinase-Mediated Phosporylation of Myosin Licht Chain in Enhancement of Cerebral Vasopasm," Circulation Research, Aug. 4, 2000, pp. 195-200.

(Continued)

*Primary Examiner*—Joseph K. McKane
*Assistant Examiner*—Rei-tsang Shiao
(74) *Attorney, Agent, or Firm*—Sughrue Mion, PLLC

(57) ABSTRACT

A compound represented by the formula (1):

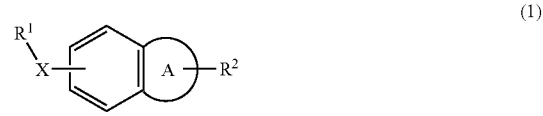

wherein $R^1$—X— indicates that 1 to 4 $R^1$—X— groups are present which may be the same or different,
the ring A is a saturated or unsaturated 5-membered heterocyclic ring,
X is a single bond, a group represented by the formula: —N($R^3$)—, —O— or —S—, or the like.
$R^1$ is a hydrogen atom, a halogen atom, a nitro group, a carboxyl group, a substituted or unsubstituted alkyl group, or the like,
$R^2$ is a hydrogen atom, a halogen atom, a nitro group, a carboxyl group, a substituted or unsubstituted alkyl group, or the like, and
$R^3$ is a hydrogen atom, a substituted or unsubstituted alkyl group, or the like;
a prodrug of said compound, or a pharmaceutically acceptable salt of said compound or prodrug is a useful compound as a therapeutic agent for diseases for which Rho kinase is responsible.

12 Claims, 1 Drawing Sheet

OTHER PUBLICATIONS

Negoro, et al., "The Kinase Inhibitor Fasudil (HA-1077) Reduces Intimal Hyperplasia through Inhibiting Migratio and Enhancing Cell Loss of Vascular Smooth Muscle Cells," Biochemical and Biophysical Research Communications 262, 211-215 (1999).

Chitaley, et al., "Antagonism of Rho-kinase stinulates rat penile erection via a nitric oxide-independent pathway," Nature Medicine, vol. 7, No. 1, Jan. 2001, pp. 119-122.

Rees, et al., "Y-27632, A Rho-Kinase Inhibitor, Inhibits Proliferation and Adrenergic Contraction of Prostatic Smooth Muscle Cells," The Journal of Urology, vol. 170, Dec. 2003, pp. 2517-2522.

Higashi et al., "Long-term inhibition of Rho-kinase suppresses angiotensin II-induced formation of coronary vascular lesions and cardiac hypertrophy in rats in vivo," Circulation, 104 (17 Supplement) Oct. 23, 2001.

Abstract of Higashi et al., "Long-term inhibition of Rho-kinase suppresses angiotension II-induced formation of coronary vascular lesions and cardiac hypertrophy in rats in vivo," Circulation, 104 (17 Supplement) Oct, 23, 2001.

Abstract of Yamagata, et al., "Effect of a calcium sensitization modulator, Y-27632, on isolated human bronchus and pulmonary artery," Pulmonary Pharmacology & Therapeutics 13(1): 25-9, 2000.

Yamagata, et al. "Effect of a Calcium Sensitization Modulator, Y-27632, on Isolated Human Bronchus and Pulmonary Artery," Pulmonary Pharmacology & Therapeutics (2000), 13, 25-29.

* cited by examiner

RHO KINASE INHIBITORS

This application is a 371 of PCT/JP02/0589 filed on Jun. 6, 2002.

TECHNICAL FIELD

The present invention relates to a Rho kinase inhibitor (ROCK-II inhibitor, ROCα inhibitor) containing a novel fused heterocyclic ring compound, a prodrug thereof or a pharmaceutically acceptable salt of said compound or prodrug.

It is known that Rho kinase participates in vasoconstriction, platelet aggregation, bronchial smooth muscle constriction, vascular smooth muscle proliferation•emigration, endothelial proliferation•emigration, stress fiber formation, cardiac hypertrophy, Na/H exchange transport system activation, adducin activation, ocular hypertension, erectile dysfunction, premature birth, retinopathy, inflammation, immune diseases, AIDS, fertilization and implantation of fertilized ovum, osteoporosis, brain functional disorder, infection of digestive tracts with bacteria, and the like.

The compound of the present invention has inhibitory effect on Rho kinase and is useful as a therapeutic agent for diseases which are such that morbidity due to them is expected to be improved by inhibition of Rho kinase and secondary effects such as inhibition of the $Na^+/H^+$ exchange transport system caused by the Rho kinase inhibition, for example, hypertension, peripheral circulatory disorder, angina, cerebral vasospasm, premature birth, and asthma, which are improved by smooth muscle relaxing effect, and diseases (chronic arterial obstruction and cerebrovascular accident) caused by hyperaggregability of platelet; diseases such as arteriosclerosis, fibroid lung, fibroid liver, liver failure, fibroid kidney, renal glomerulosclerosis, kidney failure, organ hypertrophy, prostatic hypertrophy, complications of diabetes, blood vessel restenosis, and cancer, which are improved by inhibitory effect on cell over-proliferation•emigration•fibrosing (e.g. fibroblast proliferation, smooth muscle cell proliferation, mesangial cell proliferation and hemoendothelial cell proliferation); cardiac hypertrophy; heart failure, ischemic diseases; inflammation; autoimmune diseases; AIDS; fertilization and implantation of fertilized ovum; osteopathias such as osteoporosis; brain functional disorder; infection of digestive tracts with bacteria; sepsis; adult respiratory distress syndrome; retinopathy; glaucoma; and erectile dysfunction.

BACKGROUND ART

As compounds having inhibitory activity against Rho kinase, there are exemplified the compounds disclosed in International Patent Laid-Open Nos. WO98/06433, WO99/64011 and WO00/57914.

DISCLOSURE OF THE INVENTION

A problem to be solved by the present invention is to find a compound that has inhibitory activity against Rho kinase and is useful as a therapeutic agent for the diseases described above.

The present inventors earnestly investigated in order to solve the above problem, and consequently found that the following compound, a prodrug thereof or a pharmaceutically acceptable salt of said compound or prodrug (they are hereinafter abbreviated as the compound of the present invention if necessary) has an excellent inhibitory effect against Rho kinase. Moreover, the present inventors found that the compound having inhibitory effect against Rho kinase suppresses the constriction of the detrusor of bladder and is useful as a prophylactic or therapeutic agent for urinary incontinence. That is, the present invention relates to the following.

[1] A Rho kinase inhibitor comprising a compound represented by the formula (1):

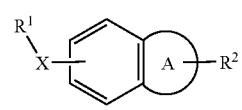

(1)

wherein $R^1$—X— indicates that 1 to 4 $R^1$—X— groups are present which may be the same or different, the ring A is a saturated or unsaturated 5-membered heterocyclic ring, X is a single bond, a group represented by the formula: —O—, —N($R^3$)—, —N($R^3$)C(=O)—, —C(=O)N($R^3$)—, —S(O)$_n$—, —N($R^3$)S(O)$_2$—, —S(O)$_2$N($R^3$)— or —C(=O)—, or a substituted or unsubstituted alkylene group (the —CH$_2$— group of said alkylene group may be substituted by one or more groups which may be the same or different and are selected from groups represented by the formula: —O—, —N($R^4$)—, —N($R^4$)C(=O)—, —C(=O)N($R^4$)—, —S(O)$_n$—, —N($R^4$)S(O)$_2$—, —S(O)$_2$N($R^4$)— or —C(=O)—, and any two adjacent carbon atoms of said alkylene group may form a double bond or a triple bond), n is 0, 1 or 2, $R^1$ is a hydrogen atom, a halogen atom, a nitro group, a carboxyl group, a cyano group, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, a substituted or unsubstituted alkylsulfonyl group, a substituted or unsubstituted arylsulfonyl group, or a cycloalkyl group substituted by a substituted or unsubstituted alkyl group, $R^2$ is a hydrogen atom, a halogen atom, a nitro group, a carboxyl group, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a group represented by the formula: —O$R^8$, —N($R^9$)$R^{10}$, —CON($R^9$)$R^{10}$, —SO$_2$N($R^9$)$R^{10}$ or —S(O)$_m$$R^{11}$, provided that in the case of $R^2$ being a substituent on a nitrogen atom, $R^2$ is a hydrogen atom, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a group represented by the formula: —CON($R^9$)$R^{10}$, —SO$_2$N($R^9$)$R^{10}$ or —S(O)$_m$$R^{11}$, each of $R^3$ and $R^4$, which may be the same or different, is a hydrogen atom, a substituted or unsubstituted alkyl group, a substituted or unsubstituted cycloalkyl group, a substituted or unsubstituted saturated heterocyclic group, a substituted or unsubstituted aromatic group, a substituted or unsubstituted arylalkyl group, or a substituted or unsubstituted acyl group, m is 0, 1 or 2, each of $R^8$, $R^9$ and $R^{10}$, which may be the same or different, is a hydrogen atom, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a substituted or unsubstituted arylalkyl group, or $R^9$ and $R^{10}$, when taken together with the nitrogen atom to which they are bonded, form a substituted or unsubstituted saturated 5- to 8-membered cyclic amino group which may contain another heteroatom, and $R^{11}$ is a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted aromatic group, or a substituted or unsubstituted arylalkyl group, a prodrug of said compound, or a pharmaceutically acceptable salt of said compound or prodrug.

[2] A Rho kinase inhibitor according to [1], which is represented by the formula (2):

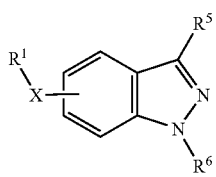

(2)

wherein $R^1$—X— indicates that 1 to 4 $R^1$—X— groups are present which may be the same or different, X and $R^1$ are as defined in [1], $R^5$ is a hydrogen atom, a halogen atom, a nitro group, a carboxyl group, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a group represented by the formula: —$OR^8$, —$N(R^9)R^{10}$, —$CON(R^9)R^{10}$, —$SO_2N(R^9)R^{10}$ or —$S(O)_mR^{11}$, $R^6$ is a hydrogen atom, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a group represented by the formula: —$CON(R^9)R^{10}$, —$SO_2N(R^9)R^{10}$ or —$S(O)_mR^{11}$, and $R^8$, $R^9$, $R^{10}$, $R^{11}$ and m are as defined in [1].

[3] A Rho kinase inhibitor according to [1] or [2], wherein X is a group represented by the formula: —$N(R^3)$—.

[4] A Rho kinase inhibitor according to [1] or [2], wherein X is a group represented by the formula: —$N(R^3)C(=O)$—.

[5] A Rho kinase inhibitor according to [1] or [2], wherein X is a group represented by the formula: —$C(=O)N(R^3)$—.

[6] A Rho kinase inhibitor according to [1] or [2], wherein X is a group represented by the formula: —O—.

[7] A Rho kinase inhibitor according to any one of [1] to [6], wherein $R^1$ is a substituted or unsubstituted cycloalkyl group, or a substituted or unsubstituted saturated heterocyclic group.

[8] A Rho kinase inhibitor according to [7], wherein the saturated heterocyclic group is a substituted or unsubstituted piperidinyl group, or a substituted or unsubstituted tetrahydropyranyl group.

[9] A Rho kinase inhibitor according to any one of [1] to [6], which is a therapeutic agent for hypertension, peripheral circulatory disorder, angina, cerebral vasospasm, premature birth, asthma, cerebrovascular accident, arteriosclerosis, fibroid lung, fibroid liver, fibroid kidney, renal glomerulosclerosis, kidney failure, prostatic hypertrophy, complications of diabetes, blood vessel restenosis, cancer, cardiac hypertrophy, heart failure, ischemic diseases, inflammation, autoimmune diseases, AIDS, fertilization and implantation of fertilized ovum, osteopathias, brain functional disorder, infection of digestive tracts with bacteria, sepsis, adult respiratory distress syndrome, retinopathy, glaucoma, or erectile dysfunction.

[10] A compound represented by the formula (3):

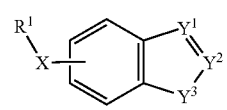

(3)

wherein $R^1$—X— indicates that 1 to 4 $R^1$—X— groups are present which may be the same or different, X is a single bond, a group represented by the formula: —O—, —$N(R^3)$—, —$N(R^3)C(=O)$—, —$C(=O)N(R^3)$—, —$S(O)_n$—, —$N(R^3)S(O)_2$—, —$S(O)_2N(R^3)$— or —$C(=O)$—, or a substituted or unsubstituted alkylene group (the —$CH_2$— group of said alkylene group may be substituted by one or more groups which may be the same or different and are selected from groups represented by the formula: —O—, —$N(R^4)$—, —$N(R^4)C(=O)$—, —$C(=O)N(R^4)$—, —$S(O)_n$—, —$N(R^4)S(O)_2$—, —$S(O)_2N(R^4)$— or —$C(=O)$—, and any two adjacent carbon atoms of said alkylene group may form a double bond or a triple bond), n is 0, 1 or 2, $Y^1$ is a group represented by the formula: —$C(R^{51})$= or a nitrogen atom, $Y^2$ is a group represented by the formula: —$C(R^{52})$— or a nitrogen atom, $Y^3$ is a group represented by the formula: —$N(R^6)$— or an oxygen atom, $R^1$ is a hydrogen atom, a halogen atom, a carboxyl group, a cyano group, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, a substituted or unsubstituted alkylsulfonyl group, a substituted or unsubstituted arylsulfonyl group, or a cycloalkyl group substituted by a substituted or unsubstituted alkyl group, each of $R^3$ and $R^4$, which may be the same or different, is a hydrogen atom, a substituted or unsubstituted alkyl group, a substituted or unsubstituted cycloalkyl group, a substituted or unsubstituted saturated heterocyclic group, a substituted or unsubstituted aromatic group, a substituted or unsubstituted arylalkyl group, or a substituted or unsubstituted acyl group, each of $R^{51}$ and $R^{52}$, which may be the same or different, is a hydrogen atom, a halogen atom, a nitro group, a carboxyl group, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a group represented by the formula: —$OR^8$, —$N(R^9)R^{10}$, —$CON(R^9)R^{10}$, —$SO_2N(R^9)R^{10}$ or —$S(O)_mR^{11}$, m is 0, 1 or 2, each of $R^8$, $R^9$ and $R^{10}$, which may be the same or different, is a hydrogen atom, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a substituted or unsubstituted arylalkyl group, or $R^9$ and $R^{10}$, when taken together with the nitrogen atom to which they are bonded, form a substituted or unsubstituted saturated 5- to 8-membered cyclic amino group which may contain another heteroatom, $R^{11}$ is a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted aromatic group, or a substituted or unsubstituted arylalkyl group, and $R^6$ is a hydrogen atom, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, or a group represented by the formula: —$CON(R^9)R^{10}$, —$SO_2N(R^9)R^{10}$ or —$S(O)_mR^{11}$, provided that when only one $R^1$—X— group is present, the following compounds are excluded:

(1) compounds in which X is a single bond and $R^1$ is a hydrogen atom, a carboxyl group or an alkoxycarbonyl group, (2) compounds in which X is a group represented by the formula: —O—, and $R^1$ is a hydrogen atom, an unsubstituted alkyl group, an alkyl group substituted by a carboxyl group, an unsubstituted benzoyl group, or an unsubstituted benzyl group, (3) compounds in which X is a group represented by the formula: —NH—, and $R^1$ is a hydrogen atom or an amino-substituted alkyl group.

(4) compounds in which X is a group represented by the formula: —C(=O)—, and $R^1$ is a hydrogen atom, (5) compounds in which X is a group represented by the formula: —NHC(=O)—, and $R^1$ is an alkyl group or an unsubstituted benzyl group, and (6) compounds in which X is an unsubstituted alkylene group (said alkylene group is not substituted by a group represented by the formula: —O—, —$N(R^4)$—, —$N(R^4)C(=O)$—, —$C(=O)N(R^4)$—, —$S(O)_n$—, —$N(R^4)S(O)_2$—, —$S(O)_2N(R^4)$— or —$C(=O)$—), and $R^1$ is a hydrogen atom or an unsubstituted amino group, a prodrug of said compound or a pharmaceutically acceptable salt of said compound or prodrug.

[11] A compound according to [10], which is represented by the formula (4):

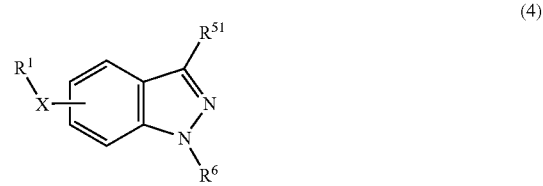

(4)

wherein X, $R^1$, $R^{51}$ and $R^6$ are as defined in [10], a prodrug thereof or a pharmaceutically acceptable salt of the compound or prodrug.

[12] A compound according to [10], which is represented by the formula (5):

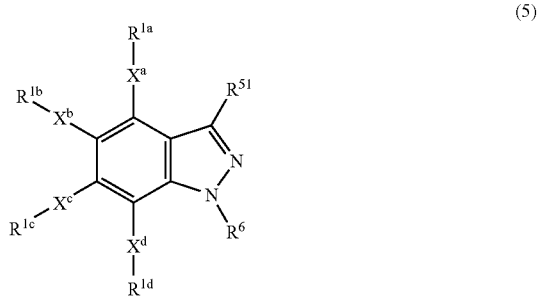

(5)

wherein $R^{51}$ and $R^6$ are as defined in [10], $X^a$, $X^b$, $X^c$ and $X^d$ are independently the same as X defined in [10], and $R^{1a}$, $R^{1b}$, $R^{1c}$ and $R^{1d}$ are independently a hydrogen atom, a carboxyl group, a substituted or unsubstituted alkyl group, a substituted or unsubstituted cycloalkyl group, a substituted or unsubstituted cycloalkenyl group, a substituted or unsubstituted saturated heterocyclic group, a substituted or unsubstituted alkoxycarbonyl group, a substituted or unsubstituted aromatic group, a substituted or unsubstituted acyl group, a substituted or unsubstituted alkylsulfonyl group, a substituted or unsubstituted arylsulfonyl group, or a cycloalkyl group substituted by a substituted or unsubstituted alkyl group, provided that three or more of the groups represented by $R^{1a}$—$X^a$, $R^{1b}$—$X^b$, $R^{1c}$—$X^c$ and $R^{1d}$—$X^d$ are not hydrogen atoms at the same time, and that when $R^{1a}$, $R^{1b}$, $R^{1c}$ or $R^{1d}$ is an unsubstituted alkyl group, the corresponding $X^a$, $X^b$, $X^c$ or $X^d$, respectively, is not a group represented by the formula: —C(=O)—, a prodrug of said compound or a pharmaceutically acceptable salt of said compound or prodrug.

[13] A compound, a prodrug thereof or a pharmaceutically acceptable salt of the compound or prodrug according to [12], wherein $R^{1b}$ is a substituted or unsubstituted cycloalkyl group, a substituted or unsubstituted cycloalkenyl group, a substituted or unsubstituted saturated heterocyclic group, a substituted or unsubstituted aromatic group, a substituted or unsubstituted aroyl group, a substituted or unsubstituted heteroaromatic acyl group, a substituted or unsubstituted saturated heterocyclic carbonyl group, or a cycloalkyl group substituted by a substituted or unsubstituted alkyl group.

[14] A compound, a prodrug thereof or a pharmaceutically acceptable salt of the compound or prodrug according to [12], wherein $R^{1a}$ is a substituted or unsubstituted cycloalkyl group, a substituted or unsubstituted cycloalkenyl group, a substituted or unsubstituted saturated heterocyclic group, a substituted or unsubstituted aromatic group, a substituted or unsubstituted aroyl group, a substituted or unsubstituted heteroaromatic acyl group, a substituted or unsubstituted saturated heterocyclic carbonyl group, or a cycloalkyl group substituted by a substituted or unsubstituted alkyl group.

[15] A compound, a prodrug thereof or a pharmaceutically acceptable salt of the compound or prodrug according to [13], wherein $X^b$ is a group represented by the formula: —O—, —N($R^3$)—, —NHC(=O)—, or —C(=O)NH—.

[16] A compound, a prodrug thereof or a pharmaceutically acceptable salt of the compound or prodrug according to [14], wherein $X^a$ is a group represented by the formula: —O—, —N($R^3$)—, —NHC(=O)—, or —C(=O)NH—.

[17] A compound, a prodrug thereof or a pharmaceutically acceptable salt of the compound or prodrug according to [13], wherein both of the groups represented by the formulas $R^{1c}$—$X^c$ and $R^{1d}$—$X^d$ are hydrogen atoms.

[18] A compound, a prodrug thereof or a pharmaceutically acceptable salt of the compound or prodrug according to [15], wherein both of the groups represented by the formulas $R^{1c}$—$X^c$ and $R^{1d}$—$X^d$ are hydrogen atoms.

[19] A compound, a prodrug thereof or a pharmaceutically acceptable salt of the compound or prodrug according to [14], wherein both of the groups represented by the formulas $R^{1c}$—$X^c$ and $R^{1d}$—$X^d$ are hydrogen atoms.

[20] A compound, a prodrug thereof or a pharmaceutically acceptable salt of the compound or prodrug according to [16], wherein both of the groups represented by the formulas $R^{1c}$—$X^c$ and $R^{1d}$—$X^d$ are hydrogen atoms.

[21] A compound, a prodrug thereof or a pharmaceutically acceptable salt of the compound or prodrug according to [17], wherein the groups represented by the formulas $R^{1a}$ and $X^a$ are as follows:
(i) $R^{1a}$ is a substituted or unsubstituted alkyl group and $X^a$ is a single bond, or
(ii) $X^a$ is a group represented by the formula: —O—, —C(=O)N($R^3$)—, —S(O)$_n$—, —S(O)$_2$N($R^3$)— or —C(=O)—.

[22] A compound, a prodrug thereof or a pharmaceutically acceptable salt of the compound or prodrug according to [18], wherein the groups represented by the formulas $R^{1a}$ and $X^a$ are as follows:
(i) $R^{1a}$ is a substituted or unsubstituted alkyl group and $X^a$ is a single bond, or
(ii) $X^a$ is a group represented by the formula: —O—, —C(=O)N($R^3$)—, —S(O)$_n$—, —S(O)$_2$N($R^3$)— or —C(=O)—.

[23] A compound, a prodrug thereof or a pharmaceutically acceptable salt of the compound or prodrug according to [22], wherein the group represented by $X^a$ is a group represented by the formula: —O—.

[24] A pharmaceutical composition comprising a compound, a prodrug thereof or a pharmaceutically acceptable salt of the compound or prodrug according to any one of [10] to [23].

[25] A pharmaceutical composition for treatment of urinary incontinence comprising a compound having inhibitory activity against Rho kinase, as an active ingredient.

[26] A pharmaceutical composition for treatment of urinary incontinence according to [25], wherein the compound having inhibitory activity against Rho kinase is a compound represented by the formula (1), a prodrug thereof or a pharmaceutically acceptable salt of the compound or prodrug according to [1].

[27] A pharmaceutical composition for treatment of urinary incontinence according to [25], wherein the compound having inhibitory activity against Rho kinase is a compound represented by the formula (3), a prodrug thereof or a pharmaceutically acceptable salt of the compound or prodrug according to [10].

[28] A pharmaceutical composition for treatment of urinary incontinence according to [25], wherein the compound having inhibitory activity against Rho kinase is a compound represented by the formula (2), a prodrug thereof or a pharmaceutically acceptable salt of the compound or prodrug according to [2].

BEST MODE FOR CARRYING OUT THE INVENTION

Figure 1:
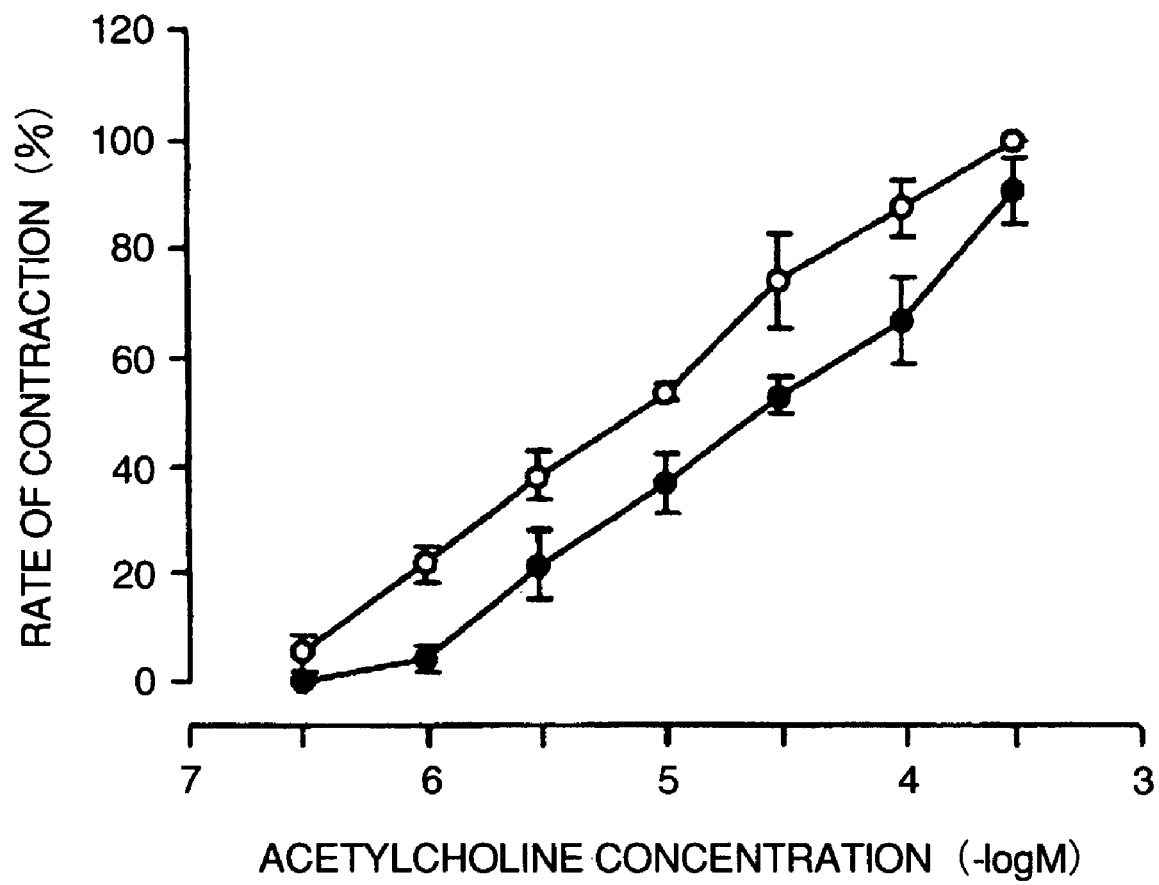
FIG. 1 is a graph showing the results of Test Example 2. The axis of abscissa refers to acetylcholine concentration (plotted as the common logarithm of the reciprocal of the molar concentration) and the axis of ordinate refers to the rate of constriction of bladder (plotted as %). The open circles indicate an untreated group to which no drug has been added, and the closed circles indicate a group to which the compound of Example 57 has been added in an amount of 100 μg/ml. Each value is shown as average value± standard error.

The various groups in the present invention are explained below. Unless otherwise specified, the following explanation applies to the case where each group is a portion of another group.

As the saturated or unsaturated heterocyclic 5-membered ring represented by the ring A, there are exemplified rings in which the three atoms other than the carbon atoms which the ring A shares with the benzene ring in the compound of formula (1) are as follows.

(a) 5-Membered rings having two nitrogen atoms and one carbon atom.

Specific examples of the 5-membered ring fused with the benzene ring are 1H-indazole, 1H-benzimidazole, 2,3-dihydro-1H-indazole and 2,3-dihydro-1H-benzimidazole.

(b) 5-Membered rings having one nitrogen atom and two carbon atoms.

Specific examples of the 5-membered ring fused with the benzene ring are 1H-indole and 2,3-dihydro-1H-indole.

(c) 5-Membered rings having one nitrogen atom, one oxygen or sulfur atom and one carbon atom.

Specific examples of the 5-membered ring fused with the benzene ring are 1,3-benzothiazole, 1,3-benzoxazole, 2,3-dihydro-1,3-benzothiazole and 2,3-dihydro-1,3-benzoxazole.

(d) 5-Membered rings having one oxygen or sulfur atom and two carbon atoms.

Specific examples of the 5-membered ring fused with the benzene ring are 1-benzofuran, 1-benzothiophene, 2,3-dihydro-1-benzofuran and 2,3-dihydro-1-benzothiophene.

Preferable examples of the saturated or unsaturated heterocyclic 5-membered ring represented by the ring A are rings represented by the following structural formula when fused with the benzene ring in the compound of the formula (1):

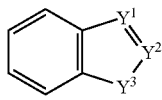

wherein $Y^1$, $Y^2$ and $Y^3$ are as defined above.

As the alkylene group, there are exemplified linear or branched alkylene groups of 8 or less carbon atoms, such as methylene, ethylene, trimethylene, tetramethylene, etc. Preferable examples thereof are alkylene groups of 1 to 4 carbon atoms.

The alkyl group includes lower alkyl groups. Specific examples thereof are linear or branched alkyl groups of 8 or less carbon atoms, such as methyl, ethyl, propyl, 2-propyl, butyl, 2-butyl, 2-methylpropyl, 1,1-dimethylethyl, pentyl, hexyl, heptyl, octyl, etc.

The cycloalkyl group includes lower cycloalkyl groups. Specific examples thereof are 3- to 8-membered cycloalkyl groups such as cyclopropyl, cyclobutyl, cyclopentyl, cyclohexyl, cycloheptyl, etc.; groups having a crosslinkage, such as adamantyl, bicyclo[2.2.2]octane, bicyclo[3.3.3]undecane, etc.; and fused-ring cycloalkyl groups such as decahydronaphthalene, octahydro-1H-indene, etc.

The cycloalkenyl group includes lower cycloalkenyl groups. Specific examples thereof are 3- to 8-membered cycloalkenyl groups having a double bond, such as 1-cyclopentenyl, 2-cyclopentenyl, 3-cyclopentenyl, 1-cyclohexenyl, 2-cyclohexenyl, 3-cyclohexenyl, etc.; and cycloalkenyl group having a crosslinkage, such as bicyclo[2.2.2]oct-2-ene, bicyclo[3.3.3]undec-2-ene, etc.

As the aromatic group, aryl group and heteroaryl group are exemplified.

As the aryl group, there are exemplified aryl groups of 10 or less carbon atoms, such as phenyl group, naphthyl group, etc. The aryl group also includes those having an unsaturated heterocyclic ring fused therewith, such as 2,3-dihydro-1-benzofuran-5-yl, etc.

As the heteroaryl group, there are exemplified 5- or 6-membered monocyclic groups containing one or two nitrogen atoms, 5- or 6-membered monocyclic groups containing one or two nitrogen atoms and one oxygen atom or one sulfur atom, 5-membered monocyclic groups containing one oxygen atom or one sulfur atom, and bicyclic groups formed by the fusion of a 6-membered ring and a 5- or 6-membered ring and containing 1 to 4 nitrogen atoms. Specific examples thereof are 2-pyridyl, 3-pyridyl, 4-pyridyl, 2-thienyl, 3-thienyl, 3-oxadiazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolyl, 8-purinyl, etc.

As the halogen atom, iodine, fluorine, chlorine and bromine atoms are exemplified.

As the arylalkyl group, alkyl groups substituted by any of the above-exemplified aryl groups are exemplified.

As the cycloalkylalkyl group, alkyl groups substituted by any of the above-exemplified cycloalkyl groups are exemplified.

As the saturated heterocyclic alkyl group, alkyl groups substituted by any of the saturated heterocyclic groups exemplified below are exemplified.

As the saturated heterocyclic group, there are exemplified 5- to 8-membered cyclic groups having a nitrogen atom, such as 1-piperidinyl, 1-pyrrolidinyl, etc.; 6- to 8-membered cyclic groups having two nitrogen atoms, such as 1-piperazinyl, etc.; 6- to 8-membered cyclic groups having a nitrogen atom and an oxygen atom, such as morpholino, etc.; and 5- to 8-membered cyclic groups having a group represented by the formula: —O—, —S—, —S(O)— or —S(O)$_2$—, such as tetrahydro-2H-pyran-4-yl, tetrahydro-2H-thiopyran-4-yl, 1-oxytetrahydro-2H-thiopyran-4-yl, 1,1-dioxytetrahydro-2H-thiopyran-4-yl, etc.; groups having a crosslinkage, such as quinuclidinyl, 1-azabicyclo[2.2.1]heptyl, 1-azabicyclo[3.2.1]octyl, etc.; and fused saturated heterocyclic groups such as decahydroquinoline, octahydro-1H-indole, etc. The saturated heterocyclic group also includes those having an aromatic ring fused therewith, such as 1H-isoindole 1,3(2H)-dion-2-yl, etc.

As the substituent of each of the saturated heterocyclic group and the saturated heterocyclic carbonyl group, there are exemplified substituents on a carbon atom, such as substituted or unsubstituted alkyl groups, hydroxyl group, oxo group, carboxyl group, halogen atoms, alkoxycarbonyl groups, etc.; and substituents on a nitrogen atom, such as substituted or unsubstituted alkyl groups, substituted or unsubstituted alkenyl groups, substituted or unsubstituted alkynyl groups, substituted or unsubstituted cycloalkyl groups, substituted or unsubstituted cycloalkylalkyl groups, alkyl-substituted or unsubstituted saturated heterocyclic groups, saturated heterocyclic groups which may be substituted by an aryl group, arylalkyl group, alkoxycarbonyl group, alkanoyl group or lower alkyl group, and groups represented by the formula: —CON($R^9$)$R^{10}$, —SO$^2$N($R^9$)$R^{10}$ or —S(O)$_m R^{11}$ ($R^9$, $R^{10}$, $R^{11}$ and m are as defined above).

As the acyl group, there are exemplified formyl group; alkanoyl groups of 2 to 6 carbon atoms, such as acetyl, propanoyl, etc.; cycloalkanecarbonyl groups of 4 to 7 carbon atoms, such as cyclopropanecarbonyl, cyclobutanecarbonyl, cyclopentanecarbonyl, cyclohexanecarbonyl, etc.; cycloalkenecarbonyl groups of 3 to 6 carbon atoms, such as cyclopentenecarbonyl, cyclohexenecarbonyl, etc.; aroyl groups of 6 to 10 carbon atoms, such as benzoyl, toluoyl, naphthoyl, etc.; saturated heterocyclic carbonyl groups having a 5- or 6-membered saturated heterocyclic ring containing one or two heteroatoms selected from nitrogen atom, oxygen atom and sulfur atom, such as 2-piperidinecarbonyl, 3-morpholinecarbonyl, etc.; and heteroaromatic acyl groups having a 5- or 6-membered heteroaromatic ring containing one or two heteroatoms selected from nitrogen atom, oxygen atom and sulfur atom, or heteroaromatic acyl groups having a heteroaromatic ring having a benzene ring fused therewith, such as 2-furoyl, 3-furoyl, 2-thenoyl, 3-thenoyl, nicotinoyl, isonicotinoyl, 5-indazolylcarbonyl, etc.

Each of the alkylene group, the alkyl group, the cycloalkyl group, the alkanoyl group, the cycloalkanecarbonyl group, the cycloalkenecarbonyl group, and the alkyl portion of the arylalkyl group may have one or more substituents which may be the same or different. As the substituents, there are exemplified halogen atoms, cyano group, aromatic groups, alkenyl groups, phenoxy group, benzyloxy group, trifluoromethyl group, hydroxyl group, lower alkoxy groups, saturated heterocyclic ring-oxy groups, lower alkoxy-lower alkoxy groups, lower alkanoyloxy groups, amino group, nitro group, carbamoyl group, lower alkylaminocarbonyl groups, di-lower-alkylaminocarbonyl group, lower alkoxycarbonylamino groups, benzyloxycarbonylamino group, lower alkylsulfonylamino-lower alkyl groups, carboxyl group, lower alkoxycarbonyl groups, lower alkylthio groups, lower alkylsulfinyl groups, lower alkylsulfonyl groups, lower alkylsulfonamide groups, tri-lower-alkylsilyl groups, phthalimide group, aryl groups, heteroaryl groups, cycloalkyl groups, cycloalkenyl groups, alkyl groups, alkynyl groups, lower alkylaminoalkyl groups, di-lower-alkylaminoalkyl groups, saturated heterocyclic groups, saturated heterocyclic ring-oxy groups, oxo group, saturated heterocyclic carbonylamino groups, cycloalkanecarbonylamino groups, and amino groups substituted by one or more groups which may be the same or different and are represented by the formula: $R^{12}-R^{13}-$ wherein $R^{12}$ is a lower alkoxycarbonyl group, a lower alkyl group, an aromatic group, a cycloalkyl group, a saturated heterocyclic group, a benzoyl group or a lower alkanoyl group (said lower alkoxycarbonyl group, lower alkyl group, aromatic group, cycloalkyl group, saturated heterocyclic group, benzoyl group or lower alkanoyl group may be substituted by one or more substituents which may be the same or different and are selected from hydroxyl group, amino group, mono-lower-alkylamino groups, di-lower-alkylamino groups, halogen atoms, lower alkoxy groups, benzyloxy group, benzyl group, methylenedioxy group and trifluoromethyl group; and $R^{13}$ is a single bond or a lower alkylene group).

Each of the aromatic group, the aroyl group, the phenyl group, the heteroaromatic acyl group and the aryl portion of the arylalkyl group may have one or more substituents which may be the same or different. As the substituents, there are exemplified halogen atoms, cyano group, trifluoromethyl group, trifluoromethoxy group, nitro group, hydroxyl group, methylenedioxy group, lower alkyl groups which may be substituted, lower alkoxy groups, benzyloxy group, lower alkanoyloxy groups, amino group, mono-lower-alkylamino groups, di-lower-alkylamino groups, monocycloalkylamino groups, dicycloalkylamino groups, carboxyl group, lower alkoxycarbonyl groups, lower alkylthio groups, lower alkylsulfinyl groups, lower alkylsulfonyl groups, lower alkanoylamino groups, lower alkylsulfonamide groups, aminosulfonyl group, and carbamoyl groups substituted by one or more lower alkyl groups or cycloalkyl groups, which may be substituted and may be the same or different. There are also exemplified saturated heterocyclic carbonyl groups that may be substituted by a benzyl group or a hydroxyl group.

As the heteroatom of the substituted or unsubstituted saturated 5- to 8-membered cyclic amino group which may contain another heteroatom in the ring and which $R^9$ and $R^{10}$ form when taken together with the nitrogen atom to which they are bonded, there are exemplified oxygen atom, sulfur atom and nitrogen atom. Specific examples of such cyclic amino group are pyrrolidine and piperidine. As the substituent, there are exemplified substituted or unsubstituted alkyl groups and groups represented by the formula: $-OR^{81}$. Here, as $R^{81}$, there are exemplified hydrogen atom, substituted or unsubstituted alkyl groups, substituted or unsubstituted cycloalkyl groups, substituted or unsubstituted cycloalkenyl groups, substituted or unsubstituted saturated heterocyclic groups, substituted or unsubstituted alkoxycarbonyl groups, substituted or unsubstituted aromatic groups, substituted or unsubstituted acyl groups, and substituted or unsubstituted arylalkyl groups.

The term "lower" means that the alkyl portion of the substituent concerned is a lower alkyl group. As such a lower alkyl group, there are exemplified groups of 4 or less carbon atoms, such as methyl, ethyl, propyl, isopropyl, butyl, isobutyl, sec-butyl, tert-butyl, etc.

The term "alkoxy group" means a group having the above-mentioned alkyl group bonded to one of the direct links of an oxygen atom.

The term "alkoxycarbonyl group" means a group having the above-mentioned alkoxy group bonded to one of the direct links of a carbonyl group.

The term "alkanoyl group" means a group having the above-mentioned alkyl group bonded to one of the direct links of a carbonyl group.

The term "cycloalkylalkyl group" means a group having on its alkyl group one or more cycloalkyl groups which may be the same or different, as substituent(s).

The term "haloalkyl group" means a group having on its alkyl group one or more halogen atoms which may be the same or different, as substituent(s).

The term "hydroxyalkyl group" means a group having on its alkyl group one or more hydroxyl groups as substituent(s).

The passage "when X is a group represented by the formula: $-N(R^3)C(=O)-$, $-C(=O)N(R^3)-$, $-N(R^3)S(O)_2-$ or $-S(O)_2N(R^3)-$ in the compound represented by the formula (1)" means that $R^1$ is bonded to the left side of X and a benzene ring fused with the ring A is bonded to the right side of X. Also in other definitions, when different compounds are formed depending on the directions of bonding of divalent groups, each structural formula means that the divalent groups are bonded in the directions shown in the structural formula, unless otherwise specified.

As the compounds according to the above items [13] to [16] which have inhibitory effect on Rho kinase in the invention of the pharmaceutical composition for treatment of urinary incontinence, there are exemplified the compounds disclosed in International Patent Laid-Open No. WO98/06433, in particular, (+)-trans-4-(1-aminoethyl)-1-(4-pyridylcarbamoyl)cyclohexane; the compounds disclosed in International Patent Laid-Open No. WO99/64011; the compounds disclosed in International Patent Laid-Open No. WO00/57914; and the compounds represented by the above general formula (1), prodrugs thereof, and pharmaceutically acceptable salts of the compounds or prodrugs.

The compound represented by the formula (1) may be synthesized from a well-known compound by a combination of well-known synthesis processes. It may be synthesized, for example, by any of the following processes.

(A) A compound of the formula (1) in which X is a group represented by the formula: $-NH-$ may be synthesized, for example, as follows.

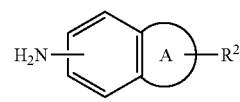

(2)

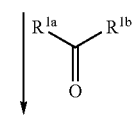

-continued

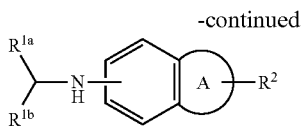

wherein each of $R^{1a}$ and $R^{1b}$ is a hydrogen atom or a substituted or unsubstituted alkyl group, or $R^{1a}$ and $R^{1b}$, when taken together with the carbon atoms to which they are bonded, form a substituted or unsubstituted cycloalkyl group, a substituted or unsubstituted cycloalkenyl group, or a substituted or unsubstituted saturated heterocyclic group; and the ring A and $R^2$ are as defined above.

The compound of the formula (1) in which X is a group represented by the formula: —NH— may be produced, for example, by subjecting a compound represented by the formula (2) to reductive amination reaction with a compound represented by the formula: $R^{1a}C(=O)R^{1b}$ in an inert solvent in the presence of a reducing agent at room temperature or with heating.

As the reducing agent, there may be used reducing agents including composite hydrogen compounds such as sodium triacetoxyborohydride, lithium aluminum hydride, sodium borohydride, sodium cyanoborohydride, etc.; and diborane. There may also be employed reduction with sodium, sodium amalgam or zinc-acid, and electrical reduction using lead or platinum as a cathode. As the solvent, there are exemplified alcohol solvents such as methanol, ethanol, etc.; ether solvents such as tetrahydrofuran, 1,4-dioxane, etc.; halogenated hydrocarbon solvents such as dichloromethane, chloroform, 1,2-dichloroethane, etc.; and mixed solvents thereof.

(B) A compound of the formula (1) in which X is a group represented by the formula: —CONH— may be synthesized, for example, as follows.

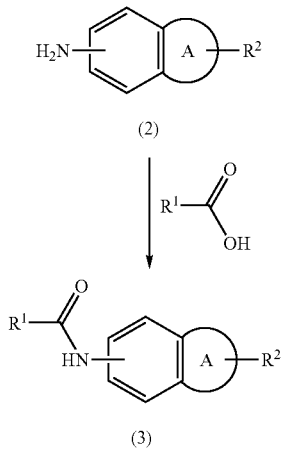

wherein the ring A, $R^1$ and $R^2$ are as defined above.

The compound of the formula (1) in which X is a group represented by the formula: —CONH—, i.e., a compound of the formula (3) may be produced by reacting a compound represented by the formula (2) with a compound represented by the formula: $R^1COOH$ in an inert solvent in the presence of a condensing agent at room temperature or with heating, or by reacting a compound represented by the formula (2) with a corresponding acid halide or acid anhydride in an inert solvent in the presence of a base at room temperature or with heating.

As the condensing agent, there are used condensing agents such as dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium•hexafluorophosphate (BOP), diphenylphosphonyldiamide (DPPA), N,N-carbonyldiimidazole (Angew. Chem. Int. Ed. Engl., Vol. 1, 351(1962)), etc. If necessary, there may be added additives such as N-hydroxysuccinimide (HOSu), 1-hydroxybenzotriazole (HOBt), 3-hydroxy-4-oxo-3,4-dihydro-1,2,3-benzotriazine (HOOBt), etc. As the solvent, there are exemplified aromatic hydrocarbon solvents such as benzene, toluene, xylene, etc.; ether solvents such as tetrahydrofuran, 1,4-dioxane, etc.; halogenated hydrocarbon solvents such as dichloromethane, chloroform, 1,2-dichloroethane, etc.; amide solvents such as dimethylformamide, dimethylacetamide, etc.; basic solvents such as pyridine, etc.; and mixed solvents thereof. As the base, there are exemplified inorganic bases such as sodium hydroxide, potassium hydroxide, sodium carbonate, potassium carbonate, sodium hydrogencarbonate, etc.; and organic bases such as triethylamine, pyridine, etc. As the acid halide, acid chlorides and acid bromides are exemplified.

(C) A compound of the formula (1) in which X is a group represented by the formula: —CH$_2$NH— may be synthesized, for example, as follows.

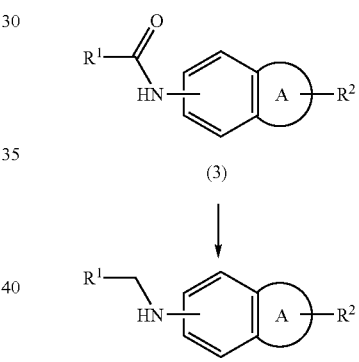

wherein the ring A, $R^1$ and $R^2$ are as defined above.

The compound of the formula (1) in which X is a group represented by the formula: —CH$_2$NH— may be produced, for example, by reducing an amide derivative represented by the formula (3) with a reducing agent such as lithium aluminum hydride, diborane or the like in an inert solvent such as tetrahydrofuran, 1,4-dioxane or the like at room temperature or with heating.

(D) A compound of the formula (1) in which X is a group (an oxygen atom) represented by the formula: —O— may be synthesized, for example, as follows.

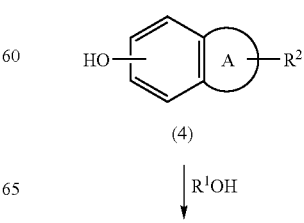

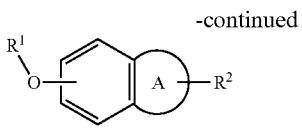

wherein the ring A, $R^1$ and $R^2$ are as defined above.

The compound of the formula (1) in which X is a group represented by the formula: —O— may be produced, for example, by reacting a compound represented by the formula (4) with a compound represented by the formula: $R^1OH$ in an inert solvent in the presence of, for example, diethyl azodicarboxylate and triphenylphosphine at room temperature or with heating.

(E) A compound of the formula (1) in which X is a group represented by the formula: —NHCO— may be synthesized, for example, as follows.

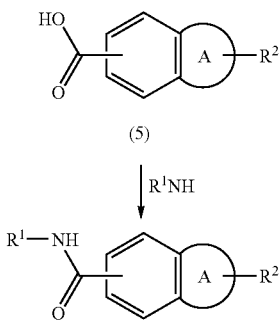

wherein the ring A, $R^1$ and $R^2$ are as defined above.

The compound of the formula (1) in which X is a group represented by the formula: —NHCO— may be produced, for example, by reacting a compound of the formula (5) with a compound represented by the formula: $R^1NH$ in an inert solvent in the presence of a condensing agent at room temperature or with heating.

As the condensing agent, there are used condensing agents such as dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium•hexafluorophosphate (BOP), diphenylphosphonyldiamide (DPPA), N,N-carbonyldiimidazole (Angew. Chem. Int. Ed. Engl., Vol. 1, 351(1962)), etc. If necessary, there may be used additives such as N-hydroxysuccinimide (HOSu), 1-hydroxybenzotriazole (HOBt), 3-hydroxy-4-oxo-3,4-dihydro-1,2,3-benzotriazine (HOOBt), etc.

As the solvent, there are exemplified aromatic hydrocarbon solvents such as benzene, toluene, xylene, etc.; ether solvents such as tetrahydrofuran, 1,4-dioxane, etc.; halogenated hydrocarbon solvents such as dichloromethane, chloroform, 1,2-dichloroethane, etc.; amide solvents such as dimethylformamide, dimethylacetamide, etc.; basic solvents such as pyridine, etc.; and mixed solvents thereof.

(F) A compound of the formula (1) in which X is a group represented by the formula: —N($R^3$)— may be synthesized, for example, as follows.

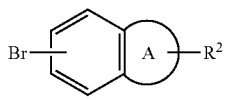

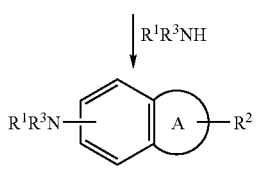

wherein the ring A, $R^1$, $R^2$ and $R^3$ are as defined above.

The compound of the formula (1) in which X is a group represented by the formula: —N($R^3$)— may be produced, for example, by reacting a compound represented by the formula (6) with a compound represented by the formula: $R^1R^3NH$ in an inert solvent in the presence of, a palladium catalyst at room temperature or with heating.

As the palladium catalyst, there may be used catalysts such as bis(tri-O-tolylphosphine)-palladium(II) dichloride, palladium acetate, etc. As the solvent, toluene, 1,4-dioxane and dimethylacetamide are exemplified.

(G) The compound of the formula (2) used as a staring material in the above production processes may be a per se well-known compound, or produced by a well-known process or a combination of well-known processes (as references, there are exemplified A. R. Katritzky and C. W. Rees, COMPREHENSIVE HETEROCYCLIC CHEMISTRY The structure, Reactions, Synthesis and Uses of Heterocyclic Compounds Volume 5, PERGAMON PRESS; Heterocycles, 1995, 41(3), 487–496; J. Chem. Research, Synop, 1990, (11), 350–351; J. Chem. Research, Miniprint, 1990, (11), 2601–2615; Synth. Commun., 1996, 26(13), 2443–2447; and Synth. Commun., 1999, 29(14), 2435–2445).

The compound of the formula (4) used as a staring material in the above production process may be a per se well-known compound, or produced by a well-known process or a combination of well-known processes (as references, there are exemplified Helv. Chim. Acta, 1976, 59, 2618–2620; J. Chem. Soc., 1955, 2412–2418; and J. Chem. Soc., 1960, 2735–2738).

The compound of the formula (5) used as a staring material in the above production process may be a per se well-known compound, or produced by a well-known process or a combination of well-known processes (as references, there are exemplified J. Med. Chem., 2000, 43, 41–58; and Helv. Chim. Acta, 1976, 59, 2618–2620).

The compound of the formula (6) used as a staring material in the above production process may be a per se well-known compound, or produced by a well-known process or a combination of well-known processes (as references, there are exemplified Tetrahedron, 1994, 50(11), 3529–3536; and International Patent Laid-Open No. WO2000-063207).

In each of the above production processes, when the starting compound in each reaction has a reactive group such as a hydroxyl group, amino group or carboxylic acid group, such a group other than a site desired to be reacted is previously protected with a suitable protective group if necessary, and the protective group is removed after carrying out each reaction or several reactions, whereby a desired compound may be obtained. As the protective group for protecting the hydroxyl group, amino group or carboxyl group, an ordinary protective group used in the field of organic synthetic chemistry may be used. The introduction and removal of such a protective group may be carried out according to a usual method (for example, the method described in T. W. Green and P. G. M. Wuts, Protective Groups in Organic Synthesis, Second Edition, John Wiley & Sons, Inc. (1991)).

For example, as a protective group for the hydroxyl group, methoxymethyl group and tetrahydropyranyl group are exemplified. As a protective group for the amino group, tert-butoxycarbonyl group is exemplified. The protective group for the hydroxyl group may be removed by reaction in a solvent such as aqueous methanol, aqueous ethanol or aqueous tetrahydrofuran in the presence of an acid such as hydrochloric acid, sulfuric acid or acetic acid. The protective group for the amino group may be removed by reaction in a solvent such as aqueous tetrahydrofuran, methylene chloride, chloroform or aqueous methanol in the presence of an acid such as hydrochloric acid or trifluoroacetic acid.

As a protective form for protecting the carboxyl group, tert-butyl esters, orthoestes and acid amides are exemplified. Such a protective group is removed as follows. In the case of the tert-butyl ester, the removal is carried out, for example, by reaction in an aqueous solvent in the presence of hydrochloric acid. In the case of the orthoester, the removal is carried out by treatment with an acid and then an alkali such as sodium hydroxide in a solvent such as aqueous methanol, aqueous tetrahydrofuran or aqueous 1,2-dimethoxyethane. In the case of the acid amide, the removal is carried out by reaction in a solvent such as water, aqueous methanol or aqueous tetrahydrofuran in the presence of an acid such as hydrochloric acid or sulfuric acid.

The compound represented by the formula (1) includes those having an optical center of asymmetry. Therefore, the compound having an optical center of asymmetry may be obtained as a racemate, or it may be obtained as an optically active substance when an optically active starting material is used. If necessary, the racemic modification obtained may be physically or chemically resolved into optical antipodes by a well-known method. Preferably, diastereomers are formed from the racemic modification by a reaction using a reagent for optical resolution. The diastereomers different in form may be resolved by a well-known method such as fractional crystallization.

As the "prodrug", there are exemplified those which are easily hydrolyzed in a living body to regenerate the compound of the formula (1). For example, when the compound of the formula (1) has a carboxyl group, examples of the prodrug are compounds obtained by converting the carboxyl group to an alkoxycarbonyl group, an alkylthiocarbonyl group or an alkylaminocarbonyl group. For example, when the compound of the formula (1) has an amino group, examples of the prodrug are compounds obtained by converting the amino group to an alkanoylamino group by substitution by the alkanoyl group, compounds obtained by converting the amino group to an alkoxycarbonylamino group by substitution by the alkoxycarbonyl group, and compounds obtained by converting the amino group to an acyloxymethylamino group or hydroxylamine. For example, when the compound of the formula (1) has a hydroxyl group, examples of the prodrug are compounds obtained by converting the hydroxyl group to an acyloxy group by substitution by the above-exemplified acyl group, and compounds obtained by converting the hydroxyl group to a phosphoric ester or an acyloxymethyloxy group. Examples of the alkyl portion of the group used for such conversion to the prodrug are the above-exemplified alkyl groups. The alkyl groups may be substituted by, for example, an alkoxy group of 1 to 6 carbon atoms. Preferable examples of the alkyl portion are as follows. For example, in the case of compounds obtained by converting the carboxyl group to an alkoxycarbonyl group, the alkoxycarbonyl group includes lower (number of carbon atoms: for example, 1 to 6) alkoxycarbonyls such as methoxycarbonyl, ethoxycarbonyl, etc.; and lower (number of carbon atoms: for example, 1 to 6) alkoxycarbonyls substituted by an alkoxy group, such as methoxymethoxycarbonyl, ethoxymethoxycarbonyl, 2-methoxyethoxycarbonyl, 2-methoxyethoxymethoxycarbonyl, pivaloyloxymethoxy-carbonyl, etc.

If necessary, the compound represented by the formula (1) or the prodrug thereof may be converted to a pharmaceutically acceptable salt. As such a salt, there are exemplified salts with mineral acids such as hydrochloric acid, hydrobromic acid, sulfuric acid, phosphoric acid, etc.; salts with organic carboxylic acids such as formic acid, acetic acid, fumaric acid, maleic acid, oxalic acid, citric acid, malic acid, tartaric acid, aspartic acid, glutamic acid, etc.; salts with sulfonic acids such as methanesulfonic acid, benzenesulfonic acid, p-toluenesulfonic acid, hydroxybenzenesulfonic acid, dihydroxybenzenesulfonic acid, etc.; and alkali metal salts such as sodium salt, potassium salt, etc.; alkaline earth metal salts such as calcium salt, magnesium salt, etc.; ammonium salt; triethylamine salt, pyridine salt, picoline salt, ethanolamine salt, dicyclohexylamine salt, and salt with N,N'-dibenzylethylenediamine.

Each of the compounds represented by the formula (1), the prodrugs thereof and the pharmaceutically acceptable salts of the compounds or prodrugs may be in the form of an anhydride, hydrate or solvate.

When used as a pharmaceutical composition, the compound of the present invention may be orally or parenterally administered. That is, the compound may be orally administered in a usual dosage form such as powder, granules, tablets, capsules, syrup, suspension or the like, or the compound may be parenterally administered, for example, by injection of a solution, emulsion or suspension prepared from the compound. The compound may be administered rectally in the form of a suppository. The above-exemplified suitable dosage forms may be prepared by blending the compound of the present invention with, for example, a carrier, excipient, binder, stabilizer and diluent which are acceptable and ordinary. When the compound is used in the form of an injection, the injection may be incorporated with, for example, a buffer, solubilizer and tonicity agent which are acceptable. Although the dose and the number of administrations are varied depending on, for example, a disease to be cured, the condition of the disease, age, body weight and administration route, the compound may be administered to an adult in a dose of usually 0.1 to 2,000 mg, preferably 1 to 200 mg per day in one portion or several portions (for example, 2 to 4 portions).

Examples of the compound of the present invention are given below. In the following general formulas, Me denotes a methyl group, Et an ethyl group, Pr a n-propyl group, Bu a n-butyl group, and Ms a methanesulfonyl group.

[1] Compounds represented by the following formula
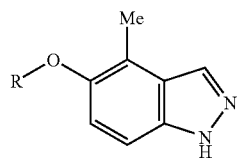
wherein R is any of the groups listed in the following Table 1, Table 2 or Table 3.

TABLE 1-continued

| | R |
|---|---|
| 18 | N-Bn piperidin-3-yl |
| 19 | azepan-4-yl (NH) |
| 20 | 1-Me-azepan-4-yl |
| 21 | 1-Et-azepan-4-yl |
| 22 | 1-Pr-azepan-4-yl |
| 23 | 1-iPr-azepan-4-yl |
| 24 | 1-(2-hydroxyethyl)-azepan-4-yl |
| 25 | 1-cyclopentyl-azepan-4-yl |
| 26 | 1-acetyl-azepan-4-yl |
| 27 | 1-Bn-azepan-4-yl |
| 28 | azepan-3-yl (NH) |
| 29 | 1-Me-azepan-3-yl |
| 30 | 1-Et-azepan-3-yl |
| 31 | 1-Pr-azepan-3-yl |
| 32 | 1-iPr-azepan-3-yl |
| 33 | 1-(2-hydroxyethyl)-azepan-3-yl |
| 34 | 1-cyclopentyl-azepan-3-yl |
| 35 | 1-acetyl-azepan-3-yl |
| 36 | 1-Bn-azepan-3-yl |

TABLE 1-continued

| | R |
|---|---|
| 37 | cyclohexyl with H₂N substituent |
| 38 | cyclohexyl with Me₂N substituent |
| 39 | cyclohexyl with EtHN substituent |

TABLE 2

| | R |
|---|---|
| 40 | cyclohexyl with Et₂N substituent |
| 41 | cyclohexyl with PrHN substituent |
| 42 | cyclohexyl with iPrNH substituent |
| 43 | cyclohexyl with BuHN substituent |
| 44 | cyclohexyl with cyclopentyl-NH substituent |
| 45 | cyclohexyl with MeC(O)NH substituent |

TABLE 2-continued

| | R |
|---|---|
| 46 | cyclohexyl with BnHN substituent (trans) |
| 47 | cyclohexyl with H₂N substituent (trans) |
| 48 | cyclohexyl with Me₂N substituent (trans) |
| 49 | cyclohexyl with EtHN substituent (trans) |
| 50 | cyclohexyl with Et₂N substituent (trans) |
| 51 | cyclohexyl with PrHN substituent (trans) |
| 52 | cyclohexyl with iPrNH substituent (trans) |
| 53 | cyclohexyl with BuHN substituent (trans) |
| 54 | cyclohexyl with cyclopentyl-NH substituent (trans) |
| 55 | cyclohexyl with MeC(O)NH substituent (trans) |

TABLE 2-continued

| | R |
|---|---|
| 56 | BnHN-cyclohexyl- (trans) |
| 57 | H₂N-cyclohexyl- |
| 58 | Me₂N-cyclohexyl- |
| 59 | EtHN-cyclohexyl- |
| 60 | Et₂N-cyclohexyl- |
| 61 | PrHN-cyclohexyl- |
| 62 | iPrHN-cyclohexyl- |
| 63 | BuHN-cyclohexyl- |
| 64 | cyclopentyl-HN-cyclohexyl- |
| 65 | MeC(O)NH-cyclohexyl- |
| 66 | BnHN-cyclohexyl- |
| 67 | H₂N-cyclohexyl- (cis) |
| 68 | Me₂N-cyclohexyl- |
| 69 | EtHN-cyclohexyl- |
| 70 | Et₂N-cyclohexyl- |
| 71 | PrHN-cyclohexyl- |
| 72 | iPrHN-cyclohexyl- |
| 73 | BuHN-cyclohexyl- |
| 74 | cyclopentyl-HN-cyclohexyl- |
| 75 | MeC(O)NH-cyclohexyl- |
| 76 | BnHN-cyclohexyl- |
| 77 | 1-(methylsulfonyl)piperidin-4-yl |

TABLE 2-continued

| | R |
|---|---|
| 78 | (Me-SO2-N-piperidin-3-yl) |

TABLE 3

| | R |
|---|---|
| 79 | (Me-SO2-N-azepan-4-yl) |
| 80 | (Me-SO2-N-azepan-3-yl) |
| 81 | (Me-SO2-NH-cyclohexyl, trans) |
| 82 | (Me-SO2-NH-cyclohexyl, cis) |
| 83 | (Me-SO2-NH-cyclohexyl-1,3) |
| 84 | (Me-SO2-NH-cyclohexyl-1,3, stereo) |

[2] Compounds represented by the following formula:

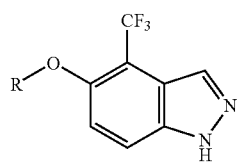

wherein R is any of the groups listed in the above Table 1, Table 2 or Table 3.

[3] Compounds represented by the following formula:

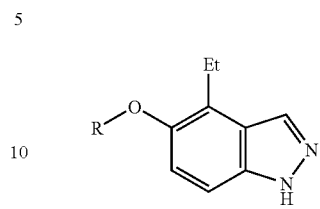

wherein R is any of the groups listed in the above Table 1, Table 2 or Table 3.

[4] Compounds represented by the following formula:

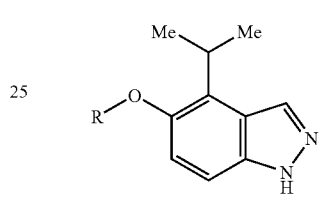

wherein R is any of the groups listed in the above Table 1, Table 2 or Table 3.

[5] Compounds represented by the following formula:

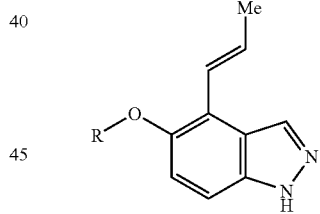

wherein R is any of the groups listed in the above Table 1, Table 2 or Table 3.

[6] Compounds represented by the following formula:

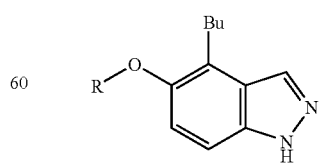

wherein R is any of the groups listed in the above Table 1, Table 2 or Table 3.

[7] Compounds represented by the following formula:

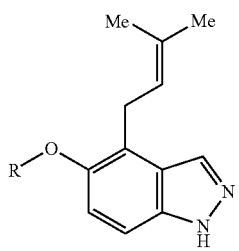

wherein R is any of the groups listed in the above Table 1, Table 2 or Table 3.

[8] Compounds represented by the following formula:

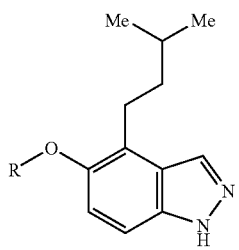

wherein R is any of the groups listed in the above Table 1, Table 2 or Table 3.

[9] Compounds represented by the following formula:

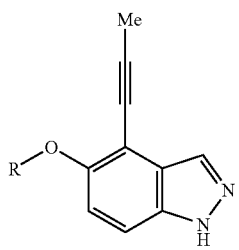

wherein R is any of the groups listed in the above Table 1, Table 2 or Table 3.

[10] Compounds represented by the following formula:

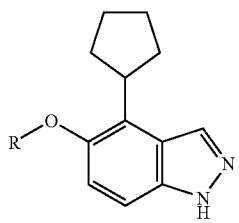

wherein R is any of the groups listed in the above Table 1, Table 2 or Table 3.

[11] Compounds represented by the following formula:

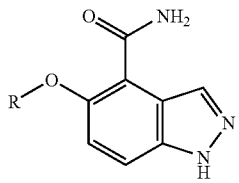

wherein R is any of the groups listed in the above Table 1, Table 2 or Table 3.

[12] Compounds represented by the following formula:

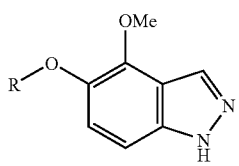

wherein R is any of the groups listed in the above Table 1, Table 2 or Table 3.

[13] Compounds represented by the following formula:

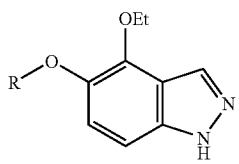

wherein R is any of the groups listed in the above Table 1, Table 2 or Table 3.

[14] Compounds represented by the following formula:

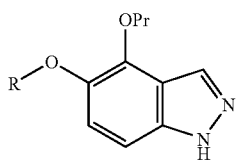

wherein R is any of the groups listed in the above Table 1, Table 2 or Table 3.

[15] Compounds represented by the following formula:

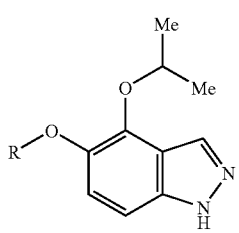

wherein R is any of the groups listed in the above Table 1, Table 2 or Table 3.

[16] Compounds represented by the following formula:

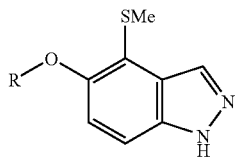

wherein R is any of the groups listed in the above Table 1, Table 2 or Table 3.

[17] Compounds represented by the following formula:

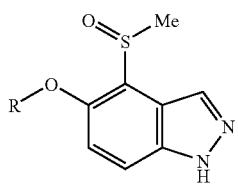

wherein R is any of the groups listed in the above Table 1, Table 2 or Table 3.

[18] Compounds represented by the following formula:

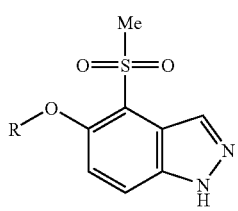

wherein R is any of the groups listed in the above Table 1, Table 2 or Table 3.

[19] Compounds represented by the following formula:

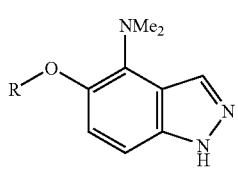

wherein R is any of the groups listed in the above Table 1, Table 2 or Table 3.

[20] Compounds represented by the following formula:

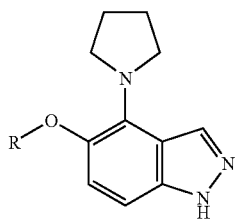

wherein R is any of the groups listed in the above Table 1, Table 2 or Table 3.

[21] Compounds represented by the following formula:

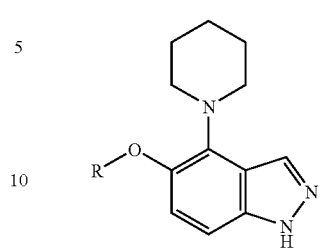

wherein R is any of the groups listed in the above Table 1, Table 2 or Table 3.

[22] Compounds represented by the following formula:

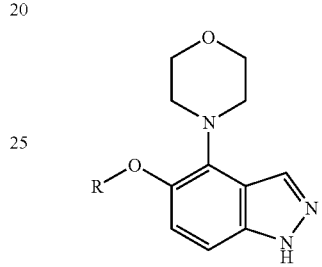

wherein R is any of the groups listed in the above Table 1, Table 2 or Table 3.

[23] Compounds represented by the following formula:

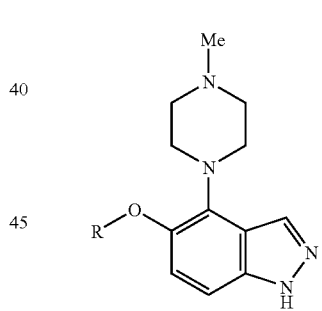

wherein R is any of the groups listed in the above Table 1, Table 2 or Table 3.

[24] Compounds represented by the following formula:

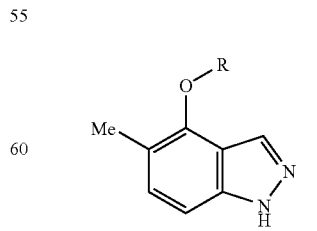

wherein R is any of the groups listed in the above Table 1, Table 2 or Table 3.

[25] Compounds represented by the following formula:

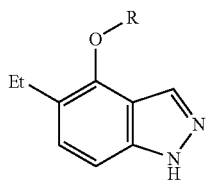

wherein R is any of the groups listed in the above Table 1, Table 2 or Table 3.

[26] Compounds represented by the following formula:

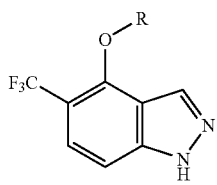

wherein R is any of the groups listed in the above Table 1, Table 2 or Table 3.

[27] Compounds represented by the following formula:

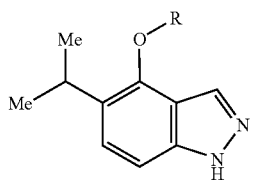

wherein R is any of the groups listed in the above Table 1, Table 2 or Table 3.

[28] Compounds represented by the following formula:

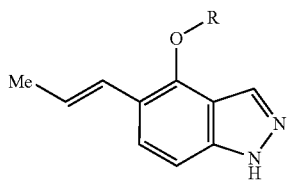

wherein R is any of the groups listed in the above Table 1, Table 2 or Table 3.

[29] Compounds represented by the following formula:

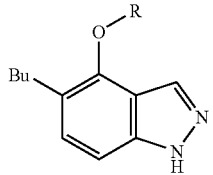

wherein R is any of the groups listed in the above Table 1, Table 2 or Table 3.

[30] Compounds represented by the following formula:

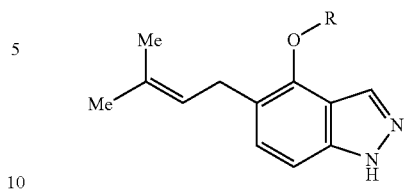

wherein R is any of the groups listed in the above Table 1, Table 2 or Table 3.

[31] Compounds represented by the following formula:

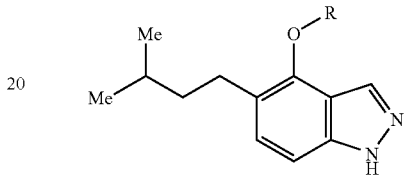

wherein R is any of the groups listed in the above Table 1, Table 2 or Table 3.

[32] Compounds represented by the following formula:

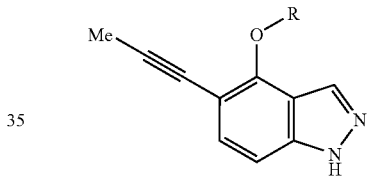

wherein R is any of the groups listed in the above Table 1, Table 2 or Table 3.

[33] Compounds represented by the following formula:

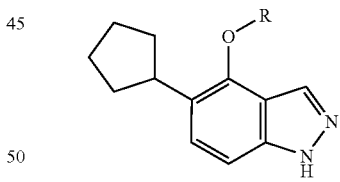

wherein R is any of the groups listed in the above Table 1, Table 2 or Table 3.

[34] Compounds represented by the following formula:

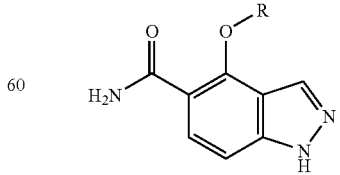

wherein R is any of the groups listed in the above Table 1, Table 2 or Table 3.

[35] Compounds represented by the following formula:

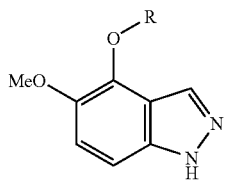

wherein R is any of the groups listed in the above Table 1, Table 2 or Table 3.

[36] Compounds represented by the following formula:

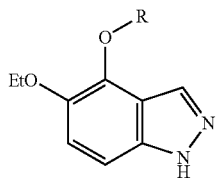

wherein R is any of the groups listed in the above Table 1, Table 2 or Table 3.

[37] Compounds represented by the following formula:

wherein R is any of the groups listed in the above Table 1, Table 2 or Table 3.

[38] Compounds represented by the following formula:

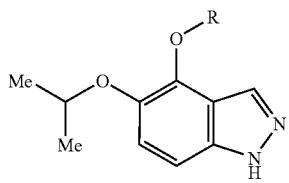

wherein R is any of the groups listed in the above Table 1, Table 2 or Table 3.

[39] Compounds represented by the following formula:

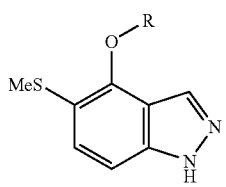

wherein R is any of the groups listed in the above Table 1, Table 2 or Table 3.

[40] Compounds represented by the following formula:

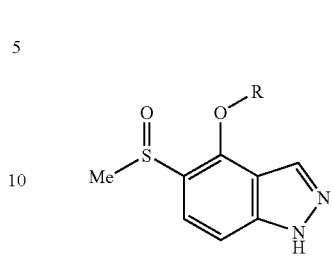

wherein R is any of the groups listed in the above Table 1, Table 2 or Table 3.

[41] Compounds represented by the following formula:

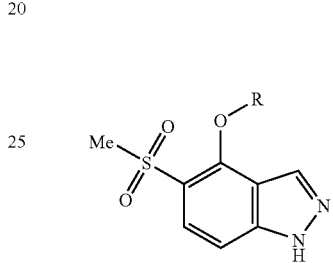

wherein R is any of the groups listed in the above Table 1, Table 2 or Table 3.

[42] Compounds represented by the following formula:

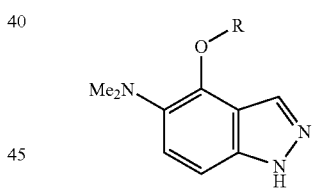

wherein R is any of the groups listed in the above Table 1, Table 2 or Table 3.

[43] Compounds represented by the following formula:

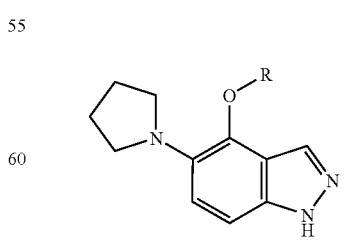

wherein R is any of the groups listed in the above Table 1, Table 2 or Table 3.

[44] Compounds represented by the following formula:

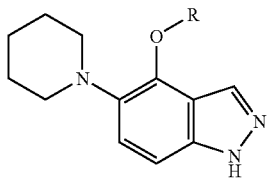

wherein R is any of the groups listed in the above Table 1, Table 2 or Table 3.

[45] Compounds represented by the following formula:

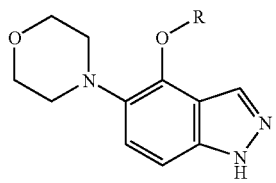

wherein R is any of the groups listed in the above Table 1, Table 2 or Table 3.

[46] Compounds represented by the following formula:

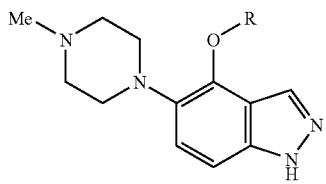

wherein R is any of the groups listed in the above Table 1, Table 2 or Table 3.

[47] Compounds represented by the following formula:

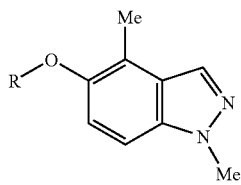

wherein R is any of the groups listed in the above Table 1, Table 2 or Table 3.

[48] Compounds represented by the following formula:

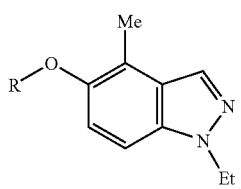

wherein R is any of the groups listed in the above Table 1, Table 2 or Table 3.

[49] Compounds represented by the following formula:

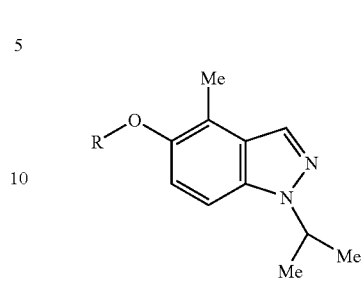

wherein R is any of the groups listed in the above Table 1, Table 2 or Table 3.

[50] Compounds represented by the following formula:

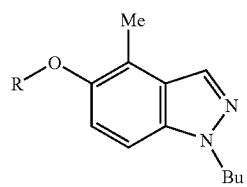

wherein R is any of the groups listed in the above Table 1, Table 2 or Table 3.

[51] Compounds represented by the following formula:

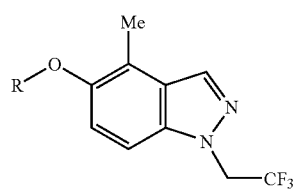

wherein R is any of the groups listed in the above Table 1, Table 2 or Table 3.

[52] Compounds represented by the following formula:

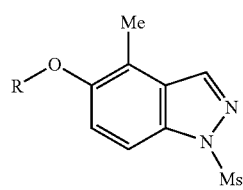

wherein R is any of the groups listed in the above Table 1, Table 2 or Table 3.

[53] Compounds represented by the following formula:

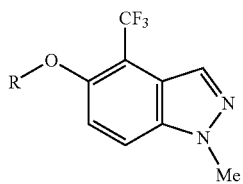

wherein R is any of the groups listed in the above Table 1, Table 2 or Table 3.

[54] Compounds represented by the following formula:

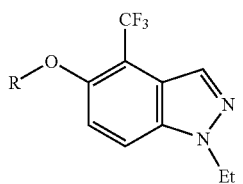

wherein R is any of the groups listed in the above Table 1, Table 2 or Table 3.

[55] Compounds represented by the following formula:

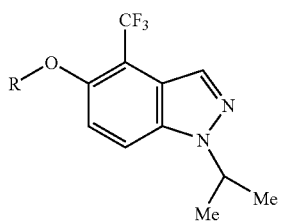

wherein R is any of the groups listed in the above Table 1, Table 2 or Table 3.

[56] Compounds represented by the following formula:

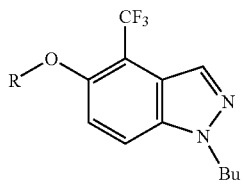

wherein R is any of the groups listed in the above Table 1, Table 2 or Table 3.

[57] Compounds represented by the following formula:

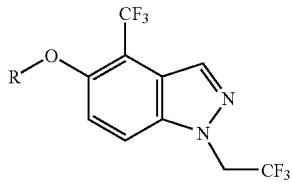

wherein R is any of the groups listed in the above Table 1, Table 2 or Table 3.

[58] Compounds represented by the following formula:

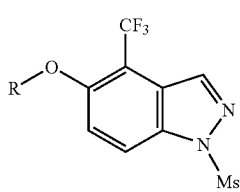

wherein R is any of the groups listed in the above Table 1, Table 2 or Table 3.

[59] Compounds represented by the following formula:

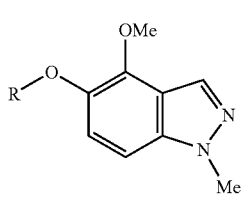

wherein R is any of the groups listed in the above Table 1, Table 2 or Table 3.

[60] Compounds represented by the following formula:

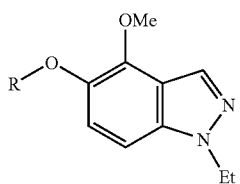

wherein R is any of the groups listed in the above Table 1, Table 2 or Table 3.

[61] Compounds represented by the following formula:

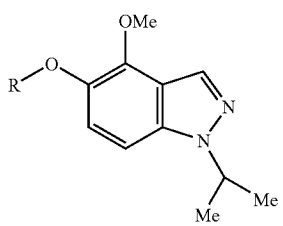

wherein R is any of the groups listed in the above Table 1, Table 2 or Table 3.

[62] Compounds represented by the following formula:

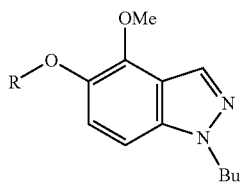

wherein R is any of the groups listed in the above Table 1, Table 2 or Table 3.

[63] Compounds represented by the following formula:

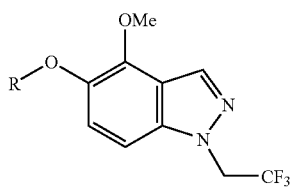

wherein R is any of the groups listed in the above Table 1, Table 2 or Table 3.

[64] Compounds represented by the following formula:

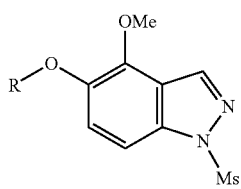

wherein R is any of the groups listed in the above Table 1, Table 2 or Table 3.

[65] Compounds represented by the following formula:

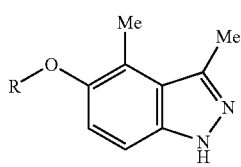

wherein R is any of the groups listed in the above Table 1, Table 2 or Table 3.

[66] Compounds represented by the following formula:

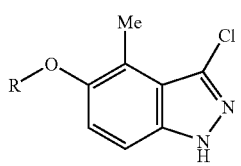

wherein R is any of the groups listed in the above Table 1, Table 2 or Table 3.

[67] Compounds represented by the following formula:

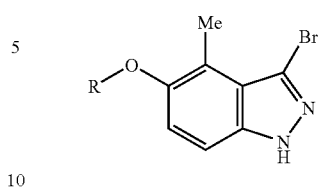

wherein R is any of the groups listed in the above Table 1, Table 2 or Table 3.

[68] Compounds represented by the following formula:

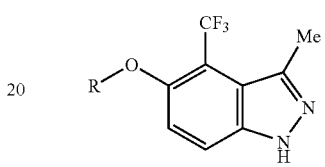

wherein R is any of the groups listed in the above Table 1, Table 2 or Table 3.

[69] Compounds represented by the following formula:

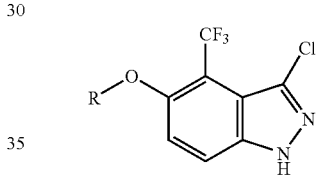

wherein R is any of the groups listed in the above Table 1, Table 2 or Table 3.

[70] Compounds represented by the following formula:

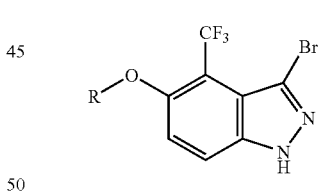

wherein R is any of the groups listed in the above Table 1, Table 2 or Table 3.

[71] Compounds represented by the following formula:

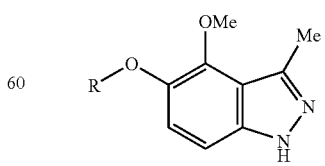

wherein R is any of the groups listed in the above Table 1, Table 2 or Table 3.

[72] Compounds represented by the following formula:

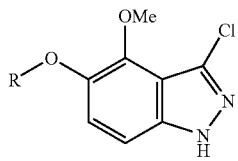

wherein R is any of the groups listed in the above Table 1, Table 2 or Table 3.

[73] Compounds represented by the following formula:

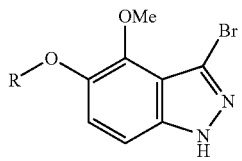

wherein R is any of the groups listed in the above Table 1, Table 2 or Table 3.

[74] Compounds represented by the following formula:

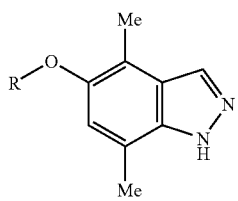

wherein R is any of the groups listed in the above Table 1, Table 2 or Table 3.

[75] Compounds represented by the following formula:

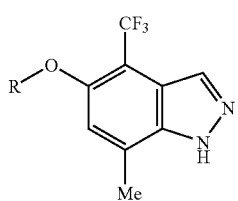

wherein R is any of the groups listed in the above Table 1, Table 2 or Table 3.

[76] Compounds represented by the following formula:

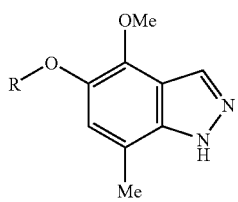

wherein R is any of the groups listed in the above Table 1, Table 2 or Table 3.

[77] Compounds represented by the following formula:

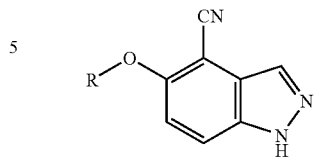

wherein R is any of the groups listed in the above Table 1, Table 2 or Table 3.

[78] Compounds represented by the following formula:

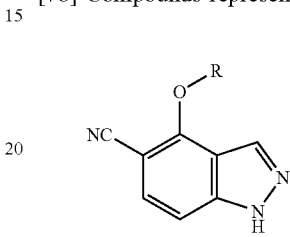

wherein R is any of the groups listed in the above Table 1, Table 2 or Table 3.

The present invention is more concretely illustrated below with reference examples, working examples and test examples, which should not be construed as limiting the scope of the invention. The nomenclature of compounds shown in the reference examples and working examples mentioned below is not always based on IUPAC.

REFERENCE EXAMPLE 1

Synthesis of 1H-indazole-5-carboxylic acid

Water (20 ml) and concentrated sulfuric acid (20 ml) were added to a solution of 1H-indazole-5-carbonitrile (3.00 g, 20.1 mmol) in acetic acid (20 ml) at room temperature, and the resulting mixture was heated at 100° C. for 3 hours. Then, the reaction solution was poured onto ice and the solid precipitated was collected by filtration and dried under reduced pressure to obtain 1H-indazole-5-carboxylic acid (2.88 g, 88%).

$^1$H-NMR (DMSO-$d_6$) δ; 7.58 (1H, d, J=8.6 Hz), 7.90 (1H, dd, J=8.6, 1.4 Hz), 8.23 (1H, s), 8.44 (1H, d, J=0.7 Hz), 12.75 (1H, brs), 13.59 (1H, brs).

REFERENCE EXAMPLE 2

Synthesis of 1H-indazol-5-ylmethanol (a) Synthesis of methyl 1H-indazole-5-carboxylate A solution of sodium nitrite (836 mg, 59.1 mmol) in water (2 ml) was added to a solution of methyl 4-amino-3-methylbenzoate (2.00 g, 12.1 mmol) in acetic acid (80 ml) at room temperature and stirred at room temperature for 5 hours. The reaction solution was concentrated and the resulting residue was diluted with chloroform and washed with a 5% aqueous sodium hydrogencarbonate solution and then a saturated aqueous sodium chloride solution. The organic layer was dried over anhydrous sodium sulfate and distilled under reduced pressure to remove the solvent, and the resulting residue was purified by a silica gel column chromatography (eluent: hexane/ethyl acetate=3/1) to obtain methyl 1H-indazole-5-carboxylate (645 mg, 30%).

$^1$H-NMR (DMSO-d$_6$) δ; 3.86 (3H, s), 7.61 (1H, d, J=8.8 Hz), 7.91 (1H, d, J=8.8 Hz), 8.25 (1H, s), 8.48 (1H, brs), 13.41 (1H, brs).

(b) Synthesis of 1H-indazole-5-ylmethanol

A solution of methyl 1H-indazole-5-carboxylate (825 mg, 4.68 mmol) in tetrahydrofuran (20 ml) was added to a solution of lithium aluminum hydride (580 mg, 14.1 mmol) in tetrahydrofuran (16 ml) at 0° C. and stirred at 0° C. for 1 hour. A mixture of tetrahydrofuran (10 ml) and water (10 ml) was added to the reaction solution and the resulting mixture was filtered. The filtrate was concentrated and the resulting residue was diluted with chloroform and washed with a 1N-aqueous sodium hydroxide solution and then a saturated aqueous sodium chloride solution. The organic layer was dried over anhydrous sodium sulfate and distilled under reduced pressure to remove the solvent, whereby 1H-indazole-5-ylmethanol (260 mg, 38%) was obtained.

$^1$H-NMR (DMSO-d$_6$) δ; 4.55 (1H, d, J=5.5 Hz), 5.14 (1H, t, J=5.5 Hz), 7.30 (1H, dd, J=1.1, 8.4 Hz), 7.47 (1H, d, J=8.4 Hz), 7.46 (1H, s), 8.01 (1H, s), 12.97 (1H, brs).

REFERENCE EXAMPLE 3

Synthesis of 5-(bromomethyl)-1H-indazole hydrobromide 1H-indazole-5-ylmethanol (100 mg, 0.675 mmol) was added to a 48% aqueous hydrogen bromide solution (2.0 ml) at room temperature and stirred at room temperature for 15 hours and then at 50° C. for 5 hours. Subsequently, the reaction solution was filtered and the resulting solid was dried under reduced pressure to obtain 5-(bromomethyl)-1H-indazole hydrobromide (156 mg, 79%).

$^1$H-NMR (DMSO-d$_6$) δ; 4.86 (2H, s), 7.42 (1H, dd, J=8.6, 1.7 Hz), 7.51 (1H, d, J=8.6 Hz), 7.84 (1H, s), 8.07 (1H, d, J=1.7 Hz).

REFERENCE EXAMPLE 4

Synthesis of 1H-indazol-5-ol (a) Synthesis of 5-methoxy-1H-indazole

A solution of sodium nitrite (3.38 g, 49.0 mmol) in water (8.1 ml) was added to a solution of 4-methoxy-2-methylaniline (6.69 g, 48.8 mmol) in acetic acid (350 ml) in an ice-water bath while maintaining the temperature at 25° C. or lower, and stirred overnight at room temperature. Then, the reaction solution was poured into water and extracted with chloroform. The organic layer was washed with a saturated aqueous sodium chloride solution, dried over anhydrous magnesium sulfate and then distilled under reduced pressure to remove the solvent, and the resulting residue was purified by a silica gel column chromatography (eluent: chloroform/methanol=9/1) to obtain 5-methoxy-1H-indazole (1.30 g, 18%).

$^1$H-NMR (DMSO-d$_6$) δ; 3.76 (3H, s), 6.98 (1H, dd, J=8.8, 1.8 Hz), 7.15 (1H, d, J=1.8 Hz), 7.42 (1H, d, J=8.8 Hz), 7.93 (1H, s), 12.89 (1H, brs).

(b) Synthesis of 1H-indazol-5-ol

A methylene chloride solution of boron tribromide (18.5 ml, 18.5 mmol) was added to a solution of 5-methoxy-1H-indazole (1.24 g, 8.40 mmol) in methylene chloride (84 ml) at 0° C. and stirred at room temperature for 10 hours. Then, water was poured into the reaction solution in an ice-water bath, followed by extraction with ethyl acetate. The organic layer was washed with a saturated aqueous sodium hydrogencarbonate solution and then a saturated aqueous sodium chloride solution, dried over anhydrous magnesium sulfate, and distilled under reduced pressure to remove the solvent, and the resulting residue was purified by a silica gel column chromatography (eluent: chloroform/methanol=96/4) to obtain 1H-indazol-5-ol (877 mg, 71%).

$^1$H-NMR (DMSO-d$_6$) δ; 6.88 (1H, dd, J=8.8, 2.2 Hz), 6.96 (1H, d, J=2.2 Hz), 7.34 (1H, d, J=8.8 Hz), 7.84 (1H, s).

REFERENCE EXAMPLE 5

Synthesis of 5-bromo-1-tetrahydro-2H-pyran-2-yl-1H-indazole 3,4-dihydro-2H-pyran (0.84 ml, 9.21 mmol) and pyridinium p-toluenesulfonate (202 mg, 0.804 mmol) were added to a solution of 5-bromo-1H-indazole (790 mg, 4.01 mmol) in methylene chloride (15 ml) at room temperature, and the resulting mixture was refluxed for 6 hours. Then, the reaction solution was poured into a saturated aqueous sodium hydrogencarbonate solution and extracted with chloroform. The organic layer was washed with a saturated aqueous sodium chloride solution and then dried over anhydrous magnesium sulfate. The solvent was distilled off under reduced pressure and the resulting residue was purified by a silica gel column chromatography (eluent: hexane/ethyl acetate=93/7) to obtain 5-bromo-1-tetrahydro-2H-pyran-2-yl-1H-indazole (1.06 g, 94%).

$^1$H-NMR (DMSO-d$_6$) δ; 1.64–1.85 (3H, m), 2.06–2.17 (2H, m), 2.48–2.59 (1H, m), 3.70–3.78 (1H, m), 3.99–4.03 (1H, m), 5.66 (1H, dd, J=8.9, 2.9 Hz), 7.46 (1H, dd, J=9.0, 1.7 Hz), 7.48–7.52 (1H, m), 7.87 (1H, dd, J=1.7, 0.9 Hz), 7.96 (1H, d, J=0.6 Hz), 7.84 (1H, s).

EXAMPLE 1

Synthesis of N-(1-benzyl-4-piperidinyl)-1H-indazol-5-amine dihydrochloride monohydrate (a) Synthesis of N-(1-benzyl-4-piperidinyl)-1H-indazol-5-amine To a solution of 1-benzyl-4-piperidone (7.11 g, 37.6 mmol) in 1,2-dichloroethane (125 ml) were added 5-aminoindazole (5.00 g, 37.6 mmol), sodium triacetoxyborohydride (11.5 g, 52.6 mmol) and acetic acid (2.15 ml, 37.6 mmol) at room temperature, and stirred overnight at room temperature. Then, the reaction solution was poured into a 1N-aqueous sodium hydroxide solution and extracted with ethyl acetate. The organic layer was washed with a saturated aqueous sodium chloride solution and then dried over anhydrous magnesium sulfate. The solvent was distilled off under reduced pressure and the resulting residue was purified by a silica gel column chromatography (eluent: ethyl acetate/methanol=100/1) to obtain N-(1-benzyl-4-piperidinyl)-1H-indazol-5-amine (8.56 g, 74%).

Melting point: 174–176° C.

(b) Synthesis of N-(1-benzyl-4-piperidinyl)-1H-indazol-5-amine dihydrochloride monohydrate To a solution of N-(1-benzyl-4-piperidinyl)-1H-indazol-5-amine (3.06 g, 10.0 mmol) in tetrahydrofuran (31 ml) was added a 1N-hydrochloric acid/ether solution (25 ml) at room temperature, and stirred at room temperature for 30 minutes. The solid precipitated was collected by filtration and recrystallized from methanol to obtain N-(1-benzyl-4-piperidinyl)-1H-indazol-5-amine dihydrochloride monohydrate (2.86 g, 72%).

Melting point: 257–259° C. (decomp.).

The following compounds of Example 2 to Example 14 were synthesized by carrying out reaction according to the method described in Example 1.

EXAMPLE 2

N-[1-(2-phenylethyl)-4-piperidinyl)]-1H-indazol-5-amine dihydrochloride

Melting point: 285–287° C. (decomp.)

EXAMPLE 3

N-(1-isopropyl-4-piperidinyl)-1H-indazol-5-amine

Melting point: 140–141° C.

EXAMPLE 4

N-(1-benzoyl-4-piperidinyl)-1H-indazol-5-amine $^1$H-NMR (DMSO-$d_6$) δ; 1.32 (2H, m), 1.98 (2H, m), 3.12 (2H, m), 3.52 (2H, m), 4.32 (1H, m), 5.22 (1H, d, J=8.3 Hz), 6.72 (1H, m), 6.82 (1H, dd, J=8.8, 2.0 Hz), 7.26 (1H, J=8.8 Hz), 7.35–7.45 (5H, m), 7.73 (1H, d, brs), 12.58 (1H, brs).

EXAMPLE 5

N-{[4-(dimethylamino)-1-naphthyl]methyl}-1H-indazol-5-amine

Melting point: 143–144° C.

EXAMPLE 6

N-[(2-methoxy-1-naphthyl)methyl]-1H-indazol-5-amine

Melting point: 183–185° C.

EXAMPLE 7

1-[(1H-indazol-5-ylamino)methyl}-2-naphtohol

Melting point: 142–144° C.

EXAMPLE 8

N-(1H-indol-3-ylmethyl)-1H-indazol-5-amine $^1$H-NMR (DMSO-$d_6$) δ; 4.13 (2H, s), 4.56 (2H, s), 6.80–6.86 (2H, m), 6.97–7.02 (1H, m), 7.08 (1H, d, J=2.2 Hz), 7.12 (1H, d, J=9.0 Hz), 7.28 (1H, d, J=8.1 Hz), 7.49 (1H, d, J=7.7 Hz), 7.84 (1H, brs), 10.72 (1H, s), 12.53 (1H, brs).

EXAMPLE 9

N-(4-quinolinylmethyl)-1H-indazol-5-amine

Melting point: 244–246° C. (decomp.)

EXAMPLE 10

N-(1,2,3,4-tetrahydro-2-naphthalenyl)-1H-indazol-5-amine $^1$H-NMR (DMSO-$d_6$) δ; 1.53–1.56 (1H, m), 2.12 (1H, m), 2.62–2.70 (1H, m), 2.85–2.89 (2H, m), 3.08–3.15 (1H, m), 3.64 (1H, m), 5.29 (1H, m), 6.75 (1H, brs), 6.86 (1H, dd, J=9.0, 2.2 Hz), 7.06–7.10 (4H, m), 7.27 (1H, d, J=8.6 Hz), 7.74 (1H, brs), 12.58 (1H, brs).

EXAMPLE 11

N-cyclohexyl-1H-indazol-5-amine monohydrochloride $^1$H-NMR (DMSO-$d_6$) δ; 1.19 (3H, m), 1.42 (2H, m), 1.60 (1H, m), 1.72 (2H, m), 1.90 (2H, m), 3.36 (1H, br), 3.62 (1H, brs), 7.47 (1H, d, J=8.8 Hz), 7.68 (1H, d, J=8.8 Hz), 7.92 (1H, s), 8.20 (1H, s), 11.07 (1H, brs), 13.39 (1H, brs).

EXAMPLE 12

N-tetrahydro-2H-pyran-4-yl-1H-indazol-5-amine Trifluoroacetate

Melting point: 242–245° C. (decomp.)

EXAMPLE 13

N-tetrahydro-2H-thiopyran-4-yl-1H-indazol-5-amine $^1$H-NMR (DMSO-$d_6$) δ; 1.41–1.54 (2H, m), 2.18–2.23 (2H, m), 2.64–2.75 (4H, m), 3.23–3.27 (1H, m), 5.22 (1H, d, J=8.4 Hz), 6.66 (1H, s), 6.80 (1H, dd, J=8.8 Hz), 7.68 (1H, dd, J=2.0, 8.8 Hz), 7.25 (1H, d, J=8.8 Hz), 7.73 (1H, s), 12.57 (1H, brs).

EXAMPLE 14

Ethyl 3-(1H-indazol-5-ylamino)-8-azabicyclo[3.2.1]octane-8-carboxylate

Melting point: 158–159° C.

EXAMPLE 15

Synthesis of N-(4-piperidinyl)-1H-indazol-5-amine dihydrochloride monohydrate

(a) Synthesis of N-(4-piperidinyl)-1H-indazol-5-amine

Ammonium formate (5.38 g) and 10% Pd—C (1.08 g) were added to a mixture of the N-(1-benzyl-4-piperidinyl)-1H-indazol-5-amine (5.38 g, 17.6 mmol) obtained in Example 1, (a) and ethanol (200 ml), and the resulting mixture was refluxed for 4 hours. The reaction mixture was filtered by the use of Celite and the filtrate was concentrated. The resulting residue was dissolved in a mixture of chloroform and methanol, followed by adding thereto hexane. The solid precipitated was collected by filtration and dried under reduced pressure to obtain N-(4-piperidinyl)-1H-indazol-5-amine (2.29 g, 60%).

Melting point: 212–214° C.

(b) Synthesis of
N-(4-piperidinyl)-1H-indazol-5-amine
dihydrochloride monohydrate A 1N-hydrochloric acid/ether solution (5 ml) was added to a solution of N-(4-piperidinyl)-1H-indazol-5-amine (433 mg, 2.00 mmol) in a mixture of chloroform (4 ml) and methanol (4 ml) at room temperature and stirred at room temperature for 30 minutes. The solid precipitated was collected by filtration and recrystallized from a mixture of chloroform and methanol to obtain N-(4-piperidinyl)-1H-indazol-5-amine dihydrochloride monohydrate (2.86 g, 72%).

Melting point: 263–265° C. (decomp.).

EXAMPLE 16

Synthesis of
N-(1-acetyl-4-piperidinyl)-1H-indazol-5-amine

Triethylamine (0.39 ml, 2.80 mmol) was added to a solution of the N-(4-piperidinyl)-1H-indazol-5-amine (0.301 g, 1.39 mmol) obtained in Example 15, (a) in tetrahydrofuran (5 ml) at room temperature, followed by adding thereto a solution of acetyl chloride (0.12 g, 1.53 mmol) in tetrahydrofuran (2 ml) at 0° C., and the resulting mixture was stirred at room temperature for 1 hour. Then, the reaction solution was poured into a 1N-aqueous sodium hydroxide solution and extracted with ethyl acetate. The organic layer was washed with a saturated aqueous sodium chloride solution and then dried over anhydrous sodium sulfate. The solvent was distilled off under reduced pressure and the resulting residue was suspended in acetone and stirred. Thereafter, the solid was collected by filtration and dried under reduced pressure to obtain N-(1-acetyl-4-piperidinyl)-1H-indazol-5-amine (0.216 g, 60%).

Melting point: 193–195° C. (decomp.).

The following compounds of Example 17 and Example 18 were synthesized by carrying out reaction according to the method described in Example 16.

EXAMPLE 17

N-(1-propionyl-4-piperidinyl)-1H-indazol-5-amine $^1$H-NMR (DMSO-$d_6$) δ; 0.99 (3H, t, J=7.5 Hz), 1.13–1.31 (2H, m), 1.89–2.02 (2H, m), 2.32 (2H, q, J=7.5 Hz), 2.86–2.76 (1H, m), 3.11–3.20 (1H, m), 3.40–3.51 (1H, m), 3.78–3.86 (1H, m), 4.21–4.29 (1H, m), 5.21 (1H, d, J=7.1 Hz), 6.72 (1H, brs), 6.82 (1H, dd, J=2.1, 8.8 Hz), 7.26 (1H, d, J=8.8 Hz), 7.75 (1H, s), 12.59 (1H, brs).

EXAMPLE 18

N-[1-(cyclohexylcarbonyl)-4-piperidinyl]-1H-indazol-5-amine $^1$H-NMR (DMSO-$d_6$) δ; 1.09–1.40 (7H, m), 1.56–1.75 (5H, m), 1.89–2.04 (2H, m), 2.55–2.63 (1H, m), 2.73–2.83 (1H, m), 3.13–3.22 (1H, m), 3.41–3.52 (1H, m), 3.87–3.94 (1H, m), 4.22–4.29 (1H, m), 5.21 (1H, d, J=8.4 Hz), 6.72 (1H, d, J=2.0 Hz), 6.81 (1H, dd, J=2.0, 8.9 Hz), 7.27 (1H, d, J=9.0 Hz), 7.75 (1H, s), 12.59 (1H, brs).

EXAMPLE 19

Synthesis of N-[1-(cyclohexylmethyl)-4-piperidinyl]-1H-indazol-5-amine

A solution of the N-[1-(cyclohexylcarbonyl)-4-piperidinyl]-1H-indazol-5-amine (0.301 g, 0.92 mmol) obtained in Example 18 in tetrahydrofuran (2 ml) was added to a solution of lithium aluminum hydride (0.071 g, 1.88 mmol) in tetrahydrofuran (2 ml) at 0° C. and stirred at 0° C. for 1 hour. The reaction solution was cooled on an ice-water bath, followed by adding thereto water (0.07 ml), a 2N-aqueous sodium hydroxide solution (0.14 ml) and water (0.21 ml) in that order. The resulting mixture was stirred and then filtered by the use of Celite. Then, the filtrate was poured into a 1N-aqueous sodium hydroxide solution and extracted with ethyl acetate. The organic layer was washed with a saturated aqueous sodium chloride solution and then dried over anhydrous sodium sulfate. The solvent was distilled off under reduced pressure and the resulting residue was suspended in ethyl acetate and stirred. Thereafter, the solid was collected by filtration and dried under reduced pressure to obtain N-[1-(cyclohexylmethyl)-4-piperidinyl]-1H-indazol-5-amine (0.121 g, 73%).

Melting point: 179–180° C.

EXAMPLE 20

Synthesis of N-[1-(methylsulfonyl)-4-piperidinyl]-1H-indazol-5-amine

Triethylamine (0.39 ml, 2.80 mmol) was added to a solution of the N-(4-piperidinyl)-1H-indazol-5-amine (0.300 g, 1.39 mmol) obtained in Example 15, (a) in tetrahydrofuran (5 ml) at room temperature, followed by adding thereto a solution of methanesulfonyl chloride (0.175 g, 1.53 mmol) in tetrahydrofuran (2 ml) at 0° C., and the resulting mixture was stirred at room temperature for 1 hour. Then, the reaction solution was poured into a 1N-aqueous sodium hydroxide solution and extracted with ethyl acetate. The organic layer was washed with a saturated aqueous sodium chloride solution and then dried over anhydrous sodium sulfate. The solvent was distilled off under reduced pressure and the resulting residue was purified by a silica gel column chromatography (eluent: chloroform/methanol=30/1) to obtain N-[1-(methylsulfonyl)-4-piperidinyl]-1H-indazol-5-amine (0.088 g, 22%).

Melting point: 219–220° C. (decomp.).

The following compounds of Example 21 and Example 22 were synthesized by carrying out reaction according to the method described in Example 20.

EXAMPLE 21

N-[1-(ethylsulfonyl)-4-piperidinyl]-1H-indazol-5-amine

Melting point: 182–183° C.

EXAMPLE 22

N-[1-(phenylsulfonyl)-4-piperidinyl]-1H-indazol-5-amine

Melting point: 132–136° C.

EXAMPLE 23

Synthesis of $N^3$-benzyl-$N^1$-(1H-indazol-5-yl)-$N^3$-methyl-β-alaninamide (a) Synthesis of 3-chloro-N-(1H-indazol-5-yl)propanamide Triethylamine (1.6 ml, 30.0 mmol) was added to a solution of 5-aminoindazole (2.0 g, 15.0 mmol) in tetrahydrofuran (50 ml) at room temperature, followed by adding thereto 3-chloropropionyl chloride (1.43 ml, 15.0 mmol) at 0° C., and the resulting mixture was stirred at room temperature for 30 minutes. Then, the reaction solution was distilled under reduced pressure to remove the solvent, and the resulting residue was suspended in ethanol and stirred. Thereafter, the solid was collected by filtration and dried under reduced pressure to obtain 3-chloro-N-(1H-indazol-5-yl)propanamide (1.49 g, 44%).

Melting point: 158–160° C.

(b) Synthesis of $N^3$-benzyl-$N^1$-(1H-indazol-5-yl)-$N^3$-methyl-β-alaninamide 3-Chloro-N-(1H-indazol-5-yl)propanamide (1.10 g, 4.92 mmol) was added to N-benzylmethylamine (6.3 ml, 49.2 mmol) at room temperature and stirred at 80° C. for 1 hour. Then, the reaction solution was cooled to 0° C. and hexane was added thereto to effect suspension. The solid precipitated was collected by filtration and purified by a silica gel column chromatography (eluent: chloroform/methanol=20/1) to obtain $N^3$-benzyl-$N^1$-(1H-indazol-5-yl)-$N^3$-methyl-β-alaninamide (1.30 g, 86%).

Melting point: 140–141° C.

EXAMPLE 24

Synthesis of $N^3$-benzyl-$N^1$-(1H-indazol-5-yl)-β-alaninamide

N-benzylamine (4.0 ml, 36.5 mmol) was added to a solution of 3-chloro-N-(1H-indazol-5-yl)propanamide (1.70 g, 7.60 mmol) in N,N-dimethylformamide (2 ml), and the resulting mixture was stirred at 80° C. for 1 hour. Then, the reaction solution was cooled to 0° C. and hexane was added thereto to effect suspension. The solid precipitated was collected by filtration and purified by a silica gel column chromatography (eluent: chloroform/methanol=20/1) to obtain $N^3$-benzyl-$N^1$-(1H-indazol-5-yl)-β-alaninamide (1.00 g, 45%).

$^1$H-NMR (DMSO-$d_6$) δ; 3.95 (3H, s), 6.56 (1H, d, J=16 Hz), 7.39 (1H, d, J=8.8 Hz), 7.57 (1H, d, J=16 Hz), 8.00 (1H, dd, J=2.0, 8.8 Hz), 8.23 (1H, d, J=2.0 Hz), 12.42 (1H, brs).

The following compounds of Example 25 and Example 26 were synthesized by carrying out reaction according to the method described in Example 24.

EXAMPLE 25

$N^1$-(1H-indazol-5-yl)-$N^3$,$N^3$-dimethyl-β-alaninamide

Melting point: 152–153° C.

EXAMPLE 26

N-(1H-indazol-5-yl)-3-(1-piperidinyl)propanamide

Melting point: 178–179° C.

EXAMPLE 27

Synthesis of N-(1H-indazol-5-yl)-4-methylpentanamide

To a solution of 5-aminoindazole (1.00 g, 7.51 mmol) in N,N-dimethylformamide (15 ml) were added 4-methylvaleric acid (960 mg, 8.26 mmol), 1-ethyl-3-(3'-dimethylaminopropyl)carbodiimide monohydrochloride (1.72 g, 9.01 mmol), hydroxybenzotriazole (1.12 g, 8.26 mmol) and triethylamine (1.7 ml, 12.0 mmol), and the resulting mixture was stirred overnight at room temperature. Then, the reaction solution was cooled to 0° C. and a 1N-aqueous sodium hydroxide solution was added thereto, followed by extraction with chloroform. The organic layer was washed with water and then a saturated aqueous sodium chloride solution and dried over anhydrous sodium sulfate. The solvent was distilled off under reduced pressure and the resulting residue was dissolved in a mixture of diethyl ether and methanol, followed by adding thereto hexane. The solid precipitated was collected by filtration and dried under reduced pressure to obtain N-(1H-indazol-5-yl)-4-methylpentanamide (1.24 g, 71%).

Melting point: 215–216° C. (decomp.)

The following compounds of Example 28 to Example 30 were synthesized by carrying out reaction according to the method described in Example 27.

EXAMPLE 28

N-(1H-indazol-5-yl)-3-methoxypropanamide

Melting point: 173–174° C.

EXAMPLE 29

4,4,4-Trifluoro-N-(1H-indazol-5-yl)butanamide

Melting point: 243–244° C. (decomp.)

EXAMPLE 30

3-(Benzyloxy)-N-(1H-indazol-5-yl)propanamide

Melting point: 167–169° C.

EXAMPLE 31

Synthesis of $N^1$-benzyl-$N^3$-(1H-indazol-5-yl)-$N^1$-methyl-1,3-propanediamine Lithium aluminum hydride (107 mg, 2.60 mmol) was added to a solution of $N^3$-benzyl-$N^1$-(1H-indazol-5-yl)-$N^3$-methyl-β-alaninamide (200 mg, 0.973 mmol) in tetrahydrofuran (30 ml) at 0° C., and the resulting mixture was refluxed for one and a half hours. Then, the reaction solution was cooled to 0° C. and a mixture of tetrahydrofuran (10 ml) and water (10 ml) was added thereto, followed by filtration. The filtrate was concentrated and the resulting residue was diluted with chloroform and washed with a 1N-aqueous sodium hydroxide solution and then a saturated aqueous sodium chloride solution. The organic layer was dried over potassium carbonate and distilled under reduced pressure to remove the solvent, and the resulting residue was purified by a silica gel column chromatography (eluent: chloroform/methanol=20/1) to obtain $N^1$-benzyl-$N^3$-(1H-indazol-5-yl)-$N^1$-methyl-1,3-propanediamine (138 mg, 72%).

Melting point: 112–114° C.

The following compound of Example 32 was synthesized by carrying out reaction according to the method described in Example 31.

EXAMPLE 32

$N^1$-benzyl-$N^3$-(1H-indazol-5-yl)-1,3-propanediamine $^1$H-NMR (DMSO-$d_6$) δ; 1.88 (2H, dq, J=6.5, 6.5 Hz), 2.82 (2H, t, J=6.5 Hz), 3.24 (2H, t, J=6.5 Hz), 3.82 (2H, s), 6.77–6.85 (2H, m), 7.23–7.35 (7H, m), 7.88 (1H, brs).

EXAMPLE 33

Synthesis of 3-hydroxy-N-(1H-indazol-5-yl)propanamide

To a solution of 3-(benzyloxy)-N-(1H-indazol-5-yl)propanamide (500 mg, 1.69 mmol) in methanol (100 ml) were added 1N-hydrochloric acid and 10% Pd—C (70 mg), and catalytic reduction was carried out at ordinary temperature and atmospheric pressure. After completion of the reaction, the catalyst was filtered off and the filtrate was concentrated under reduced pressure. The resulting residue was dissolved in a mixture of chloroform and methanol, followed by adding thereto hexane. The solid precipitated was collected by filtration and dried under reduced pressure to obtain 3-hydroxy-N-(1H-indazol-5-yl)propanamide (201 mg, 58%).

$^1$H-NMR (DMSO-$d_6$) δ; 2.47 (2H, t, J=6.4 Hz), 3.71 (2H, t, J=6.4 Hz), 7.42 (1H, dd, J=1.7, 8.8 Hz), 7.46 (1H, d, J=8.8 Hz), 8.00 (1H, s), 8.14 (1H, s), 9.94 (1H, brs).

EXAMPLE 34

Synthesis of 4-(1H-indazol-5-ylamino)-4-oxobutanoic Acid

Phthalic anhydride (827 mg, 8.26 mmol) was added to a solution of 5-aminoindazole (1.0 g, 7.51 mmol) in acetone (60 ml) at room temperature, and the resulting mixture was refluxed for 4 hours. The solid precipitated was collected by filtration and dried under reduced pressure to obtain 4-(1H-indazol-5-ylamino)-4-oxobutanoic acid (1.79 g, 100%).

Melting point: 218–220° C. (decomp.)

EXAMPLE 35

Synthesis of $N^2$-benzyl-$N^1$-(1H-indazol-5-yl)-$N^2$-methylglycinamide (a) Synthesis of 2-chloro-N-(1H-indazol-5-yl)acetamide Chloroacetyl chloride (3.14 ml, 39.4 mmol) was added to a solution of 5-aminoindazole (5.0 g, 37.5 mmol) in tetrahydrofuran (100 ml) at room temperature, followed by adding thereto a solution of triethylamine (5.76 ml, 41.3 mmol) in tetrahydrofuran (30 ml) at 0° C., and the resulting mixture was stirred at 0° C. for 30 minutes. Subsequently, a saturated aqueous sodium carbonate solution and then water were added to the reaction solution, followed by extraction with ethyl acetate. The organic layer was dried over anhydrous magnesium sulfate and distilled under reduced pressure to remove the solvent, and the resulting residue was suspended in ethanol and stirred, followed by filtration. To a solution of the solid collected by the filtration and dissolved in a mixture of tetrahydrofuran (25 ml) and methanol (25 ml) was added a 2N-aqueous lithium hydroxide solution (9.3 ml) at 0° C., and stirred at room temperature for 30 minutes. Then, the reaction solution was poured into water and extracted with ethyl acetate. The organic layer was washed with a saturated aqueous sodium chloride solution and then dried over anhydrous magnesium sulfate. The solvent was distilled off under reduced pressure to obtain 2-chloro-N-(1H-indazol-5-yl)acetamide (1.90 g, 46%).

$^1$H-NMR (DMSO-$d_6$) δ; 4.25 (2H, s), 7.41 (1H, d, J=9.0 Hz), 7.48 (1H, d, J=9.0 Hz), 8.03 (1H, s), 8.11 (1H, s), 10.29 (1H, s), 13.01 (1H, brs).

(b) Synthesis of $N^2$-benzyl-$N^1$-(1H-indazol-5-yl)-$N^2$-methylglycinamide

2-Chloro-N-(1H-indazol-5-yl)acetamide (300 mg, 1.43 mmol) was added to N-benzylmethylamine (1 ml) at room temperature and stirred at 80° C. for 30 minutes. Then, ethyl acetate was added to the reaction solution to effect suspension. The solid precipitated was collected by filtration and purified by a silica gel column chromatography (eluent: chloroform/methanol=50/1) to obtain $N^2$-benzyl-$N^1$-(1H-indazol-5-yl)-$N^2$-methylglycinamide (163 mg, 39%).

Melting point: 159–160° C.

The following compounds of Example 36 and Example 37 were synthesized by carrying out reaction according to the method described in Example 35.

EXAMPLE 36

$N^2$-benzyl-$N^1$-(1H-indazol-5-yl)glycinamide

Melting point: 256–258° C. (decomp.)

EXAMPLE 37

N-(1H-indazol-5-yl)-2-(1-piperidinyl)acetamide

Melting point: 189–190° C.

EXAMPLE 38

Synthesis of 4-[benzyl(methyl)amino]-N-(1H-indazol-5-yl)butanamide (a) Synthesis of 4-chloro-N-(1H-indazol-5-yl)butanamide Triethylamine (2.1 ml, 15 mmol) was added to a suspension of 5-aminoindazole (1.00 g, 7.51 mmol) in tetrahydrofuran (10 ml) at room temperature, followed by adding thereto a solution of 4-chlorobutyryl chloride (1.16 g, 8.26 mmol) in tetrahydrofuran (5 ml) at 0° C., and the resulting mixture was stirred at 0° C. for 1 hour. Then, a 1N-aqueous sodium hydroxide solution was added to the reaction solution, followed by extraction with ethyl acetate. The organic layer was washed with a saturated aqueous sodium chloride solution and dried over anhydrous magnesium sulfate. The solvent was distilled off under reduced pressure and the resulting residue was suspended in ethanol and stirred, followed by filtration. The solid collected by the filtration was dried under reduced pressure to obtain 4-chloro-N-(1H-indazol-5-yl)butanamide (572 mg, 32%).

Melting point: 160–161° C.

(b) Synthesis of 4-[benzyl(methyl)amino]-N-(1H-indazol-5-yl)butanamide

4-Chloro-N-(1H-indazol-5-yl)butanamide (300 mg, 1.26 mmol) was added to N-benzylmethylamine (1 ml) at room temperature and stirred at 80° C. for 1 hour. Then, hexane was added to the reaction solution to effect suspension. The supernatant was removed and the resulting solid was purified by a silica gel column chromatography (eluent: chloroform/methanol=40/1) to obtain 4-[benzyl(methyl)amino]-N-(1H-indazol-5-yl)butanamide (134 mg, 33%).

Melting point: 115–117° C.

EXAMPLE 39

Synthesis of N-methyl-1H-indazol-5-amine (a) Synthesis of 2,2,2-trifluoro-N-(1H-indazol-5-yl)acetamide Trifluoroacetic anhydride (13.3 ml, 94.2 mmol) was added dropwise to a solution of 5-aminoindazole (5.00 g, 37.6 mmol) in pyridine (188 ml) at 0° C. and stirred at 0° C. for 1.5 hours and then at room temperature for 2.5 hours. Subsequently, the reaction solution was concentrated and the resulting residue was poured into water and extracted with ethyl acetate. The organic layer was washed with 1N-hydrochloric acid and then a saturated aqueous sodium chloride solution and dried over anhydrous magnesium sulfate. The solvent was distilled off under reduced pressure to obtain 2,2,2-trifluoro-N-(1H-indazol-5-yl)acetamide (8.37 g, 97%).

Melting point: 249–250° C. (decomp.)

(b) Synthesis of 2,2,2-trifluoro-N-(1H-indazol-5-yl)-N-methylacetamide

Potassium carbonate (415 mg, 3.00 mmol) and methyl iodide (0.20 ml, 3.21 mmol) were added to a solution of 2,2,2-trifluoro-N-(1H-indazol-5-yl)acetamide (688 mg, 3.00 mmol) in N,N-dimethylformamide (4 ml) at room temperature and stirred overnight at room temperature. Then, the reaction solution was poured into water and extracted with ethyl acetate. The organic layer was washed with a saturated aqueous sodium chloride solution and then dried over anhydrous magnesium sulfate. The solvent was distilled off under reduced pressure and the resulting residue was purified by a silica gel column chromatography (eluent: chloroform/methanol=99/1) to obtain 2,2,2-trifluoro-N-(1H-indazol-5-yl)-N-methylacetamide (466 mg, 64%).

Melting point: 172–174° C.

(c) Synthesis of N-methyl-1H-indazol-5-amine

Potassium carbonate (8.64 g, 62.5 mmol) was added to a solution of 2,2,2-trifluoro-N-(1H-indazol-5-yl)-N-methylacetamide (3.80 g, 15.6 mmol) in a mixture of methanol (95 ml) and water (16 ml) at room temperature, and the resulting mixture was refluxed for 1.5 hours. Then, the reaction solution was concentrated and the resulting residue was poured into water and extracted with ethyl acetate. The organic layer was washed with a saturated aqueous sodium chloride solution and then dried over anhydrous magnesium sulfate. The solvent was distilled off under reduced pressure to obtain N-methyl-1H-indazol-5-amine (2.30 g, 100%).

Melting point: 144–146° C.

The following compound of Example 40 was synthesized by carrying out reaction according to the method described in Example 1, (a), except for using the N-methyl-1H-indazol-5-amine obtained in Example 39, as a starting material.

EXAMPLE 40

N-(1-benzyl-4-piperidinyl)-N-methyl-1H-indazol-5-amine

Melting point: 152–154° C.

The following compound of Example 41 was synthesized by carrying out reaction according to the method described in Example 15, (a), except for using the N-(1-benzyl-4-piperidinyl)-N-methyl-1H-indazol-5-amine obtained in Example 40, as a starting material.

EXAMPLE 41

N-methyl-N-(4-piperidinyl)-1H-indazol-5-amine

Melting point: 175–177° C.

EXAMPLE 42

Synthesis of 5-(4-piperidinyloxy)-1H-indazole (a) Synthesis of tert-butyl 4-(1H-indazol-5-yloxy)-1-piperidinecarboxylate To a suspension of 1H-indazol-5-ol (134 mg, 0.999 mmol) in tetrahydrofuran (4 ml) were added tert-butyl 4-hydroxy-1-piperidinecarboxylate (201 mg, 0.999 mmol) and triphenylphosphine (262 mg, 0.999 mmol) at room temperature, followed by adding thereto diethyl azodicarboxylate (0.46 ml, 1.01 mmol) at 0° C., and the resulting mixture was stirred at 0° C. for 30 minutes and then at room temperature for 4 hours. Subsequently, the solvent of the reaction mixture was distilled off under reduced pressure and the resulting residue was purified by a silica gel column chromatography (eluent: hexane/ethyl acetate=7/3) to obtain tert-butyl 4-(1H-indazol-5-yloxy)-1-piperidinecarboxylate (77 mg, 24%).

$^1$H-NMR (DMSO-d$_6$) δ; 1.42 (9H, s), 1.47–1.57 (2H, m), 1.89 (2H, m), 3.16–3.24 (2H, m), 3.63–3.70 (2H, m), 4.49 (1H, m), 7.01 (1H, dd, J=9.0, 2.2 Hz), 7.26 (1H, d, J=2.2 Hz), 7.42 (1H, d, J=9.0 Hz), 7.91 (1H, s), 12.89 (1H, brs).

(b) Synthesis of 5-(4-piperidinyloxy)-1H-indazole

Trifluoroacetic acid (0.20 ml, 2.60 mmol) was added to a solution of tert-butyl 4-(1H-indazol-5-yloxy)-1-piperidinecarboxylate (70 mg, 0.221 mmol) in methylene chloride (5 ml) at room temperature and stirred overnight at room temperature. Then, the solvent of the reaction solution was distilled off under reduced pressure and the resulting residue was poured into a 1N-aqueous sodium hydroxide solution and extracted with ethyl acetate. The organic layer was washed with a saturated aqueous sodium chloride solution and then dried over anhydrous magnesium sulfate. The solvent was distilled off under reduced pressure to obtain 5-(4-piperidinyloxy)-1H-indazole (25 mg, 52%).

$^1$H-NMR (DMSO-d$_6$) δ; 1.49–1.59 (2H, m), 1.89–1.98 (2H, m), 2.65–2.74 (2H, m), 2.99–3.05 (2H, m), 4.37–4.42 (1H, m), 7.00 (1H, dd, J=9.0, 2.4 Hz), 7.23 (1H, d, J=2.2 Hz), 7.42 (1H, d, J=9.0 Hz), 7.91 (1H, s), 12.90 (1H, brs).

The following compounds of Example 43 and Example 44 were synthesized by carrying out reaction according to the method described in Example 42, (a).

EXAMPLE 43

5-{[1-(Methylsulfonyl)-4-piperidinyl]oxy}-1H-indazole $^1$H-NMR (DMSO-d$_6$) δ; 1.76 (2H, m), 1.98 (2H, m), 2.88 (3H, s), 3.11 (2H, m), 3.39 (2H, m), 4.50 (1H, m), 7.05 (1H, dd, J=2.2, 8.8 Hz), 7.27 (1H, d, J=2.2 Hz), 7.42 (1H, d, J=8.8 Hz), 12.91 (1H, brs).

EXAMPLE 44

5-(Tetrahydro-2H-pyran-4-yloxy)-1H-indazole

Melting point: 151–152° C.

EXAMPLE 45

Synthesis of 5-[(4-benzyl-1-piperazinyl)carbonyl]-1H-indazole

To a solution of 1H-indazole-5-carboxylic acid (400 mg, 2.47 mmol) in N,N-dimethylformamide (8 ml) were added 1-benzylpiperazine (435 mg 2.47 mmol), 1-ethyl-3-(3'-dimethylaminopropyl)carbodiimide monohydrochloride (565 mg, 2.96 mmol), hydroxybenzotriazole (367 mg, 2.72 mmol) and triethylamine (0.56 ml, 3.95 mmol), and the resulting mixture was stirred overnight at room temperature. Then, a 10% aqueous potassium hydrogensulfate solution was added to the reaction solution, followed by extraction with chloroform. A 1N-aqueous sodium hydroxide solution was added to the aqueous layer, followed by extraction with chloroform. The combined organic layer was washed with a saturated aqueous sodium chloride solution and then dried over anhydrous sodium sulfate. The solvent was distilled off under reduced pressure and the resulting residue was purified by a silica gel column chromatography (eluent: chloroform/methanol=20/1) to obtain 5-[(4-benzyl-1-piperazinyl)carbonyl]-1H-indazole (624 mg, 79%).

$^1$H-NMR (DMSO-d$_6$) δ; 2.38 (4H, br), 3.50 (6H, br), 7.20–7.35 (5H, m), 7.05 (1H, dd, J=2.2, 8.8 Hz), 7.34 (1H, dd, J=1.5, 8.4 Hz), 7.56 (1H, d, J=8.4 Hz), 7.81 (1H, brs), 8.13 (1H, brs), 13.23 (1H, brs).

The following compound of Example 46 was synthesized by carrying out reaction according to the method described in Example 15, (a), except for using the 5-[(4-benzyl-1-piperazinyl)carbonyl]-1H-indazole obtained in Example 45, as a starting material.

EXAMPLE 46

5-(1-Piperazinylcarbonyl)-1H-indazole

Melting point: 190–191° C.

The following compound of Example 47 was synthesized by carrying out reaction according to the method described in Example 31, except for using the 5-[(4-benzyl-1-piperazinyl)carbonyl]-1H-indazole obtained in Example 45, as a starting material.

EXAMPLE 47

5-[(4-benzyl-1-piperazinyl)methyl]-1H-indazole

Melting point: 147–149° C.

EXAMPLE 48

Synthesis of 1-benzyl-N-(1H-indazol-5-yl)-4-piperidinecarboxamide

Thionyl chloride (10.5 ml) was added to 1-benzyl-4-piperidinecarboxylic acid (4.85 g, 22.1 mmol), and the resulting mixture was refluxed for 2 hours. The reaction solution was distilled under reduced pressure to remove the solvent. To a solution of the resulting residue in methylene chloride (65 ml) were added 5-aminoindazole (4.41 g, 33.2 mmol), triethylamine (1.8 ml), pyridine (30 ml) and a catalytic amount of 4-dimethylaminopyridine at 0° C., and then stirred at room temperature for 3 hours. Then, the reaction solution was poured into a 1N-aqueous sodium hydroxide solution and extracted with chloroform. The organic layer was washed with a saturated aqueous sodium chloride solution and then dried over anhydrous sodium sulfate. The solvent was distilled off under reduced pressure and the resulting residue was purified by a silica gel column chromatography (eluent: chloroform/methanol=20/1) to obtain 1-benzyl-N-(1H-indazol-5-yl)-4-piperidinecarboxamide (2.2 g, 30%).

$^1$H-NMR (DMSO-d$_6$) δ; 1.58–1.80 (4H, m), 1.94 (2H, br), 2.31 (1H, br), 2.86 (2H, br), 3.45 (2H, s), 7.24–7.27 (5H, m), 7.39 (1H, d, J=9.2 Hz), 7.44 (1H, d, J=9.2 Hz), 7.97 (1H, s), 8.12 (1H, s), 9.92 (1H, s), 12.93 (1H, brs).

The following compound of Example 49 was synthesized by carrying out reaction according to the method described in Example 15, (a), except for using the 1-benzyl-N-(1H-indazol-5-yl)-4-piperidinecarboxamide obtained in Example 48, as a starting material.

EXAMPLE 49

N-(1H-indazol-5-yl)-4-piperidinecarboxamide $^1$H-NMR (DMSO-d$_6$) δ; 1.40–1.75 (4H, m), 2.30–2.55 (3H, m), 2.97 (2H, d, J=12.3 Hz), 7.40 (1H, dd, J=1.7, 8.8 Hz), 7.44 (1H, d, J=8.8 Hz), 7.98 (1H, s), 8.12 (1H, s), 9.78 (1H, s), 12.94 (1H, brs).

EXAMPLE 50

Synthesis of N-(1H-indazol-5-yl)-1-(methylsulfonyl)-4-piperidinecarboxamide

A catalytic amount of N,N-dimethylformamide and a solution of oxalyl dichloride (0.367 g, 2.89 mmol) in methylene chloride (3 ml) were added to a solution of 1-(methylsulfonyl)-4-piperidinecarboxylic acid (500 mg, 2.41 mmol) in methylene chloride (7 ml), and the resulting mixture was stirred at room temperature for three and a half hours. The reaction solution was distilled under reduced pressure to remove the solvent, and a solution of the resulting residue in methylene chloride (5 ml) was added to a solution of 5-aminoindazole (322 mg, 2.42 mmol) and triethylamine (0.67 ml, 4.8 mmol) in methylene chloride (10 ml) at 0° C. and stirred overnight at room temperature. Then, the reaction solution was poured into a saturated aqueous sodium hydrogencarbonate solution and the organic solvent was distilled off under reduced pressure. The solid precipitated was collected by filtration and suspended in methanol, and the resulting suspension was stirred at 50° C., followed by filtration. The solid collected by this filtration was dried under reduced pressure to obtain N-(1H-indazol-5-yl)-1-(methylsulfonyl)-4-piperidinecarboxamide (670 mg, 86%).

Melting point: 291–293° C. (decomp.)

The following compound of Example 51 was synthesized by carrying out reaction according to the method described in Example 50.

EXAMPLE 51

N-(1H-indazol-5-yl)tetrahydro-2H-pyran-4-carboxamide

Melting point: 286–288° C. (decomp.)

The following compound of Example 52 was synthesized by carrying out reaction according to the method described in Example 31, except for using the 1-benzyl-N-(1H-indazol-5-yl)-4-piperidinecarboxamide obtained in Example 48, as a starting material.

EXAMPLE 52

5-[(1-Benzyl-4-piperidinyl)methyl]-1H-indazol-5-amine $^1$H-NMR (DMSO-d$_6$) δ; 1.13–1.30 (2H, m), 1.57 (1H, br), 1.75 (2H, br), 1.88 (2H, br), 2.80 (2H, br), 2.87 (2H, dd, J=6.1, 6.1 Hz), 3.42 (2H, s), 5.33 (1H, dd, J=6.1, 6.1 Hz), 6.57 (1H, brs), 6.82 (1H, dd, J=2.2, 9.0 Hz), 7.17–7.40 (6H, m), 7.71 (1H, s), 12.55 (1H, brs).

The following compound of Example 53 was synthesized by carrying out reaction according to the method described in Example 15, (a), except for using the 5-[(1-benzyl-4-piperidinyl)methyl]-1H-indazol-5-amine obtained in Example 52, as a starting material.

EXAMPLE 53

N-(4-piperidinylmethyl)-1H-indazol-5-amine $^1$H-NMR (DMSO-d$_6$) δ; 0.95–1.15 (2H, m), 1.55–1.72 (2H, m), 2.35–2.55 (2H, m), 2.85 (2H, d, J=5.9 Hz), 2.94 (2H, d, J=12.1 Hz), 3.16 (1H, s), 5.33 (1H, t, J=5.9 Hz), 6.57 (1H, d, J=2.0 Hz), 6.82 (1H, dd, J=2.0, 9.0 Hz), 7.24 (1H, d, J=9.0 Hz), 7.72 (1H, s), 12.56 (1H, brs).

The following compound of Example 54 was synthesized by carrying out reaction according to the method described in Example 31, except for using the N-(1H-indazol-5-yl)-1-(methylsulfonyl)-4-piperidinecarboxamide obtained in Example 50, as a starting material.

EXAMPLE 54

N-{[1-(methylsufonyl)-4-piperidinyl]methyl}-1H-indazol-5-amine

Melting point: 262–263° C. (decomp.)

The following compound of Example 55 was synthesized by carrying out reaction according to the method described in Example 31, except for using the N-(1H-indazol-5-yl) tetrahydro-2H-pyran-4-carboxamide obtained in Example 51, as a starting material.

EXAMPLE 55

N-(tetrahydro-2H-pyran-4-ylmethyl)-1H-indazol-5-amine

Melting point: 293–294° C. (decomp.)

The following compounds of Example 56 and Example 57 were synthesized by carrying out reaction according to the method described in Example 45.

EXAMPLE 56

N-(1-benzyl-4-piperidinyl)-1H-indazole-5-carboxamide

Melting point: 240–242° C. (decomp.)

EXAMPLE 57

N-tetrahydro-2H-pyran-4-yl-1H-indazole-5-carboxamide

Melting point: 285–286° C.

$^1$H-NMR (DMSO-d$_6$) δ; 1.58 (2H, dddd, J=4.3, 11.9, 11.9, 11.9 Hz), 1.72–1.82 (2H, m), 3.38 (2H, ddd, J=2.0, 11.9, 11.9 Hz), 3.80–3.93 (2H, m), 3.9–4.10 (1H, m), 7.55 (1H, d, J=8.8 Hz), 7.84 (1H, dd, J=1.7, 8.8 Hz), 8.30 (1H, s), 8.32 (1H, s), 13.26 (1H, s).

The following compound of Example 58 was synthesized by carrying out reaction according to the method described in Example 15, (a), except for using the N-(1-benzyl-4-piperidinyl)-1H-indazole-5-carboxamide obtained in Example 56, as a starting material.

EXAMPLE 58

N-(4-piperidinyl)-1H-indazole-5-carboxamide

Melting point: 273–275° C. (decomp.)

The following compound of Example 59 was synthesized by carrying out reaction according to the method described in Example 20, except for using the N-(4-piperidinyl)-1H-indazole-5-carboxamide obtained in Example 58, as a starting material.

EXAMPLE 59

N-[1-(methylsulfonyl)-4-piperidinyl]-1H-indazole-5-carboxamide $^1$H-NMR (DMSO-$d_6$) δ; 1.63 (2H, m), 2.86 (2H, m), 3.55 (2H, m), 3.95 (1H, m), 7.57 (1H, d, J=8.8 Hz), 7.82 (1H, d, J=8.8 Hz), 8.20 (1H, s), 8.32 (1H, s), 8.35 (1H, d, J=9.6 Hz), 13.26 (1H, s).

The following compounds of Example 60 and Example 61 were synthesized by carrying out reaction according to the method described in Example 27.

EXAMPLE 60

2-(1-Benzyl-4-piperidinyl)-N-(1H-indazol-5-yl)acetamide

Melting point: 195–197° C.

EXAMPLE 61

2-(1-Benzyl-4-piperidinylidene)-N-(1H-indazol-5-yl)acetamide

Melting point: 169–172° C.

The following compound of Example 62 was synthesized by carrying out reaction according to the method described in Example 15, (a), except for using the 2-(1-benzyl-4-piperidinyl)-N-(1H-indazol-5-yl)acetamide obtained in Example 60, as a starting material.

EXAMPLE 62

N-(1H-indazol-5-yl)-2-(4-piperidinyl)acetamide $^1$H-NMR (DMSO-$d_6$) δ; 1.08 (2H, m), 1.56 (2H, m), 1.82 (1H, m), 2.18 (2H, d, J=7.2 Hz), 2.42 (2H, m), 2.86 (2H, m), 7.40 (1H, dd, J=1.6, 8.8 Hz), 7.43 (1H, d, J=8.8 Hz), 7.98 (1H, s), 8.11 (1H, s), 9.84 (1H, s), 12.95 (1H, s).

The following compound of Example 63 was synthesized by carrying out reaction according to the method described in Example 19, except for using the 2-(1-benzyl-4-piperidinyl)-N-(1H-indazol-5-yl)acetamide obtained in Example 60, as a starting material.

EXAMPLE 63

N-[2-(1-benzyl-4-piperidinyl)ethyl]-1H-indazol-5-amine

Melting point: 117–118° C.

The following compound of Example 64 was synthesized by carrying out reaction according to the method described in Example 15, (a), except for using the N-[2-(1-benzyl-4-piperidinyl)ethyl]-1H-indazol-5-amine obtained in Example 63, as a starting material.

EXAMPLE 64

N-[2-(4-piperidinyl)ethyl]-1H-indazol-5-amine

Melting point: 184–186° C. (decomp.)

EXAMPLE 65

Synthesis of N-(1H-indazol-5-ylmethyl)-4-piperidinecarboxamide (a) Synthesis of 1-(1H-indazol-5-yl)methanamine A solution of 1H-indazole-5-carbonitrile (100 mg, 0.699 mmol) in tetrahydrofuran (4 ml) was added to a solution of lithium aluminum hydride (53 mg, 1.40 mmol) in tetrahydrofuran (4 ml) at room temperature, and the resulting mixture was refluxed for 2 hours. Subsequently, water (0.053 ml), a 2N-aqueous lithium hydroxide solution (0.106 ml) and water (0.212 ml) were added in that order to the reaction solution and stirred, followed by filtration. The solvent was distilled off under reduced pressure and the residue was dried under reduced pressure to obtain 1-(1H-indazol-5-yl)methanamine (97 mg, 94%).

(b) Synthesis of tert-butyl 4{[(1H-indazol-5-ylmethyl)amino]carbonyl}-1-piperidinecarboxylate To a solution of 1-(1H-indazol-5-yl)methanamine (291 mg) in N,N-dimethylformamide (8 ml) were added 1-(tert-butoxycarbonyl)-4-piperidinecarboxylic acid (507 mg, 2.21 mmol), 1-ethyl-3-(3'-dimethylaminopropyl)carbodiimide monohydrochloride (578 mg, 3.02 mmol) and hydroxybenzotriazole (229 mg, 2.21 mmol), and the resulting mixture was stirred at room temperature for 14 hours. Subsequently, a saturated aqueous sodium hydrogencarbonate solution and then water were added to the reaction solution, followed by extraction with ethyl acetate. The organic layer was dried over anhydrous magnesium sulfate and distilled under reduced pressure to remove the solvent. The resulting residue was purified by a silica gel column chromatography (eluent: chloroform/methanol=40/1). To a solution of the resulting solid in a mixture of methanol (1 ml) and tetrahydrofuran (1 ml) was added a 2N-aqueous lithium hydroxide solution (0.68 ml), and the resulting mixture was stirred at room temperature for 30 minutes. Then, the reaction solution was poured into water and extracted with ethyl acetate. The organic layer was dried over anhydrous magnesium sulfate and distilled under reduced pressure to remove the solvent. The resulting residue was purified by a silica gel column chromatography (eluent: chloroform/methanol=30/1) to obtain tert-butyl 4{[(1H-indazol-5-ylmethyl)amino]carbonyl}-1-piperidinecarboxylate (179 mg).

(c) Synthesis of N-(1H-indazol-5-ylmethyl)-4-piperidinecarboxamide

A 4N-hydrochloric acid/dioxane solution (2.0 ml) was added to tert-butyl 4{[(1H-indazol-5-ylmethyl)amino]carbonyl}-1-piperidinecarboxylate (160 mg, 0.446 mmol), and the resulting mixture was stirred at room temperature for 2 hours. Then, the reaction solution was poured into a saturated aqueous sodium hydrogencarbonate solution and extracted with chloroform. The organic layer was dried over anhydrous magnesium sulfate and distilled under reduced pressure to remove the solvent. The resulting residue was recrystallized from a mixture of ethanol and diethyl ether to obtain N-(1H-indazol-5-ylmethyl)-4-piperidinecarboxamide (10 mg, 9%).

$^1$H-NMR (DMSO-$d_6$) δ; 1.42 (2H, m), 2.22 (1H, m), 2.42 (2H, m), 3.46 (2H, m), 4.30 (2H, d, J=5.9 Hz), 7.23 (1H, d, J=8.7 Hz), 7.45 (1H, d, J=8.7 Hz), 7.55 (1H, s), 8.01 (1H, s), 8.23 (1H, t, J=5.9 Hz), 13.00 (1H, s).

EXAMPLE 66

Synthesis of 5-(4-benzyl-1-piperazinyl)-1H-indazole (a) Synthesis of 5-(4-benzyl-1-piperazinyl)-1-tetrahydro-2H-pyran-2-yl-1H-indazole To a solution of the 5-bromo-1-tetrahydro-2H-pyran-2-yl-1H-indazole (250 mg, 0.889 mmol) obtained in Reference Example 5 in toluene (12 ml) were added 1-benzylpiperazine (0.24 ml, 1.35 mmol) and sodium tert-butoxide (128 mg, 1.33 mmol) at room temperature. After deaeration, bis(tri-o-tolylphosphine)-palladium(II) dichloride (70 mg, 0.0891 mmol) was added thereto and the resulting mixture was stirred at 75° C. for three and a half hours. Then, the reaction solution was poured into water and extracted with ethyl acetate. The organic layer was washed with a saturated aqueous sodium chloride solution and then dried over anhydrous magnesium sulfate. The solvent was distilled off under reduced pressure and the resulting residue was purified by a silica gel column chromatography (eluent: chloroform/ethyl acetate=5/2) to obtain 5-(4-benzyl-1-piperazinyl)-1-tetrahydro-2H-pyran-2-yl-1H-indazole (183 mg, 55%).

(b) Synthesis of 5-(4-benzyl-1-piperazinyl)-1H-indazole

Acetic acid (2.6 ml) and water (0.7 ml) were added to a solution of 5-(4-benzyl-1-piperazinyl)-1-tetrahydro-2H-pyran-2-yl-1H-indazole (100 mg, 0.266 mmol) in tetrahydrofuran (1.3 ml) at room temperature and stirred 80° C. for 7 hours. Then, the reaction solution was concentrated and the resulting residue was diluted with ethyl acetate and washed with a saturated aqueous sodium hydrogencarbonate solution and then a saturated aqueous sodium chloride solution. The organic layer was dried over anhydrous sodium sulfate and distilled under reduced pressure to remove the solvent, and the resulting residue was purified by a thin-layer chromatography (eluent: chloroform/methanol=95/5) to obtain 5-(4-benzyl-1-piperazinyl)-1H-indazole (37 mg, 47%).

Melting point: 196–198° C. (decomp.)

The following compound of Example 67 was synthesized by carrying out reaction according to the method described in Example 66.

EXAMPLE 67

5-(4-Morpholinyl)-1H-indazole $^1$H-NMR (DMSO-$d_6$) δ; 3.02–3.05 (4H, m), 3.73–3.76 (4H, m), 7.08 (1H, m), 7.18 (1H, dd, J=9.2, 2.2 Hz), 7.41 (1H, d, J=9.0 Hz), 7.89 (1H, s), 12.80 (1H, brs).

The following compound of Example 68 was synthesized by carrying out reaction according to the method described in Example 15, (a), except for using the 5-(4-benzyl-1-piperazinyl)-1H-indazole obtained in Example 66, as a starting material.

EXAMPLE 68

5-(1-Piperazinyl)-1H-indazole $^1$H-NMR (DMSO-$d_6$) δ; 2.85–2.86 (2H, m), 2.95–2.98 (2H, m), 3.06 (1H, m), 7.05 (1H, brs), 7.14–7.16 (1H, m), 7.39 (1H, d, J=9.0 Hz), 7.87 (1H, s), 12.79 (1H, brs).

EXAMPLE 69

Synthesis of 2-(1H-indazol-5-ylamino)-N,N-dimethylbenzamide

To a solution of 2-(1H-indazol-5-ylamino)benzoic acid (80 mg, 0.316 mmol) in N,N-dimethylformamide (0.5 ml) were added 1-ethyl-3-(3'-dimethylaminopropyl)carbodiimide monohydrochloride (73 mg, 0.379 mmol), hydroxybenzotriazole (58 mg, 0.379 mmol) and a 40%-aqueous dimethylamine solution (107 mg, 0.948 mmol), and the resulting mixture was stirred at room temperature for 4 hours. Then, a 5%-aqueous sodium hydrogencarbonate solution was added to the reaction solution, followed by extraction with a mixed solvent of ethyl acetate and toluene. The organic layer was washed with a 5%-aqueous sodium hydrogencarbonate solution and then a 5%-aqueous sodium chloride solution and dried over anhydrous sodium sulfate. The solvent was distilled off under reduced pressure and the resulting residue was purified by a silica gel column chromatography (eluent: hexane/ethyl acetate/methanol=1/1/0.05) to obtain 2-(1H-indazol-5-ylamino)-N,N-dimethylbenzamide (59 mg, 67%).

Melting point: 234–235° C. (decomp.)

The following compounds of Example 70 to Example 73 were synthesized by carrying out reaction according to the method described in Example 1, except for using 1H-indazol-4-amine as a starting material.

EXAMPLE 70

N-(1-benzyl-4-piperidinyl)-1H-indazol-4-amine $^1$H-NMR (DMSO-$d_6$) δ; 1.45–1.57 (2H, m), 1.93–2.01 (2H, m), 2.05–2.13 (2H, m), 2.80–2.87 (2H, m), 3.32–3.42 (1H, m), 3.49 (2H, s), 5.90 (1H, d, J=8.1 Hz), 6.05 (1H, d, J=7.9 Hz), 6.62 (1H, d, J=7.9 Hz), 7.03 (1H, t, J=7.9 Hz), 7.22–7.36 (5H, m), 8.18 (1H, br), 12.64 (1H, b).

EXAMPLE 71

N-[1-(2-phenethyl)-4-piperidinyl]-1H-indazol-4-amine

Melting point: 196–198° C. (decomp.)

EXAMPLE 72

N-(1-benzyl-4-piperidinyl)-1H-indazol-4-amine dihydrochloride

Melting point: 257–260° C. (decomp.)

EXAMPLE 73

N-[1-(2-phenethyl)-4-piperidinyl]-1H-indazol-4-amine dimethanesulfonate

Melting point: 213–215° C. (decomp.)

The following compounds of Example 74 and Example 75 were synthesized by carrying out reaction according to the method described in Example 15, except for using N-(1-benzyl-4-piperidinyl)-1H-indazol-4-amine as a starting material.

EXAMPLE 74

N-(4-piperidinyl)-1H-indazol-4-amine $^1$H-NMR (DMSO-$d_6$) δ; 1.57–1.69 (2H, m), 2.05–2.12 (2H, m), 2.88–2.98 (2H, m), 3.23–3.31 (2H, m), 3.60–3.71 (1H, m), 6.10 (1H, d, J=8.1 Hz), 6.12 (1H, d, J=7.5 Hz), 6.67 (1H, d, J=8.0 Hz), 7.06 (1H, dd, J=7.5, 8.0 Hz), 8.21 (1H, d, J=12 Hz), 12.7 (1H, b).

EXAMPLE 75

N-(4-piperidinyl)-1H-indazol-4-amine dihydrochloride

Melting point: 270–271° C.

The following compounds of Example 76 and Example 77 were synthesized by carrying out reaction according to the method described in Example 1, except for using 1H-indazol-6-amine as a starting material.

EXAMPLE 76

N-(1-benzyl-4-piperidinyl)-1H-indazol-6-amine $^1$H-NMR (DMSO-$d_6$) δ; 1.35–1.47 (2H, m), 1.89–1.97 (2H, m), 2.04–2.14 (2H, m), 2.75–2.83 (2H, m), 3.17–3.27 (1H, m), 3.48 (2H, s), 5.66 (1H, d, J=7.5 Hz), 6.34 (1H, br), 6.52 (1H, dd, J=1.8, 8.9 Hz), 7.21–7.34 (5H, m), 7.36 (1H, dd, J=8.9 Hz), 7.71 (1H, s), 12.26 (1H, br).

EXAMPLE 77

N-(1-benzyl-4-piperidinyl)-1H-indazol-6-amine dihydrochloride $^1$H-NMR (DMSO-$d_6$) δ; 1.88–2.19 (4H, m), 2.95–3.43 (4H, m), 3.55–3.86 (1H, m), 4.26–4.35 (2H, m), 6.80–7.10 (2H, m), 7.44–7.48 (3H, m), 7.58–7.68 (3H, m), 8.06–8.09 (1H, m), 11.0 (1H, br).

The following compounds of Example 78 and Example 79 were synthesized by carrying out reaction according to the method described in Example 15, except for using N-(1-benzyl-4-piperidinyl)-1H-indazol-6-amine as a starting material.

EXAMPLE 78

N-(4-piperidinyl)-1H-indazol-6-amine

Melting point: 196–197° C. (decomp.)

EXAMPLE 79

N-(4-piperidinyl)-1H-indazol-6-amine dihydrochloride $^1$H-NMR (DMSO-$d_6$) δ; 1.74–1.88 (2H, m), 2.05–2.13 (2H, m), 2.89–3.02 (2H, m), 3.28–3.36 (2H, m), 3.65–3.74 (1H, m), 6.93 (1H, br), 7.05 (1H, br), 7.68 (1H, d, J=8.9 Hz), 7.95 (1H, s), 8.90 (1H, br), 9.10 (1H, br), 13.30 (1H, br).

The following compounds of Example 80 to Example 82 were synthesized by carrying out reaction according to the method described in Example 1, except for using 1-methyl-1H-indazol-5-amine as a starting material.

EXAMPLE 80

N-(1-benzyl-4-piperidinyl)-1-methyl-1H-indazol-5-amine

Melting point: 116–117° C.

EXAMPLE 81

1-Methyl-N-[1-(2-phenylethyl)-4-piperidinyl]-1H-indazol-5-amine

N-(1-benzyl-4-piperidinyl)-1H-benzimidazol-5-amine $^1$H-NMR (DMSO-$d_6$) 67; 1.31–1.41 (2H, m), 1.92–1.98 (2H, m), 2.06–2.13 (2H, m), 2.48–2.53 (2H, m), 2.69–2.75 (2H, m), 2.88–2.92 (2H, m), 3.16 (1H, m), 3.91 (3H, s), 5.17 (1H, d, J=8.3 Hz), 6.64 (1H, d, J=1.8 Hz), 6.85 (1H, dd, J=9.0, 1.8 Hz), 7.14–7.29 (5H, m), 7.33 (1H, d, J=9.0 Hz), 7.68 (1H, s).

EXAMPLE 82

N-(1-benzyl-4-piperidinyl)-1-methyl-1H-indazol-5-amine dihydrochloride

N-(1-benzyl-4-piperidinyl)-1H-benzimidazol-5-amine $^1$H-NMR (DMSO-$d_6$) δ; 2.12 (4H, m), 2.71–3.66 (5H, m), 4.05 (3H, s), 4.05–4.41 (2H, m), 7.43–7.57 (5H, m), 7.67–7.79 (2H, m), 8.13 (1H, s), 10.87 (1H, brs).

The following compounds of Example 83 and Example 84 were synthesized by carrying out reaction according to the method described in Example 15, except for using N-(1-benzyl-4-piperidinyl)-1-methyl-1H-indazol-5-amine as a starting material.

EXAMPLE 83

1-Methyl-N-(4-piperidinyl)-1H-indazol-5-amine

Melting point: 111–113° C.

EXAMPLE 84

1-Methyl-N-(4-piperidinyl)-1H-indazol-5-amine dihydrochloride $^1$H-NMR (DMSO-$d_6$) δ; 1.92–2.12 (4H, m), 2.86–2.90 (2H, m), 3.32–3.36 (2H, m), 3.71 (1H, m), 7.44 (1H, brs), 7.67–7.69 (1H, m), 7.88 (1H, m), 8.17 (1H, s), 8.68 (1H, m), 9.13 (1H, m).

The following compounds of Example 85 and Example 86 were synthesized by carrying out reaction according to the method described in Example 1, except for using 2-methyl-2H-indazol-5-amine as a starting material.

EXAMPLE 85

N-(1-benzyl-4-piperidinyl)-2-methyl-2H-indazol-5-amine

Melting point: 108–110° C.

EXAMPLE 86

N-(1-benzyl-4-piperidinyl)-2-methyl-2H-indazol-5-amine dihydrochloride $^1$H-NMR (DMSO-d$_6$) δ; 2.12 (4H, m), 2.93–3.65 (5H, m), 4.17 (3H, s), 4.17–4.41 (2H, m), 7.24–7.28 (1H, m), 7.43–7.56 (5H, m), 7.69–7.73 (2H, m), 8.44 (1H, s), 10.84 (1H, brs).

The following compounds of Example 87 and Example 88 were synthesized by carrying out reaction according to the method described in Example 15, except for using N-(1-benzyl-4-piperidinyl)-2-methyl-2H-indazol-5-amine as a starting material.

EXAMPLE 87

2-Methyl-N-(4-piperidinyl)-2H-indazol-5-amine

Melting point: 144–147° C.

EXAMPLE 88

2-Methyl-N-(4-piperidinyl)-2H-indazol-5-amine dihydrochloride $^1$H-NMR (DMSO-d$_6$) δ; 1.95–2.26 (4H, m), 2.86–2.90 (2H, m), 3.32–3.36 (2H, m), 3.71 (1H, m), 4.18 (3H, s), 7.30–7.33 (1H, m), 7.73–7.86 (1H, m), 8.48 (1H, s), 8.89 (1H, m), 9.20 (1H, m).

The following compounds of Example 89 to Example 91 were synthesized by carrying out reaction according to the method described in Example 1, except for using 3-methyl-1H-indazol-5-amine as a starting material.

EXAMPLE 89

N-(1-benzyl-4-piperidinyl)-3-methyl-1H-indazol-5-amine

Melting point: 160–162° C.

EXAMPLE 90

3-Methyl-N-[1-(2-phenylethyl)-4-piperidinyl]-1H-indazol-5-amine $^1$H-NMR (DMSO-d$_6$) δ; 1.31–1.41 (2H, m), 1.92–1.95 (2H, m), 2.08–2.14 (2H, m), 2.36 (3H, s), 2.48–2.53 (2H, m), 2.70–2.75 (2H, m), 2.88–2.92 (2H, m), 3.16 (1H, m), 5.06 (1H, d, J=8.3 Hz), 6.58 (1H, s), 6.78 (1H, dd, J=8.8, 2.0 Hz), 7.15–7.29 (6H, m), 12.11 (1H, brs).

EXAMPLE 91

N-(1-benzyl-4-piperidinyl)-3-methyl-1H-indazol-5-amine dihydrochloride $^1$H-NMR (DMSO-d$_6$) 67; 2.13 (4H, m), 2.49 (3H, s), 2.92 (2H, m), 3.27–3.86 (3H, m), 4.23–4.41 (2H, m), 7.43–7.81 (9H, m), 10.86 (1H, brs).

The following compounds of Example 92 and Example 93 were synthesized by carrying out reaction according to the method described in Example 15, except for using N-(1-benzyl-4-piperidinyl)-3-methyl-1H-indazol-5-amine as a starting material.

EXAMPLE 92

3-Methyl-N-(4-piperidinyl)-1H-indazol-5-amine

Melting point: 175–177° C.

EXAMPLE 93

3-Methyl-N-(4-piperidinyl)-1H-indazol-5-amine dihydrochloride $^1$H-NMR (DMSO-d$_6$) δ; 1.92–2.03 (4H, m), 2.50 (3H, s), 2.70–2.95 (2H, m), 3.33–3.88 (3H, m), 7.41–7.85 (3H, m), 8.86–8.92 (1H, m), 9.19 (1H, m).

The following compound of Example 94 was synthesized by carrying out reaction according to the method described in Example 1, (a), except for using 1H-benzimidazol-5-amine as a starting material.

EXAMPLE 94

N-(1-benzyl-4-piperidinyl)-1H-benzimidazol-5-amine $^1$H-NMR (DMSO-d$_6$) δ; 1.36–1.39 (2H, m), 1.90–1.93 (2H, m), 2.03–2.10 (2H, m), 2.76–2.80 (2H, m), 3.19 (1H, m), 3.46 (2H, s), 5.21 (1H, brs), 6.53–6.59 (2H, m), 7.23–7.34 (6H, m), 7.84 (1H, brs), 11.81 (1H, brs).

The following compound of Example 95 was synthesized by carrying out reaction according to the method described in Example 15, (a), except for using N-(1-benzyl-4-piperidinyl)-1H-benzimidazol-5-amine as a starting material.

EXAMPLE 95

N-(4-piperidinyl)-1H-benzimidazol-5-amine $^1$H-NMR (DMSO-d$_6$) δ; 1.14–1.27 (2H, m), 1.86–1.89 (2H, m), 2.49–2.56 (2H, m), 2.92–2.98 (2H, m), 3.29 (1H, m), 5.15 (1H, brs), 6.53–6.66 (2H, m), 7.26 (1H, d, J=8.4 Hz), 7.84 (1H, brs), 11.81 (1H, brs).

The following compound of Example 96 was synthesized by carrying out reaction according to the method described in Example 1, (a), except for using 1,2-benzisoxazol-5-amine as a starting material.

EXAMPLE 96

N-(1-benzyl-4-piperidinyl)-1,2-benzisoxazol-5-amine

Melting point: 89–90° C.

The following compound of Example 97 was synthesized by carrying out reaction according to the method described in Example 1, (a), except for using 5-amino-1,3-dihydro-2H-benzimidazol-2-one as a starting material.

EXAMPLE 97

5-[(1-Benzyl-4-piperidinyl)amino]-1,3-dihydro-2H-benzimidazol-2-one $^1$H-NMR (DMSO-d$_6$) δ; 1.32 (2H, m), 1.84 (2H, m), 2.02 (2H, m), 2.74 (2H, m), 3.06 (1H, m), 3.44 (2H, s), 4.94 (1H, d, J=8.6 Hz), 6.20 (1H, d, J=8.1 Hz), 6.20 (1H, s), 6.59 (1H, d, J=8.1 Hz), 7.25 (5H, m), 10.03 (1H, s), 10.17 (1H, s).

The following compound of Example 98 was synthesized by carrying out reaction according to the method described in Example 15, (a), except for using 5-[(1-benzyl-4-piperidinyl)amino]-1,3-dihydro-2H-benzimidazol-2-one as a starting material.

EXAMPLE 98

5-(4-Piperidinylamino)-1,3-dihydro-2H-benzimidazol-2-one $^1$H-NMR (DMSO-d$_6$) δ; 1.14 (2H, m), 1.80 (2H, m), 2.48 (2H, m), 2.89 (2H, m), 3.11 (1H, brs), 4.92 (1H, d, J=7.9 Hz), 6.20 (1H, d, J=8.1 Hz), 6.20 (1H, s), 6.59 (1H, d, J=8.1 Hz), 10.03 (1H, s), 10.17 (1H, s).

EXAMPLE 99

Synthesis of N-(1-propylpiperidin-4-yl)-1H-indazole-5-carboxamide

Acetic acid (0.048 ml) was added to a solution of the N-(4-piperidinyl)-1H-indazole-5-carboxamide (40.0 mg, 0.164 mmol) obtained in Example 58 in methanol (1.2 ml), and the resulting solution was maintained at room temperature for 30 minutes. Propionaldehyde (48.0 mg, 0.826 mmol) was added to the solution and the resulting mixture was maintained at room temperature for another 2 hours. Then, a solution of sodium cyanoborohydride (51.5 mg, 0.820 mmol) in methanol (3.0 ml) was added dropwise thereto, and the resulting mixture was stirred for 18 hours while being maintained at room temperature. A 1N-aqueous sodium hydroxide solution (0.8 ml) was added to the reaction solution, and the resulting mixture was stirred while being maintained at room temperature, and then was concentrated to dryness. The resulting crude product residue was purified by a silica gel column chromatography (eluent: chloroform/methanol/aqueous ammonia=20/1/0.1) to obtain N-(1-propylpiperidin-4-yl)-1H-indazole-5-carboxamide (31 mg, 46%).

MS: m/z=287 (M+1)

The following compounds of Example 100 to Example 114 were synthesized by carrying out reaction according to the method described in Example 99.

EXAMPLE 100

N-(1-butylpiperidin-4-yl)-1H-indazole-5-carboxamide

MS: m/z=301 (M+1)

EXAMPLE 101

N-(1-isobutylpiperidin-4-yl)-1H-indazole-5-carboxamide

MS: m/z=301 (M+1)

EXAMPLE 102

N-(1-isopentylpiperidin-4-yl)-1H-indazole-5-carboxamide

MS: m/z=315 (M+1)

EXAMPLE 103

N-[1-(3,3-dimethylbutyl)piperidin-4-yl]-1H-indazole-5-carboxamide

MS: m/z 329 (M+1)

EXAMPLE 104

N-(1-cyclobutylpiperidin-4-yl)-1H-indazole-5-carboxamide

MS: m/z=299 (M+1)

EXAMPLE 105

N-(1-cyclopentylpiperidin-4-yl)-1H-indazole-5-carboxamide

MS: m/z=313 (M+1)

EXAMPLE 106

N-(1-cyclohexylpiperidin-4-yl)-1H-indazole-5-carboxamide

MS: m/z=327 (M+1)

EXAMPLE 107

N-(1-tetrahydro-2H-pyran-4-ylpiperidin-4-yl)-1H-indazole-5-carboxamide

MS: m/z=329 (M+1)

EXAMPLE 108

N-(1'-methyl-1,4'-piperidin-4-yl)-1H-indazole-5-carboxamide

MS: m/z=342 (M+1)

EXAMPLE 109

N-(1-cycloheptylpiperidin-4-yl)-1H-indazole-5-carboxamide

MS: m/z=341 (M+1)

EXAMPLE 110

N-[1-(cyclopropylmethyl)piperidin-4-yl]-1H-indazole-5-carboxamide

MS: m/z=299 (M+1)

EXAMPLE 111

N-[1-(cyclohexylmethyl)piperidin-4-yl]-1H-indazole-5-carboxamide

MS: m/z=341 (M+1)

EXAMPLE 112

N-[1-(2-phenylethyl)piperidin-4-yl]-1H-indazole-5-carboxamide

MS: m/z=349 (M+1)

EXAMPLE 113

N-(1-methylpiperidin-4-yl)-1H-indazole-5-carboxamide $^1$H-NMR (DMSO-d$_6$) δ; 1.53–1.65 (2H, m), 1.73–1.81 (2H, m), 1.89–1.98 (2H, m), 2.16 (3H, s), 2.73–2.81 (2H, m), 3.69–3.80 (1H, m), 7.55 (1H, d, J=8.8 Hz), 7.84 (1H, dd, J=8.8, 1.5 Hz), 8.20 (1H, s), 8.22 (1H, d, J=7.6 Hz), 8.32 (1H, s), 13.25 (1H, br).

EXAMPLE 114

N-(1-isopropylpiperidin-4-yl)-1H-indazole-5-carboxamide $^1$H-NMR (DMSO-d$_6$) δ; 0.97 (6H, d, J=6.6 Hz), 1.47–1.59 (2H, m), 1.75–1.84 (2H, m), 2.12–2.21 (2H, m), 2.69 (1H, q, J=6.6 Hz), 2.76–2.83 (2H, m), 3.68–3.80 (1H, m), 7.55 (1H, d, J=8.9 Hz), 7.84 (1H, dd, J=8.9, 1.7 Hz), 8.20 (1H, s), 8.21 (1H, d, J=7.6 Hz), 8.31 (1H, s), 13.25 (1H, br).

EXAMPLE 115

Synthesis of N-[1-(but-2-enyl)piperidin-4-yl]-1H-indazole-5-carboxamide

Potassium carbonate (55.0 mg, 0.398 mmol) and 1-chloro-2-butene (17.8 mg, 0.197 mmol) were added to a solution of the N-(4-piperidinyl)-1H-indazole-5-carboxamide (40.0 mg, 0.164 mmol) obtained in Example 58 in N,N-dimethylformamide (1.2 ml), and the resulting mixture was stirred for 20 hours while being maintained at room temperature. The reaction solution was filtered and the filtrate was concentrated to dryness. The resulting crude product residue was purified by a silica gel column chromatography (eluent: chloroform/methanol/aqueous ammonia=20/1/0.1) to obtain N-[1-(but-2-enyl)piperidin-4-yl]-1H-indazole-5-carboxamide (26 mg, 54%).

MS: m/z=299 (M+1)

The following compounds of Example 116 to Example 134 were synthesized by carrying out reaction according to the method described in Example 115.

EXAMPLE 116

N-[1-(3-methylbut-2-enyl)piperidin-4-yl]-1H-indazole-5-carboxamide

MS: m/z=313 (M+1)

EXAMPLE 117

N-(1-prop-2-ynylpiperidin-4-yl)-1H-indazole-5-carboxamide

MS: m/z=283 (M+1)

EXAMPLE 118

N-[1-(2-hydroxyethyl)piperidin-4-yl]-1H-indazole-5-carboxamide

MS: m/z=289 (M+1)

EXAMPLE 119

N-[1-(2-hydroxypropyl)piperidin-4-yl]-1H-indazole-5-carboxamide

MS: m/z=303 (M+1)

EXAMPLE 120

N-[1-(2-hydroxy-2-methylpropyl)piperidin-4-yl]-1H-indazole-5-carboxamide

MS: m/z=317 (M+1)

EXAMPLE 121

N-[1-(3-hydroxypropyl)piperidin-4-yl]-1H-indazole-5-carboxamide

MS: m/z=303 (M+1)

EXAMPLE 122

N-[1-(2-methoxyethyl)piperidin-4-yl]-1H-indazole-5-carboxamide

MS: m/z=303 (M+1)

EXAMPLE 123

N-{1-[2-(2-methoxyethoxy)ethyl]piperidin-4-yl]-1H-indazole-5-carboxamide

MS: m/z=347 (M+1)

EXAMPLE 124

N-[1-(2-phenoxyethyl)piperidin-4-yl]-1H-indazole-5-carboxamide

MS: m/z=365 (M+1)

EXAMPLE 125

N-[1-(2-fluoroethyl)piperidin-4-yl]-1H-indazole-5-carboxamide

MS: m/z=291 (M+1)

EXAMPLE 126

N-[1-(2,2,2-trifluoroethyl)piperidin-4-yl]-1H-indazole-5-carboxamide

MS: m/z=327 (M+1)

EXAMPLE 127

N-[1-(3,3,3-trifluoropropyl)piperidin-4-yl]-1H-indazole-5-carboxamide

MS: m/z=341 (M+1)

EXAMPLE 128

N-[1-(cyanomethyl)piperidin-4-yl]-1H-indazole-5-carboxamide

MS: m/z=284 (M+1)

EXAMPLE 129

N-[1-(2-cyanoethyl)piperidin-4-yl]-1H-indazole-5-carboxamide

MS: m/z=298 (M+1)

EXAMPLE 130

N-[1-(2-amino-2-oxoethyl)piperidin-4-yl]-1H-indazole-5-carboxamide

MS: m/z=302 (M+1)

EXAMPLE 131

N-[1-(2-oxopropyl)piperidin-4-yl]-1H-indazole-5-carboxamide

MS: m/z=301 (M+1)

EXAMPLE 132

N-{1-[2-(dimethylamino)ethyl]piperidin-4-yl}-1H-indazole-5-carboxamide

MS: m/z=316 (M+1)

EXAMPLE 133

N-[1-(cyclobutylmethyl)piperidin-4-yl]-1H-indazole-5-carboxamide

MS: m/z=313 (M+1)

EXAMPLE 134

N-[1-(tetrahydro-2H-pyran-2-ylmethyl)piperidin-4-yl]-1H-indazole-5-carboxamide

MS: m/z=343 (M+1)

The following compounds of Examples 135 and 136 were synthesized by carrying out reaction according to the method described in Example 45.

EXAMPLE 135

N-(1-phenylpiperidin-4-yl)-1H-indazole-5-carboxamide

MS: m/z=321 (M+1)

EXAMPLE 136

N-(1-benzylpyrrolidin-3-yl)-1H-indazole-5-carboxamide

Melting point: 187–189° C.

The following compound of Example 137 was synthesized by carrying out reaction according to the method described in Example 15, (a), except for using the N-(1-benzylpyrrolidin-3-yl)-1H-indazole-5-carboxamide obtained in Example 136, as a starting material.

EXAMPLE 137

N-(3-pyrrolidinyl)-1H-indazole-5-carboxamide $^1$H-NMR (DMSO-$d_6$) δ; 1.63–1.73 (1H, m), 1.93–2.02 (1H, m), 2.65–2.78 (2H, m), 2.89–2.98 (2H, m), 4.28–4.37 (1H, m), 7.55 (1H, d, J=8.9 Hz), 7.85 (1H, dd, J=1.4, 8.9 Hz), 8.20 (1H, s), 8.31 (1H, d, J=7.3 Hz), 8.33 (1H, s), 13.2 (1H, br).

EXAMPLE 138

Synthesis of N-(1-benzylpiperidin-3-yl)-1H-indazole-5-carboxamide (a) Synthesis of ethyl 1-benzyl-3-piperidinecarboxylate Benzyl chloride (5.5 ml, 47.8 mmol) and potassium carbonate (8.3 g, 60.1 mmol) were added to a solution of ethyl 3-piperidinecarboxylate (6.55 g, 40.0 mmol) in N,N-dimethylformamide (20 ml), and the resulting mixture was stirred at 100° C. for 10 hours. After completion of the reaction, the reaction solution was filtered and the filtrate was subjected to azeotropic concentration with toluene. The resulting residue was purified by a silica gel column chromatography (eluent: n-hexane/ethyl acetate=20/1) to obtain ethyl 1-benzyl-3-piperidinecarboxylate (7.45 g, 75.3%).

(b) Synthesis of 1-benzyl-3-piperidinecarboxylic acid

A 4N-aqueous sodium hydroxide solution (15 ml) was added to a solution of ethyl 1-benzyl-3-piperidinecarboxylate (7.00 g, 28.3 mmol) in a mixture of tetrahydrofuran (30 ml) and 1,4-dioxane (30 ml), and the resulting mixture was stirred at room temperature for 4 hours. After a 4N-aqueous sodium hydroxide solution (15 ml) was added again, the resulting mixture was stirred overnight at room temperature. After completion of the reaction, the reaction solution was neutralized by the addition of 2N-hydrochloric acid (15 ml) under ice-cooling and the resulting mixture was subjected to azeotropic concentration with toluene. The residue was suspended in ethanol, followed by filtration, and the filtrate was concentrated to obtain 1-benzyl-3-piperidinecarboxylic acid (6.3 g, 100%).

(c) Synthesis of tert-butyl 1-benzyl-3-piperidinylcarbamate

Triethylamine (0.38 ml, 2.73 mmol) and diphenylphosphoryl azide (0.692 g, 2.52 mmol) were added to a solution of 1-benzyl-3-piperidinecarboxylic acid (0.501 g, 2.28 mmol) in toluene (10 ml), and the resulting mixture was stirred for 2 hours with heating under reflux. The solvent was distilled off under reduced pressure and a solution of the resulting residue in tert-butanol (10 ml) was stirred for 4 hours with heating under reflux. The solvent was distilled off under reduced pressure and a 1N-aqueous sodium hydroxide solution was added to the residue, followed by extraction with ethyl acetate (three times). The extract solution was dried over anhydrous sodium sulfate. The solvent was distilled off under reduced pressure and the residue was purified by a silica gel chromatography (eluent: hexane/ethyl acetate=5/1) to obtain tert-butyl 1-benzyl-3-piperidinylcarbamate (0.475 g, 72%).

(d) Synthesis of 1-benzyl-3-piperidinamine dihydrochloride

A 4N-hydrochloric acid/1,4-dioxane solution (4 ml) was added to a solution of tert-butyl 1-benzyl-3-piperidinylcarbamate (0.448 g, 1.54 mmol) in tetrahydrofuran (4 ml) and stirred overnight. After the solvent was distilled off under reduced pressure, diethyl ether was added to the residue to precipitate a solid, and the supernatant was decanted and then dried under reduced pressure to obtain 1-benzyl-3-piperidinamine dihydrochloride (0.384 g, 95%).

(e) Synthesis of N-(1-benzylpiperidin-3-yl)-1H-indazole-5-carboxamide

The 1H-indazole-5-carboxylic acid (0.225 g, 1.39 mmol) obtained in Reference Example 1, triethylamine (0.57 ml, 4.1 mmol), 1-hydroxybenztriazole (0.222 g, 1.64 mmol) and 1-ethyl-3-(3'-dimethylaminopropyl)carbodiimide monohydrochloride (0.314 g, 1.64 mmol) were added to a solution of 1-benzyl-3-piperidinamine dihydrochloride (0.360 g, 1.37 mmol) in N,N-dimethylformamide (5 ml) and stirred overnight. The resulting mixture was added to a 1N-aqueous sodium hydroxide solution and extracted three times with ethyl acetate, and the extract solution was dried over anhydrous sodium sulfate. The solvent was distilled off under reduced pressure and the residue was purified by a silica gel chromatography (eluent: chloroform/methanol=20/1) to obtain N-(1-benzylpiperidin-3-yl)-1H-indazole-5-carboxamide (0.384 g, 83%).

Melting point: 203–204° C.

EXAMPLE 139

Synthesis of N-(3-piperidinyl)-1H-indazole-5-carboxamide

Ammonium formate (0.363 g) and 10% Pd—C (0.074 g) were added to a suspension of the N-(1-benzylpiperidin-3-yl)-1H-indazole-5-carboxamide (0.357 g, 1.06 mmol) obtained in Example 138 in ethanol (10 ml), and the resulting mixture was stirred for 4 hours with heating under reflux. The resulting solution was filtered by the use of Celite and then the solvent was distilled off from the filtrate to obtain a solid. The solid obtained was suspended in ethyl acetate, stirred to be washed, collected by filtration and dried under reduced pressure to obtain N-(3-piperidinyl)-1H-indazole-5-carboxamide (0.250 g, 96%).

Melting point: 265–266° C.

EXAMPLE 140

Synthesis of N-(1-methylpiperidin-3-yl)-1H-indazole-5-carboxamide

Acetic acid (0.12 ml, 2.1 mmol) was added to a suspension of the N-(3-piperidinyl)-1H-indazole-5-carboxamide (0.100 g, 0.409 mmol) obtained in Example 139 and paraformaldehyde (0.101 g, 3.34 mmol) in methanol (3 ml), and the resulting mixture was stirred for 15 minutes and then ice-cooled. Sodium cyanoborohydride (0.128 g, 2.04 mmol) was added thereto and the resulting mixture was slowly warmed up to room temperature and stirred overnight. After a 1N-aqueous sodium hydroxide solution was added thereto, the solvent was distilled off under reduced pressure and the residue was dried up and then purified by a silica gel chromatography (eluent: chloroform/methanol/30% aqueous ammonia=100/10/1). Ethyl acetate was added thereto to precipitate a solid and the resulting suspension was stirred to wash the solid. The solid was collected by filtration and dried under reduced pressure to obtain N-(1-methylpiperidin-3-yl)-1H-indazole-5-carboxamide (0.0718 g, 68%).

Melting point: 228–229° C.

The following compounds of Example 141 to Example 146 were synthesized by carrying out reaction according to the method described in Example 99, except for using the N-(3-piperidinyl)-1H-indazole-5-carboxamide obtained in Example 139, as a starting material.

EXAMPLE 141

N-(1-butylpiperidin-3-yl)-1H-indazole-5-carboxamide

MS: m/z=301 (M+1)

EXAMPLE 142

N-[1-(cyclohexylmethyl)piperidin-3-yl]-1H-indazole-5-carboxamide

MS: m/z=341 (M+1)

EXAMPLE 143

N-(1-isopropylpiperidin-3-yl)-1H-indazole-5-carboxamide

MS: m/z=287 (M+1)

EXAMPLE 144

N-(1-cyclobutylpiperidin-3-yl)-1H-indazole-5-carboxamide

MS: m/z=299 (M+1)

EXAMPLE 145

N-(1-cyclopentylpiperidin-3-yl)-1H-indazole-5-carboxamide

MS: m/z=313 (M+1)

EXAMPLE 146

N-(1-cyclohexylpiperidin-3-yl)-1H-indazole-5-carboxamide

MS: m/z=327 (M+1)

EXAMPLE 147

Synthesis of N-(1-benzylazepan-3-yl)-1H-indazole-5-carboxamide (a) Synthesis of 3-amino-2-azepanone Hexamethyldisilazane (30 ml) and chloro-trimethylsilane (several drops) were added to a suspension of DL-lysine (3.0 g, 20.5 mmol) in xylene (270 ml) at room temperature, and the reaction was carried out at 140° C. for 48 hours. The reaction mixture was cooled and then poured into ethanol (600 ml), and the resulting mixture was concentrated. The resulting residue was suspended in chloroform, followed by filtration and concentration, whereby 3-amino-2-azepanone (1.59 g, 60%) was obtained.

$^1$H-NMR (DMSO-$d_6$): 1.08–1.36 (2H, m), 1.51–1.84 (6H, m), 3.00–3.12 (2H, m), 3.95–3.96 (1H, m), 7.56 (1H, brs).

(b) Synthesis of 3-(tritylamino)-2-azepanone

Triethylamine (1.75 ml, 12.6 mmol) and triphenylmethyl chloride (3.50 g, 12.6 mmol) were added to a solution of 3-amino-2-azepanone (1.46 g, 11.4 mmol) in chloroform (44 ml) at room temperature and stirred overnight at room temperature. The reaction mixture was poured into water and then extracted with chloroform. The organic layer was washed with a saturated aqueous sodium chloride solution and then dried over anhydrous magnesium sulfate. The solvent was distilled off under reduced pressure and the resulting residue was purified by a silica gel column chromatography (eluent: chloroform/ethyl acetate) to obtain 3-(tritylamino)-2-azepanone (2.93 g, 69%).

$^1$H-NMR (DMSO-$d_6$): 0.98–1.36 (4H, m), 1.48–1.54 (2H, m), 2.63–2.81 (2H, m), 3.22 (1H, m), 3.95–3.96 (1H, m), 7.16–7.49 (15H, m), 7.51–7.52 (1H, m).

(c) Synthesis of 1-benzyl-3-(tritylamino)-2-azepanone

To a suspension of 3-(tritylamino)-2-azepanone (2.85 g, 7.69 mmol) in tetrahydrofuran (30 ml) was added 60%-sodium hydride (462 mg, 11.6 mmol) at 0° C., and then stirred at room temperature for 30 minutes. Subsequently, a solution of benzyl bromide (1.0 ml, 8.41 mmol) in tetrahydrofuran (5 ml) was added dropwise thereto at room temperature over a period of 3 minutes, followed by adding thereto tetra-n-butylammonium iodide (57 mg, 0.15 mmol), and the resulting mixture was stirred at room temperature for 6 hours. The reaction mixture was cooled on an ice-water bath and t-butanol (0.7 ml) and water (1 ml) were added thereto at 0° C. The resulting mixture was poured into water and then extracted with ethyl acetate. The organic layer was washed with a saturated aqueous sodium chloride solution and then dried over anhydrous magnesium sulfate. The solvent was distilled off under reduced pressure and the resulting residue was purified by a silica gel column chromatography (eluent: n-hexane/chloroform) to obtain 1-benzyl-3-(tritylamino)-2-azepanone (2.22 g, 63%).

$^1$H-NMR (DMSO-$d_6$): 1.05 (1H, m), 1.22–1.44 (4H, m), 1.59–1.65 (2H, m), 2.85–3.02 (2H, m), 3.41–3.45 (1H, m), 3.97 (1H, d, J=5.9 Hz), 4.00 (1H, d, J=15.0 Hz), 4.60 (1H, d, J=14.7 Hz), 6.96–6.99 (2H, m), 7.18–7.41 (18H, m).

(d) Synthesis of 1-benzyl-N-trityl-3-azepanamine

A solution of 1-benzyl-3-(tritylamino)-2-azepanone (425 mg, 0.922 mmol) in tetrahydrofuran (11 ml) was added dropwise to a suspension of lithium aluminum hydride (140 mg, 3.69 mmol) in tetrahydrofuran (22 ml) at room temperature, and the resulting mixture was stirred for 30 minutes and then refluxed for 3 hours. After the reaction mixture was cooled, water (0.14 ml), a 2N-aqueous sodium hydroxide solution (0.3 ml) and water (0.14 ml) were added thereto under ice-cooling. The resulting mixture was filtered and the solvent of the filtrate was distilled off under reduced pressure. The resulting residue was purified by a silica gel column chromatography (eluent: chloroform/methanol) to obtain 1-benzyl-N-trityl-3-azepanamine (319 mg, 78%).

$^1$H-NMR (DMSO-$d_6$): 1.22–1.65 (7H, m), 2.08–2.23 (2H, m) 2.43–2.50 (1H, m), 2.59 (2H, brs), 3.17 (1H, d, J=13.6 Hz), 3.24 (1H, d, J=13.6 Hz), 7.12–7.27 (14H, m), 7.44 (6H, m).

(e) Synthesis of 1-benzyl-3-azepanamine

Formic acid (0.25 ml, 6.63 mmol) was added dropwise to a solution of 1-benzyl-N-trityl-3-azepanamine (300 mg, 0.672 mmol) in methylene chloride (7 ml) under ice-cooling and stirred under ice-cooling for 3.5 hours. After the reaction mixture was concentrated, the residue was diluted with ether and washed with 1N-hydrochloric acid. After extraction, a 1N-aqueous sodium hydroxide solution was added to the aqueous layer under ice-cooling to make the aqueous layer basic, followed by extraction with chloroform. The organic layer was dried over magnesium sulfate and then concentrated to obtain 1-benzyl-3-azepanamine (100 mg, 73%).

$^1$H-NMR (DMSO-$d_6$): 1.26–1.60 (5H, m), 1.70–1.74 (1H, m), 2.28 (1H, dd, J=8.1, 13.0 Hz), 2.68 (1H, dd, J=4.0, 13.0 Hz), 2.77–2.86 (1H, m), 3.25 (2H, br), 3.57 (1H, d, J=15.2 Hz), 3.62 (1H, d, J=15.4 Hz), 7.18–7.31 (5H, m).

(f) Synthesis of N-(1-benzylazepan-3-yl)-1H-indazole-5-carboxamide

N-(1-benzylazepan-3-yl)-1H-indazole-5-carboxamide was obtained by carrying out reaction according to the method described in Example 45, except for using 1-benzyl-3-azepanamine.

MS: m/z=349 (M+1)

EXAMPLE 148

Synthesis of N-azepan-3-yl-1H-indazole-5-carboxamide

Ammonium formate (716 mg, 11.4 mmol) and 10% palladium carbon (containing 50% water, 100 mg) were added to a solution of the N-(1-benzylazepan-3-yl)-1H-indazole-5-carboxamide (494 mg, 1.42 mmol) obtained in Example 147 in ethanol (28 ml) at room temperature, and the resulting mixture was stirred with heating under reflux for 5 hours. The reaction mixture was filtered to remove the catalyst and the solvent of the filtrate was distilled off under reduced pressure. The resulting residue was purified by a silica gel column chromatography (eluent: ethyl acetate/ methanol/aqueous ammonia=10/1/0.1) to obtain N-azepan-3-yl-1H-indazole-5-carboxamide (267 mg, 73%).

MS: m/z=259 (M+1)

The following compounds of Example 149 to Example 154 were synthesized by carrying out reaction according to the method described in Example 99, except for using the N-azepan-3-yl-1H-indazole-5-carboxamide obtained in Example 148, as a starting material.

EXAMPLE 149

N-(1-methylazepan-3-yl)-1H-indazole-5-carboxamide

MS: m/z=273 (M+1)

EXAMPLE 150

N-(1-butylazepan-3-yl)-1H-indazole-5-carboxamide

MS: m/z=315 (M+1)

EXAMPLE 151

N-(1-isopropylazepan-3-yl)-1H-indazole-5-carboxamide

MS: m/z=301 (M+1)

EXAMPLE 152

N-(1-cyclobutylazepan-3-yl)-1H-indazole-5-carboxamide

MS: m/z=313 (M+1)

EXAMPLE 153

N-(1-cyclopentylazepan-3-yl)-1H-indazole-5-carboxamide

MS: m/z=327 (M+1)

EXAMPLE 154

N-(1-tetrahydro-2H-pyran-4-ylazepan-3-yl)-1H-indazole-5-carboxamide

MS: m/z=343 (M+1)

EXAMPLE 155

Synthesis of N-(8-benzyl-8-azabicyclo[3.2.1]oct-3-yl)-1H-indazole-5-carboxamide (a) Synthesis of 8-benzyl-8-azabicyclo[3.2.1]octan-3-one oxime A 50%-aqueous hydroxylamine solution (182 mg, 2.76 mmol) was added to a solution of 8-benzyl-8-azabicyclo[3.2.1]octan-3-one (538 mg, 2.50 mmol) in ethanol (5 ml) at room temperature and stirred at room temperature for 4 hours. The reaction mixture was concentrated and the resulting residue was purified by a silica gel column chromatography (eluent: chloroform/methanol) to obtain 8-benzyl-8-azabicyclo[3.2.1]octan-3-one oxime (516 mg, 90%).

$^1$H-NMR (DMSO-d$_6$) δ; 1.49–1.69 (2H, m), 2.04–2.25 (4H, m), 2.59 (1H, dd, J=3.3, 14.9 Hz), 2.98 (1H, d, J=15.4 Hz), 3.35 (2H, m), 3.65 (2H, s), 7.23–7.41 (6H, m).

(b) Synthesis of 8-benzyl-8-azabicyclo[3.2.1]octan-3-amine

A suspension of 8-benzyl-8-azabicyclo[3.2.1]octan-3-one oxime (230 mg, 0.999 mmol) in tetrahydrofuran (4 ml) was added dropwise to a suspension of lithium aluminum hydride (152 mg, 4.01 mmol) in tetrahydrofuran (3 ml) at room temperature, and the resulting mixture was refluxed for 8 hours. The reaction mixture was cooled on an ice-water bath, and water (0.2 ml), a 2N-aqueous sodium hydroxide solution (0.4 ml) and water (0.2 ml) were added thereto in that order and stirred. Subsequently, the resulting mixture was filtered and the solvent of the filtrate was distilled off to obtain 8-benzyl-8-azabicyclo[3.2.1]octan-3-amine (246 mg) containing a small amount of impurities.

(c) Synthesis of N-(8-benzyl-8-azabicyclo[3.2.1]oct-3-yl)-1H-indazole-5-carboxamide N-(8-benzyl-8-azabicyclo[3.2.1]oct-3-yl)-1H-indazole-5-carboxamide was obtained by carrying out reaction according to the method described in Example 45, except for using 8-benzyl-8-azabicyclo[3.2.1]octan-3-amine.

MS: m/z=361 (M+1)

The following compound of Example 156 was synthesized by carrying out reaction according to the method described in Example 148, except for using the N-(8-benzyl-8-azabicyclo[3.2.1]oct-3-yl)-1H-indazole-5-carboxamide obtained in Example 155, as a starting material.

EXAMPLE 156

N-(8-azabicyclo[3,2,1]oct-3-yl)-1H-indazole-5-carboxamide

MS: m/z=271 (M+1)

The following compound of Example 157 was synthesized by carrying out reaction according to the method described in Example 45.

EXAMPLE 157

N-(1-azabicyclo[2,2,2]oct-3-yl)-1H-indazole-5-carboxamide

MS: m/z=271 (M+1)

EXAMPLE 158

Synthesis of trans-tert-butyl-4-[(1H-indazol-5-ylcarbonyl)amino]cyclohexylcarbamate (a) Trans-tert-butyl 4-aminocyclohexylcarbamate A solution of di-tert-butyldicarbonate (4.78 g, 21.9 mmol) in chloroform (75 ml) was added to a solution of trans-1,4-diaminocyclohexane (5.0 g, 43.8 mmol) in chloroform (100 ml) at room temperature and stirred for 1.5 hours. The reaction solution was concentrated, diluted with methylene chloride, and then washed with a saturated aqueous sodium hydrogencarbonate solution. The organic layer was dried over anhydrous magnesium sulfate and distilled under reduced pressure to remove the solvent. The resulting residue was purified by a silica gel column chromatography (eluent: chloroform/methanol/aqueous ammonia=90/10/1) to obtain trans-tert-butyl 4-aminocyclohexylcarbamate (2.81 g, 60%).

(b) Synthesis of trans-tert-butyl-4-[(1H-indazol-5-ylcarbonyl)amino]cyclohexylcarbamate To a solution of the 1H-indazole-5-carboxylic acid (200 mg, 1.23 mmol) obtained in Reference Example 1 in N,N-dimethylformamide (15 ml) were added trans-tert-butyl 4-aminocyclohexylcarbamate (317 mg, 1.48 mmol), triethylamine (0.172 ml, 1.23 mmol), 1-ethyl-3-(3'-dimethylaminopropyl)carbodiimide monohydrochloride (355 mg, 1.85 mmol) and hydroxybenzotriazole (200 mg, 1.48 mmol), and the resulting mixture was stirred at room temperature for 1 hour. After the reaction solution was heated at 50° C. for 1 hour, water was added thereto at 0° C. The resulting solid was filtered and then dried under reduced pressure to obtain trans-tert-butyl-4-[(1H-indazol-5-ylcarbonyl)amino]cyclohexylcarbamate (435 mg, 98%).

$^1$H-NMR (DMSO-$d_6$) δ; 1.18–1.44 (6H, m), 1.36 (9H, s), 1.82 (4H, m), 7.54 (1H, d, J=8.6 Hz), 7.81 (1H, d, J=8.6 Hz), 8.17 (1H, s), 8.19 (1H, d, J=7.6 Hz), 8.29 (1H, s).

EXAMPLE 159

Synthesis of N-(4-aminocyclohexyl)-1H-indazole-5-carboxamide trifluoroacetate

Trifluoroacetic acid (6.0 ml) was added to the trans-tert-butyl-4-[(1H-indazol-5-ylcarbonyl)amino]cyclo-hexylcarbamate (420 mg, 1.17 mmol) obtained in Example 158, and the resulting mixture was stirred at room temperature for 1 hour. After the reaction solution was concentrated under reduced pressure, ethanol (10 ml) was added to the concentration residue, followed by washing by repulping. The residue washed was filtered and then dried under reduced pressure to obtain N-(4-aminocyclohexyl)-1H-indazole-5-carboxamide trifluoroacetate (363 mg, 83%).

$^1$H-NMR (DMSO-$d_6$) δ; 1.44 (4H, m), 1.96 (4H, m), 3.00 (1H, m), 3.73 (1H, m), 7.56 (1H, d, J=8.9 Hz), 7.80 (2H, m), 8.19 (1H, s), 8.28 (1H, d, J=7.7 Hz), 8.30 (1H, s), 13.27 (1H, s).

EXAMPLE 160

Synthesis of N-(4-oxocyclohexyl)-1H-indazole-5-carboxamide (a) Synthesis of tert-butyl 4-hydroxycyclohexylcarbamate An aqueous solution (52.5 ml) of sodium hydroxide (2.91 g, 72.8 mmol) was added to a t-butanol suspension (122.5 ml) of trans-4-aminocyclohexanol (8.06 g, 70.0 mmol) at room temperature, followed by adding thereto di-t-butyl dicarbonate (15.9 g, 72.9 mmol), and the resulting mixture was stirred overnight at room temperature. Water was added to the reaction mixture, followed by extraction with n-hexane. The suspended organic layer was filtered and the precipitate was dried to obtain tert-butyl 4-hydroxycyclohexylcarbamate (2.70 g) as a white solid. The aqueous layer was neutralized with 1N-hydrochloric acid and then extracted with ethyl acetate. The organic layer was washed with a saturated aqueous sodium chloride solution and then dried over magnesium sulfate. The solvent was distilled off under reduced pressure and the resulting residue was purified by a silica gel column chromatography (eluent: chloroform/ethyl acetate) to obtain tert-butyl 4-hydroxycyclohexylcarbamate (11.3 g) (14.0 g in total, 93%).

$^1$H-NMR (DMSO-$d_6$): 1.06–1.20 (4H, m), 1.35 (9H, s), 1.69–1.76 (4H, m), 3.12–3.31 (2H, m), 4.48 (1H, s), 6.64 (1H, d, J=7.5 Hz).

(b) Synthesis of Tert-butyl 4-oxocyclohexylcarbamate

A methylene chloride solution (6 ml) of dimethyl sulfoxide (2.0 ml, 28.2 mmol) was added dropwise to a methylene chloride solution (30 ml) of oxalyl chloride (1.7 ml, 19.5 mmol) at −60° C. over a period of 10 minutes and stirred at −60° C. for another 10 minutes. Then, a methylene chloride solution (140 ml) of tert-butyl 4-hydroxycyclohexylcarbamate (2.56 g, 11.9 mmol) was added dropwise thereto over a period of 35 minutes, and the resulting mixture was stirred at −60° C. for 40 minutes. After triethylamine (8.4 ml, 60.3 mmol) was added thereto at −60° C., the resulting mixture was warmed up to room temperature spontaneously. Water was added to the reaction mixture, followed by extraction with chloroform. The organic layer was washed with a saturated aqueous ammonium chloride solution and a saturated aqueous sodium chloride solution and then dried over magnesium sulfate. The solvent was distilled off under reduced pressure and the resulting residue was purified by a silica gel column chromatography (eluent: chloroform/ethyl acetate) to obtain tert-butyl 4-oxocyclohexylcarbamate (2.23 g, 87%).

$^1$H-NMR (DMSO-$d_6$): 1.06–1.20 (4H, m), 1.35 (9H, s), 1.69–1.76 (4H, m), 3.12–3.31 (2H, m), 4.48 (1H, s), 6.64 (1H, d, J=7.5 Hz)

(c) Synthesis of 4-aminocyclohexanone

Trifluoroacetic acid (4.3 ml, 55.8 mmol) was added to a solution of tert-butyl 4-oxocyclohexylcarbamate (1.00 g, 4.69 mmol) in methylene chloride (47 ml) at room temperature and stirred overnight at room temperature. Then, the solvent of the reaction solution was distilled off under reduced pressure and the resulting residue was poured into a 1N-aqueous sodium hydroxide solution and extracted with ethyl acetate and chloroform. The organic layer was washed with a saturated aqueous sodium chloride solution and then dried over anhydrous magnesium sulfate. The solvent was distilled off under reduced pressure to obtain 4-aminocyclohexanone (378 mg) containing a small amount of impurities.

(d) Synthesis of N-(4-oxocyclohexyl)-1H-indazole-5-carboxamide

N-(4-oxocyclohexyl)-1H-indazole-5-carboxamide was obtained by carrying out reaction according to the method described in Example 45, except for using 4-aminocyclohexanone.

MS: m/z=258 (M+1)

EXAMPLE 161

Synthesis of N-[4-(methylamino)cyclohexyl]-1H-indazole-5-carboxamide

Acetic acid (0.096 ml) was added to a solution of the N-(4-oxocyclohexyl)-1H-indazole-5-carboxamide (40.0 mg, 0.155 mmol) obtained in Example 160 in methanol (1.2 ml), and the resulting solution was maintained at room temperature for 30 minutes. To this solution was added a 40% aqueous methylamine solution (60.0 mg, 0.777 mmol), and the resulting mixture was maintained at room temperature for another 2 hours. Then, a solution of sodium cyanotrihydroborate (48.7 mg, 0.777 mmol) in methanol (0.6 ml) was added dropwise thereto, and the resulting mixture was stirred for 22 hours while being maintained at room temperature. A 1N aqueous sodium hydroxide solution (0.8 ml) was added to the reaction solution, and the resulting mixture was stirred while being maintained at room temperature, and was then concentrated to dryness. The resulting crude product residue was purified by a silica gel column chromatography (eluent: chloroform/methanol/aqueous ammonia=10/1/0.1) to obtain N-[4-(methylamino)cyclohexyl]-1H-indazole-5-carboxamide (an isomer having a lower polarity) (12.2 mg, 29%) and N-[4-(methylamino)cyclohexyl]-1H-indazole-5-carboxamide (an isomer having a higher polarity) (28.3 mg, 67%).

MS: m/z=273 (M+1) for both isomers.

The following compounds of Example 162 to Example 170 were synthesized by carrying out reaction according to the method described in Example 9, except for using the trans-N-(4-aminocyclohexyl)-1H-indazole-5-carboxamide trifluoroacetate obtained in Example 159, as a starting material.

EXAMPLE 162 trans-N-[4-(dimethylamino)cyclohexyl]-1H-indazole-5-carboxamide

MS: m/z=287 (M+1)

EXAMPLE 163 trans-N-[4-(butylamino)cyclohexyl]-1H-indazole-5-carboxamide

MS: m/z=315 (M+1)

EXAMPLE 164 trans-N-[4-(isopropylamino)cyclohexyl]-1H-indazole-5-carboxamide

MS: m/z=301 (M+1)

EXAMPLE 165 trans-N-[4-(cyclobutylamino)cyclohexyl]-1H-indazole-5-carboxamide

MS: m/z=313 (M+1)

EXAMPLE 166 trans-N-[4-(cyclopentylamino)cyclohexyl]-1H-indazole-5-carboxamide

MS: m/z=327 (M+1)

EXAMPLE 167 trans-N-[4-(cyclohexylamino)cyclohexyl]-1H-indazole-5-carboxamide

MS: m/z=341 (M+1)

EXAMPLE 168 trans-N-[4-(tetrahydro-2H-pyran-4-ylamino)cyclohexyl]-1H-indazole-5-carboxamide

MS: m/z=343 (M+1)

EXAMPLE 169 trans-N-(4-{[2-(benzyloxy)ethyl]amino}cyclohexyl)-1H-indazole-5-carboxamide

MS: m/z=393 (M+1)

EXAMPLE 170 trans-N-(4-piperidin-1-ylcyclohexyl)-1H-indazole-5-carboxamide

MS: m/z=327 (M+1)

The following compounds of Examples 171 and 172 were synthesized by carrying out reaction according to the method described in Example 161.

EXAMPLE 171

N-(4-azetidin-1-ylcyclohexyl)-1H-indazole-5-carboxamide (Two Isomers Different in Polarity)
MS: m/z=299 (M+1) for both isomers.

EXAMPLE 172

N-(4-pyrrolidin-1-ylcyclohexyl)-1H-indazole-5-carboxamide (Two Isomers Different in Polarity)
MS: m/z=313 (M+1) for both isomers.

The following compound of Example 173 was synthesized by carrying out reaction according to the method described in Example 138, except for using 4-({[(benzyloxy)carbonyl]amino}methyl)cyclohexanecarboxylic acid as a starting material.

EXAMPLE 173 trans-Benzyl {4-[(1H-indazol-5-ylcarbonyl)amino]cyclohexyl}methylcarbamate $^1$H-NMR (DMSO-$d_6$) δ; 0.92–1.05 (2H, m), 1.25–1.43 (3H, m), 1.70–1.78 (2H, m), 1.82–1.91 (2H, m), 2.88 (2H, d, J=6.3 Hz), 3.68–3.80 (1H, m), 5.01 (2H, s), 7.28–7.40 (6H, m), 7.54 (1H, d, J=8.6 Hz), 7.84 (1H, dd, J=1.5, 8.6 Hz), 8.18 (1H, d, J=7.4 Hz), 8.19 (1H, br), 8.31 (1H, s), 13.24 (1H, br)

The following compound of Example 174 was synthesized by carrying out reaction according to the method described in Example 139, except for using the trans-benzyl {4-[(1H-indazol-5-ylcarbonyl)amino]cyclohexyl}methylcarbamate obtained in Example 173, as a starting material.

EXAMPLE 174 trans-N-[4-(aminomethy)]cyclohexyl]-1H-indazole-5-carboxamide

Melting point: 259–261° C.

The following compounds of Example 175 to Example 183 were synthesized by carrying out reaction according to the method described in Example 99, except for using the trans-N-[4-(aminomethy)cyclohexyl]-1H-indazole-5-carboxamide obtained in Example 174, as a starting material.

EXAMPLE 175 trans-N-{4-[(dimethylamino)methyl]cyclohexyl}-1H-indazole-5-carboxamide

MS: m/z=301 (M+1)

EXAMPLE 176 trans-N-{4-[(butylamino)methyl]cyclohexyl}-1H-indazole-5-carboxamide

MS: m/z=329 (M+1)

EXAMPLE 177 trans-N-{4-[(isopropylamino)methyl]cyclohexyl}-1H-indazole-5-carboxamide

MS: m/z=315 (M+1)

EXAMPLE 178 trans-N-{4-[(cyclobutylamino)methyl]cyclohexyl}-1H-indazole-5-carboxamide

MS: m/z=327 (M+1)

EXAMPLE 179 trans-N-{4-[(dicyclobutylamino)methyl]cyclohexyl}-1H-indazole-5-carboxamide

MS: m/z=381 (M+1)

EXAMPLE 180 trans-N-{4-[(cyclopentylamino)methyl]cyclohexyl}-1H-indazole-5-carboxamide

MS: m/z=341 (M+1)

EXAMPLE 181 trans-N-{4-[(cyclohexylamino)methyl]cyclohexyl}-1H-indazole-5-carboxamide

MS: m/z=355 (M+1)

EXAMPLE 182 trans-N-{4-[(tetrahydro-2H-pyran-4-ylamino)methyl]cyclohexyl}-1H-indazole-5-carboxamide MS: m/z=357 (M+1)

EXAMPLE 183 trans-N-[4-(piperidin-1-ylmethyl)cyclohexyl]-1H-indazole-5-carboxamide

MS: m/z=341 (M+1)

The following compounds of Example 184 to Example 186 were synthesized by carrying out reaction according to the method described in Example 45.

EXAMPLE 184 trans-N-(4-hydroxycyclohexyl)-1H-indazole-5-carboxamide

MS: m/z=260 (M+1)

EXAMPLE 185

N-(4-methylcyclohexyl)-1H-indazole-5-carboxamide

MS: m/z=258 (M+1)

EXAMPLE 186

Methyl 4-[(1H-indazol-5-ylcarbonyl)amino]cyclohexanecarboxylate

MS: m/z=302 (M+1)

EXAMPLE 187

Synthesis of N-(4-hydroxymethylcyclohexyl)-1H-indazole-5-carboxamide

Lithium borohydride (10.0 mg, 0.459 mmol) was added to a solution of the methyl 4-[(1H-indazol-5-ylcarbonyl)amino]cyclohexanecarboxylate (30.0 mg, 0.0951 mmol) obtained in Example 186 in tetrahydrofuran (3.0 ml) at room temperature, and the resulting mixture was stirred for 2 hours with heating under reflux while maintaining the temperature. A 1N aqueous sodium hydroxide solution (0.8 ml) was added to the reaction solution, and the resulting mixture was stirred while being maintained at room temperature, and then was concentrated to dryness. The resulting crude product residue was stirred in methanol (3.0 ml) for another 1 hour with heating under reflux while maintaining the temperature. The resulting mixture was concentrated to dryness and purified by a silica gel column chromatography (eluent: chloroform/methanol=20/1) to obtain N-(4-hydroxymethylcyclohexyl)-1H-indazole-5-carboxamide (23.5 mg, 91%).

MS: m/z=274 (M+1)

EXAMPLE 188

Synthesis of tert-butyl-3-[(1H-indazol-5-ylcarbonyl)amino]cyclohexyl carbamate (a) Synthesis of tert-butyl 3-aminocyclohexanecarbamate A solution of di-tert-butyl dicarbonate (14.3 mg, 65.5 mmol) in chloroform (210 ml) was added dropwise to a solution of 1,3-diaminocyclohexane (15.0 g, 131 mmol) in chloroform (300 ml), and the resulting mixture was stirred overnight at room temperature. After completion of the reaction, the precipitate was removed. The solvent was distilled off from the filtrate under reduced pressure, and the residue was purified by a silica gel chromatography (eluent: chloroform/methanol) to obtain tert-butyl 3-aminocyclohexanecarbamate (13.0 g, yield 92%).

(b) Synthesis of tert-butyl-3-[(1H-indazol-5-ylcarbonyl)amino]cyclohexyl carbamate The title compound was synthesized by carrying out reaction according to the method described in Example 138, (e), except for using tert-butyl 3-aminocyclohexanecarbamate as a starting material.

$^1$H-NMR (DMSO-d$_6$) δ; 1.10 (4H, m), 1.72 (4H, m), 1.94 (1H, m), 3.79 (1H, m), 7.54 (1H, d), 7.83 (1H, d, J=7.1 Hz), 8.17 (1H, s), 8.25 (1H, d, J=7.9 Hz), 8.31 (1H, s), 13.23 (1H, s).

EXAMPLE 189

Synthesis of N-(3-aminocyclohexyl)-1H-indazole-5-carboxamide

The tert-butyl-3-[(1H-indazol-5-ylcarbonyl)amino]cyclohexyl carbamate (3.0 g, 8.3 mmol) obtained in Example 188 was suspended in dichloromethane (32 ml), followed by adding dropwise thereto trifluoroacetic acid (30 ml), and the resulting mixture was stirred overnight at room temperature. The solvent was distilled off under reduced pressure and the trifluoroacetic acid was removed as an azeotrope with toluene and ethanol as much as possible. The concentration residue was dissolved in water (10 ml), followed by adding thereto a saturated aqueous sodium hydrogencarbonate solution (50 ml), and the resulting mixture was stirred at room temperature for 2 hours. Thereafter, the precipitate formed was collected by filtration. The precipitate on a filter was washed with water and dried under reduced pressure to obtain N-(3-aminocyclohexyl)-1H-indazole-5-carboxamide (2.2 g, yield 99%).

$^1$H-NMR (DMSO-d$_6$) δ; 1.14 (4H, m), 1.76 (3H, m), 1.96 (1H, m), 2.72 (1H, m), 3.28 (1H, m), 3.80 (1H, m), 6.72 (1H, d, J=8.3 Hz), 7.54 (1H, d, J=8.8 Hz), 7.83 (1H, dd, J=1.5, 8.8 Hz), 8.25 (1H, d, J=7.9 Hz), 8.31 (1H, s).

The following compounds of Examples 190 to 193 were synthesized by carrying out reaction according to the method described in Example 140, except for using the N-[3-(aminomethyl)]cyclohexyl]-1H-indazole-5-carboxamide obtained in Example 189, as a starting material.

EXAMPLE 190

N-[3-(dimethylamino)]cyclohexyl]-1H-indazole-5-carboxamide

Melting point: 225–226° C.

EXAMPLE 191

N-[3-(isopropylamino)]cyclohexyl]-1H-indazole-5-carboxamide

Melting point: 222–223° C.

EXAMPLE 192

N-[3-(butylamino)]cyclohexyl]-1H-indazole-5-carboxamide

Melting point: 216–218° C.

EXAMPLE 193

N-[3-(cyclobutylamino)]cyclohexyl]-1H-indazole-5-carboxamide

Melting point: 247–249° C.

The following compound of Example 194 was synthesized by carrying out reaction according to the method described in Example 45.

EXAMPLE 194

Methyl 3-[(1H-indazol-5-ylcarbonyl)amino]cyclohexanecarboxylate

MS: m/z=302 (M+1)

The following compound of Example 195 was synthesized by carrying out reaction according to the method described in Example 187, except for using the methyl 3-[(1H-indazol-5-ylcarbonyl)amino]cyclohexanecarboxylate obtained in Example 194, as a starting material.

EXAMPLE 195

N-[3-(hydroxymethyl)cyclohexyl]-1H-indazole-5-carboxamide

MS: m/z=274 (M+1)

EXAMPLE 196

Synthesis of N-{3-[(dibenzylamino)methyl]cyclohexyl}-1H-indazole-5-carboxamide (a) Synthesis of 3-[(tert-butoxycarbonyl)amino]cyclohexanecarboxylic acid A solution of 3-aminocyclohexanecarboxylic acid (1.005 g, 7.02 mmol) in a mixture of a 2N-aqueous sodium hydroxide solution (14 ml, 28 mmol) and 1,4-dioxane (15 ml) was cooled on a water bath, and di-tert-butyl dicarbonate (3.25 ml, 14.1 mmol) was added thereto and stirred overnight. The resulting solution was diluted with water and washed with diethyl ether, and the aqueous layer was adjusted to pH 6 to 7 with 1N-hydrochloric acid and then to pH 2 to 3 with a 5%-aqueous potassium hydrogensulfate solution. The aqueous layer was extracted three times with ethyl acetate, and the extract solution was washed with a saturated aqueous sodium chloride solution and dried over anhydrous magnesium sulfate. The solvent was distilled off under reduced pressure to obtain 3-[(tert-butoxycarbonyl)amino]cyclohexanecarboxylic acid (1.587 g, 93%).

(b) Synthesis of tert-butyl 3-[(dibenzylamino)carbonyl]cyclohexanecarbamate

A solution of dibenzylamine (0.448 g, 2.27 mmol) in dichloromethane (3 ml), 1-hydroxybenztriazole (0.337 g, 2.49 mmol) and 1-ethyl-3-(3'-dimethylaminopropyl)carbodiimide monohydrochloride (0.477 g, 2.49 mmol) were added to a solution of 3-[(tert-butoxycarbonyl)amino]cyclohexanecarboxylic acid (0.502 g, 2.06 mmol) in dichloromethane (7 ml) and stirred overnight. The resulting solution was diluted with ethyl acetate and washed with a 5%-aqueous potassium hydrogensulfate solution (twice), a saturated aqueous sodium hydrogencarbonate solution (twice) and a saturated aqueous sodium chloride solution, and dried over anhydrous magnesium sulfate. The solvent was distilled off under reduced pressure and the residue was purified by a silica gel chromatography (eluent: chloroform/ethyl acetate=20/1) to obtain tert-butyl 3-[(dibenzylamino)carbonyl]cyclohexanecarbamate (0.796 g, 91%).

(c) Synthesis of 3-amino-N,N-dibenzylcyclohexane-carboxamide monohydrochloride A 4N-hydrochloric acid/1,4-dioxane solution (4.5 ml) was added to a solution of tert-butyl 3-[(dibenzylamino)carbonyl]cyclohexanecarbamate (0.749 g, 1.773 mmol) in tetrahydrofuran (4.5 ml) and stirred overnight. The solvent was distilled off under reduced pressure, followed by replacement with toluene (twice), whereby 3-amino-N,N-dibenzylcyclohexanecarboxamide monohydrochloride (0.848 g, >99%) was obtained.

(d) Synthesis of 3-[(dibenzylamino)methyl]cyclohexanamine

A solution of 3-amino-N,N-dibenzylcyclohexane-carboxamide monohydrochloride (0.848 g) in tetrahydrofuran (5 ml) was added dropwise to a suspension of lithium aluminum hydride (0.337 g, 8.89 mmol) in tetrahydrofuran (5 ml), and the resulting mixture was stirred with heating under reflux for 3 hours. The resulting solution was cooled on an ice bath, followed by adding dropwise thereto water (0.33 ml), a 2N-aqueous sodium hydroxide solution (0.66 ml) and water (1.0 ml) in that order. Thereafter, the insoluble material was removed by filtration using Celite. The solvent was distilled off from the filtrate under reduced pressure, followed by replacement with ethanol (once) and toluene (twice). Then, the residue was dried under reduced pressure to obtain 3-[(dibenzylamino)methyl]cyclohexanamine (0.550 g, 99%).

(e) Synthesis of N-{3-[(dibenzylamino)methyl]cyclohexyl}-1H-indazole-5-carboxamide The 1H-indazole-5-carboxylic acid (0.285 g, 1.75 mmol) obtained in Reference Example 1, 1-hydroxybenztriazole (0.285 g, 2.11 mmol) and 1-ethyl-3-(3'-dimethylaminopropyl)carbodiimide monohydrochloride (0.409 g, 2.13 mmol) were added to a solution of 3-[(dibenzylamino)methyl]cyclohexanamine (0.542 g, 1.76 mmol) in N,N-dimethylformamide (5 ml) and stirred overnight. A 1N-aqueous sodium hydroxide solution was added thereto, followed by extraction with ethyl acetate (three times), and the extract solution was dried over anhydrous magnesium sulfate. The solvent was distilled off under reduced pressure and the residue was purified by a silica gel chromatography (eluent: chloroform/methanol=30/1) to obtain N-{3-[(dibenzylamino)methyl]cyclohexyl}-1H-indazole-5-carboxamide (0.605 g, 76%).

$^1$H-NMR (DMSO-$d_6$) δ; 0.52–0.63 (1H, m), 0.75–0.86 (1H, m), 1.13–1.37 (2H, m), 1.69–1.88 (4H, m), 1.93–2.03 (1H, m), 2.19 (2H, d, J=7.3 Hz), 3.49 (4H, s), 3.75–3.87 (1H, m), 7.20–7.26 (2H, m), 7.30–7.37 (8H, m), 7.55 (1H, d, J=8.7 Hz), 7.84 (1H, dd, J=1.6, 8.7), 8.17 (1H, d, J=7.9 Hz), 8.19 (1H, br), 8.31 (1H, s), 13.25 (1H, br).

The following compound of Example 197 was synthesized by carrying out reaction according to the method described in Example 139, except for using the N-{3-[(dibenzylamino)methyl]cyclohexyl}-1H-indazole-5-carboxamide obtained in Example 196, as a starting material.

EXAMPLE 197

N-[3-(aminomethyl)]cyclohexyl]-1H-indazole-5-carboxamide

Melting point: 230–231° C.

The following compounds of Example 198 to Example 201 were synthesized by carrying out reaction according to the method described in Example 45.

EXAMPLE 198 cis-N-(2-hydroxycyclohexyl)-1H-indazole-5-carboxamide

MS: m/z=260 (M+1)

EXAMPLE 199

N-(2-hydroxycyclohexyl)-1H-indazole-5-carboxamide

MS: m/z=260 (M+1)

EXAMPLE 200

N-(2-methylcyclohexyl)-1H-indazole-5-carboxamide

MS: m/z=258 (M+1)

EXAMPLE 201 cis-ethyl 2-{(1H-indazol-5-ylcarbonyl)amino}cyclohexanecarboxylate

MS: m/z=316 (M+1)

The following compound of Example 202 was synthesized by carrying out reaction according to the method described in Example 187, except for using the cis-ethyl 2-[(1H-indazol-5-ylcarbonyl)amino]cyclohexanecarboxylate obtained in Example 201, as a starting material.

EXAMPLE 202 cis-N-[2-(hydroxymethyl)cyclohexyl]-1H-indazole-5-carboxamide

MS: m/z=274 (M+1)

The following compound of Example 203 was synthesized by carrying out reaction according to the method described in Example 45.

EXAMPLE 203 trans-ethyl 2-[(1H-indazol-5-ylcarbonyl)amino]cyclohexanecarboxylate

MS: m/z=316 (M+1)

The following compound of Example 204 was synthesized by carrying out reaction according to the method described in Example 187, except for using the trans-ethyl 2-{(1H-indazol-5-ylcarbonyl)amino]cyclohexanecarboxylate obtained in Example 203, as a starting material.

EXAMPLE 204 trans-N-[2-(hydroxymethyl)cyclohexyl]-1H-indazole-5-carboxamide

MS: m/z=274 (M+1)

The following compound of Example 205 was synthesized by carrying out reaction according to the method described in Example 45.

EXAMPLE 205

Methyl 1-{(1H-indazol-5-ylcarbonyl)amino}cyclohexanecarboxylate

MS: m/z=302 (M+1)

The following compound of Example 206 was synthesized by carrying out reaction according to the method described in Example 187, except for using the methyl 1-[(1H-indazol-5-ylcarbonyl)amino]cyclohexanecarboxylate obtained in Example 205, as a starting material.

EXAMPLE 206

N-[1-(hydroxymethyl)cyclohexyl]-1H-indazole-5-carboxamide

MS: m/z=274 (M+1)

EXAMPLE 207

Synthesis of N-(1-benzyl-5-oxopyrrolidin-3-yl)-1H-indazole-5-carboxamide (a) Synthesis of 1-benzyl-5-oxo-3-pyrrolidinecarboxylic acid Methyl 1-benzyl-5-oxo-3-pyrrolidinecarboxylate (2.00 g, 8.57 mmol) was dissolved in a mixed solvent of methanol (10 ml) and tetrahydrofuran (10 ml), followed by adding thereto a 2N aqueous lithium hydroxide solution (8.6 ml, 17.2 mmol), and the resulting mixture was heated under reflux for 20 minutes. After completion of the reaction, the reaction solution was ice-cooled, made into an acidic solution with an aqueous potassium hydrogensulfate solution, and then extracted with ethyl acetate. The ethyl acetate layer was concentrated, washed by repulping (ethyl acetate/hexane), and then dried to obtain 1-benzyl-5-oxo-3-pyrrolidinecarboxylic acid (1.83 g, 97%).

$^1$H-NMR (DMSO-$d_6$) δ; 2.56 (2H, m), 3.80 (1H, m), 3.15 (2H, m), 3.25 (2H, m), 4.36 (2H, q, J=8.6 Hz), 7.27 (5H, m), 12.61 (1H, s)

(b) Synthesis of tert-butyl 1-benzyl-5-oxo-3-pyrrolidinylcarbamate

In tert-butyl alcohol (6 ml) was dissolved 1-benzyl-5-oxo-3-pyrrolidinecarboxylic acid (1.00 g, 4.56 mmol), and triethylamine (0.76 ml, 5.5 mmol) was added thereto. Then, a solution of diphenylphosphoryl azide (1.38 g, 5.02 mmol) in tert-butyl alcohol (4 ml) was added thereto, and the resulting mixture was refluxed for 2 hours. After completion of the reaction, the reaction solution was concentrated and the tert-butyl alcohol was removed as an azeotrope with toluene as much as possible. The residue was purified by a silica gel chromatography (eluent: ethyl acetate/hexane) to obtain tert-butyl 1-benzyl-5-oxo-3-pyrrolidinylcarbamate (480 mg, 51%).

$^1$H-NMR (DMSO-$d_6$) δ; 1.34 (9H, s), 2.23 (1H, dd, J=5.7, 16.8 Hz), 2.61 (1H, dd, J=8.6, 16.8 Hz), 3.01 (1H, dd, J=5.7, 9.9 Hz), 3.43 (1H, dd, J=8.6, 9.9 Hz), 4.03 (1H, m), 4.36 (2H, s), 7.30 (6H, m).

(c) Synthesis of 4-amino-1-benzyl-2-pyrrolidinone hydrochloride

In tetrahydrofuran (6 ml) was dissolved tert-butyl 1-benzyl-5-oxo-3-pyrrolidinylcarbamate (480 mg, 1.65 mmol), followed by adding thereto 4N-hydrogen chloride/dioxane (6.0 ml, 24 mmol), and the resulting mixture was stirred overnight at room temperature. After completion of the reaction, diethyl ether (35 ml) was added to the reaction solution, and the resulting mixture was stirred at room temperature for 30 minutes and the precipitate was collected by filtration. The precipitate was washed with diethyl ether and dried to obtain 4-amino-1-benzyl-2-pyrrolidinone hydrochloride (380 mg, 99%).

$^1$H-NMR (DMSO-$d_6$) δ; 2.23 (1H, dd, J=4.0, 17.2 Hz), 2.76 (1H, dd, J=8.6, 17.2 Hz), 3.22 (1H, dd, J=4.0, 10.8 Hz), 3.53 (1H, dd, J=7.7, 10.8 Hz), 3.89 (1H, bs), 4.30 (1H, d, J=15.0 Hz), 4.45 (1H, d, J=15.0 Hz), 7.30 (5H, m), 8.32 (2H, bs).

(d) Synthesis of N-(1-benzyl-5-oxo-3-pyrrolidinyl)-1H-indazole-5-carboxamide

N-(1-benzyl-5-oxo-3-pyrrolidinyl)-1H-indazole-5-carboxamide was obtained by carrying out reaction according to the method described in Example 45, except for using 4-amino-1-benzyl-2-pyrrolidinone hydrochloride.

$^1$H-NMR (DMSO-$d_6$) δ; 2.74 (1H, dd, J=8.6, 16.8 Hz), 3.17 (1H, dd, J=5.7, 10.2 Hz), 3.53 (1H, dd, J=7.3, 10.5 Hz), 3.59 (1H, bs), 4.36 (1H, d, J=15.0 Hz), 4.53 (1H, d, J=15.0 Hz), 4.55 (1H, m), 7.28 (5H, m), 7.55 (1H, d, J=8.7 Hz), 7.82 (1H, dd, J=1.5, 8.7 Hz), 8.20 (1H, s), 8.32 (1H, s), 8.74 (1H, d, J=6.6 Hz), 13.26 (1H, s).

The following compounds of Example 208 to Example 233 were synthesized by carrying out reaction according to the method described in Example 45.

EXAMPLE 208

N-(2-oxoazepan-3-yl)-1H-indazole-5-carboxamide

MS: m/z=273 (M+1)

EXAMPLE 209

N-cyclopropyl-1H-indazole-5-carboxamide

MS: m/z=202 (M+1)

EXAMPLE 210

N-cyclobutyl-1H-indazole-5-carboxamide

MS: m/z=216 (M+1)

EXAMPLE 211

N-cyclopentyl-1H-indazole-5-carboxamide

MS: m/z=230 (M+1)

EXAMPLE 212

N-cyclohexyl-1H-indazole-5-carboxamide $^1$H-NMR (DMSO-$d_6$) δ; 1.14–1.34 (5H, m), 1.59–1.81 (5H, m), 3.77 (1H, m), 7.53 (1H, d, J=8.8 Hz), 7.83 (1H, dd, J=1.5, 8.8 Hz), 8.16–8.18 (2H, m), 8.31 (1H, s), 13.23 (1H, brs).

EXAMPLE 213

N-cycloheptyl-1H-indazole-5-carboxamide

MS: m/z=258 (M+1)

EXAMPLE 214

N-cyclooctyl-1H-indazole-5-carboxamide

MS: m/z=272 (M+1)

EXAMPLE 215

N-(1-adamantyl)-1H-indazole-5-carboxamide

MS: m/z=296 (M+1)

EXAMPLE 216

N-phenyl-1H-indazole-5-carboxamide $^1$H-NMR (DMSO-$d_6$) δ; 7.08 (1H, t, J=7.3 Hz), 7.35 (2H, t, J=7.5 Hz), 7.63 (1H, d, J=8.8 Hz), 7.79 (2H, d, J=7.5 Hz), 7.94 (1H, d, J=8.8 Hz), 8.26 (1H, s), 8.47 (1H, s), 10.26 (1H, s), 13.34 (1H, brs).

EXAMPLE 217

N-(2-methylphenyl)-1H-indazole-5-carboxamide

MS: m/z=252 (M+1)

EXAMPLE 218

N-(3-methylphenyl)-1H-indazole-5-carboxamide

MS: m/z=252 (M+1)

EXAMPLE 219

N-(4-methylphenyl)-1H-indazole-5-carboxamide

MS: m/z=252 (M+1)

EXAMPLE 220

N-(1H-imidazol-2-yl)-1H-indazole-5-carboxamide

MS: m/z=228 (M+1)

EXAMPLE 221

N-(4,5-dihydro-1,3-thiazol-2-yl)-1H-indazole-5-carboxamide

MS: m/z=247 (M+1)

EXAMPLE 222

N-benzyl-1H-indazole-5-carboxamide

MS: m/z=252 (M+1)

EXAMPLE 223

N-[2-(trifluoromethyl)benzyl]-1H-indazole-5-carboxamide

MS: m/z=320 (M+1)

EXAMPLE 224

N-[3-(trifluoromethyl)benzyl]-1H-indazole-5-carboxamide

MS: m/z=320 (M+1)

EXAMPLE 225

N-[4-(trifluoromethyl)benzyl]-1H-indazole-5-carboxamide

MS: m/z=320 (M+1)

EXAMPLE 226

N-[2-(trifluoromethoxy)benzyl]-1H-indazole-5-carboxamide

MS: m/z=336 (M+1)

EXAMPLE 227

N-[3-(trifluoromethoxy)benzyl]-1H-indazole-5-carboxamide

MS: m/z=336 (M+1)

EXAMPLE 228

N-[4-(trifluoromethoxy)benzyl]-1H-indazole-5-carboxamide

MS: m/z=336 (M+1)

EXAMPLE 229

N-[4-(dimethylamino)benzyl]-1H-indazole-5-carboxamide

MS: m/z=295 (M+1)

EXAMPLE 230

N-[4-(aminosulfonyl)benzyl]-1H-indazole-5-carboxamide

MS: m/z=331 (M+1)

EXAMPLE 231

N-[4-(methylsulfonyl)benzyl]-1H-indazole-5-carboxamide

MS: m/z 330 (M+1)

EXAMPLE 232

N-(4-nitrobenzyl)-1H-indazole-5-carboxamide

MS: m/z=297 (M+1)

EXAMPLE 233

Methyl 4-{[(1H-indazol-5-ylcarbonyl)amino]methyl}benzoate

MS: m/z=310 (M+1)

The following compound of Example 234 was synthesized by carrying out reaction according to the method described in Example 187, except for using the methyl 4-{[(1H-indazol-5-ylcarbonyl)amino]methyl}benzoate obtained in Example 233, as a starting material.

EXAMPLE 234

N-[4-(hydroxymethyl)benzyl]-1H-indazole-5-carboxamide

MS: m/z=282 (M+1)

The following compounds of Example 235 to Example 249 were synthesized by carrying out reaction according to the method described in Example 45.

EXAMPLE 235

N-(4-tert-butylbenzyl)-1H-indazole-5-carboxamide

MS: m/z=308 (M+1)

EXAMPLE 236

N-(2,3-dimethoxybenzyl)-1H-indazole-5-carboxamide

MS: m/z=312 (M+1)

EXAMPLE 237

N-(2,4-dimethoxybenzyl)-1H-indazole-5-carboxamide

MS: m/z=312 (M+1)

EXAMPLE 238

N-(2,5-dimethoxybenzyl)-1H-indazole-5-carboxamide

MS: m/z=312 (M+1)

EXAMPLE 239

N-(2,6-dimethoxybenzyl)-1H-indazole-5-carboxamide

MS: m/z=312 (M+1)

EXAMPLE 240

N-(3,4-dimethoxybenzyl)-1H-indazole-5-carboxamide

MS: m/z=312 (M+1)

EXAMPLE 241

N-(3,5-dimethoxybenzyl)-1H-indazole-5-carboxamide

MS: m/z=312 (M+1)

EXAMPLE 242

N-(2,3-difluorobenzyl)-1H-indazole-5-carboxamide

MS: m/z=288 (M+1)

EXAMPLE 243

N-(2,4-difluorobenzyl)-1H-indazole-5-carboxamide

MS: m/z=288 (M+1)

EXAMPLE 244

N-(2,5-difluorobenzyl)-1H-indazole-5-carboxamide

MS: m/z=288 (M+1)

EXAMPLE 245

N-(2,6-difluorobenzyl)-1H-indazole-5-carboxamide

MS: m/z=288 (M+1)

EXAMPLE 246

N-(3,4-difluorobenzyl)-1H-indazole-5-carboxamide

MS: m/z=288 (M+1)

EXAMPLE 247

N-(3,5-difluorobenzyl)-1H-indazole-5-carboxamide

MS: m/z=288 (M+1)

EXAMPLE 248

N-(2,3-dihydro-1-benzofuran-5-ylmethyl)-1H-indazole-5-carboxamide

MS: m/z=294 (M+1)

EXAMPLE 249

N-(2-phenylethyl)-1H-indazole-5-carboxamide

MS: m/z=266 (M+1)

EXAMPLE 250

Synthesis of N-(piperidin-4-ylmethyl)-1H-indazole-5-carboxamide hydrochloride (a) Synthesis of tert-butyl 4-{[(1H-indazol-5-ylcarbonyl)amino]methyl}piperidine-1-carboxylate tert-Butyl 4-{[(1H-indazol-5-ylcarbonyl)amino]methyl}piperidine-1-carboxylate was obtained by carrying out reaction according to the method described in Example 45.

MS: m/z=359 (M+1)

(b) Synthesis of N-(piperidin-4-ylmethyl)-1H-indazole-5-carboxamide hydrochloride A 4N-hydrogen chloride-1,4-dioxane solution (0.200 mg, 0.800 mmol) was added to a solution of tert-butyl 4-{[(1H-indazol-5-ylcarbonyl)amino]methyl}piperidine-1-carboxylate (36.0 mg, 0.100 mmol) in a mixture of 1,4-dioxane (0.4 ml) and acetic acid (0.7 ml) at room temperature, and the resulting mixture was stirred for 3 hours while being maintained at room temperature. Toluene was added to the reaction solution and the resulting mixture was stirred while being maintained at room temperature. Then, the resulting slurry was collected by filtration and dried under reduced pressure, and the resulting crude product residue was stirred in methanol (3.0 ml) for 1 hour with heating under reflux while maintaining the temperature. The resulting mixture was concentrated to dryness to obtain N-(piperidin-4-ylmethyl)-1H-indazole-5-carboxamide hydrochloride (29.8 mg, 100%).

MS: m/z=259 (M+1)

The following compounds of Example 251 to Example 270 were synthesized by carrying out reaction according to the method described in Example 45.

EXAMPLE 251

N-(tetrahydro-2H-pyran-4-ylmethyl)-1H-indazole-5-carboxamide

MS: m/z=260 (M+1)

EXAMPLE 252

1H-indazole-5-carboxamide

MS: m/z=162 (M+1)

EXAMPLE 253

N-methyl-1H-indazole-5-carboxamide

MS: m/z=176 (M+1)

EXAMPLE 254

N-propyl-1H-indazole-5-carboxamide

MS: m/z=204 (M+1)

EXAMPLE 255

N-(2,2,2-trifluoroethyl)-1H-indazole-5-carboxamide

MS: m/z=244 (M+1)

EXAMPLE 256

N-(3,3,3-trifluoropropyl)-1H-indazole-5-carboxamide

MS: m/z=258 (M+1)

EXAMPLE 257

N-isopropyl-1H-indazole-5-carboxamide

MS: m/z=204 (M+1)

EXAMPLE 258

N-(tert-butyl)-1H-indazole-5-carboxamide

MS: m/z=218 (M+1)

EXAMPLE 259

N-(2-hydroxy-1,1-dimethylethyl)-1H-indazole-5-carboxamide

MS: m/z=234 (M+1)

EXAMPLE 260

N-isopentyl-1H-indazole-5-carboxamide $^1$H-NMR (CDCl$_3$) δ; 0.98 (6H, d, J=6.4 Hz), 1.51–1.58 (2H, m), 1.65–1.77 (1H, m), 3.49–3.56 (2H, m), 6.11 (1H, brs), 7.53 (1H, d, J=8.8 Hz), 7.84 (1H, d, J=8.8 Hz), 8.16 (1H, s), 8.21 (1H, s), 10.33 (1H, brs).

EXAMPLE 261

N-(2-methoxyethyl)-1H-indazole-5-carboxamide

MS: m/z=220 (M+1)

EXAMPLE 262

N-(3-methoxypropyl)-1H-indazole-5-carboxamide

MS: m/z=234 (M+1)

EXAMPLE 263

N-(2-hydroxyethyl)-1H-indazole-5-carboxamide

MS: m/z=206 (M+1)

EXAMPLE 264

N-[2-(dimethylamino)ethyl]-1H-indazole-5-carboxamide

MS: m/z=233 (M+1)

EXAMPLE 265

N-[3-(dimethylamino)propyl]-1H-indazole-5-carboxamide

MS: m/z=247 (M+1)

EXAMPLE 266

N-[2-(dimethylamino)-1-methylethyl]-1H-indazole-5-carboxamide

MS: m/z=247 (M+1)

EXAMPLE 267

N-(2-pyrrolidin-1-ylethyl)-1H-indazole-5-carboxamide

MS: m/z=259 (M+1)

EXAMPLE 268

N-(2-piperidin-1-ylethyl)-1H-indazole-5-carboxamide

MS: m/z=273 (M+1)

EXAMPLE 269

N-(2-morpholin-4-ylethyl)-1H-indazole-5-carboxamide

MS: m/z=275 (M+1)

EXAMPLE 270

N-[2-(4-benzylpiperazin-1-yl)ethyl]-1H-indazole-5-carboxamide

MS: m/z=364 (M+1)

The following compound of Example 271 was synthesized by carrying out reaction according to the method described in Example 148, except for using the N-[2-(4-benzylpiperazin-1-yl)ethyl]-1H-indazole-5-carboxamide obtained in Example 270, as a starting material.

EXAMPLE 271

N-(2-piperazin-1-ylethyl)-1H-indazole-5-carboxamide

MS: m/z=274 (M+1)

The following compound of Example 272 was synthesized by carrying out reaction according to the method described in Example 45.

EXAMPLE 272

N-[2-(1-benzylpiperidin-4-yl)ethyl]-1H-indazole-5-carboxamide

MS: m/z=363 (M+1)

The following compound of Example 273 was synthesized by carrying out reaction according to the method described in Example 148, except for using the N-[2-(1-benzylpiperidin-4-yl)ethyl]-1H-indazole-5-carboxamide obtained in Example 272, as a starting material.

EXAMPLE 273

N-(2-piperidin-4-ylethyl)-1H-indazole-5-carboxamide

MS: m/z=273 (M+1)

The following compounds of Example 274 and Example 275 were synthesized by carrying out reaction according to the method described in Example 45.

EXAMPLE 274

N,N-dimethyl-1H-indazole-5-carboxamide

MS: m/z=190 (M+1)

EXAMPLE 275

N,N-dipropyl-1H-indazole-5-carboxamide

MS: m/z=246 (M+1)

EXAMPLE 276

Synthesis of N-(1-phenylcyclohexyl)-1H-indazole-5-carboxamide

Oxalyl dichloride (38.7 μl, 0.444 mmol) and N,N-dimethylformamide (about 1 μl) were added to a solution of the 1H-indazole-5-carboxylic acid (40.0 mg, 0.247 mmol) obtained in Reference Example 1 in dichloromethane (2.5 ml), and the resulting mixture was stirred at room temperature for 0.5 hour and then was stirred with heating under reflux for 2 hours while maintaining the temperature. The reaction solution was concentrated to dryness and a solution of the resulting residue in tetrahydrofuran (1.5 ml) was added dropwise to a solution of 1-phenylcyclohexylamine (130 mg, 0.742 mmol) in tetrahydrofuran (2.0 ml). The resulting mixture was stirred for 18 hours while being maintained at room temperature. A 5% aqueous sodium bicarbonate solution was added to the reaction solution and stirred, followed by extraction with ethyl acetate. The organic phase was washed with a 5% aqueous sodium chloride solution and then dried over anhydrous sodium sulfate. The organic phase dried was concentrated under reduced pressure, and the resulting crude product was purified by a silica gel column chromatography (eluent: chloroform/methanol=50/1 to 30/1) to obtain N-(1-phenylcyclohexyl)-1H-indazole-5-carboxamide (62 mg, 78%).

MS: m/z=320 (M+1)

The following compounds of Example 277 to Example 316 were synthesized by carrying out reaction according to the method described in Example 276.

EXAMPLE 277

1,3-bis[(1H-indazol-5-ylcarbonyl)amino]cyclohexane

MS: m/z=403 (M+1)

EXAMPLE 278 cis-N-(2-aminocyclohexyl)-1H-indazole-5-carboxamide

MS: m/z=259 (M+1)

EXAMPLE 279 trans-N-(2-aminocyclohexyl)-1H-indazole-5-carboxamide

MS: m/z=259 (M+1)

EXAMPLE 280

N-(1-ethynylcyclohexyl)-1H-indazole-5-carboxamide

MS: m/z=268 (M+1)

EXAMPLE 281

N-(2-methoxyphenyl)-1H-indazole-5-carboxamide

MS: m/z=268 (M+1)

EXAMPLE 282

N-(3-methoxyphenyl)-1H-indazole-5-carboxamide

MS: m/z=268 (M+1)

EXAMPLE 283

N-(4-methoxyphenyl)-1H-indazole-5-carboxamide

MS: m/z=268 (M+1)

EXAMPLE 284

N-[2-(aminocarbonyl)phenyl]-1H-indazole-5-carboxamide

MS: m/z=281 (M+1)

EXAMPLE 285

N-[3-(aminocarbonyl)phenyl]-1H-indazole-5-carboxamide

MS: m/z=281 (M+1)

EXAMPLE 286

N-(2-fluorophenyl)-1H-indazole-5-carboxamide

MS: m/z=256 (M+1)

EXAMPLE 287

N-(3-fluorophenyl)-1H-indazole-5-carboxamide

MS: m/z=256 (M+1)

EXAMPLE 288

N-(4-fluorophenyl)-1H-indazole-5-carboxamide

MS: m/z=256 (M+1)

EXAMPLE 289

N-pyridin-2-yl-1H-indazole-5-carboxamide

MS: m/z=239 (M+1)

EXAMPLE 290

N-pyridin-3-yl-1H-indazole-5-carboxamide

MS: m/z=239 (M+1)

EXAMPLE 291

N-pyridin-4-yl-1H-indazole-5-carboxamide

MS: m/z=239 (M+1)

EXAMPLE 292

N-pyrimidin-2-yl-1H-indazole-5-carboxamide

MS: m/z=240 (M+1)

EXAMPLE 293

N-(1H-1,2,4-triazol-3-yl)-1H-indazole-5-carboxamide

MS: m/z=229 (M+1)

EXAMPLE 294

N-(1H-tetrazol-5-yl)-1H-indazole-5-carboxamide

MS: m/z=230 (M+1)

EXAMPLE 295

N-(1,3-thiazol-2-yl)-1H-indazole-5-carboxamide

MS: m/z=245 (M+1)

EXAMPLE 296

N-(1,3,4-thiadiazol-2-yl)-1H-indazole-5-carboxamide

MS: m/z=246 (M+1)

EXAMPLE 297

N-(1H-benzimidazol-2-yl)-1H-indazole-5-carboxamide

MS: m/z=278 (M+1)

EXAMPLE 298

N-(1H-indazol-5-yl)-1H-indazole-5-carboxamide

MS: m/z=278 (M+1)

EXAMPLE 299

N-(2-methylbenzyl)-1H-indazole-5-carboxamide

MS: m/z=266 (M+1)

EXAMPLE 300

N-(3-methylbenzyl)-1H-indazole-5-carboxamide

MS: m/z=266 (M+1)

EXAMPLE 301

N-(4-methylbenzyl)-1H-indazole-5-carboxamide

MS: m/z=266 (M+1)

EXAMPLE 302

N-(2-methoxybenzyl)-1H-indazole-5-carboxamide

MS: m/z=282 (M+1)

EXAMPLE 303

N-(3-methoxybenzyl)-1H-indazole-5-carboxamide

MS: m/z=282 (M+1)

EXAMPLE 304

N-(4-methoxybenzyl)-1H-indazole-5-carboxamide

MS: m/z=282 (M+1)

EXAMPLE 305

N-(2-fluorobenzyl)-1H-indazole-5-carboxamide

MS: m/z=270 (M+1)

EXAMPLE 306

N-(3-fluorobenzyl)-1H-indazole-5-carboxamide

MS: m/z=270 (M+1)

EXAMPLE 307

N-(4-fluorobenzyl)-1H-indazole-5-carboxamide

MS: m/z=270 (M+1)

EXAMPLE 308

N-[4-(aminomethyl)benzyl]-1H-indazole-5-carboxamide

MS: m/z=281 (M+1)

EXAMPLE 309

N-[3-(aminomethyl)benzyl]-1H-indazole-5-carboxamide

MS: m/z=281 (M+1)

EXAMPLE 310

1,4-bis[(1H-indazol-5-ylcarobonyl)aminomethyl]benzene

MS: m/z=425 (M+1)

EXAMPLE 311

1,3-bis[(1H-indazol-5-ylcarobonyl)aminomethyl]benzene

MS: m/z=425 (M+1)

EXAMPLE 312

N-(pyridin-2-ylmethyl)-1H-indazole-5-carboxamide

MS: m/z=253 (M+1)

EXAMPLE 313

N-(pyridin-3-ylmethyl)-1H-indazole-5-carboxamide

MS: m/z=253 (M+1)

EXAMPLE 314

N-(pyridin-4-ylmethyl)-1H-indazole-5-carboxamide

MS: m/z=253 (M+1)

EXAMPLE 315

N-(2-furylmethyl)-1H-indazole-5-carboxamide

MS: m/z=242 (M+1)

EXAMPLE 316

N-(thien-2-ylmethyl)-1H-indazole-5-carboxamide

MS: m/z=258 (M+1)

EXAMPLE 317

Synthesis of N-(1H-indazol-5-yl)piperidine-4-sulfonamide (a) Synthesis of benzyl 4-bromo-1-piperidinecarboxylate To a solution of 4-bromopiperidine hydrobromide (3.0 g, 12.2 mmol) in tetrahydrofuran (30 ml) were added 1-{[(benzyloxy)carbonyl]oxy}-2,5-pyrrolidinedione (3.20 g, 12.9 mmol), N-methylmorpholine (1.62 ml, 14.7 mmol) and 4-N,N-dimethylaminopyridine (30 mg) at room temperature, and stirred at room temperature for 16 hours. The reaction solution was poured into water and extracted with ethyl acetate. The organic layer was washed with a 1N-aqueous hydrochloric acid solution, dried over anhydrous magnesium sulfate and distilled under reduced pressure to remove the solvent, and the resulting residue was purified by a silica gel column chromatography (eluent: hexane/ethyl acetate=1/1) to obtain benzyl 4-bromo-1-piperidinecarboxylate (3.58 g, 98%).

(b) Synthesis of benzyl 4-(acetylthio)-1-piperidinecarboxylate

Potassium thiosulfate (1.47 g, 12.9 mmol) was added to a solution of benzyl 4-bromo-1-piperidinecarboxylate (3.5 g, 11.7 mmol) in N,N-dimethylformamide (25 ml) at room temperature and stirred at room temperature for 16 hours and then at 60° C. for 3 hours. The reaction solution was poured into water and extracted with ethyl acetate. The organic layer was washed with a saturated aqueous sodium chloride solution, dried over anhydrous magnesium sulfate and distilled under reduced pressure to remove the solvent, and the resulting residue was purified by a silica gel column chromatography (eluent: hexane/ethyl acetate=8/1) to obtain benzyl 4-(acetylthio)-1-piperidinecarboxylate (2.61 g, 76%).

(c) Synthesis of Benzyl 4-(chlorosulfonyl)-1-piperidinecarboxylate

A solution of benzyl 4-(acetylthio)-1-piperidinecarboxylate (1.45 g, 4.94 mmol) in a mixture of methylene chloride (10 ml) and water (40 ml) was stirred at 0° C. for 4 hours while bubbling chlorine gas therethrough. After the organic layer was separated, the aqueous layer was extracted with methylene chloride. The resulting organic layer was dried over anhydrous magnesium sulfate and distilled under reduced pressure to remove the solvent, whereby benzyl 4-(chlorosulfonyl)-1-piperidinecarboxylate (1.58 g, 100%) was obtained.

(d) Synthesis of 5-nitro-1-tetrahydro-2H-pyran-2-yl-1H-indazole

To a solution of 5-nitroindazole (20.0 g, 123 mmol) in methylene chloride (400 ml) were added 3,4-dihydro-2H-pyran (16.8 ml, 184 mmol) and p-toluenesulfonic acid (4.22 g, 24.5 mmol) at room temperature, and stirred for 2 hours. After the reaction solution was concentrated, a saturated aqueous sodium hydrogencarbonate solution was added thereto, followed by extraction with chloroform. The organic layer was dried over anhydrous magnesium sulfate and distilled under reduced pressure to remove the solvent, and resulting residue was purified by a silica gel column chromatography (eluent: hexane/ethyl acetate=5/1) to obtain 5-nitro-1-tetrahydro-2H-pyran-2-yl-1H-indazole (26.6 g, 88%).

(e) Synthesis of 1-tetrahydro-2H-pyran-2-yl-1H-indazol-5-amine

To a solution of 5-nitro-1-tetrahydro-2H-pyran-2-yl-1H-indazole (3.69 g, 14.9 mmol) in a mixture of ethyl acetate (50 ml) and ethanol (50 ml) was added 10% Pd—C (300 mg), followed by catalytic reduction at ordinary temperature and atmospheric pressure. After completion or the reaction, the catalyst was filtered off, and the filtrate was concentrated under reduced pressure. The resulting residue was suspended in ethyl acetate, and the solid precipitated was collected by filtration and dried under reduced pressure to obtain 1-tetrahydro-2H-pyran-2-yl-1H-indazol-5-amine (1.79 g, 55%).

(f) Synthesis of benzyl 4-{[(1-tetrahydro-2H-pyran-2-yl-1H-indazol-5-yl)amino]sulfonyl}-1-piperidinecarboxylate Triethylamine (0.789 ml, 5.69 mmol) was added to a solution of 1-tetrahydro-2H-pyran-2-yl-1H-indazol-5-amine (1.04 g, 4.79 mmol) and benzyl 4-(chlorosulfonyl)-1-piperidinecarboxylate (1.5 g, 4.74 mmol) in methylene chloride (50 ml) at 0° C. and stirred at 0° C. for 30 minutes and then at room temperature for 15 hours. The reaction solution was poured into water and extracted with chloroform. The organic layer was dried over anhydrous magnesium sulfate and distilled under reduced pressure to remove the solvent, and the resulting residue was purified by a silica gel column chromatography (eluent: chloroform/ethyl acetate=3/1) to obtain benzyl 4-{[(1-tetrahydro-2H-pyran-2-yl-1H-indazol-5-yl)amino]sulfonyl}-1-piperidinecarboxylate (1.32 g, 56%).

(g) Synthesis of Benzyl 4-[(1H-indazol-5-ylamino)sulfonyl]-piperidine-1-carboxylate Trifluoroacetic acid (5.0 ml) was added to a solution of benzyl 4-{[(1-tetrahydro-2H-pyran-2-yl-1H-indazol-5-yl)amino]sulfonyl}-1-piperidinecarboxylate (500 mg, 1.00 mmol) in methylene chloride (50 ml) at room temperature and stirred for 2 hours. After the reaction solution was concentrated, a saturated aqueous sodium hydrogencarbonate solution was added thereto, followed by extraction with ethyl acetate. The organic layer was dried over anhydrous magnesium sulfate and distilled under reduced pressure to remove the solvent, and resulting residue was purified by a silica gel column chromatography (eluent: chloroform/methanol=50/1) to obtain benzyl 4-[(1H-indazol-5-ylamino)sulfonyl]piperidine-1-carboxylate (317 mg, 76%).

(h) Synthesis of N-(1H-indazol-5-yl)piperidine-4-sulfonamide

Ammonium formate (250 mg) and 10%-Pd/C (50 mg) were added to a solution of benzyl 4-[(1H-indazol-5-ylamino)sulfonyl]piperidine-1-carboxylate (250 mg, 0.603 mmol) in ethanol (15 ml) at room temperature, and the resulting mixture was refluxed for 1 hour. The reaction mixture was filtered by the use of Celite, and the filtrate was concentrated and the resulting residue was dissolved in a mixture of chloroform and methanol, followed by adding thereto diethyl ether. The solid precipitated was collected by filtration and dried under reduced pressure to obtain N-(1H-indazol-5-yl)piperidine-4-sulfonamide (116 mg, 69%).

Melting point: 120–123° C.

EXAMPLE 318

Synthesis of N-(1-benzylpiperidin-4-yl)-N-methyl-1H-indazole-5-carboxamide (a) Synthesis of N-(1-benzyl-4-piperidinyl)-2,2,2-trifluoro-N-methylacetamide N-(1-benzyl-4-piperidinyl)-2,2,2-trifluoroacetamide (1.0 g, 3.49 mmol) was added to a suspension of 60%-sodium hydride (147 mg, 3.67 mmol) in tetrahydrofuran (20 ml) at room temperature and stirred for 30 minutes. Then, methyl iodide (0.239 ml, 3.84 mmol) was added thereto and stirred for 5 hours. The reaction solution was poured into water and extracted with ethyl acetate. The organic layer was dried over anhydrous magnesium sulfate and distilled under reduced pressure to remove the solvent, and the resulting residue was purified by a silica gel column chromatography (eluent: chloroform/methanol=100/1) to obtain N-(1-benzyl-4-piperidinyl)-2,2,2-trifluoro-N-methylacetamide (731 mg, 70%).

(b) Synthesis of 1-benzyl-N-methylpiperidin-4-amine

Potassium carbonate (662 mg, 4.79 mmol) was added to a solution of N-(1-benzyl-4-piperidinyl)-2,2,2-trifluoro-N-methylacetamide (720 mg, 2.40 mmol) in a mixture of methanol (14 ml) and water (2 ml) at room temperature and stirred at 50° C. for 1.5 hours. After the reaction solution was concentrated, a saturated aqueous sodium hydrogencarbonate solution was added thereto, followed by extraction with ethyl acetate. The organic layer was dried over anhydrous magnesium sulfate and then distilled under reduced pressure to remove the solvent, whereby 1-benzyl-N-methylpiperidin-4-amine (629 mg, 100%) was obtained.

(c) Synthesis of N-(1-benzylpiperidin-4-yl)-N-methyl-1H-indazole-5-carboxamide

To a solution of the 1H-indazole-5-carboxylic acid (281 mg, 1.73 mmol) obtained in Reference Example 1 in N,N-dimethylformamide (10 ml) were added 1-benzyl-N-methylpiperidin-4-amine (390 mg, 1.91 mmol), triethylamine (0.29 ml, 2.08 mmol), 1-ethyl-3-(3'-dimethylaminopropyl)-carbodiimide monohydrochloride (499 mg, 2.60 mmol) and hydroxybenzotriazole (281 mg, 2.08 mmol), and the resulting mixture was stirred overnight at room temperature. An aqueous sodium hydrogencarbonate solution was added to the reaction solution, followed by extraction with chloroform, and the organic layer was dried over anhydrous magnesium sulfate. The solvent was concentrated under reduced pressure and the resulting residue was purified by a silica gel column chromatography (eluent: chloroform/ethyl acetate→chloroform/methanol) to obtain N-(1-benzylpiperidin-4-yl)-N-methyl-1H-indazole-5-carboxamide (502 mg, 83%).

$^1$H-NMR (DMSO-$d_6$) δ; 1.61 (2H, m), 1.78 (2H, m), 2.83 (5H, m), 3.39 (2H, s), 7.29 (6H, m), 7.57 (1H, d, J=8.5 Hz), 7.78 (1H, s), 8.12 (1H, s), 13.22 (1H, s).

EXAMPLE 319

Synthesis of N-methyl-N-piperidin-4-yl-1H-indazole-5-carboxamide

Ammonium formate (400 mg) and 10%-Pd/C (80 mg) were added to a solution of the N-(1-benzylpiperidin-4-yl)-N-methyl-1H-indazole-5-carboxamide (435.1 mg, 1.25 mmol) obtained in Example 318 in ethanol (10 ml) at room temperature, and the resulting mixture was refluxed for 2 hours. The reaction mixture was filtered by the use of Celite, and the filtrate was concentrated and the resulting residue was purified by a silica gel column chromatography (eluent: chloroform/methanol (1%-aqueous ammonia)) to obtain N-methyl-N-piperidin-4-yl-1H-indazole-5-carboxamide (247 mg, 77%).

$^1$H-NMR (DMSO-$d_6$) δ; 1.61 (4H, m), 2.12 (2H, m), 2.92 (3H, s), 3.32 (2H, m), 3.32 (1H, m), 7.33 (1H, d, J=8.5 Hz), 7.54 (1H, d, J=8.5 Hz), 7.78 (1H, s), 8.13 (1H, s), 13.23 (1H, s).

EXAMPLE 320

Synthesis of 4-(piperidin-4-yloxy)-1H-indazole (a) Synthesis of 3-(acetylamino)-2-methylphenyl acetate Under a nitrogen atmosphere, 10% Pd—C (1.0 g) was added to a solution of 3-nitro-o-cresol (10.0 g, 65.3 mmol) in methanol (200 ml) at room temperature, and catalytic reduction was carried out at ordinary temperature and atmospheric pressure. After completion of the reaction, the catalyst was filtered off and the filtrate was concentrated under reduced pressure. The resulting residue was dissolved in ethyl acetate, followed by adding thereto acetic anhydride (10.0 ml, 170 mmol) and pyridine (10.6 ml, 131 mmol), and the resulting mixture was refluxed for 2 hours. After completion of the reaction, the reaction mixture was concentrated and hexane was added thereto. The resulting suspension was filtered and the precipitate was dried under reduced pressure to obtain 3-(acetylamino)-2-methylphenyl acetate (12.7 g, 94%).

$^1$H-NMR (DMSO-$d_6$) δ; 1.96 (3H, s), 2.04 (3H, s), 2.29 (3H, s), 6.89 (1H, d, J=8.0 Hz), 7.16 (1H, dd, J=8.0, 8.0 Hz), 7.28 (1H, d, J=8.0 Hz), 9.39 (1H, s).

(b) Synthesis of 1H-indazol-4-ol

Acetic anhydride (16.4 ml, 174 mmol), tetrabutylammonium bromide (933 mg, 2.90 mmol), potassium acetate (11.4 g, 116 mmol) and isoamyl nitrite (11.7 ml, 86.9 mmol) were added to a solution of 3-(acetylamino)-2-methylphenyl acetate (12.0 g, 57.9 mmol) in ethyl acetate (120 ml) at room temperature, and the resulting mixture was refluxed for 7 hours. The reaction solution was poured into water and extracted with ethyl acetate. The organic layer was dried over anhydrous magnesium sulfate and distilled under reduced pressure to remove the solvent, and the resulting residue was purified by a silica gel column chromatography (eluent: hexane/ethyl acetate=3/1). Subsequently, the residue purified was dissolved in methanol (50 ml) and a 2N-aqueous sodium hydroxide solution (47.9 ml) was added thereto at room temperature and stirred for 1 hour. The methanol was distilled off under reduced pressure, and the resulting aqueous solution was adjusted to pH 4 to 5 by dropwise addition of hydrochloric acid and then extracted with acetic acid. The organic layer was dried over anhydrous magnesium sulfate and distilled under reduced pressure to remove the solvent, and the resulting residue was purified by a silica gel column chromatography (eluent: hexane/ethyl acetate=2/1) to obtain 1H-indazol-4-ol (3.62 g, 47%).

$^1$H-NMR (DMSO-$d_6$) δ; 6.36 (1H, d, J=7.9 Hz), 6.92 (1H, d, J=7.9 Hz), 7.19 (1H, dd, J=7.9, 7.9 Hz), 8.01 (1H, s), 10.00 (1H, s), 12.85 (1H, brs).

(c) Synthesis of 4-(piperidin-4-yloxy)-1H-indazole

To a solution of 1H-indazol-4-ol (200 mg, 1.49 mmol) in tetrahydrofuran (10 ml) were added tert-butyl 4-hydroxypiperidine-1-carboxylate (300 mg, 1.49 mmol), triphenylphosphine (430 mg, 1.64 mmol) and a 40%-dibenzyl azodicarboxylate-dichloromethane solution (0.855 ml, 1.79 mmol) at 0° C. After 1 hour, the mixture thus obtained was warmed up to room temperature. After stirring overnight, the reaction solution was concentrated under reduced pressure, and the resulting residue was dissolved in chloroform (30 ml) and washed with a 1M-aqueous sodium hydroxide solution (20 ml). Extraction with chloroform (30 ml) was carried out again and the organic layer was dried over anhydrous magnesium sulfate. The organic layer dried was concentrated under reduced pressure and the resulting residue was purified by a silica gel column chromatography (eluent: hexane/ethyl acetate). The mixture thus obtained was dissolved in methanol (2 ml) and 4N-hydrochloric acid-dioxane (2 ml) was added thereto at room temperature. After 2 hours, the reaction solution was concentrated under reduced pressure, and the resulting residue was dissolved in methanol (5 ml) and the pH was adjusted to 10 by dropwise addition of a 2M aqueous sodium hydroxide solution. The resulting mixed solution was concentrated under reduced pressure, dried and then purified by a silica gel column chromatography (eluent: chloroform/methanol=10/1→chloroform/methanol/(1%-NH$_3$ aq)=10/1) to obtain 4-(piperidin-4-yloxy)-1H-indazole (103 mg, 32%).

Melting point: 162–165° C.

EXAMPLE 321

4-(Piperidin-3-yloxy)-1H-indazole (a) Synthesis of Tert-butyl 3-hydroxy-1-piperidinecarboxylate A solution of di-tert-butyl dicarbonate (5.83 g, 26.7 mmol) in dichloromethane (10 ml) was added to a solution of 3-hydroxypiperidine (3.0 g, 29.7 mmol) in dichloromethane (30 ml) at room temperature and stirred for 15 hours.

The reaction solution was concentrated, diluted with ethyl acetate, and then washed with a saturated aqueous sodium hydrogencarbonate solution, a 0.5M-aqueous potassium hydrogensulfate solution, a saturated aqueous sodium hydrogencarbonate solution and then a saturated aqueous sodium chloride solution. The organic layer was dried over anhydrous magnesium sulfate and distilled under reduced pressure to remove the solvent, and the resulting residue was crystallized by the addition of hexane, filtered, and then dried to obtain tert-butyl 3-hydroxy-1-piperidinecarboxylate (5.17 g, 87%).

$^1$H-NMR (DMSO-d$_6$) δ; 1.46 (9H, s, 1.99 (2H, m), 3.34–3.49 (4H, m), 4.45 (1H, m).

(b) Synthesis of 4-(piperidin-3-yloxy)-1H-indazole 4-(Piperidin-3-yloxy)-1H-indazole was obtained by carrying out reaction according to the method described in Example 320, except for using tert-butyl 3-hydroxy-1-piperidinecarboxylate.

$^1$H-NMR (DMSO-d$_6$) δ; 1.67 (1H, m), 1.94 (3H, m), 3.08 (2H, m), 3.27 (2H, m), 4.88 (1H, m), 6.64 (1H, d, J=8.0 Hz), 7.12 (1H, d, J=8.0 Hz), 7.24 (1H, dd, J=8.0, 8.0 Hz), 8.19 (1H, s), 8.73 (1H, brs.), 13.06 (1H, s).

EXAMPLE 322

Synthesis of 4-(azepan-4-yloxy)-1H-indazole (a) Synthesis of 1-benzyl-4-azepanone N-methyl-N-nitrosourethane (1.39 ml, 10.8 mmol) was added dropwise to a solution of 1-benzyl-4-piperidone (2.0 g, 10.6 mmol) in methanol (4 ml) at −15° C. over a period of 30 minutes while maintaining the temperature at −5° C. or lower. During the addition, barium oxide (65 mg, 0.423 mmol) was added thereto in small portions. The resulting mixture was stirred overnight at −15° C. and then filtered, and the filtrate was distilled under reduced pressure to remove the solvent and diethyl ether was added to the residue. The insoluble material was filtered off and a saturated aqueous sodium hydrogencarbonate solution was added to the filtrate, followed by extraction with diethyl ether. The organic layer was dried over anhydrous magnesium sulfate and distilled under reduced pressure to remove the solvent, and the resulting residue was purified by a silica gel column chromatography (eluent: hexane/ethyl acetate=2/1) to obtain 1-benzyl-4-azepanone (662 mg, 31%).

$^1$H-NMR (CDCl$_3$) δ; 1.84 (2H, m), 2.54 (2H, m), 2.60 (2H, m), 2.73 (4H, s), 3.65 (2H, s), 7.25 (5H, m)

(b) Synthesis of 1-benzyl-4-azepanol

A solution of 1-benzyl-4-azepanone (610 mg, 3.00 mmol) in diethyl ether (8 ml) was added to a suspension of lithium aluminum hydride (57 mg, 1.50 mmol) in diethyl ether (5 ml) at 0° C. and stirred for 1 hour. Water (0.057 ml), a 2N-aqueous sodium hydroxide solution (0.114 ml) and then water (0.171 ml) were added to the reaction mixture, and the resulting mixture was dried over anhydrous magnesium sulfate and distilled under reduced pressure to remove the solvent. The resulting residue was purified by a silica gel column chromatography (eluent: hexane/ethyl acetate 1/1, chloroform/methanol=30/1) to obtain 1-benzyl-4-azepanol (516 mg, 84%).

$^1$H-NMR (CDCl$_3$) δ; 1.52–1.81 (4H, m), 1.87 (1H, m), 1.96 (1H, m), 2.44 (1H, m), 2.53 (1H, m), 2.77 (1H, m), 2.87 (1H, m), 3.67 (2H, m), 4.08 (1H, m), 7.28 (5H, m).

(c) Synthesis of Tert-butyl 4-hydroxyazepane-1-carboxylate

Ammonium formate (900 mg) and 10% Pd—C (200 mg) were added to a solution of 1-benzyl-4-azepanol (450 mg, 2.19 mmol) in ethanol (10 ml), and the resulting mixture was refluxed for 1 hour. The reaction mixture was filtered by the use of Celite and the filtrate was concentrated. To a solution of the resulting residue in dichloromethane (10 ml) was added di-tert-butyl dicarbonate (0.504 ml, 2.19 mmol) at room temperature, and stirred for 19 hours. A saturated aqueous sodium hydrogencarbonate solution and then water were added to the reaction mixture, followed by extraction with chloroform. The organic layer was dried over anhydrous magnesium sulfate and distilled under reduced pressure to remove the solvent, and the resulting residue was purified by a silica gel column chromatography (eluent: hexane/ethyl acetate=2/1) to obtain tert-butyl 4-hydroxyazepane-1-carboxylate (333 mg, 70%).

$^1$H-NMR (CDCl$_3$) δ; 1.50–1.92 (6H, m), 2.39 (1H, s), 3.11–3.42 (4H, m), 3.77 (1H, m).

(d) Synthesis of 4-(azepan-4-yloxy)-1H-indazole 4-(Azepan-4-yloxy)-1H-indazol was obtained by carrying out reaction according to the method described in Example 320, except for using tert-butyl 4-hydroxyazepane-1-carboxylate.

Melting point: 187–188° C.

EXAMPLE 323

Synthesis of trans-4-(1H-indazol-4-yloxy)-cyclohexanamine

(a) Synthesis of trans-2-(4-hydroxycyclohexyl)-1H-isoindole-1,3(2H)-dione

Potassium carbonate (1.64 g, 11.9 mmol) and N-carboethoxyphthalimide (1.59 g, 7.25 mmol) were added to a solution of 4-aminocyclohexanol hydrochloride (1.0 g, 6.59 mmol) in water (15 ml) at room temperature and stirred for 30 minutes. The reaction solution was filtered and the resulting precipitate was purified by a silica gel column chromatography (eluent: hexane/ethyl acetate=2/1) to obtain trans-2-(4-hydroxycyclohexyl)-1H-isoindole-1,3(2H)-dione (823 mg, 51%).

$^1$H-NMR (DMSO-d$_6$) δ; 1.27 (2H, m), 1.68 (2H, m), 1.88 (2H, m), 2.11 (2H, m), 3.44 (1H, m), 3.94 (1H, m), 4.63 (1H, d, J=4.2 Hz), 7.83 (4H, m).

(b) Synthesis of cis-4-(1,3-dioxo-1,3-dihydro-2H-isoindol-2-yl)cyclohexyl 4-nitrobenzoate To a solution of trans-2-(4-hydroxycyclohexyl)-1H-isoindole-1,3(2H)-dione (359 mg, 1.46 mmol) in tetrahydrofuran (15 ml) were added p-nitrobenzoic acid (245 mg, 1.46 mmol), triphenylphosphine (422 mg, 1.61 mmol) and a 40%-diethyl azodicarboxylate/toluene solution (0.73 ml, 1.61 mmol) at 0° C., and stirred at 0° C. for 30 minutes and then at room temperature for 3 hours. The reaction solution was concentrated and the resulting residue was dissolve in a mixed solution of ethanol (10 ml) and diisopropyl ether (10 ml) at 60° C. Then, the resulting solution was allowed to cool and the crystals formed were filtered under reduced pressure to obtain cis-4-(1,3-dioxo-1,3-dihydro-2H-isoindol-2-yl)cyclohexyl 4-nitrobenzoate (427 mg, 74%).

$^1$H-NMR (DMSO-d$_6$) δ; 1.66 (2H, m), 1.80 (2H, m), 2.05 (2H, m), 2.54 (2H, m), 4.18 (1H, m), 5.23 (1H, m), 7.85 (4H, m), 8.31 (2H, d, J=9.0 Hz), 8.40 (2H, d, J=9.0 Hz).

(c) Synthesis of cis-2-(4-hydroxycyclohexyl)-1H-isoindole-1,3(2H)-dione

To a suspension of cis-4-(1,3-dioxo-1,3-dihydro-2H-isoindol-2-yl)cyclohexyl 4-nitrobenzoate (2.0 g, 5.07 mmol) in a mixture of methanol (40 ml) and tetrahydrofuran (40 ml) was added 28%-sodium methoxide (1.04 ml, 5.07 mmol) at 0° C., and stirred at 0° C. for 30 minutes and then at room temperature for 3.5 hours. The reaction solution was adjusted to pH 4 with a 0.5M-aqueous potassium hydrogensulfate solution and distilled under reduced pressure to remove the solvent. The residue was added to water and extracted with ethyl acetate. The organic layer was dried over anhydrous magnesium sulfate and distilled under reduced pressure to remove the solvent, and the resulting residue was purified by a silica gel column chromatography (eluent: hexane/ethyl acetate=3/1) to obtain cis-2-(4-hydroxycyclohexyl)-1H-isoindole-1,3(2H)-dione (932 mg, 75%).

$^1$H-NMR (DMSO-d$_6$) δ; 1.42 (2H, m), 1.48 (2H, m), 1.73 (2H, m), 2.50 (2H, m), 3.85 (1H, m), 3.96 (1H, m), 4.38 (1H, d, J=2.2 Hz), 7.82 (4H, m).

(d) Synthesis of trans-4-(1H-indazol-4-yloxy)-cyclohexanamine

To a solution of the 1H-indazol-4-ol (131 mg, 0.977 mmol) obtained in Example 320, (b) in tetrahydrofuran (10 ml) were added dropwise cis-2-(4-hydroxycyclohexyl)-1H-isoindole-1,3(2H)-dione (215 mg, 0.879 mmol), triphenylphosphine (283 mg, 1.07 mmol) and 40%-dibenzyl azodicarboxylate-dichloromethane solution (0.672 ml, 1.17 mmol) at 0° C. The resulting mixture was warmed up to room temperature 30 minutes after the addition. After stirring overnight, the reaction solution was concentrated under reduced pressure and the resulting residue was dissolved in chloroform (50 ml) and washed with a 1M-aqueous sodium hydroxide solution (20 ml). Extraction with chloroform (20 ml) was carried out again, and the organic layer was dried over anhydrous magnesium sulfate. The organic layer dried was concentrated under reduced pressure and the resulting residue was purified by a silica gel column chromatography (eluent: hexane/ethyl acetate). To the resulting mixture was added 30%-methylamine/ethanol (2 ml) at room temperature, and the resulting mixture was refluxed for 15 minutes. After 4 hours, the reaction solution was concentrated under reduced pressure at room temperature and the resulting residue was purified by a silica gel column chromatography (eluent: chloroform/methanol=10/1→chloroform/methanol/(1%-aqueous ammonia)=10/1) to obtain trans-4-(1H-indazol-4-yloxy)-cyclohexanamine (11 mg, 5.6%).

$^1$H-NMR (DMSO-d$_6$) δ; 1.22 (2H, m), 1.48 (2H, m), 1.69 (2H, brs), 1.78 (2H, m), 2.07 (2H, m), 2.65 (1H, m), 4.43 (1H, m), 6.56 (1H, d, J=7.5 Hz), 7.04 (1H, d, J=7.5 Hz), 7.20 (1H, dd, J=7.5, 7.5 Hz), 7.94 (1H, s), 12.97 (1H, s).

The following compounds of Example 324 and Example 325 were synthesized by carrying out reaction according to the method described in Example 323.

EXAMPLE 324 cis-4-(1H-indazol-4-yloxy)-cyclohexanamine $^1$H-NMR (DMSO-d$_6$) δ; 1.44–1.65 (8H, m), 1.94 (2H, m), 2.70 (1H, m), 4.65 (1H, m), 6.55 (1H, d, J=7.8 Hz), 7.04 (1H, d, J=7.8 Hz), 7.20 (1H, dd, J=7.8, 7.8 Hz), 8.00 (1H, s), 12.97 (1H, s).

EXAMPLE 325

Synthesis of cis-3-(1H-indazol-4-yloxy)-cyclohexanamine

Melting point: 166–168° C.

EXAMPLE 326

Synthesis of trans-3-(1H-indazol-4-yloxy)-cyclohexanamine

(a) Synthesis of 2-(2-cyclohexen-1-yl)-1H-isoindole-1,3 (2H)-dione

Phthalimide (7.08 g, 48.1 mmol), triphenylphosphine (13.2 g, 50.4 mmol) and a 40%-diethyl azodicarboxylate/toluene solution (23.3 ml, 51.4 mmol) were added to a solution of cyclohexenol (4.5 g, 45.9 mmol) in tetrahydrofuran (90 ml) at 0° C. and stirred at 0° C. for 30 minutes and then at room temperature for 2.5 hours. The reaction solution was concentrated under reduced pressure and the resulting residue was purified by a silica gel column chromatography (eluent: hexane/ethyl acetate=15/1) to obtain 2-(2-cyclohexen-1-yl)-1H-isoindole-1,3(2H)-dione (3.36 g, 32%).

$^1$H-NMR (CDCl$_3$) δ; 1.73 (1H, m), 1.93 (2H, m), 2.16 (3H, m), 4.90 (1H, m), 5.58 (1H, m), 5.94 (1H, m), 7.72 (2H, m), 7.81 (2H, m).

(b) Synthesis of (2S, 6R, 12bS, 13S)-13-bromo-12b-propyl-3,4,5,6-tetrahydro-2H-2,6-methano[2,3-a]isoindol-8(12bH)-one Ethanol (3 ml) and N-bromosuccinimide (2.94 g, 16.5 mmol) were added to a solution of 2-(2-cyclohexen-1-yl)-1H-isoindole-1,3(2H)-dione (3.0 g, 13.2 mmol) in chloroform (90 ml) at room temperature and stirred for 14 hours. A 1M-aqueous sodium thiosulfate solution was added to the reaction solution, followed by extraction with chloroform. The organic layer was dried over anhydrous magnesium sulfate and the solvent was concentrated under reduced pressure, and the resulting residue was purified by a silica gel column chromatography (eluent: hexane/ethyl acetate=10/1) to obtain (2S, 6R, 12bS, 13S)-13-bromo-12b-propyl-3,4,5,6-tetrahydro-2H-2,6-methano[2,3-a]isoindol-8(12bH)-one (3.60 g, 77%).

$^1$H-NMR (CDCl$_3$) δ; 1.14 (3H, t, J=7.1 Hz), 1.34 (1H, m), 1.68 (2H, m), 2.11 (2H, m), 2.54 (1H, m), 3.05 (1H, m), 3.38 (1H, m), 4.37 (1H, m), 4.56 (1H, m), 5.57 (1H, m), 7.56 (3H, m), 7.76 (1H, m).

(c) Synthesis of 2-[(1R, 2S, 3S)-2-bromo-3-hydroxycyclohexyl]-1H-isoindole-1,3(2H)-dione A 2N-aqueous hydrochloric acid solution (18 ml) was added to a solution of (2S, 6R, 12bS, 13S)-13-bromo-12b-propyl-3,4,5,6-tetrahydro-2H-2,6-methano[2,3-a]isoindol-8(12bH)-one (3.56 g, 10.1 mmol) in methanol (70 ml) at room temperature and stirred for 1 hour. The reaction solution was concentrated and the resulting residue was dissolved in chloroform and washed with water. The organic layer was dried over anhydrous magnesium sulfate and the solvent was concentrated under reduced pressure, and the resulting residue was crystallized from hexane/ethyl acetate to obtain 2-[(1R, 2S, 3S)-2-bromo-3-hydroxycyclohexyl]-1H-isoindole-1,3(2H)-dione (2.19 g, 67%).

$^1$H-NMR (CDCl$_3$) δ; 1.51 (2H, m), 1.91 (2H, m), 2.20 (2H, m), 2.52 (1H, s), 3.76 (1H, m), 4.38 (1H, m), 4.81 (1H, dd, J=9.5, 11.2 Hz), 7.76 (2H, m), 7.86 (2H, m).

(d) Synthesis of cis-2-(3-hydroxycyclohexyl)-1H-isoindole-1,3(2H)-dione

Tributyltin hydride (1.99 ml, 7.40 mmol) and 2,2'-azobis(isobutyronitrile) (8 mg) were added to a solution of 2-[(1R, 2S, 3S)-2-bromo-3-hydroxycyclohexyl]-1H-isoindole-1,3(2H)-dione (2.0 g, 6.17 mmol) in a mixture of toluene (40 ml) and methanol (4 ml) at room temperature, and the resulting mixture was refluxed for 3 hours. Tributyltin hydride (1.99 ml, 7.40 mmol) and 2,2'-azobis(isobutyronitrile) (8 mg) were further added thereto, and the resulting mixture was refluxed for 1 hour. The reaction solution was concentrated and the resulting residue was purified by a silica gel column chromatography (eluent: hexane/ethyl acetate=2/1) to obtain cis-2-(3-hydroxycyclohexyl)-1H-isoindole-1,3(2H)-dione (1.33 g, 88%).

$^1$H-NMR (CDCl$_3$) δ; 1.37 (2H, m), 1.51 (1H, d, J=5.3 Hz), 1.71 (1H, m), 1.88 (1H, m), 2.04–2.32 (4H, m), 3.69 (1H, m), 4.17 (1H, m), 7.73 (2H, m), 7.80 (2H, m).

(e) Synthesis of trans-3-(1H-indazol-4-yloxy)-cyclohexanamine

Except for using cis-2-(3-hydroxycyclohexyl)-1H-isoindole-1,3(2H)-dione, trans-3-(1H-indazol-4-yloxy)-cyclohexanamine was synthesized by carrying out reaction according to the method described in Example 323, (d).

$^1$H-NMR (CDCl$_3$) δ; 1.14 (1H, m), 1.32–1.58 (3H, m), 1.71 (1H, m), 1.81 (1H, m), 1.91 (1H, m), 2.15 (1H, m), 3.19 (1H, m), 4.78 (1H, m), 6.37 (1H, d, J=7.7 Hz), 6.95 (1H, d, J=7.7 Hz), 7.12 (1H, dd, J=7.7, 7.7 Hz), 8.05 (1H, s).

EXAMPLE 327

Synthesis of trans-3-(1H-indazol-4-yloxy)-cyclohexanamine hydrochloride

To a solution of the trans-3-(1H-indazol-4-yloxy)-cyclohexanamine (163.1 mg, 0.705 mmol) obtained in Example 326 in ethanol (3 ml) was added 1M-hydrochloric acid/diethyl ether (0.776 ml, 0.776 mmol) at room temperature. After 1 hour, the resulting solution was concentrated under reduced pressure, and the resulting oil was crystallized by the addition of acetonitrile, followed by filtration. The precipitate was dried under reduced pressure to obtain trans-3-(1H-indazol-4-yloxy)-cyclohexanamine hydrochloride (166 mg, 88%).

$^1$H-NMR (DMSO-d$_6$) δ; 1.39–1.56 (2H, m), 1.71 (3H, m), 1.96 (2H, m), 2.26 (1H, m), 3.39 (1H, m), 5.01 (1H, m), 6.59 (1H, d, J=8.2 Hz), 7.08 (1H, d, J=8.2 Hz), 7.23 (1H, dd, J=8.2, 8.2 Hz), 7.92 (3H, brs.), 8.05 (1H, s), 13.03 (1H, s).

EXAMPLE 328

Synthesis of 5-[(4-methylpentyl)oxy]-1H-indazole

To a solution of the 1H-indazol-5-ol (100 mg, 0.745 mmol) obtained in Reference Example 4 in N,N-dimethylformamide (2 ml) were added 1-bromo-4-methylpentane (0.109 ml, 0.745 mmol), tetrabutylammonium iodide (28 mg, 0.1 mmol) and potassium carbonate (103 mg, 0.745 mmol), and the resulting mixture was heated to 60° C. After 9 hours, the mixture was poured into water (20 ml) and extracted with ethyl acetate (20 ml×2). The organic layer was dried over anhydrous magnesium sulfate and concentrated under reduced pressure, and the resulting residue was purified by a silica gel column chromatography (eluent: hexane/ethyl acetate) to obtain 5-[(4-methylpentyl)oxy]-1H-indazole (60 mg, 37%).

Melting point: 124–126° C.

The following compounds of Example 329 and Example 330 were synthesized by carrying out reaction according to the method described in Example 328.

EXAMPLE 329

5-(Isopentyloxy)-1H-indazole

Melting point: 139–140° C.

EXAMPLE 330

5-Isobutyloxy-1H-indazole

Melting point: 151–153° C.

EXAMPLE 331

Synthesis of 5-(benzyloxy)-1H-indazole

Benzyl bromide (0.089 ml, 0.745 mmol) and potassium carbonate (103 mg, 0.745 mmol) were added to a solution of the 1H-indazol-5-ol (100 mg, 0.745 mmol) obtained in Reference Example 4 in N,N-dimethylformamide (2 ml), and the resulting mixture was heated to 40° C. After 2 hours, the mixture was poured into water (20 ml) and extracted with ethyl acetate (20 ml×2). The organic layer was dried over anhydrous magnesium sulfate. The organic layer dried was concentrated under reduced pressure and the resulting residue was purified by a silica gel column chromatography (eluent: hexane/ethyl acetate) to obtain 5-(benzyloxy)-1H-indazole (63 mg, 38%).

Melting point: 179–181° C.

EXAMPLE 332

Synthesis of 5-(piperidin-4-ylmethoxy)-1H-indazole dihydrochloride (a) Synthesis of tert-butyl 4-(hydroxymethyl)piperidine-1-carboxylate A 1M-borane/tetrahydrofuran solution (4.36 ml, 4.36 mmol) was added dropwise to a solution of 1-(tert-butoxycarbonyl)piperidine-4-carboxylic acid (1.0 g, 4.36 mmol) in tetrahydrofuran (20 ml) at 0° C. After 1 hour, the mixture thus obtained was warmed up to room temperature. After another 6 hours, a saturated aqueous sodium hydrogencarbonate solution was added to the reaction mixture and the resulting mixture was poured into water (100 ml) and extracted with ethyl acetate (50 ml×2). The organic layer was dried over anhydrous magnesium sulfate. The organic layer dried was concentrated under reduced pressure and the resulting residue was purified by a silica gel column chromatography (eluent: hexane/ethyl acetate) to obtain tert-butyl 4-(hydroxymethyl)piperidine-1-carboxylate (715 mg, 76%).

(b) Synthesis of tert-butyl 4-[(1H-indazol-5-yloxy)methyl]piperidine-1-carboxylate Triethylamine (0.155 ml, 1.11 mmol) and methanesulfonyl chloride (0.075 ml, 0.975 mmol) were added to a solution of tert-butyl 4-(hydroxymethyl)piperidine-1-carboxylate (200 mg, 0.929 mmol) in dichloromethane (6 ml). After 2 hours, the mixture thus obtained was poured into water (20 ml), adjusted to pH 4 with a 0.5M-aqueous potassium hydrogensulfate solution and then extracted with chloroform (20 ml×2). The organic layer was dried over anhydrous magnesium sulfate. The organic layer dried was concentrated under reduced pressure and the resulting residue was dissolved in N,N-dimethylformamide (3 ml). The 1H-indazol-5-ol (125 mg, 0.929 mmol) obtained in Reference Example 4, potassium carbonate (128 mg, 0.929 mmol) and tetrabutylammonium bromide (34 mg, 0.0929 mmol) were added thereto, and the resulting mixture was heated to 60° C. After 1 hour, the mixture was heated to 80° C. After another 5 hours, a 1M-aqueous sodium hydroxide solution was added thereto and the resulting mixture was poured into water (30 ml) and extracted with chloroform (20 ml×2). The organic layer was washed with a saturated aqueous sodium chloride solution and then dried over anhydrous magnesium sulfate. The organic layer dried was concentrated under reduced pressure and the resulting residue was purified by a silica gel column chromatography (eluent: chloroform/ethyl acetate) to obtain tert-butyl 4-[(1H-indazol-5-yloxy)methyl]piperidine-1-carboxylate (90 mg, 29%).

(c) Synthesis of 5-(piperidin-4-ylmethoxy)-1H-indazole dihydrochloride

To tert-butyl 4-[(1H-indazol-5-yloxy)methyl]piperidine-1-carboxylate (81.2 mg, 0.245 mmol) was added 4N-hydrochloric acid-dioxane (1 ml). After 1 hour, the resulting mixture was concentrated under reduced pressure, and the resulting residue was dissolved in methanol (0.5 ml) and crystallized from diethyl ether (10 ml). The crystals were filtered and then dried under reduced pressure to obtain 5-(piperidin-4-ylmethoxy)-1H-indazole dihydrochloride (71 mg, 95%).

$^1$H-NMR (DMSO-d$_6$) δ; 1.48 (2H, m), 1.90 (2H, m), 2.07 (1H, m), 2.89 (2H, m), 3.27 (2H, m), 3.86 (2H, d, J=6.3 Hz), 7.00 (1H, d, J=9.0 Hz), 7.18 (1H, s), 7.42 (1H, d, J=9.0 Hz), 7.92 (1H, s), 8.51 (1H, br), 8.82 (1H, br).

EXAMPLE 333

Synthesis of 5-(2-phenylethoxy)-1H-indazole

Potassium carbonate (68 mg, 0.492 mmol), tetrabutylammonium iodide (17 mg, 0.0447 mmol) and phenethyl bromide (0.061 ml, 0.447 mmol) were added to a solution of the 1H-indazol-5-ol (60 mg, 0.447 mmol) obtained in Reference Example 4 in N,N-dimethylformamide (2 ml), and the resulting mixture was heated to 60° C. After 7 hours, chloroform (3 ml) and a 1M-aqueous sodium hydroxide solution (4 ml) were added to the reaction mixture and stirred. After removing the aqueous layer, water (3 ml) was added to the organic layer and stirred. After removing the aqueous layer, the organic layer was dried over anhydrous magnesium sulfate. The organic layer dried was concentrated and the resulting residue was purified by a silica gel column chromatography (eluent: hexane/ethyl acetate) to obtain 5-(2-phenylethoxy)-1H-indazole (8.4 mg, 8%).

MS: m/z=239 (M+1)

The following compounds of Example 334 to Example 350 were synthesized by carrying out reaction according to the method described in Example 333.

EXAMPLE 334

5-(Cyclopropylmethoxy)-1H-indazole

MS m/z=189 (M+1)

EXAMPLE 335

5-(Cyclobutylmethoxy)-1H-indazole

MS: m/z=203 (M+1)

EXAMPLE 336

5-(Cyclohexylmethoxy)-1H-indazole

MS: m/z=231 (M+1)

EXAMPLE 337

Ethyl(1H-indazol-5-yloxy)acetate

MS: m/z=221 (M+1)

EXAMPLE 338

5-(2-Methoxyethoxy)-1H-indazole

MS m/z=193 (M+1)

EXAMPLE 339

5-(2-Phenoxyethoxy)-1H-indazole

MS: m/z=255 (M+1)

EXAMPLE 340

2-(1H-indazol-5-yloxy)ethanol

MS: m/z=179 (M+1)

EXAMPLE 341

5-(Pyridin-2-ylmethoxy)-1H-indazole

MS: m/z=226 (M+1)

EXAMPLE 342

5-(Pyridin-3-ylmethoxy)-1H-indazole

MS: m/z=226 (M+1)

EXAMPLE 343

5-(Pyridin-4-ylmethoxy)-1H-indazole

MS: m/z=226 (M+1)

EXAMPLE 344

2-[(1H-indazol-5-yloxy)methyl]quinoline

MS: m/z=276 (M+1)

EXAMPLE 345

5-[2-(1H-pyrrol-1-yl)ethoxy]-1H-indazole

MS: m/z=228 (M+1)

EXAMPLE 346

2-[(1H-indazol-5-yloxy)methyl]benzonitrile

MS: m/z=250 (M+1)

EXAMPLE 347

3-[(1H-indazol-5-yloxy)methyl]benzonitrile

Melting point: 158–161° C.

EXAMPLE 348

4-[(1H-indazol-5-yloxy)methyl]benzonitrile

MS: m/z=250 (M+1)

EXAMPLE 349

2-[2-(1H-indazol-5-yloxy)ethyl]-1H-isoindole-1,3 (2H)-dione

MS: m/z=308 (M+1)

EXAMPLE 350

2-(Tetrahydro-2H-pyran-2-ylmethoxy)-1H-indazole

MS: m/z=233 (M+1)

EXAMPLE 351

Synthesis of 5-(cyclohexyloxy)-1H-indazole

Cyclohexanol (0.315 ml, 2.98 mmol), triphenylphosphine (442 mg, 1.64 mmol) and dibenzyl azodicarboxylate (534 mg, 1.17 mmol) were added at 0° C. to a solution of the 1H-indazol-5-ol (200 mg, 1.49 mmol) obtained in Reference Example 4 in tetrahydrofuran (16 ml). After 30 minutes, the mixture thus obtained was warmed up to room temperature. After stirring overnight, the reaction solution was concentrated under reduced pressure and a-1M aqueous sodium hydroxide solution (20 ml) was added to the resulting residue, followed by extraction with ethyl acetate (20 ml×2). The organic layer was dried over anhydrous magnesium sulfate. The organic layer dried was concentrated under reduced pressure and the resulting residue was purified by a silica gel column chromatography (eluent: chloroform/methanol, hexane/ethyl acetate) to obtain 5-(cyclohexyloxy)-1H-indazole (140 mg, 43%).

Melting point: 144–146° C.

EXAMPLE 352

Synthesis of 5-(2-nitrophenoxy)-1H-indazole

To a solution of the 1H-indazol-5-ol (300 mg, 2.24 mmol) obtained in Reference Example 4 in N,N-dimethylformamide (6 ml) were added 2-bromonitrobenzene (497 mg, 2.46 mmol) and potassium carbonate (402 mg, 2.91 mmol), and the resulting mixture was heated to 120° C. After 6 hours, the mixture was poured into water (20 ml) and extracted with ethyl acetate (20 ml×2). The organic layer was dried over anhydrous magnesium sulfate. The organic layer dried was concentrated under reduced pressure and the resulting residue was purified by a silica gel column chromatography (eluent: hexane/ethyl acetate) to obtain 5-(2-nitrophenoxy)-1H-indazole (57 mg, 10%).

$^1$H-NMR (DMSO-$d_6$) δ; 7.02 (1H, d, J=8.5 Hz), 7.29 (1H, d, J=8.0 Hz), 7.29 (1H, dd, J=7.5, 7.5 Hz), 7.46 (1H, s), 7.60 (2H, m), 8.04 (2H, m), 13.18 (1H, s)

EXAMPLE 353

Synthesis of 5-(cyclopentyloxy)-1H-indazole

Cyclopentanol (0.068 ml, 0.745 mmol), triphenylphosphine (221 mg, 0.820 mmol) and dibenzyl azodicarboxylate (267 mg, 0.895 mmol) were added at 0° C. to a solution of the 1H-indazol-5-ol (100 mg, 0.745 mmol) obtained in Reference Example 4 in tetrahydrofuran (6 ml). After 30 minutes, the mixture thus obtained was heated to room temperature. After stirring overnight, the reaction solution was concentrated under reduced pressure and a 1M-aqueous sodium hydroxide solution (4 ml) and chloroform (3 ml) were added to the resulting residue. After removing the aqueous layer, water (2 ml) was added to the residue. The aqueous layer was removed and the organic layer was dried over anhydrous magnesium sulfate. The organic layer dried was concentrated and the resulting residue was purified by a silica gel column chromatography (eluent: chloroform/methanol, hexane/ethyl acetate) to obtain 5-(cyclopentyloxy)-1H-indazole (24 mg, 16%).

Melting point: 141–142° C.

The following compounds of Example 354 to Example 360 were synthesized by carrying out reaction according to the method described in Example 353.

EXAMPLE 354

5-(Cycloheptyloxy)-1H-indazole

MS: m/z=231 (M+1)

EXAMPLE 355

5-(1-Methyl-2-phenoxyethoxy)-1H-indazole

MS: m/z=269 (M+1)

EXAMPLE 356

5-(Tetrahydrofuran-3-yloxy)-1H-indazole

MS: m/z=205 (M+1)

EXAMPLE 357

5-(2-Methoxy-1-methylethoxy)-1H-indazole

MS: m/z=207 (M+1)

EXAMPLE 358

5-(Cyclobutyloxy)-1H-indazole

MS: m/z=189 (M+1)

EXAMPLE 359

5-[(2-Methylcyclohexyl)oxy]-1H-indazole

MS: m/z=231 (M+1)

EXAMPLE 360

4-[1-(1H-indazol-5-yloxy)ethyl]benzonitrile $^1$H-NMR (CDCl$_3$) δ; 1.64 (3H, d, J=6.5 Hz), 5.34 (1H, q, J=6.5 Hz), 6.92 (1H, d, J=2.2 Hz), 7.10 (1H, dd, J=9.0, 2.2 Hz), 7.36 (1H, d, J=9.0 Hz), 7.52 (2H, d, J=8.2 Hz), 7.62 (1H, d, J=8.2 Hz), 7.90 (1H, s), 10.91 (1H, brs.).

EXAMPLE 361

Synthesis of 2-[(1H-indazol-5-yloxy)methyl]benzylamine

Lithium aluminum hydride (44 mg, 1.12 mmol) was added to a solution of the 2-[(1H-indazol-5-yloxy)methyl]benzonitrile (70 mg, 0.281 mmol) obtained in Example 346 in tetrahydrofuran (8 ml), and the resulting mixture was refluxed. After 2 hours, water, a 2M-aqueous sodium hydroxide solution and then water were added to the reaction mixture, and the resulting solution was filtered by the use of Celite. The filtrate was concentrated under reduced pressure and the resulting residue was purified by a silica gel column chromatography (eluent: chloroform/methanol→chloroform/methanol (1% aqueous ammonia)) to obtain 2-[(1H-indazol-5-yloxy)methyl]benzyl-amine (52 mg, 74%).

$^1$H-NMR (DMSO-d$_6$) δ; 1.80 (2H, brs.), 3.80 (2H, s), 5.16 (2H, s), 7.08 (1H, dd, J=2.2, 8.8 Hz), 7.23 (1H, m), 7.31 (2H, m), 7.45 (3H, m), 7.94 (1H, s), 12.90 (1H, brs.).

The following compound of Example 362 was synthesized by carrying out reaction according to the method described in Example 361, except for using the 4-[(1H-indazol-5-yloxy)methyl]benzonitrile obtained in Example 348, as a starting material.

EXAMPLE 362

4-[(1H-indazol-5-yloxy)methyl]benzylamine

Melting point: 197–198° C.

The following compound of Example 363 was synthesized by carrying out reaction according to the method described in Example 361, except for using the 3-[(1H-indazol-5-yloxy)methyl]benzonitrile obtained in Example 347, as a starting material.

EXAMPLE 363

3-[(1H-indazol-5-yloxy)methyl]benzylamine

Melting point: 179–183° C.

The following compound of Example 364 was synthesized by carrying out reaction according to the method described in Example 361, except for using the 4-[1-(1H-indazol-5-yloxy)ethyl]benzonitrile obtained in Example 360, as a starting material.

EXAMPLE 364

1-{4-[1-(1H-indazol-5-yloxy)ethyl]phenyl}-methanamine $^1$H-NMR (CDCl$_3$) δ; 1.64 (3H, d, J=6.4 Hz), 3.81 (2H, s), 5.29 (1H, q, J=6.4 Hz), 6.97 (1H, d, J=2.2 Hz), 7.06 (1H, dd, J=8.9, 2.2 Hz), 7.26 (3H, m), 7.34 (2H, d, J=8.2 Hz), 7.84 (1H, s).

EXAMPLE 365

Synthesis of 5-(tetrahydro-2H-pyran-4-yloxy)-1H-indazole

To a solution of the 1H-indazol-5-ol (150 mg, 1.12 mmol) obtained in Reference Example 4 in tetrahydrofuran (6 ml) were added 4-hydroxytetrahydropyran (0.107 ml, 1.12 mmol), triphenylphosphine (293 mg, 1.12 mmol) and a 40%-diethyl azodicarboxylate-toluene solution (0.517 ml, 1.14 mmol) at 0° C. After 30 minutes, the mixture thus obtained was heated to room temperature. After stirring overnight, the reaction solution was concentrated under reduced pressure, and the resulting residue was purified by a silica gel column chromatography (eluent: chloroform/methanol) to obtain 5-(tetrahydro-2H-pyran-4-yloxy)-1H-indazole (11.4 mg, 47%).

Melting point: 151–153° C.

EXAMPLE 366

Synthesis of 5-[(1-isopropylpiperidin-4-yl)oxy]-1H-indazole

The 5-(piperidin-4-yloxy)-1H-indazole (80 mg, 0.368 mmol) obtained in Example 42 was suspended in methanol (2 ml), and acetone (0.031 ml, 1.10 mmol) and acetic acid (0.105 ml, 1.84 mmol) were added dropwise thereto. Then, sodium cyanoborohydride (116 mg, 1.84 mmol) was added thereto. After 18 hours, acetone, acetic acid and sodium cyanoborohydride were further added in the same amounts, respectively, as above. After 3 days, a saturated aqueous sodium hydrogencarbonate solution was added to the reaction solution, and the resulting mixture was poured into water (20 ml) and extracted with chloroform (20 ml×3). The organic layer was dried over anhydrous magnesium sulfate. The organic layer dried was concentrated under reduced pressure and the resulting residue was purified by a silica gel column chromatography (eluent: chloroform/methanol→chloroform/methanol (1%-aqueous ammonia)) to obtain 5-[(1-isopropylpiperidin-4-yl)oxy]-1H-indazole (30 mg, 31%).

Melting point: 125–126° C.

EXAMPLE 367

Synthesis of Ethyl 4-(1H-indazol-5-yloxy)cyclohexanecarboxylate

Ethyl 4-hydroxycyclohexylcarboxylate (1.44 ml, 8.95 mmol), triphenylphosphine (2.15 g, 8.20 mmol) and dibenzyl azodicarboxylate (3.34 g, 11.18 mmol) were added at 0° C. to a solution of the 1H-indazol-5-ol (1.0 g, 7.45 mmol) obtained in Reference Example 4 in tetrahydrofuran (40 ml). After 1 hour, the mixture thus obtained was warmed up to room temperature. After stirring overnight, the reaction solution was concentrated under reduced pressure, and the resulting residue was purified by a silica gel column chromatography (eluent: chloroform/ethyl acetate, hexane/ethyl acetate) to obtain ethyl 4-(1H-indazol-5-yloxy)cyclohexanecarboxylate (928 mg, 43%).

MS: m/z=289 (M+1)

EXAMPLE 368

Synthesis of 4-(1H-indazol-5-yloxy)cyclohexanecarboxylic acid

The ethyl 4-(1H-indazol-5-yloxy)cyclo-hexanecarboxylate (728.4 mg, 2.53 mmol) obtained in Example 367 was dissolved in a mixture of methanol (2.5 ml) and tetrahydrofuran (2.5 ml), and a 2M-aqueous lithium hydroxide solution (2.53 ml, 5.05 mmol) was added dropwise thereto. After 2 hours, the reaction mixture was concentrated under reduced pressure and the resulting residue was dissolved in water (5 ml). The resulting aqueous solution was adjusted to pH 4 with a 0.5M-aqueous potassium hydrogensulfate solution. The crystals formed were filtered under reduced pressure and then dried to obtain 4-(1H-indazol-5-yloxy)cyclohexanecarboxylic acid (381 mg, 58%).

$^1$H-NMR (DMSO-d$_6$) δ; 1.47 (2H, m), 1.65 (2H, m), 1.78 (4H, m), 1.91 (1H, m), 2.10 (1H, m), 2.24 (0.5H, m), 2.36 (0.5H, m), 4.24 (0.5H, m), 4.47 (0.5H, m), 6.98 (1H, m), 7.21 (1H, m), 7.40 (1H, m), 7.90 (1H, s), 12.84 (1H, br).

EXAMPLE 369

Synthesis of 4-(1H-indazol-5-yloxy)cyclohexanecarboxamide

Ammonium chloride (173 ml, 3.23 mmol) and diisopropylethylamine (0.75 ml, 4.30 mmol) were added to a solution of the 4-(1H-indazol-5-yloxy)cyclohexanecarboxylic acid (280 mg, 1.08 mmol) obtained in Example 368 in N,N-dimethylformamide (10 ml). After aqueous ammonia (1 ml) was added thereto to effect dissolution, 1-ethyl-3-(3'-dimethylaminopropyl)carbodiimide monohydrochloride (309 mg, 1.61 mmol) and hydroxybenzotriazole (160 mg, 1.18 mmol) were added thereto. After 16 hours, it was confirmed that the starting material remained. Therefore, 1-ethyl-3-(3'-dimethylaminopropyl)carbodiimide monohydrochloride (309 mg, 1.61 mmol) and hydroxybenzotriazole (160 mg, 1.18 mmol) were further added thereto. After 7 hours, a saturated aqueous sodium hydrogencarbonate solution was added to the reaction solution, and the resulting mixture was poured into water (100 ml) and extracted with ethyl acetate (50 ml×3) and chloroform (20 ml×2). The organic layer was washed with a saturated aqueous sodium chloride solution and then dried over anhydrous magnesium sulfate. The organic layer dried was concentrated under reduced pressure and the resulting residue was washed with diethyl ether by repulping to obtain 4-(1H-indazol-5-yloxy)cyclohexanecarboxamide (265 mg, 95%).

$^1$H-NMR (DMSO-d$_6$) δ; 1.45 (1H, m), 1.66 (3H, m), 1.94 (2H, m), 2.11 (1H, m), 2.26 (2H, m), 4.35 (0.5H, m), 4.65 (0.5H, m), 6.85 (1H, s), 7.15 (1H, m), 7.37 (2H, m), 7.56 (1H, m), 8.05 (1H, s), 13.01 (1H, s).

EXAMPLE 370

Synthesis of [4-(1H-indazol-5-yloxy)cyclohexyl]methanol

Lithium aluminum hydride (52 mg, 1.39 mmol) was added to a solution of the ethyl 4-(1H-indazol-5-yloxy)cyclohexanecarboxylate (100 mg, 0.347 mmol) obtained in Example 367 in tetrahydrofuran (2 ml), and the resulting mixture was refluxed. After 2 hours, water (52 μl), a 2M-aqueous sodium hydroxide solution (0.104 ml) and then water (0.156 ml) were added to the reaction mixture, and the resulting solution was filtered by the use of Celite. The filtrate was concentrated under reduced pressure, and the resulting oil was crystallized by the addition of diisopropyl ether. The crystals were filtered under reduced pressure and then dried to obtain [4-(1H-indazol-5-yloxy)cyclohexyl]methanol (72 mg, 84%, trans/cis=4/1).

$^1$H-NMR (DMSO-d$_6$): 1.04 (1.6H, m), 1.33 (3.8H, m), 1.79 (1.6H, m), 1.95 (0.4H, m), 2.11 (1.6H, m), 3.24 (2H, m), 4.18 (0.8H, m), 4.42 (1H, m), 4.55 (0.2H, m), 7.01 (1H, m), 7.19 (1H, s), 7.39 (1H, m), 7.90 (1H, s), 12.85 (1H, s).

EXAMPLE 371

Synthesis of
1-[4-(1H-indazol-5-yloxy)cyclohexyl]methanamine

Lithium aluminum hydride (58 mg, 1.54 mmol) was added to a solution of the 4-(1H-indazol-5-yloxy)cyclohexanecarboxamide (100 mg, 0.386 mmol) obtained in Example 369 in tetrahydrofuran (3 ml), and the resulting mixture was refluxed. After 6 hours, water (0.087 ml), a 2M-aqueous sodium hydroxide solution (0.176 ml) and then water (0.261 ml) were added to the reaction mixture, and the resulting solution was filtered by the use of Celite. The filtrate was concentrated under reduced pressure, and the resulting residue was purified by a silica gel column chromatography (eluent: chloroform/methanol→chloroform/methanol (1%-aqueous ammonia)) to obtain 1-[4-(1H-indazol-5-yloxy)cyclohexyl]methanamine (49 mg, 52%).

$^1$H-NMR (DMSO-$d_6$) δ; 1.02 (2H, m), 1.28 (3H, m), 1.52 (2H, m), 1.79 (2H, m), 2.08 (2H, m), 2.39 (2H, m), 4.18 (1H, m), 6.98 (1H, dd, J=9.0, 2.0 Hz), 7.19 (1H, d, J=2.0 Hz), 7.38 (1H, d, J=9.0 Hz), 7.90 (1H, s), 12.87 (1H, s)

EXAMPLE 372

Synthesis of 4-(1H-indazol-5-yloxy)cyclo-hexanol (a) Synthesis of
4-(tetrahydro-2H-pyran-2-yloxy)cyclo-hexanol An acidic resin (Dowex 50W×8, trade name, Dow Chemical Company, 800 mg) and dihydropyran (1.89 ml, 20.7 mol) were added dropwise to a solution of 1,4-cyclohexanediol (4.0 g, 34.4 mol) in toluene (80 ml) at room temperature and vigorously stirred. After 17 hours, the reaction mixture was filtered by the use of Celite and the filtrate was concentrated under reduced pressure. The resulting residue was purified by a silica gel column chromatography (eluent: hexane/ethyl acetate) to obtain 4-(tetrahydro-2H-pyran-2-yloxy)cyclo-hexanol (2.69 g, 65%).

(b) Synthesis of 5-{[4-(tetrahydro-2H-pyran-2-yloxy)cyclohexyl]oxy}-1H-indazole

To a solution of the 1H-indazol-5-ol (250 mg) obtained in Reference Example 4 in tetrahydrofuran (15 ml) were added 4-(tetrahydro-2H-pyran-2-yloxy)cyclohexanol (373 mg, 1.86 mmol), triphenylphosphine (538 mg, 2.05 mmol) and dibenzyl azodicarboxylate (667 mg, 2.24 mmol) at 0° C. After 1 hour, the mixture thus obtained was heated to room temperature. After stirring overnight, the reaction solution was concentrated under reduced pressure, and a 1M-aqueous sodium hydroxide solution (50 ml) was added to the resulting residue, followed by extraction with chloroform (50 ml×2). The organic layer was washed with a saturated aqueous sodium chloride solution and then dried over anhydrous magnesium sulfate. The organic layer dried was concentrated under reduced pressure, and the resulting residue was purified by a silica gel column chromatography (eluent: hexane/ethyl acetate) to obtain 5-{[4-(tetrahydro-2H-pyran-2-yloxy)cyclohexyl]oxy}-1H-indazole (244 mg, 41%).

(c) Synthesis of
4-(1H-indazol-5-yloxy)cyclohexanol

An acidic resin (Dowex 50W×8, trade name, Dow Chemical Company, 46 mg) was added to a solution of 5-{[4-(tetrahydro-2H-pyran-2-yloxy)cyclohexyl]oxy}-1H-indazole (232 mg, 0.733 mmol) in methanol (10 ml), and the resulting mixture was heated to 50° C. After 5 hours, the reaction solution was filtered by the use of Celite and the filtrate was concentrated under reduced pressure. The resulting residue was purified by a silica gel column chromatography (eluent: chloroform/methanol) to obtain 4-(1H-indazol-5-yloxy)cyclohexanol (132 g, 78%).

Melting point: 112–118° C.

The following compound of Example 373 was synthesized by carrying out reaction according to the method described in Example 372, except for using 1,3-cyclohexanediol as a starting material.

EXAMPLE 373

3-(1H-indazol-5-yloxy)cyclohexanol $^1$H-NMR (DMSO-$d_6$) δ; 1.04–1.37 (2.5H, m), 1.60–1.78 (5H, m), 1.99 (0.5H, m), 3.51 (0.5H, m), 3.89 (0.5H, m), 4.20 (0.5H, m), 4.51 (0.5H, d, J=4.0 Hz), 4.61 (0.5H, m), 4.64 (0.5H, d, J=4.6 Hz), 6.98 (1H, dd, J=2.4, 9.0 Hz), 7.18 (1H, m), 7.39 (1H, d, J=9.0 Hz), 7.91 (1H, s), 12.86 (1H, s)

The following compound of Example 374 was synthesized by carrying out reaction according to the method described in Example 372, except for using 1,3-cyclopentanediol as a starting material.

EXAMPLE 374

3-(1H-indazol-5-yloxy)cyclopentanol

Melting point: 147–148° C.

EXAMPLE 375

Synthesis of
2-[4-(1H-indazol-5-yloxy)piperidin-1-yl]ethanol

To a solution of the 5-(piperidin-4-yloxy)-1H-indazole (31 mg, 0.143 mmol) obtained in Example 42 in N,N-dimethylformamide (1 ml) were added 2-bromoethanol (0.0121 ml, 0.171 mmol) and potassium carbonate (49 mg, 0.357 mmol). After 17 hours, 2-bromoethanol (0.0121 ml, 0.171 mmol) was further added thereto. After another 24 hours, the reaction mixture was filtered by the use of Celite and the filtrate was concentrated under reduced pressure. The resulting residue was purified by a silica gel column chromatography (eluent: chloroform/methanol→chloroform/methanol/(1%-aqueous ammonia)) to obtain 2-[4-(1H-indazol-5-yloxy)piperidin-1-yl]ethanol (14 mg, 38%).

$^1$H-NMR (DMSO-$d_6$) δ; 1.62 (2H, m), 1.9 (2H, m), 2.25 (2H, m), 2.39 (2H, t), 2.73 (2H, m), 3.47 (2H, dt), 4.30 (1H, m), 4.36 (1H, t), 7.00 (1H, d), 7.21 (1H, s), 7.49 (1H, d), 7.90 (1H, s), 12.87 (1H, s).

The following compound of Example 376 was synthesized by carrying out reaction according to the method described in Example 372, (b).

EXAMPLE 376 tert-Butyl 3-(1H-indazol-5-yloxy)piperidine-1-carboxylate $^1$H-NMR (DMSO-$d_6$) δ; 1.22–1.37 (10H, m), 1.72 (2H, m), 1.92 (1H, m), 3.32 (2H, m), 3.55 (2H, m), 5.32 (1H, m), 7.00 (1H, dd, J=2.3, 9.0 Hz), 7.22 (1H, d, J=2.3 Hz), 7.42 (1H, d, J=9.0 Hz), 7.91 (1H, s), 12.89 (1H, brs).

EXAMPLE 377

Synthesis of 5-(piperidin-3-yloxy)-1H-indazole

To a solution of the tert-butyl 3-(1H-indazol-5-yloxy)piperidine-1-carboxylate (150 mg, 0.473 mmol) obtained in Example 376 in methanol (2 ml) was added a 4N-hydrochloric acid-dioxane solution (1 ml) at room temperature. After 3 hours, the mixture thus obtained was concentrated under reduced pressure, and the resulting residue was dissolved in methanol. The resulting solution was adjusted to pH 8 to 9 with a 2M-aqueous sodium hydroxide solution and concentrated under reduced pressure. The residue was purified by a silica gel column chromatography (eluent: chloroform/methanol/chloroform/methanol/(1%-aqueous ammonia)) to obtain 5-(piperidin-3-yloxy)-1H-indazole (104 mg, 65%).

$^1$H-NMR (DMSO-$d_6$) δ; 1.55 (2H, m), 1.74 (1H, m), 1.98 (1H, m), 2.70 (2H, m), 2.85 (1H, m), 3.16 (1H, m), 4.34 (1H, m), 7.04 (1H, dd, J=2.2, 9.0 Hz), 7.25 (1H, d, J=2.2 Hz), 7.42 (1H, d, J=9.0 Hz), 7.92 (1H, s), 12.92 (1H, s).

The following compound of Example 378 was synthesized by carrying out reactions according to the methods described in Example 372, (b) and Example 377, except for using tert-butyl 3-hydroxypyrrolidine-1-carboxylate as a reagent.

EXAMPLE 378

5-(Pyrrolidin-3-yloxy)-1H-indazole $^1$H-NMR (DMSO-$d_6$) δ; 2.08 (2H, m), 3.17–3.38 (5H, m), 5.04 (1H, m), 7.02 (1H, dd, J=2.2, 9.0 Hz), 7.23 (1H, d, J=2.2 Hz), 7.45 (1H, d, J=9.0 Hz), 7.95 (1H, s), 12.97 (1H, s).

The following compound of Example 379 was synthesized by carrying out reactions according to the methods described in Example 372, (b) and Example 377 except for using the tert-butyl 4-hydroxyazepane-1-carboxylate obtained in Example 322, (c), as a reagent.

EXAMPLE 379

5-(Azepan-4-yloxy)-1H-indazole

Melting point: 159–160° C.

The following compound of Example 380 was synthesized by carrying out reaction according to the method described in Example 372, (b), except for using the trans-2-(4-hydroxycyclohexyl)-1H-isoindole-1,3(2H)-dione obtained in Example 323, (a), as a starting material.

EXAMPLE 380 cis-2-[4-(1H-indazol-5-yloxy)cyclohexyl]-1H-isoindole-1,3(2H)-dione

Melting point: 194–196° C.

EXAMPLE 381

Synthesis of cis-4-(1H-indazol-5-yloxy)cyclo-hexanamine

A 30%-methylamine-ethanolamine solution (1.0 ml) was added to the cis-2-[4-(1H-indazol-5-yloxy)cyclohexyl]-1H-isoindole-1,3(2H)-dione (100 mg, 0.277 mmol) obtained in Example 380. After 22 hours, the mixture thus obtained was poured into water (20 ml) and extracted with ethyl acetate (20 ml×2), and the organic layer was dried over anhydrous magnesium sulfate. The organic layer dried was concentrated under reduced pressure, and the resulting residue was purified by a silica gel column chromatography (eluent: chloroform/methanol→chloroform/methanol/(1%-aqueous ammonia)) to obtain cis-4-(1H-indazol-5-yloxy)cyclo-hexanamine (36 mg, 57%).

Melting point: 144–146° C.

The following compound of Example 382 was synthesized by carrying out reaction according to the method described in Example 372, (b), except for using the cis-2-(3-hydroxycyclohexyl)-1H-isoindole-1,3(2H)-dione obtained in Example 326, (d), as a reagent.

EXAMPLE 382 trans-2-[3-(1H-indazol-5-yloxy)cyclohexyl]-1H-isoindole-1,3(2H)-dione

Melting point: 197–198° C.

The following compound of Example 383 was synthesized by carrying out reaction according to the method described in Example 381, except for using the cis-2-[3-(1H-indazol-5-yloxy)cyclohexyl]-1H-isoindole-1,3(2H)-dione synthesized in Example 382, as a starting material.

EXAMPLE 383 trans-3-(1H-indazol-5-yloxy)cyclohexanamine

Melting point: 179–180° C.

The following compound of Example 384 was synthesized by carrying out reactions according to the methods described in Example 372, (b) and Example 381, except for using the cis-2-(4-hydroxycyclohexyl)-1H-isoindole-1,3(2H)-dione obtained in Example 323, (c), as a starting material.

EXAMPLE 384 trans-4-(1H-indazol-5-yloxy)cyclohexanamine $^1$H-NMR (DMSO-$d_6$) δ; 1.16 (2H, m), 1.34 (2H, m), 1.69 (2H, brs), 1.76 (2H, m), 2.01 (2H, m), 2.64 (1H, m), 4.19 (1H, m), 6.97 (1H, dd, J=2.4, 9.0 Hz), 7.19 (1H, d, J=2.4 Hz), 7.38 (1H, d, J=9.0 Hz), 7.90 (1H, s), 12.87 (1H, s).

127

EXAMPLE 385

Synthesis of cis-3-(1H-indazol-5-yloxy)cyclo-hexanamine (a) Synthesis of trans-3-(1,3-dioxo-1,3-dihydro-2H-isoindol-2-yl)cyclohexyl 4-nitrobenzoate Except for using the cis-2-(3-hydroxycyclohexyl)-1H-isoindole-1,3(2H)-dione obtained in Example 326, (d), trans-3-(1,3-dioxo-1,3-dihydro-2H-isoindol-2-yl)cyclohexyl 4-nitrobenzoate was obtained by carrying out reaction according to the method described in Example 323, (b).

(b) Synthesis of trans-2-(3-hydroxycyclohexyl)-1H-isoindole-1,3(2H)-dione

Except for using trans-3-(1,3-dioxo-1,3-dihydro-2H-isoindol-2-yl)cyclohexyl 4-nitrobenzoate, trans-2-(3-hydroxycyclohexyl)-1H-isoindole-1,3(2H)-dione was obtained by carrying out reaction according to the method described in Example 323, (c).

(c) Synthesis of cis-3-(1H-indazol-5-yloxy)cyclohexanamine

To a solution of the 1H-indazol-5-ol (200 mg, 1.49 mmol) obtained in Reference Example 4 in tetrahydrofuran (15 ml) were added dropwise trans-2-[3-(1H-indazol-5-yloxy)cyclohexyl]-1H-isoindole-1,3(2H)-dione (366 mg, 1.49 mmol), triphenylphosphine (430 mg, 1.64 mmol) and a 40%-dibenzyl azodicarboxylate-dichloromethane solution (1.03 ml, 1.79 mmol) at 0° C. After 1 hour, the mixture thus obtained was warmed up to room temperature. After stirring overnight, the reaction solution was concentrated under reduced pressure, and the resulting residue was dissolved in chloroform (50 ml) and washed with a 1M-aqueous sodium hydroxide solution (20 ml). Extraction with chloroform (20 ml) was carried out again and the organic layer was dried over anhydrous magnesium sulfate. The organic layer dried was concentrated under reduced pressure and the resulting residue was purified by a silica gel column chromatography (eluent: hexane/ethyl acetate) to obtain a mixture. To this mixture was added 30%-methylamine/ethanol (6 ml) under a nitrogen atmosphere at room temperature, after 15 minutes, then the resulting mixture was refluxed. After 3 hours, the reaction mixture was concentrated under reduced pressure at room temperature and the resulting residue was purified by a silica gel column chromatography (eluent: chloroform/methanol→chloroform/methanol/(1% aqueous ammonia)) to obtain cis-3-(1H-indazol-5-yloxy)cyclohexanamine (98 mg, 29%).

$^1$H-NMR (DMSO-$d_6$) δ; 0.92–1.32 (4H, m), 1.45 (2H, s), 1.68 (2H, m), 2.04 (1H, m), 2.17 (1H, m), 2.63 (1H, m), 4.20 (1H, m), 6.98 (1H, dd, J=2.4, 9.0 Hz), 7.19 (1H, d, J=2.4 Hz), 7.39 (1H, d, J=9.0 Hz), 7.90 (1H, s), 12.87 (1H, s).

The following compounds of Example 386 and Example 387 were synthesized by carrying out reaction according to the method described in Example 140, except for using the trans-4-(1H-indazol-5-yloxy)cyclohexanamine obtained in Example 384, as a starting material.

128

EXAMPLE 386 trans-N-butyl-4-(1H-indazol-5-yloxy)cyclohexanamine

MS: m/z=288 (M+1)

EXAMPLE 387 trans-4-(1H-indazol-5-yloxy)-N-isopropylcyclohexanamine

MS: m/z=274 (M+1)

EXAMPLE 388 trans-N-cyclopentyl-4-(1H-indazol-5-yloxy)cyclohexanamine

MS: m/z=300 (M+1)

EXAMPLE 389

Synthesis of trans-4-(1H-indazol-5-yloxy)-N,N-dimethylcyclohexanamine monohydrochloride Acetic acid (0.05 ml, 0.87 mmol) was added to a solution of the trans-4-(1H-indazol-5-yloxy)cyclohexanamine (0.044 g, 0.19 mmol) obtained in Example 384 and paraformaldehyde (0.040 g, 1.33 mmol) in methanol (4 ml), and the resulting mixture was stirred for 15 minutes and then ice-cooled. Sodium cyanoborohydride (0.055 g, 0.87 mmol) was added thereto and the resulting mixture was slowly warmed up to room temperature and stirred overnight. After a 1N-aqueous sodium hydroxide solution was added thereto, the solvent was distilled off under reduced pressure and the residue was dried up and then purified by a silica gel chromatography (eluent: chloroform/methanol/30%-aqueous ammonia=300/10/3). A solution of the purified residue in ethyl acetate was prepared, followed by adding thereto a 1N-hydrochloric acid-diethyl ether solution (0.5 ml). The solid precipitated was subjected to decantation with ethyl acetate (three times) and then dried up to obtain trans-4-(1H-indazol-5-yloxy)-N,N-dimethylcyclohexanamine monohydrochloride (0.0400 g, 86%).

MS: m/z=260 (M+1)

The following compound of Example 390 was synthesized by carrying out reaction according to the method described in Example 389.

EXAMPLE 390 trans-4-(1H-indazol-5-yloxy)-N-propylcyclohexanamine monohydrochloride

MS: m/z=274 (M+1)

EXAMPLE 391

Synthesis of trans-N-[4-(1H-indazol-5-yloxy)cyclohexyl]acetamide

Acetic acid (0.033 g, 0.58 mmol), triethylamine (0.12 ml, 0.86 mmol), 1-hydroxybenztriazole (0.088 g, 0.65 mmol) and 1-ethyl-3-(3'-dimethylaminopropyl)carbodiimide monohydrochloride (0.124 g, 0.65 mmol) were added to a solution of the trans-4-(1H-indazol-5-yloxy)cyclohexanamine (0.100 g, 0.44 mmol) obtained in Example 384 in N,N-dimethylformamide (5 ml) and stirred overnight. A 2N-aqueous lithium hydroxide solution (2 ml) was added thereto and stirred for some time, and the resulting mixture was added to water and extracted three times with toluene/ethyl acetate=1/1. The organic layer was washed with water and a saturated aqueous sodium chloride solution and dried over anhydrous sodium sulfate. The solvent was distilled off under reduced pressure and the solid precipitated was suspended in a hexane/ethyl acetate mixed solvent and stirred to be washed. The solid was collected by filtration and dried under reduced pressure to obtain trans-N-[4-(1H-indazol-5-yloxy)cyclohexyl]acetamide (0.097 g, 82%).

MS: m/z=274 (M+1)

EXAMPLE 392

Synthesis of trans-N-ethyl-4-(1H-indazol-5-yloxy)cyclohexanamine monohydrochloride The trans-N-[4-(1H-indazol-5-yloxy)cyclohexyl]acetamide (0.066 g, 0.24 mmol) obtained in Example 391 was added to a suspension of lithium aluminum hydride (0.040 g, 1.05 mmol) in tetrahydrofuran (5 ml) and stirred for 12 hours with heating under reflux. The resulting solution was cooled on an ice bath, followed by adding dropwise thereto water (0.05 ml), a 2N-aqueous sodium hydroxide solution (0.10 ml) and water (0.15 ml) in that order. Thereafter, the insoluble material was removed by filtration using Celite. The filtrate was purified by a silica gel chromatography (eluent: chloroform/methanol/30%-aqueous ammonia=10/1/0 to 100/10/1). A solution of the purified material in ethyl acetate was prepared and a 1N-hydrochloric acid/diethyl ether solution (0.5 ml) was added thereto. The solid precipitated was subjected to decantation with ethyl acetate and dried up to obtain trans-N-ethyl-4-(1H-indazol-5-yloxy)cyclohexanamine monohydrochloride (0.057 g, 80%).

MS: m/z=260 (M+1)

The following compounds of Example 393 to Example 397 were synthesized by carrying out reaction according to the method described in Example 140, except for using the trans-3-(1H-indazol-5-yloxy)cyclohexanamine obtained in Example 383, as a starting material.

EXAMPLE 393 trans-3-(1H-indazol-5-yloxy)-N,N-dimethylcyclohexanamine

Melting point: 134–135° C.

EXAMPLE 394 trans-3-(1H-indazol-5-yloxy)-N-propylcyclohexanamine

MS: m/z=274 (M+1)

EXAMPLE 395 trans-N-butyl-3-(1H-indazol-5-yloxy)cyclohexanamine

MS: m/z=288 (M+1)

EXAMPLE 396 trans-3-(1H-indazol-5-yloxy)-N-isopropylcyclohexanamine

MS: m/z=274 (M+1)

EXAMPLE 397 trans-N-cyclopentyl-3-(1H-indazol-5-yloxy)cyclohexanamine

MS: m/z=300 (M+1)

The following compound of Example 398 was synthesized by carrying out reaction according to the method described in Example 391, except for using the trans-3-(1H-indazol-5-yloxy)cyclohexanamine obtained in Example 383, as a starting material.

EXAMPLE 398 trans-N-[3-(1H-indazol-5-yloxy)cyclohexyl]-acetamide

MS: m/z=274 (M+1)

EXAMPLE 399

Synthesis of trans-N-ethyl-3-(1H-indazol-5-yloxy)cyclohexanamine

The trans-N-[3-(1H-indazol-5-yloxy)cyclohexyl]-acetamide (0.077 g, 0.28 mmol) obtained in Example 398 was added to a suspension of lithium aluminum hydride (0.040 g, 1.05 mmol) in tetrahydrofuran (5 ml) and stirred for 12 hours with heating under reflux. The resulting solution was cooled on an ice bath, followed by adding dropwise thereto water (0.05 ml), a 2N-aqueous sodium hydroxide solution (0.10 ml) and water (0.15 ml) in that order. Thereafter, the insoluble material was removed by filtration using Celite. The filtrate was purified by a silica gel chromatography (eluent: chloroform/methanol/30%-aqueous ammonia=10/1/0 to 100/10/1) to obtain trans-N-ethyl-3-(1H-indazol-5-yloxy)cyclohexanamine (0.060 g, 83%).

Melting point: 116–118° C.

EXAMPLE 400

Synthesis of trans-N,N-diethyl-3-(1H-indazol-5-yloxy)cyclohexanamine monohydrochloride (a) Synthesis of trans-N-ethyl-N-[3-(1H-indazol-5-yloxy)cyclohexyl]acetamide The title compound was synthesized by carrying out reaction according to the method described in Example 391, except for using the trans-N-ethyl-3-(1H-indazol-5-yloxy)cyclohexanamine obtained in Example 399, as a starting material.

(b) Synthesis of trans-N,N-diethyl-3-(1H-indazol-5-yloxy)cyclohexanamine monohydrochloride Except for using trans-N-ethyl-N-[3-(1H-indazol-5-yloxy)cyclohexyl]acetamide, trans-N,N-diethyl-3-(1H-indazol-5-yloxy)cyclohexanamine monohydrochloride was obtained by carrying out reaction according to the method described in Example 392.

MS: m/z=288 (M+1)

EXAMPLE 401

Synthesis of 5-methoxy-4-methyl-1H-indazole (a) Synthesis of N-(4-methoxy-2,3-dimethylphenyl)acetamide To a solution of 2,3-dimethyl-4-nitroanisole (1.04 g, 5.74 mmol) in methanol (20 ml) was added 10%-Pd/C (100 mg) at room temperature, and the resulting solution was stirred under a hydrogen atmosphere. After 1 hour, the reaction solution was filtered by the use of Celite and the filtrate was concentrated under reduced pressure and then dried. The residue was dissolved in ethyl acetate (10 ml), followed by adding thereto acetic anhydride (0.867 ml, 9.18 mmol), and the resulting mixture was refluxed. After 2 hours, hexane (70 ml) was poured into the reaction solution and the crystals formed were filtered under reduced pressure and then dried to obtain N-(4-methoxy-2,3-dimethylphenyl)acetamide (1.02 g, 92%).

(b) Synthesis of 5-methoxy-4-methyl-1H-indazole

Acetic anhydride (1.46 ml, 15.52 mmol), tetrabutylammonium bromide (83 mg, 0.259 mmol), potassium acetate (1.02 g, 10.35 mmol) and isoamyl nitrite (0.904 ml, 6.73 mmol) were added to a solution of N-(4-methoxy-2,3-dimethylphenyl)acetamide (1.0 g, 5.175 mmol) in ethyl acetate (10 ml) at room temperature, and the resulting mixture was refluxed. After 6 hours, the ethyl acetate was distilled off with heating, and a 6M-aqueous sodium hydroxide solution (10.35 ml, 62.1 mmol) was added dropwise to the residue at 60° C. After 1 hour, the reaction solution was adjusted to pH 8 to 9 with a 3M-aqueous hydrochloric acid solution and extracted with chloroform (50 ml×2), and the organic layer was dried over anhydrous magnesium sulfate. The organic layer dried was concentrated under reduced pressure and the resulting residue was purified by a silica gel column chromatography (eluent: hexane/ethyl acetate) to obtain 5-methoxy-4-methyl-1H-indazole (456 mg, 54%).

Melting point: 148–149° C.

EXAMPLE 402

Synthesis of 4-methyl-1H-indazol-5-ol

A solution of boron tribromide (0.513 ml, 5.43 mmol) in dichloromethane (5 ml) was added dropwise to a solution of the 5-methoxy-4-methyl-1H-indazole (400 mg, 2.47 mmol) obtained in Example 401 in dichloromethane (5 ml) at 0° C. After 1 hour, the reaction solution was poured onto ice (50 ml), adjusted to pH 4 to 5 with a saturated aqueous sodium hydrogencarbonate solution, and then extracted with chloroform (20 ml×2) and ethyl acetate (20 ml×2), and the organic layer was dried over anhydrous magnesium sulfate. The organic layer dried was concentrated under reduced pressure and the resulting residue was purified by a silica gel column chromatography (eluent: chloroform/ethyl acetate) to obtain 4-methyl-1H-indazol-5-ol (149 mg, 41%).

$^1$H-NMR (DMSO-$d_6$) δ; 2.31 (3H, s), 6.93 (1H, d, J=8.8 Hz), 7.13 (1H, d, J=8.8 Hz), 7.90 (1H, s), 8.72 (1H, s), 12.68 (1H, s).

EXAMPLE 403

Synthesis of 6-methyl-1H-indazol-5-ol (a) Synthesis of 4-(acetylamino)-2,5-dimethylphenyl acetate Acetic anhydride (0.894 ml, 9.48 mmol) and pyridine (1 ml) were added to a solution of 2,5-dimethy-4-aminophenol (500 mg, 3.64 mmol) in ethyl acetate (5 ml), and the resulting mixture was refluxed. After 1 hour, hexane (50 ml) was poured into the reaction solution and the crystals formed were filtered under reduced pressure and then dried to obtain 4-(acetylamino)-2,5-dimethylphenyl acetate (763 mg, 95%).

(b) Synthesis of 1-acetyl-6-methyl-1H-indazol-5-yl acetate

Acetic anhydride (0.96 ml, 10.2 mmol), tetrabutylammonium bromide (55 mg, 0.169 mmol), potassium acetate (665 mg, 6.78 mmol) and isoamyl nitrite (0.592 ml, 4.41 mmol) were added to a solution of 4-(acetylamino)-2,5-dimethylphenyl acetate (750 mg, 3.39 mmol) in ethyl acetate (7.5 ml) at room temperature, and the resulting mixture was refluxed. After 9 hours, the reaction solution was poured into water (50 ml) and extracted with ethyl acetate (50 ml×2), and the organic layer was dried over anhydrous magnesium sulfate. The organic layer dried was concentrated under reduced pressure and the resulting residue was purified by a silica gel column chromatography (eluent: hexane/ethyl acetate) to obtain 1-acetyl-6-methyl-1H-indazol-5-yl acetate (359 mg, 46%).

(c) Synthesis of 6-methyl-1H-indazol-5-ol

A 2M-aqueous lithium hydroxide solution (1.46 ml, 2.93 mmol) was added dropwise to a solution of 1-acetyl-6-methyl-1H-indazol-5-yl acetate (340 mg, 1.46 mmol) in a mixture of methanol (2.0 ml) and tetrahydrofuran (1.0 ml) at room temperature. After 1 hour, the reaction mixture was adjusted to pH 4 with a 0.5M-aqueous potassium hydrogensulfate solution. The resulting solution was poured into water (50 ml) and extracted with ethyl acetate (30 ml×3), and the extract solution was dried over anhydrous magnesium sulfate. The extract solution dried was concentrated under reduced pressure and the resulting residue was purified by a silica gel column chromatography (eluent: hexane/ethyl acetate) to obtain 6-methyl-1H-indazol-5-ol (199 mg, 92%).

$^1$H-NMR (DMSO-$d_6$) δ; 2.22 (3H, s), 6.95 (1H, s), 7.20 (1H, s), 7.76 (1H, s), 9.05 (1H, s), 12.57 (1H, brs).

The following compound of Example 404 was synthesized by carrying out reactions according to the methods described in Example 372, (b) and Example 377, except for using the 4-methyl-1H-indazol-5-ol synthesized in Example 402, as a starting material.

EXAMPLE 404

Synthesis of 4-methyl-5-(piperidin-4-yloxy)-1H-indazole $^1$H-NMR (DMSO-$d_6$) δ; 1.78 (2H, m), 2.00 (2H, m), 2.40 (3H, s), 2.89 (2H, m), 3.14 (2H, m), 4.35 (1H, m), 7.15 (1H, d, J=9.0 Hz), 7.28 (1H, d, J=9.0 Hz), 8.03 (1H, s), 12.92 (1H, brs).

The following compound of Example 405 was synthesized by carrying out reactions according to the methods described in Example 372, (b) and Example 377, except for using the 6-methyl-1H-indazol-5-ol synthesized in Example 403, as a starting material.

EXAMPLE 405

Synthesis of
6-methyl-5-(piperidin-4-yloxy)-1H-indazole $^1$H-NMR (DMSO-d$_6$) δ; 1.51 (2H, m), 1.92 (2H, m), 2.26 (3H, s), 2.57 (2H, m), 2.93 (2H, m), 4.38 (1H, m), 7.16 (1H, s), 7.28 (1H, s), 7.84 (1H, s), 12.70 (1H, brs)

The following compound of Example 406 was synthesized by carrying out reactions according to the methods described in Example 372, (b) and Example 377, except for using the 6-methyl-1H-indazol-5-ol synthesized in Example 403, as a starting material.

EXAMPLE 406

Synthesis of
6-methyl-5-(piperidin-3-yloxy)-1H-indazole $^1$H-NMR (DMSO-d$_6$) δ; 1.45 (2H, m), 1.68 (1H, m), 2.04 (1H, m), 2.25 (3H, s), 2.59 (2H, m), 3.10 (1H, m), 4.20 (1H, m), 7.17 (1H, s), 7.28 (1H, s), 7.85 (1H, s), 12.71 (1H, s).

The following compound of Example 407 was synthesized by carrying out reactions according to the methods described in Example 372, (b) and Example 377, except for using the 4-methyl-1H-indazol-5-ol synthesized in Example 402, as a starting material.

EXAMPLE 407

Synthesis of
5-(azepin-4-yloxy)-4-methyl-1H-indazole

Melting point: 157–159° C.

The following compound of Example 408 was synthesized by carrying out reaction according to the method described in Example 385, except for using the cis-2-(4-hydroxycyclohexyl)-1H-isoindole-1,3(2H)-dione obtained in Example 323, (c) and the 4-methyl-1H-indazol-5-ol obtained in Example 402, as starting materials.

EXAMPLE 408 trans-4-[(4-Methyl-1H-indazol-5-yl)oxy]cyclohexanamine

Melting point: 150–152° C.

The following compound of Example 409 was synthesized by carrying out reaction according to the method described in Example 385, except for using the cis-2-[3-(1H-indazol-5-yloxy)cyclohexyl]-1H-isoindole-1,3(2H)-dione obtained in Example 326, (d) and the 4-methyl-1H-indazol-5-ol obtained in Example 402, as starting materials.

EXAMPLE 409 trans-3-[(4-Methyl-1H-indazol-5-yl)oxy]cyclohexanamine

Melting point: 156–160° C.

The following compound of Example 410 was synthesized by carrying out reactions according to the methods described in Example 385 and Example 327, except for using the trans-2-(4-hydroxycyclohexyl)-1H-isoindole-1,3 (2H)-dione obtained in Example 323, (a) and the 4-methyl-1H-indazol-5-ol obtained in Example 402, as starting materials.

EXAMPLE 410 cis-4-[(4-Methyl-1H-indazol-5-yl)oxy]cyclohexanamine hydrochloride $^1$H-NMR (DMSO-d$_6$) δ; 1.64 (2H, m), 1.75 (4H, m), 1.92 (2H, m), 2.44 (3H, s), 3.09 (1H, m), 4.44 (1H, m), 7.13 (1H, d, J=9.0 Hz), 7.27 (1H, d, J=9.0 Hz), 7.91 (3H, brs), 8.02 (1H, s).

The following compound of Example 411 was synthesized by carrying out reaction according to the method described in Example 385, except for using the trans-2-[3-(1H-indazol-5-yloxy)cyclohexyl]-1H-isoindole-1,3(2H)-dione obtained in Example 385, (b) and the 4-methyl-1H-indazol-5-ol obtained in Example 402, as starting materials.

EXAMPLE 411 cis-3-[(4-Methyl-1H-indazol-5-yl)oxy]cyclohexanamine $^1$H-NMR (DMSO-d$_6$) δ; 0.90 (1H, m), 1.04–1.29 (3H, m), 1.46 (2H, s), 1.66 (2H, m), 1.98 (1H, m), 2.09 (1H, m), 2.50 (1H, m), 3.99 (1H, m), 7.11 (1H, d, J=9.0 Hz), 7.25 (1H, d, J=9.0 Hz), 8.00 (1H, s), 12.86 (1H, s).

The following compounds of Examples 412 to 415 were synthesized by carrying out reaction according to the method described in Example 140, except for using the trans-4-[(4-methyl-1H-indazol-5-yl)oxy]cyclohexanamine obtained in Example 408, as a starting material.

EXAMPLE 412 trans-N,N-dimethyl-4-[(4-methyl-1H-indazol-5-yl)oxy]cyclohexanamine

MS: m/z=274 (M+1)

EXAMPLE 413 trans-N-{4-[(4-methyl-1H-indazol-5-yl)oxy]cyclohexyl}-N-propylamine

MS: m/z=288 (M+1)

EXAMPLE 414 trans-N-isopropyl-4-[(4-methyl-1H-indazol-5-yl)oxy]cyclohexanamine

MS: m/z=288 (M+1)

EXAMPLE 415 trans-N-cyclopentyl-4-[(4-methyl-1H-indazol-5-yl)oxy]cyclohexanamine

MS: m/z=314 (M+1)

The following compound of Example 416 was synthesized by carrying out reaction according to the method described in Example 390, except for using the trans-4-[(4-methyl-1H-indazol-5-yl)oxy]cyclohexanamine obtained in Example 408, as a starting material.

EXAMPLE 416 trans-N-butyl-4-[(4-methyl-1H-indazol-5-yl)oxy]cyclohexanamine monohydrochloride MS: m/z=302 (M+1)

The following compound of Example 417 was synthesized by carrying out reaction according to the method described in Example 391, except for using the trans-4-[(4-methyl-1H-indazol-5-yl)oxy]cyclohexanamine obtained in Example 408, as a starting material.

EXAMPLE 417 trans-N-{4-[(4-methyl-1H-indazol-5-yl)oxy]cyclohexyl}acetamide

MS: m/z=288 (M+1)

The following compound of Example 418 was synthesized by carrying out reaction according to the method described in Example 399, except for using the trans-N-{4-[(4-methyl-1H-indazol-5-yl)oxy]cyclohexyl}acetamide obtained in Example 417, as a starting material.

EXAMPLE 418 trans-N-ethyl-4-[(4-methyl-1H-indazol-5-yl)oxy]cyclohexanamine

Melting point: 150–151° C.

EXAMPLE 419

Synthesis of trans-N,N-diethyl-4-[(4-methyl-1H-indazol-5-yl)oxy]cyclohexanamine

Synthesis of trans-N-ethyl-N-{4-[(4-methyl-1H-indazol-5-yl)oxy]cyclohexyl}acetamide The title compound was synthesized by carrying out reaction according to the method described in Example 391, except for using the trans-N-ethyl-4-[(4-methyl-1H-indazol-5-yl)oxy]cyclohexanamine obtained in Example 418, as a starting material.

(b) Synthesis of trans-N,N-diethyl-4-[(4-methyl-1H-indazol-5-yl)oxy]cyclohexanamine Except for using trans-N-ethyl-4-[(4-methyl-1H-indazol-5-yl)oxy]cyclohexanamine as a starting material, trans-N,N-diethyl-4-[(4-methyl-1H-indazol-5-yl)oxy]cyclohexanamine was obtained by carrying out reaction according to the method described in Example 399.

MS: m/z=302 (M+1)

The following compound of Example 420 was synthesized by carrying out reaction according to the method described in Example 140, except for using the trans-3-[(4-methyl-1H-indazol-5-yl)oxy]cyclohexanamine obtained in Example 409, as a starting material.

EXAMPLE 420 trans-N-isopropyl-3-[(4-methyl-1H-indazol-5-yl)oxy]cyclohexanamine

MS: m/z=287 (M+1)

The following compound of Example 421 was synthesized by carrying out reaction according to the method described in Example 390, except for using the trans-3-[(4-methyl-1H-indazol-5-yl)oxy]cyclohexanamine obtained in Example 409, as a starting material.

EXAMPLE 421 trans-N,N-diethyl-3-[(4-methyl-1H-indazol-5-yl)oxy]cyclohexanamine monohydrochloride MS: m/z=302 (M+1)

EXAMPLE 422

Synthesis of 4-methyl-5-(piperidin-3-yloxy)-1H-indazole (a) Synthesis of t-butyl 3-[(4-methyl-1H-indazol-5-yl)oxy]piperidine-1-carboxylate A solution of dibenzyl dicarboxylate (10.1 g, 33.9 mmol) in tetrahydrofuran (50 ml) was added dropwise to a mixture of the 5-hydroxy-4-methyl-1H-indazole (4.17 g, 28.1 mmol) obtained in Example 402, t-butyl 3-hydroxypiperidine-1-carboxylate (5.62 g, 27.9 mmol) and tetrahydrofuran (100 ml) under ice-cooling. After 30 minutes, the mixture thus obtained was warmed up to room temperature and stirred for 16 hours. The reaction mixture was concentrated and then a 1N-aqueous sodium hydroxide solution (250 ml) was added thereto, followed by extraction with chloroform (150 ml) (three times). The organic layer was washed with a saturated aqueous sodium chloride solution and dried over magnesium sulfate. The solvent was distilled off under reduced pressure and the resulting residue was purified by a silica gel column chromatography (eluent: hexane/ethyl acetate=3/1 to 2/1) to obtain a crude product t-butyl 3-[(4-methyl-1H-indazol-5-yl)oxy]piperidine-1-carboxylate (a mixture with t-butyl 3-hydroxypiperidine-1-carboxylate, 3.46 g).

(b) Synthesis of 4-methyl-5-(piperidin-3-yloxy)-1H-indazole

A 4N-hydrochloric acid/dioxane solution (15 ml) was added dropwise to a solution of the crude product t-butyl 3-[(4-methyl-1H-indazol-5-yl)oxy]piperidine-1-carboxylate (3.46 g) in methanol (15 ml), and the resulting mixture was stirred at room temperature for 1 hour. The solvent was distilled off, and to the hydrochloride thus obtained was added a 1N-aqueous sodium hydroxide solution (100 ml), followed by extraction with ethyl acetate (60 ml) (twice). The extract solution was dried over magnesium sulfate and distilled under reduced pressure to remove the solvent, and the resulting residue was purified by a silica gel column chromatography (eluent: chloroform/methanol=20/1~chloroform/methanol/triethylamine=20/1/1) to obtain 4-methyl-5-(piperidin-3-yloxy)-1H-indazole (1.51 g, two steps 23%).

Melting point: 183–185° C.

EXAMPLE 423

Synthesis of 4-methyl-5-[(1-methylpiperidin-3-yl)oxy]-1H-indazole

Acetic acid (0.060 ml) was added to a methanolic solution (1.0 ml) of the 4-methyl-5-(piperidin-3-yloxy)-1H-indazole (46 mg, 0.20 mmol) obtained in Example 422, followed by adding thereto paraformaldehyde (30 mg, 1.0 mmol), and the resulting mixture was stirred at room temperature for 2 hours. Then, a solution of sodium cyanoborohydride (63 mg, 1.0 mmol) in methanol (1.0 ml) was added thereto and the resulting mixture was stirred at room temperature for 18 hours. After a 1N-aqueous sodium hydroxide solution (0.8 ml) was added to the reaction solution, the solvent was distilled off under reduced pressure and the resulting residue was purified by a silica gel column chromatography (eluent: hexane/ethyl acetate/triethylamine=5/15/1) to obtain 4-methyl-5-[(1-methylpiperidin-3-yl)oxy]-1H-indazole (34 mg, 70%).

MS: m/z=246 (M+1)

The following compounds of Example 424 to Example 427 were synthesized according to the process described in Example 423.

EXAMPLE 424

4-Methyl-5-[(1-propylpiperidin-3-yl)oxy]-1H-indazole

MS: m/z=274 (M+1)

EXAMPLE 425

5-[(1-Isopropylpiperidin-3-yl)oxy]-4-methyl-1H-indazole

MS: m/z=274 (M+1)

EXAMPLE 426

5-[(1-Cyclopentylpiperidin-3-yl)oxy]-4-methyl-1H-indazole $^1$H-NMR (DMSO-$d_6$) δ; 0.91 (1H, d, J=6.6 Hz), 1.30–1.50 (2H, m), 1.67–1.78 (1H, m), 1.90-1.99 (1H, m), 2.10–2.22 (2H, m), 2.38 (3H, s), 2.53–2.61 (1H, m), 2.61–2.71 (1H, m), 2.82–2.90 (1H, m), 4.02–4.13 (3H, m), 7.10 (2H, d, J=9.0 Hz), (1H, d, J=9.0 Hz), 8.00 (1H, s), 12.86 (1H, s).

EXAMPLE 427

5-[(1-Cyclobutylpiperidin-3-yl)oxy]-4-methyl-1H-indazole

MS: m/z=286 (M+1)

The following compounds of Example 428 to Example 432 were synthesized according to the process described in Example 423, except for using the 5-(piperidin-3-yloxy)-1H-indazole obtained in Example 377, as a starting material.

EXAMPLE 428

5-[(1-Methylpiperidin-3-yl)oxy]-1H-indazole

MS: m/z=232 (M+1)

EXAMPLE 429

5-[(1-Propylpiperidin-3-yl)oxy]-1H-indazole

MS: m/z=260 (M+1)

EXAMPLE 430

5-[(1-Isopropylpiperidin-3-yl)oxy]-1H-indazole $^1$H-NMR (DMSO-$d_6$) δ; 0.91 (6H, d, J=6.6 Hz), 1.20–1.37 (1H, m), 1.37–1.57 (1H, m), 1.64–1.76 (1H, m), 1.96–2.20 (3H, m), 2.58–2.67 (1H, m), 2.67–2.76 (1H, m), 2.90–3.01 (1H, m), 4.20–4.30 (1H, m), 6.97 (1H, dd, J=2.1, 8.8 Hz), 7.20 (1H, d, J=1.9 Hz), 7.41 (1H, d, J=9.0 Hz), 7.91 (1H, s), 12.87 (1H, s).

EXAMPLE 431

5-[(1-Cyclopentylpiperidin-3-yl)oxy]-1H-indazole

MS: m/z=286 (M+1)

EXAMPLE 432

5-[(1-Cyclobutylpiperidin-3-yl)oxy]-1H-indazole

MS: m/z=272 (M+1)

The following compounds of Example 433 to Example 436 were synthesized according to the process described in Example 423, except for using the 4-methyl-5-(piperidin-4-yloxy)-1H-indazole obtained in Example 404, as a starting material.

EXAMPLE 433

4-Methyl-5-[(1-methylpiperidin-4-yl)oxy]-1H-indazole

MS: m/z=246 (M+1)

EXAMPLE 434

4-Methyl-5-[(1-propylpiperidin-4-yl)oxy]-1H-indazole

MS: m/z=274 (M+1)

EXAMPLE 435

5-[(1-Isopropylpiperidin-4-yl)oxy]-4-methyl-1H-indazole

Melting point: 134–136° C.

EXAMPLE 436

5-[(1-Cyclopentylpiperidin-4-yl)oxy]-4-methyl-1H-indazole

Melting point: 140–143° C.

The following compounds of Example 437 to Example 440 were synthesized according to the process described in Example 423, except for using the 5-(azepan-4-yloxy)-1H-indazole obtained in Example 379, as a starting material.

EXAMPLE 437

5-[(1-Methylazepan-4-yl)oxy]-1H-indazole

MS: m/z=246 (M+1)

EXAMPLE 438

5-[(1-Propylazepan-4-yl)oxy]-1H-indazole

MS: m/z=274 (M+1)

EXAMPLE 439

5-[(1-Isopropylazepan-4-yl)oxy]-1H-indazole

MS: m/z=274 (M+1)

EXAMPLE 440

5-[(1-Cyclopentylazepan-4-yl)oxy]-1H-indazole

Melting point: 138–140° C.

The following compounds of Example 441 to Example 444 were synthesized according to the process described in Example 423, except for using the 5-(azepin-4-yloxy)-4-methyl-1H-indazole obtained in Example 407, as a starting material.

EXAMPLE 441

4-Methyl-5-[(1-methylazepan-4-yl)oxy]-4-methyl-1H-indazole

MS: m/z=260 (M+1)

EXAMPLE 442

4-Methyl-5-[(1-propylazepan-4-yl)oxy]-4-methyl-1H-indazole

MS: m/z=288 (M+1)

EXAMPLE 443

5-[(1-Isopropylazepan-4-yl)oxy]-4-methyl-1H-indazole

MS: m/z=288 (M+1)

EXAMPLE 444

5-[(1-Cyclopentylazepan-4-yl)oxy]-4-methyl-1H-indazole

Melting point: 126–131° C.

The following compounds of Example 445 to Example 449 were synthesized according to the process described in Example 423, except for using the cis-4-[(4-methyl-1H-indazol-5-yl)oxy]cyclohexanamine obtained in Example 410, as a starting material.

EXAMPLE 445 cis-N,N-dimethyl-4-[(4-methyl-1H-indazol-5-yl)oxy]cyclohexanamine

MS: m/z=274 (M+1)

EXAMPLE 446 cis-N-{4-[(4-methyl-1H-indazol-5-yl)oxy]cyclohexyl}-N-propylamine

MS: m/z=288 (M+1)

EXAMPLE 447 cis-N-butyl-4-[(4-methyl-1H-indazol-5-yl)oxy]cyclohexanamine

MS: m/z=302 (M+1)

EXAMPLE 448 cis-N-isopropyl-4-[(4-methyl-1H-indazol-5-yl)oxy]cyclohexanamine

Melting point: 166–168° C.

EXAMPLE 449 cis-N-cyclopentyl-4-[(4-methyl-1H-indazol-5-yl)oxy]cyclohexanamine

Melting point: 153–155° C.

EXAMPLE 450

Synthesis of 2-[3-(1H-indazol-5-yloxy)piperidin-1-yl]ethanol

A mixture of the 5-(piperidin-3-yloxy)-1H-indazole (43 mg, 0.20 mmol) obtained in Example 377, 2-iodoethanol (84 mg, 0.49 mmol), potassium carbonate (70 mg, 0.50 mmol) and N,N-dimethylformamide (1 ml) was stirred at room temperature for 24 hours. The precipitate was removed by filtration and the solvent was distilled off as an azeotrope with toluene. The residue oil was purified by a silica gel column chromatography (eluent: ethyl acetate/triethylamine/ethanol=20/1/1) to obtain 2-[3-(1H-indazol-5-yloxy)piperidin-1-yl]ethanol (17 mg, 32%).

MS: m/z=261 (M+1)

The following compound of Example 451 was synthesized according to the process described in Example 450, except for using the 4-methyl-5-(piperidin-3-yloxy)-1H-indazole obtained in Example 422, as a starting material.

EXAMPLE 451

2-{3-[(4-Methyl-1H-indazol-5-yl)oxy]piperidin-1-yl}ethanol

MS: m/z=276 (M+1)

The following compound of Example 452 was synthesized according to the process described in Example 450, except for using the 4-methyl-5-(piperidin-4-yloxy)-1H-indazole obtained in Example 404, as a starting material.

EXAMPLE 452

2-{4-[(4-Methyl-1H-indazol-5-yl)oxy]piperidin-1-yl}ethanol

MS: m/z=276 (M+1)

The following compound of Example 453 was synthesized according to the process described in Example 450, except for using the 5-(azepan-4-yloxy)-1H-indazole obtained in Example 379, as a starting material.

EXAMPLE 453

2-[4-(1H-indazol-5-yloxy)azepan-1-yl]ethanol

MS: m/z=276 (M+1)

The following compound of Example 454 was synthesized according to the process described in Example 450, except for using the 5-(azepin-4-yloxy)-4-methyl-1H-indazole obtained in Example 407, as a starting material.

EXAMPLE 454

2-{4-[(4-Methyl-1H-indazol-5-yl)oxy]azepan-1-yl}ethanol $^1$H-NMR (DMSO-d$_6$) δ; 1.30–1.60 (1H, m), 1.65–1.85 (3H, m), 1.85–2.06 (2H, m), 2.36 (3H, s), 2.62 (2H, t, J=5.9 Hz), 2.65–2.77 (1H, m), 3.44 (2H, t, J=6.4 Hz), 4.22–4.42 (2H, m), 7.08 (1H, d, J=8.8 Hz), 7.27 (1H, d, J=8.8 Hz), 7.99 (1H, s), 12.85 (1H, s).

EXAMPLE 455

Synthesis of 5-[(1-acetylpiperidin-3-yl)oxy]-4-methyl-1H-indazole

Triethylamine (0.14 ml, 1.0 mmol) was added to a mixture of the 4-methyl-5-(piperidin-3-yloxy)-1H-indazole (92 mg, 0.40 mmol) obtained in Example 422, acetic acid (24 mg, 0.40 mmol), 1-ethyl-3-(3'-dimethylaminopropyl)carbodiimide monohydrochloride (77 mg, 0.40 mmol), 1-hydroxybenzo-triazole (54 mg, 0.40 mmol) and N,N-dimethylformamide (1.5 ml), and the resulting mixture was stirred at room temperature for 19 hours. The mixture was diluted with a mixed solution of ethyl acetate (10 ml)/toluene (10 ml) and washed with water and then a saturated aqueous sodium hydrogencarbonate solution. The mixture washed was dried over potassium carbonate and then concentrated to dryness to obtain 5-[(1-acetylpiperidin-3-yl)oxy]-4-methyl-1H-indazole (84 mg, 76%).

$^1$H-NMR (DMSO-d$_6$) δ; 1.30–1.55 (1H, m), 1.60–2.05 (6H, m), 2.34 (3H, s), 3.10–4.46 (5H, m), 7.10–7.20 (1H, m), 7.29 (1H, t, J=7.9 Hz), 8.01 (1H, s), 12.88 (1H, s).

The following compound of Example 456 was synthesized according to the process described in Example 455, except for using the 5-(piperidin-3-yloxy)-1H-indazole obtained in Example 377, as a starting material.

EXAMPLE 456

5-[(1-Acetylpiperidin-3-yl)oxy]-1H-indazole $^1$H-NMR (DMSO-d$_6$) δ; 1.30–1.58 (1H, m), 1.58–2.07 (6H, m), 2.34 (3H, s), 3.13–4.52 (5H, m), 7.29 (1H, dt, J=2.6, 9.0 Hz), 7.22–7.29 (1H, m), 7.39–7.47 (1H, m), 8.04 (1H, s), 12.91 (1H, s).

The following compound of Example 457 was synthesized according to the process described in Example 455, except for using the 4-methyl-5-(piperidin-4-yloxy)-1H-indazole obtained in Example 404, as a starting material.

EXAMPLE 457

5-[(1-Acetylpiperidin-4-yl)oxy]-4-methyl-1H-indazole

Melting point: 161–163° C.

The following compound of Example 458 was synthesized according to the process described in Example 455, except for using the 5-(azepan-4-yloxy)-1H-indazole obtained in Example 379, as a starting material.

EXAMPLE 458

5-[(1-Acetylazepan-4-yl)oxy]-1H-indazole $^1$H-NMR (CDCl$_3$) δ; 1.60–1.80 (3H, m), 1.80–2.40 (7H, m), 3.44–3.87 (3H, m), 4.43–4.56 (1H, m), 7.02–7.10 (1H, m), 7.10–7.22 (2H, m), 7.97 (1H, s).

The following compound of Example 459 was synthesized according to the process described in Example 455, except for using the 5-(azepin-4-yloxy)-4-methyl-1H-indazole obtained in Example 407, as a starting material.

EXAMPLE 459

5-[(1-Acetylazepan-4-yl)oxy]-4-methyl-1H-indazole $^1$H-NMR (DMSO-d$_6$) δ; 1.70–2.10 (10H, m), 2.37 (3H, s), 3.38–3.53 (3H, m), 4.26–4.42 (1H, m), 7.07–7.19 (1H, m), 7.19–7.31 (1H, m), 8.00 (1H, s), 12.86 (1H, s).

The following compound of Example 460 was synthesized according to the process described in Example 455, except for using the cis-4-[(4-methyl-1H-indazol-5-yl)oxy]cyclohexanamine obtained in Example 410, as a starting material.

EXAMPLE 460 cis-N-{4-[(4-methyl-1H-indazol-5-yl)oxy]cyclohexyl}acetamide $^1$H-NMR (DMSO-d$_6$) δ; 1.50–1.70 (6H, m), 1.70–1.94 (5H, m), 2.43 (3H, s), 3.63 (1H, s), 4.35 (1H, s), 7.10 (1H, d, J=9.2 Hz), 7.27 (1H, d, J=8.8 Hz), 7.94 (1H, s), 8.00 (1H, s), 12.85 (1H, s).

EXAMPLE 461

Synthesis of 5-[(1-ethylpiperidin-3-yl)oxy]-4-methyl-1H-indazole

A mixture of the 5-[(1-acetylpiperidin-3-yl)oxy]-4-methyl-1H-indazole (55.1 mg, 0.202 mmol) obtained in Example 455, lithium aluminum hydride (40 mg, 1.1 mmol) and tetrahydrofuran (2 ml) was stirred at 80° C. for 2.5 hours. The reaction mixture was ice-cooled, followed by adding thereto water (0.04 ml), a 2N-aqueous sodium hydroxide solution (0.08 ml) and water (0.12 ml) in that order. The precipitate was removed by filtration and the solvent was distilled off. Thereafter, the residue oil was purified by a silica gel column chromatography (eluent:

hexane/ethyl acetate/triethylamine=5/15/1) to obtain 5-[(1-ethylpiperidin-3-yl)oxy]-4-methyl-1H-indazole (14 mg, 28%).

MS: m/z=260 (M+1)

The following compound of Example 462 was synthesized according to the process described in Example 461, except for using the 5-[(1-acetylpiperidin-3-yl)oxy]-1H-indazole obtained in Example 456, as a starting material.

EXAMPLE 462

5-[(1-Ethylpiperidin-3-yl)oxy]-1H-indazole $^1$H-NMR (DMSO-$d_6$) δ; 0.89 (3H, t, J=7.2 Hz), 1.26–1.48 (2H, m), 1.62–1.72 (1H, m), 1.84–2.05 (3H, m), 2.27 (2H, q, J=4.2 Hz), 2.33 (3H, s), 2.50–2.60 (1H, m), 2.78–2.87 (1H, m), 4.00–4.10 (1H, m), 7.08 (1H, d, J=8.8 Hz), 7.23 (1H, d, J=9.0 Hz), 7.96 (1H, s), 12.83 (1H, s)

The following compound of Example 463 was synthesized according to the process described in Example 461, except for using the 5-[(1-acetylpiperidin-4-yl)oxy]-4-methyl-1H-indazole obtained in Example 457, as a starting material.

EXAMPLE 463

5-[(1-Ethylpiperidin-4-yl)oxy]-4-methyl-1H-indazole $^1$H-NMR (DMSO-$d_6$) δ; 0.98 (3H, t, J=7.1 Hz), 1.56–1.70 (2H, m), 1.81–1.92 (2H, m), 2.03–2.16 (2H, m), 2.30 (2H, q, J=4.2 Hz), 2.39 (3H, s), 2.62–2.72 (2H, m), 4.08–4.18 (1H, m), 7.11 (1H, d, J=8.8 Hz), 7.27 (1H, d, J=9.2 Hz), 8.00 (1H, s), 12.86 (1H, s).

The following compound of Example 464 was synthesized according to the process described in Example 461, except for using the 5-[(1-acetylazepan-4-yl)oxy]-1H-indazole obtained in Example 458, as a starting material.

EXAMPLE 464

5-[(1-Ethylazepan-4-yl)oxy]-1H-indazole

MS: m/z=260 (M+1)

The following compound of Example 465 was synthesized according to the process described in Example 461, except for using the 5-[(1-acetylazepan-4-yl)oxy]-4-methyl-1H-indazole obtained in Example 459, as a starting material.

EXAMPLE 465

5-[(1-Ethylazepan-4-yl)oxy]-4-methyl-1H-indazole $^1$H-NMR (DMSO-$d_6$) δ; 0.96 (3H, t, J=7.1 Hz), 1.40–1.57 (1H, m), 1.68–1.85 (3H, m), 1.85–2.04 (2H, m), 2.36 (3H, s), 2.40–2.68 (4H, m), 4.34–4.41 (1H, m), 7.08 (1H, d, J=9.1 Hz), 7.27 (1H, d, J=9.5 Hz), 7.99 (1H, s), 12.85 (1H, s).

The following compound of Example 466 was synthesized according to the process described in Example 461, except for using the cis-N-{4-[(4-methyl-1H-indazol-5-yl)oxy]cyclohexyl}acetamide obtained in Example 460, as a starting material.

EXAMPLE 466 cis-N-ethyl-4-[(4-methyl-1H-indazol-5-yl)oxy]cyclohexanamine

MS: m/z=274 (M+1)

EXAMPLE 467

Synthesis of 4-methoxy-1H-indazol-5-yl methanesulfonate (a) Synthesis of 2-methoxy-1-(methoxymethoxy)-4-nitrobenzene N,N-diisopropylethylamine (1.24 ml, 7.09 mmol), chloromethoxymethyl ether (0.494 ml, 6.50 mmol) and tetrabutylammonium bromide (218 mg, 0.591 mmol) were added to a solution of 2-methoxy-4-nitrophenol (1.0 g, 5.91 mmol) in dichloromethane (20 ml) at 0° C. After 1 hour, the mixture thus obtained was warmed up to room temperature. After 15 hours, the mixture was poured into water (50 ml) and extracted with chloroform (50 ml×2), and the organic layer was dried over anhydrous magnesium sulfate. The organic layer dried was concentrated under reduced pressure and the resulting residue was purified by a silica gel column chromatography (eluent: hexane/ethyl acetate) to obtain 2-methoxy-1-(methoxymethoxy)-4-nitrobenzene (1.26 g, 100%).

(b) Synthesis of N-[3-methoxy-4-(methoxymethoxy)phenyl]-2,2-dimethylpropanamide

To a solution of 2-methoxy-1-(methoxymethoxy)-4-nitrobenzene (1.2 g, 5.63 mmol) in ethyl acetate (30 ml) was added 10%-Pd/C (120 mg) at room temperature, and reaction was carried out under a hydrogen atmosphere. After 30 minutes, the mixture thus obtained was filtered by the use of Celite and the filtrate was concentrated under reduced pressure. To a solution of the resulting residue in ethyl acetate (30 ml) were added pyridine (0.546 ml, 6.75 mmol) and pivaloyl chloride (0.763 ml, 6.19 mmol) at 0° C., and the resulting mixture was warmed up to room temperature. After 15 hours, a saturated aqueous sodium hydrogencarbonate solution was added to the reaction solution and the resulting mixture was poured into water (100 ml) and extracted with ethyl acetate (50 ml×2), and the organic layer was dried over anhydrous magnesium sulfate. The organic layer dried was concentrated under reduced pressure and the resulting residue was purified by a silica gel column chromatography (eluent: hexane/ethyl acetate) to obtain N-[3-methoxy-4-(methoxymethoxy)phenyl]-2,2-dimethylpropanamide (1.48 g, 98%).

(c) Synthesis of N-[3-methoxy-4-(methoxymethoxy)-2-methylphenyl]-2,2-dimethylpropanamide To a solution of N-[3-methoxy-4-(methoxymethoxy)phenyl]-2,2-dimethylpropanamide (500 mg, 1.87 mmol) in tetrahydrofuran (10 ml) was added dropwise 1.59M-n-butyllithium (2.94 ml, 4.68 mmol) at −15° C., and the resulting mixture was slowly warmed up to 0° C. After 2 hours, a solution of methyl iodide (0.175 ml, 2.81 mmol) in tetrahydrofuran (0.5 ml) was added dropwise thereto. After 1 hour, the resulting mixture was warmed up to room temperature. After 14 hours, the reaction solution was poured into water (50 ml) and extracted with ethyl acetate (30 ml×3), and the organic layer was dried over anhydrous magnesium sulfate. The organic layer dried was concentrated under reduced pressure and the resulting residue was purified by a silica gel column chromatography (eluent: hexane/ethyl acetate) to obtain N-[3-methoxy-4-(methoxymethoxy)-2-methylphenyl]-2,2-dimethylpropanamide (424 mg, 81%).

(d) Synthesis of 4-[(2,2-dimethylpropanoyl)amino]-2-methoxy-3-methylphenyl Methanesulfonate A 6N aqueous hydrochloric acid solution (0.355 ml, 2.13 mmol) was added dropwise to a solution of N-[3-methoxy-4-(methoxymethoxy)-2-methylphenyl]-2,2-dimethylpropanamide (300 mg, 1.07 mmol) in methanol (3 ml) at room temperature. After 18 hours, the reaction solution was poured into water (30 ml) and extracted with ethyl acetate (30 ml×2), and the ethyl acetate layer was washed with a saturated aqueous sodium chloride solution and then dried over anhydrous magnesium sulfate. The ethyl acetate layer dried was concentrated under reduced pressure, and to a solution of the resulting residue in pyridine (3 ml) was added methanesulfonyl chloride (0.091 ml, 1.17 mmol) at 0° C. The resulting mixture was heated to 60° C. After 2.5 hours, the reaction solution was concentrated under reduced pressure and the resulting residue was poured into water (50 ml) and extracted with ethyl acetate (30 ml×2). The extract solution was dried over anhydrous magnesium sulfate. The extract solution dried was concentrated under reduced pressure and the resulting residue was purified by a silica gel column chromatography (eluent: hexane/ethyl acetate) to obtain 4-[(2,2-dimethylpropanoyl)amino]-2-methoxy-3-methylphenyl methanesulfonate (338 mg, 100%).

(e) Synthesis of 4-(acetylamino)-2-methoxy-3-methylphenyl methanesulfonate

A 20%-aqueous sulfuric acid solution (4 ml) was added dropwise to a solution of 4-[(2,2-dimethylpropanoyl)amino]-2-methoxy-3-methylphenyl methanesulfonate (223 mg, 0.707 mmol) in n-butanol (2 ml) at room temperature, and the resulting mixture was heated to 100° C. After 14 hours, the reaction solution was poured onto ice (50 ml) and adjusted to pH 11 with an aqueous sodium hydroxide solution. The resulting mixture was extracted with ethyl acetate (50 ml×3) and the organic layer was dried over anhydrous magnesium sulfate. The organic layer dried was concentrated under reduced pressure, and to a solution of the resulting residue in ethyl acetate (5 ml) were added pyridine (0.069 ml, 0.848 mmol) and acetic anhydride (0.073 ml, 0.778 mmol) at room temperature. The resulting mixture was heated to 60° C. After 2 hours, the reaction solution was concentrated under reduced pressure and the resulting residue was purified by a silica gel column chromatography (eluent: hexane/ethyl acetate→chloroform/ethyl acetate) to obtain 4-(acetylamino)-2-methoxy-3-methylphenyl methanesulfonate (154 mg, 79%).

(f) Synthesis of 1-acetyl-4-methoxy-1H-indazol-5-yl methanesulfonate

Acetic anhydride (155?l, 1.65 mmol), tetrabutylammonium bromide (8.8 mg, 0.0274 mmol), potassium acetate (108 mg, 1.10 mmol) and isoamyl nitrite (0.096 ml, 0.274 mmol) were added to a solution of 4-(acetylamino)-2-methoxy-3-methylphenyl methanesulfonate (150 mg, 0.549 mmol) in ethyl acetate (1.5 ml) at room temperature. After 8 hours, isoamyl nitrite (0.037 ml, 0.713 mmol) was further added thereto. After another 2 hours, the mixture thus obtained was poured into water (20 ml) and extracted with ethyl acetate (20 ml×2), and the organic layer was dried over anhydrous magnesium sulfate. The organic layer dried was concentrated under reduced pressure and the resulting residue was purified by a silica gel column chromatography (eluent: hexane/ethyl acetate) to obtain 1-acetyl-4-methoxy-1H-indazol-5-yl methanesulfonate (110 mg, 70%).

(g) Synthesis of 4-methoxy-1H-indazol-5-yl methanesulfonate

A 2M-aqueous lithium hydroxide solution (0.352 ml, 0.704 mmol) was added to a solution of 1-acetyl-4-methoxy-1H-indazol-5-yl methanesulfonate (100 mg, 0.352 mmol) in a mixture of tetrahydrofuran (1.0 ml) and methanol (1.0 ml) at room temperature. After 1 hour, the resulting mixture was poured into water (10 ml) and extracted with ethyl acetate (20 ml×2), and the organic layer was dried over anhydrous magnesium sulfate. The organic layer dried was concentrated under reduced pressure and the resulting residue was purified by a silica gel column chromatography (eluent: hexane/ethyl acetate) to obtain 4-methoxy-1H-indazol-5-yl methanesulfonate (80 mg, 94%).

Melting point: 130–131° C.

EXAMPLE 468

Synthesis of 4-chloro-1H-indazol-5-ol

To a solution of the 1H-indazol-5-ol (1.60 g, 0.0119 mol) obtained in Reference Example 4 in tetrahydrofuran (50 ml) was added N-chlorosuccinimide (1.59 g, 0.0119 mol) at room temperature. After 1 hour, the mixture thus obtained was heated to 40° C., and after another 2 hour, the mixture was heated to 50° C. After 5 hours, the reaction solution was poured into water (100 ml) and extracted with ethyl acetate (100 ml×3). The organic layer was dried over anhydrous magnesium sulfate and concentrated under reduced pressure, and the resulting residue was purified by a silica gel column chromatography (eluent: hexane/ethyl acetate) to obtain 4-chloro-1H-indazol-5-ol (1.7365 g, 86%).

$^1$H-NMR (DMSO-$d_6$) δ; 7.09 (1H, d, J=8.8 Hz), 7.33 (1H, d, J=8.8 Hz), 7.90 (1H, s), 9.71 (1H, s), 13.10 (1H, s).

EXAMPLE 469

Synthesis of 4-methoxy-1H-indazol-5-ol (a) Synthesis of 4-methoxy-1H-indazol-5-yl 2-nitrobenzenesulfonate Title compound was synthesized by carrying out reaction according to the method described in Example 467, except for using the N-[3-methoxy-4-(methoxymethoxy)-2-methylphenyl]-2,2-dimethylpropanamide synthesized in Example 467, (c), as a starting material.

(b) Synthesis of 4-methoxy-1H-indazol-5-ol

Cesium carbonate (45 mg, 0.137 mmol) and thiophenol (24 ml, 0.229 mmol) were added to a solution of 4-methoxy-1H-indazol-5-yl 2-nitrobenzenesulfonate (40 mg, 0.115 mmol) in N,N-dimethylformamide (1 ml) at 0° C. After 30 minutes, the reaction solution was poured into water (20 ml) and extracted with ethyl acetate (20 ml×2). The organic layer was dried over anhydrous magnesium sulfate and concentrated under reduced pressure, and the resulting residue was purified by a silica gel column chromatography (eluent: hexane/ethyl acetate) to obtain 4-methoxy-1H-indazol-5-ol (19 mg, 100%).

$^1$H-NMR (DMSO-d$_6$) δ; 3.97 (3H, s), 6.95 (1H, d, J=8.7 Hz), 7.00 (1H, d, J=8.7 Hz), 8.01 (1H, s), 8.57 (1H, s), 12.81 (1H, s).

The following compound of Example 470 was synthesized by carrying out reaction according to the method described in Example 385, except for using the 4-chloro-1H-indazol-5-ol synthesized in Example 468, as a starting material.

EXAMPLE 470 trans-3-[(4-Chloro-1H-indazol-5-yl)oxy]cyclohexanamine

Melting point: 142–144° C.

The following compound of Example 471 was synthesized by carrying out reaction according to the method described in Example 470, except for using the 4-chloro-1H-indazol-5-ol synthesized in Example 468, as a starting material.

EXAMPLE 471 cis-3-[(4-Chloro-1H-indazol-5-yl)oxy]cyclohexanamine $^1$H-NMR (DMSO-d$_6$) δ; 0.92 (1H, m), 1.17 (1H, m), 1.23 (2H, m), 1.70 (2H, m), 1.96 (1H, m), 2.10 (1H, m), 2.53 (1H, m), 4.16 (1H, m), 7.30 (1H, d, J=9.0 Hz), 7.45 (1H, d, J=9.0 Hz), 8.01 (1H, s).

The following compound of Example 472 was synthesized by carrying out reaction according to the method described in Example 470, except for using the 4-chloro-1H-indazol-5-ol synthesized in Example 468, as a starting material.

EXAMPLE 472 trans-4-[(4-chloro-1H-indazol-5-yl)oxy]cyclohexanamine $^1$H-NMR (DMSO-d$_6$) δ; 1.13 (2H, m), 1.42 (2H, m), 1.75 (2H, m), 1.98 (2H, m), 2.62 (1H, m), 4.17 (1H, m), 7.30 (1H, d, J=9.0 Hz), 7.44 (1H, dd, J=0.8, 9.0 Hz), 8.01 (1H, d, J=0.8 Hz).

EXAMPLE 473

Synthesis of 5-methoxy-4-(trifluoromethyl)-1H-indazole (a) Synthesis of 4-methoxy-3-(trifluoromethyl)aniline To a solution of 2-methoxy-5-nitrobenzotrifluoride (5.08 g, 23.0 mmol) in methanol (200 ml) was added 10% Pd—C (containing 50% water, 250 mg), and the resulting mixture was stirred for 3.5 hours under a hydrogen atmosphere at room temperature and atmospheric pressure while maintaining the temperature. The mixture was filtered by the use of Celite and the filtrate was concentrated to dryness under reduced pressure to obtain 4-methoxy-3-(trifluoromethyl) aniline (4.67 g, 100%).

MS: m/z=192 (M+1)

(b) Synthesis of N-[4-methoxy-3-(trifluoromethyl) phenyl]-2,2-dimethylpropanamide Triethylamine (6.24 ml, 44.8 mmol) was added to a solution of 4-methoxy-3-(trifluoromethyl)aniline (4.29 g, 22.4 mmol) in dichloromethane (45.0 ml), and the resulting mixture was ice-cooled, followed by adding dropwise thereto pivaloyl chloride (2.84 g, 23.5 mmol) at 0 to 5° C. The resulting mixture was warmed up to room temperature and stirred for 1 hour while maintaining the temperature. The mixture was partitioned by the use of a 5%-aqueous sodium hydrogencarbonate solution and ethyl acetate, and the organic layer was washed with a 5% aqueous sodium chloride solution, dried over anhydrous sodium sulfate, and then filtered. The filtrate was concentrated under reduced pressure to obtain N-[4-methoxy-3-(trifluoromethyl)phenyl]-2,2-dimethylpropanamide (6.16 g, 100%).

$^1$H-NMR (CDCl$_3$) δ; 1.32 9H, s), 3.89 (3H, s), 6.96 (1H, d, J=8.9 Hz), 7.31 (1H, br s), 7.63 (1H, d, J=2.8 Hz), 7.76 (1H, dd, J=2.8, 8.9 Hz).

(c) Synthesis of N-[4-methoxy-2-methyl-3-(trifluoromethyl)-phenyl]-2,2-dimethylpropanamide A solution of N-[4-methoxy-3-(trifluoromethyl)-phenyl]-2,2-dimethylpropanamide (5.90 g, 21.4 mmol) in tetrahydrofuran (70.0 ml) was cooled to −10 to −15° C., and then a 1.57M n-butyllithium/hexane solution (33.5 ml, 52.5 mmol) was added dropwise thereto over a period of 25 minutes while maintaining the internal temperature at 0° C. or lower. The resulting mixture was slowly warmed up to 20° C. and stirred for 3 hours while maintaining the temperature. The resulting suspension was cooled to −35 to −40° C., and then iodomethane (1.53 ml, 24.6 mmol) was added dropwise thereto over a period of 15 minutes. The resulting mixture was slowly warmed up to −5 to 0° C. and stirred for 1.5 hours while maintaining the temperature. The mixture was partitioned and extracted with water and ethyl acetate, and the organic phase was washed with a 5% aqueous sodium chloride solution, dried over anhydrous magnesium sulfate, and then filtered. The filtrate was concentrated under reduced pressure to obtain a crude product (6.23 g). The crude product was purified by a silica gel column chromatography (eluent: hexane/diisopropyl ether=1/1) to obtain N-[4-methoxy-2-methyl-3-(trifluoromethyl)phenyl]-2,2-dimethylpropanamide (3.20 g, 50%).

$^1$H-NMR (CDCl$_3$) δ; 1.35 (9H, s), 2.31 (3H, q, J=2.9 Hz), 3.86 (3H, s), 6.87 (1H, d, J=9.0 Hz), 7.08 (1H, brs), 7.57 (1H, d, J=9.0 Hz).

(d) Synthesis of 4-methoxy-2-methyl-3-(trifluoromethyl)-aniline

N-[4-methoxy-2-methyl-3-(trifluoromethyl)phenyl]-2,2-dimethylpropanamide (3.15 g, 10.9 mmol) and potassium hydroxide (3.20 g, 57.1 mmol) were slowly heated to 160° C. in ethylene glycol (31.0 ml) and stirred for 20 hours while maintaining the temperature. The reaction solution was portioned and extracted with water and chloroform, and the organic phase was extracted with a 1N aqueous hydrochloric acid solution to obtain an aqueous phase. This aqueous phase was made basic with a 2N aqueous sodium hydroxide solution and extracted three times with chloroform. The combined organic phase was dried over anhydrous magnesium sulfate and filtered, and the filtrate was concentrated under reduced pressure to obtain 4-methoxy-2-methyl-3-(trifluoromethyl)-aniline (1.10 g, 49%).

$^1$H-NMR (CDCl$_3$) δ; 2.25 (3H, q, J=2.4 Hz), 3.79 (3H, s), 6.76 (1H, d, J=8.8 Hz), 6.82 (1H, d, J=8.8 Hz).

(e) Synthesis of 1-acetyl-5-methoxy-4-(trifluoromethyl)-1H-indazole

Acetic anhydride (377 μl, 4.00 mmol) was added dropwise to a solution of 4-methoxy-2-methyl-3-(trifluoromethyl)aniline (513 mg, 2.50 mmol) in ethyl acetate (3.0 ml) at room temperature. Ethyl acetate (4.5 ml) was added to the solidified reaction solution and the resulting mixture was slowly heated to 65° C. and stirred for 15 minutes while maintaining the temperature. The resulting reaction solution was cooled to room temperature, followed by adding thereto acetic anhydride (708 μl, 7.50 mmol), tetrabutylammonium bromide (40.3 mg, 0.125 mmol), potassium acetate (491 mg, 5.00 mmol) and isopentyl nitrite (437 μl, 3.25 mmol) in that order at room temperature. The resulting mixture was slowly heated to 65° C. and stirred for 6 hours while maintaining the temperature. After cooling, the mixture was partitioned and extracted with water and ethyl acetate, and the organic layer was washed with a 5% aqueous sodium chloride solution, dried over anhydrous magnesium sulfate, and then filtered. The filtrate was concentrated under reduced pressure to obtain a crude product (800 mg). The crude product was purified by a silica gel column chromatography (eluent: hexane/ethyl acetate=9/1 to 6/1) to obtain 1-acetyl-5-methoxy-4-(trifluoromethyl)-1H-indazole (496 mg, 77%).

$^1$H-NMR (CDCl$_3$) δ; 2.79 (3H, s), 4.00 3H, s), 7.33 (1H, d, J=9.2 Hz), 8.24 (1H, m), 8.63 (1H, d, J=9.2 Hz).

(f) Synthesis of 5-methoxy-4-(trifluoromethyl)-1H-indazole

A 6N-aqueous sodium hydroxide solution (3.8 ml, 23 mmol) was added dropwise to a solution of 1-acetyl-5-methoxy-4-(trifluoromethyl)-1H-indazole (493 mg, 1.91 mmol) in a mixture of methanol (3.8 ml) and tetrahydrofuran (3.8 ml) at room temperature and stirred at room temperature for 5 hours while maintaining the temperature. The resulting reaction solution was adjusted to pH 8 to 9 by dropwise addition of 12N-aqueous hydrochloric acid solution (1.5 ml) and then a 1N aqueous hydrochloric acid solution (about 2 ml), and distilled under reduced pressure to remove the organic solvent. The white precipitate formed was diluted with water, filtered, washed with water, and then dried under reduced pressure to obtain 5-methoxy-4-(trifluoromethyl)-1H-indazole (400 mg, 97%).

$^1$H-NMR (CDCl$_3$) δ; 3.98 (3H, s), 7.27 (1H, d, J=9.0 Hz), 7.67 (1H, d, J÷9.0 Hz), 8.20 (1H, m).

EXAMPLE 474

Synthesis of 4-(trifluoromethyl)-1H-indazol-5-ol

A suspension of the 5-methoxy-4-(trifluoromethyl)-1H-indazole (395 mg, 1.83 mmol) obtained in Example 473 in dichloromethane (5.0 ml) was cooled to −30 to −40° C., and then a 1M boron tribromide/dichloromethane solution (3.84 ml, 3.84 mmol) was added dropwise thereto over a period of 5 minutes. The resulting mixture was slowly heated from −30° C. to 20° C. and stirred for 5.5 hours while maintaining the temperature. The resulting reaction solution was cooled to 0 to 5° C., poured into ice water, adjusted to pH 5 to 6 with a 5% aqueous sodium hydrogencarbonate solution, and then extracted with chloroform (an insoluble material was present) and then ethyl acetate. Each organic phase was washed with a 5% aqueous sodium chloride solution, dried over anhydrous magnesium sulfate, and then filtered, and the filtrate was concentrated under reduced pressure. A crude product (280 mg) composed mainly of the starting 5-methoxy-4-(trifluoromethyl)-1H-indazole was obtained from the chloroform phase, and a crude product (145 mg) composed mainly of 4-(trifluoromethyl)-1H-indazol-5-ol was obtained from the ethyl acetate phase. The latter crude product was purified by a silica gel column chromatography (eluent: chloroform/ethyl acetate=4/1) to obtain 4-(trifluoromethyl)-1H-indazol-5-ol (95 mg, 26%).

$^1$H-NMR (DMSO-d$_6$) δ; 7.12 (1H, d, J=8.8 Hz), 7.66 (1H, d, J=8.8 Hz), 7.91 (1H, m), 10, 23 (1H, s), 13.25 (1H, brs).

The following compound of Example 475 was synthesized by carrying out reaction according to the method described in Example 407, except for using the 4-(trifluoromethyl)-1H-indazol-5-ol obtained in Example 474, as a starting material.

EXAMPLE 475

5-(Azepan-4-yloxy)-4-(trifluoromethyl)-1H-indazole $^1$H-NMR (CDCl$_3$) δ; 1.57–1.70 (1H, m), 1.85–2.20 (5H, m), 2.86–3.12 (4H, m), 4.72 (1H, m), 7.19 (1H, d, J=9.1 Hz), 7.61 (1H, d, J=9.1 Hz), 8.16 (1H, m).

EXAMPLE 476

Synthesis of 2-(1H-indazol-5-yloxy)aniline

Under a hydrogen atmosphere at atmospheric pressure, a solution of the 5-(2-nitrophenoxy)-1H-indazole (56.7 mg, 0.222 mmol) obtained in Example 352 in a mixture of ethyl acetate (3 ml) and methanol (3 ml) was stirred at room temperature for 1.5 hours. The solution was filtered and then the filtrate was concentrated to obtain 2-(1H-indazol-5-yloxy)aniline (34.5 mg, 69%).

MS: m/z=226 (M+1)

EXAMPLE 477

Synthesis of N-[2-(1H-indazol-5-yloxy)phenyl]acetamide

Acetic anhydride (0.04 ml) was added to a solution of the 2-(1H-indazol-5-yloxy)aniline (34 mg, 0.151 mmol) obtained in Example 476 in pyridine (1 ml) at room temperature, and the resulting mixture was stirred at room temperature for 2 hours. The reaction solution was cooled to 0° C. and a saturated aqueous sodium hydrogencarbonate solution was added thereto, followed by extraction with ethyl acetate. The organic layer was washed with a saturated aqueous sodium chloride solution and then dried over anhydrous sodium sulfate. The solvent was distilled off under reduced pressure and the resulting residue was dissolved in a mixed solution of tetrahydrofuran (1 ml) and methanol (1 ml), followed by adding thereto 1N aqueous sodium hydroxide solution (1 ml). The resulting mixture was stirred at room temperature for 1 hour. The reaction solution was added to a saturated aqueous sodium chloride solution and extracted with chloroform. The organic layer was dried over anhydrous sodium sulfate and distilled under reduced pressure to remove the solvent, and the resulting residue was purified by a silica gel column chromatography (chloroform/methanol) to obtain N-[2-(1H-indazol-5-yloxy)phenyl]acetamide (32 mg, 79%).

$^1$H-NMR (DMSO-d$_6$) δ; 2.05 (3H, s), 6.70–6.79 (1H, m), 6.95–7.10 (3H, m), 7.12 (1H, dd, J=2.0, 9.0 Hz), 7.32 (1H, d, J=2.0 Hz), 7.57 (1H, d, J=9.0 Hz), 7.95–8.05 (2H, m), 9.49 (1H, s), 13.09 (1H, brs)

EXAMPLE 478

Synthesis of methyl 2-(1H-indazol-5-yloxy)benzoate (a) Synthesis of methyl 2-(3-methyl-4-nitrophenoxy)benzoate Potassium carbonate (1.16 g, 8.39 mmol) was added to a solution of 5-fluoro-2-nitrotoluene (1.0 g, 6.45 mmol) and methyl salicylate (1.18 g, 7.74 mmol) in N,N-dimethylformamide (8 ml), and the resulting mixture was stirred at 140° C. for 1 hour. After the reaction, the reaction solution was cooled to 0° C. and a saturated aqueous sodium chloride solution was added thereto, followed by extraction with ethyl acetate. The organic layer was washed with water and a saturated aqueous sodium chloride solution, and dried over anhydrous sodium sulfate. The organic layer dried was concentrated and then purified by a silica gel column chromatography (eluent: hexane/ethyl acetate=10/1) to obtain methyl 2-(3-methyl-4-nitrophenoxy)benzoate (1.88 g, 85%).

$^1$H-NMR (CDCl$_3$) δ; 2.59 (3H, s), 3.78 (3H, s), 6.70–6.82 (2H, m), 7.12 (1H, dd, J=11, 8.0 Hz), 7.35 (1H, ddd, J=1.1, 7.5, 7.5 Hz), 7.56–7.65 (1H, m), 8.02 (1H, dd, J=1.3, 7.5 Hz), 8.05 (1H, d, J=8.0 Hz).

(b) Synthesis of methyl 2-(4-amino-3-methylphenoxy)-benzoate

Under a hydrogen atmosphere at atmospheric pressure, a solution of methyl 2-(3-methyl-4-nitrophenoxy)-benzoate (1.85 g, 6.44 mmol) in a mixture of ethyl acetate (15 ml) and methanol (8 ml) was stirred at room temperature for 5 hours. The solution was filtered and the filtrate was concentrated to obtain methyl 2-(4-amino-3-methylphenoxy)-benzoate (1.52 g, 92%).

$^1$H-NMR (CDCl$_3$) δ; 2.16 (3H, s), 3.87 (3H, s), 6.65–6.82 (3H, m), 6.85 (1H, dd, J=1.1, 8.4 Hz), 7.06 (1H, dd, J=1.1, 7.7 Hz), 7.30–7.40 (1H, m), 7.85 (1H, dd, J=1.7, 7.7 Hz).

(c) Synthesis of methyl 2-(1H-indazol-5-yloxy)benzoate

Methyl 2-(4-amino-3-methylphenoxy)benzoate (500 mg, 1.94 mmol) was suspended in water (5.7 ml), followed by adding thereto concentrated hydrochloric acid (1.0 ml) and ammonium tetrafluoroborate (693 mg) at 0° C. An aqueous sodium nitrite solution (134 mg/1 ml) was added dropwise to the suspension. A saturated aqueous sodium chloride solution was added thereto, followed by extraction with chloroform. The organic layer was dried over anhydrous sodium sulfate and concentrated. The resulting dark-blue oil was dissolved in chloroform (15 ml), and potassium acetate (381 mg, 3.88 mmol) and 18-crown-6 (15 mg) were added thereto at room temperature and then stirred for 2 hours. To the resulting suspension was added a saturated aqueous sodium chloride solution, followed by extraction with chloroform. The organic layer was washed with a saturated aqueous sodium chloride solution and dried over anhydrous sodium sulfate. The organic layer dried was concentrated and then purified by a silica gel column chromatography (chloroform/methanol=70/1) to obtain methyl 2-(1H-indazol-5-yloxy)benzoate (157 mg, two steps 30%).

$^1$H-NMR (CDCl$_3$) δ; 3.85 (3H, s), 6.92 (1H, dd, J=1.0, 8.3 Hz), 7.12–7.28 (3H, m), 7.40–7.52 (2H, m), 7.92 (1H, dd, J=1.8, 7.9 Hz), 8.00 (1H, s).

EXAMPLE 479

Synthesis of 2-(1H-indazol-5-yloxy)benzoic Acid

The methyl 2-(1H-indazol-5-yloxy)benzoate (960 mg, 3.58 mmol) synthesized in Example 478 was dissolved in a mixture of tetrahydrofuran (10 ml) and methanol (5 ml), and a 1N-aqueous sodium hydroxide solution (7 ml) was added thereto at room temperature and then stirred at 60° C. for 40 minutes. After the reaction, the reaction solution was cooled to 0° C., adjusted to pH 4 with a 2N-aqueous hydrochloric acid solution, and then extracted with ethyl acetate. The organic layer was washed with a saturated aqueous sodium chloride solution, dried over anhydrous sodium sulfate, and then concentrated to obtain 2-(1H-indazol-5-yloxy)benzoic acid (790 mg, 86%).

MS: m/z=255 (M+1)

EXAMPLE 480

Synthesis of 2-(1H-indazol-5-yloxy)-N-isobutylbenzamide

The 2-(1H-indazol-5-yloxy)benzoic acid (80.6 mg, 0.317 mmol) synthesized in Example 479 and isobutylamine (301 mg, 0.412 mmol) were dissolved in N,N-dimethylformamide (2 ml), and dimethylamine hydrochloride (72.5 mg, 0.380 mmol), hydroxybenzotriazole (47.1 mg, 0.349 mmol) and triethylamine (0.09 ml, 0.634 mmol) were added thereto at room temperature and then stirred for 2.5 hours. After the reaction, a saturated aqueous sodium hydrogencarbonate solution was added thereto, followed by extraction with chloroform. The organic layer was washed with a saturated aqueous sodium chloride solution, dried over anhydrous sodium sulfate, and then concentrated to obtain 2-(1H-indazol-5-yloxy)-N-isobutylbenzamide (47 mg, 48%) as a brown solid.

$^1$H-NMR (DMSO-d$_6$) δ; 0.80 (6H, d, J=6.8 Hz), 1.60–1.80 (1H, m), 3.06 (2H, t, J=6.3 Hz), 6.79 (1H, d, J=8.3 Hz), 7.10–7.30 (2H, m), 7.30–7.45 (2H, m), 7.50–7.70 (2H, m), 8.02 (1H, s), 8.22 (1H, brs), 13.1 (1H, brs).

EXAMPLE 481

Synthesis of 2-(1H-indazol-5-yloxy)-N,N-dimethylbenzamide

The 2-(1H-indazol-5-yloxy)benzoic acid (80.8 mg, 0.318 mmol) synthesized in Example 479 and dimethylamine hydrochloride (33.7 mg, 0.413 mmol) were dissolved in N,N-dimethylformamide (2 ml), and 1-ethyl-3-(3'-dimethylaminopropyl)carbodiimide monohydrochloride (72.5 mg, 0.380 mmol), hydroxybenzotriazole (47.1 mg, 0.349 mmol) and triethylamine (0.13 ml, 0.954 mmol) were added thereto at room temperature and then stirred for 2.5 hours. After the reaction, a saturated aqueous sodium hydrogencarbonate solution was added thereto, followed by extraction with chloroform. The organic layer was washed with a saturated aqueous sodium chloride solution, dried over anhydrous sodium sulfate, and then concentrated to obtain 2-(1H-indazol-5-yloxy)-N,N-dimethylbenzamide (51 mg, 57%).

$^1$H-NMR (DMSO-d$_6$) δ; 2.93 (3H, s), 2.89 (3H, s), 6.78 (1H, d, J=9.2 Hz), 7.05–7.20 (2H, m), 7.40–7.62 (3H, m), 7.57 (1H, d, J=9.2 Hz), 8.02 (1H, s), 13.1 (1H, brs)

EXAMPLE 482

Synthesis of 3-(1H-indazol-5-yloxy)-N,N-dimethylbenzamide (a) Synthesis of 3-(1H-indazol-5-yloxy)benzoic acid 3-(1H-indazol-5-yloxy)benzoic acid was synthesized by carrying out reaction according to the method described in Example 479, except for using methyl 3-hydroxybenzoate as a starting material.

(b) Synthesis of 3-(1H-indazol-5-yloxy)-N,N-dimethylbenzamide 3-(1H-indazol-5-yloxy)-N,N-dimethylbenzamide was synthesized by carrying out reaction according to the method described in Example 481, except for using 3-(1H-indazol-5-yloxy)benzoic acid as a starting material.

MS: m/z=282 (M+1)

EXAMPLE 483

Synthesis of [2-(1H-indazol-5-yloxy)phenyl]-methanol

The methyl 2-(1H-indazol-5-yloxy)benzoate (95.6 g, 0.36 mmol) obtained in Example 478 was dissolved in tetrahydrofuran (5 ml), and lithium aluminum hydride (44.1 mg, 1.07 mmol) was added thereto at 0° C. and stirred for 30 minutes. Water (0.3 ml), a 2N-aqueous sodium hydroxide solution (0.6 ml) and water (0.9 ml) was added dropwise thereto in that order, and the precipitate formed was removed by filtration. A saturated aqueous sodium hydrogencarbonate solution was added to the filtrate, followed by extraction with ethyl acetate. The organic layer was washed with a saturated aqueous sodium chloride solution, dried over anhydrous sodium sulfate, and then concentrated to obtain [2-(1H-indazol-5-yloxy)phenyl]methanol (56 mg, 65%).

MS: m/z=241 (M+1)

EXAMPLE 484

Synthesis of 1-[2-(1H-indazol-5-yloxy)phenyl]-N, N-dimethylmethanamine monohydrochloride (a) Synthesis of 1-[2-(1H-indazol-5-yloxy)phenyl]-N,N-dimethylmethanamine 1-[2-(1H-indazol-5-yloxy)phenyl]-N,N-dimethylmethanamine was synthesized by carrying out reaction according to the method described in Example 483, except for using the 2-(1H-indazol-5-yloxy)-N,N-dimethylbenzamide obtained in Example 481, as a starting material.

MS: m/z=268 (M+1)

(b) Synthesis of 1-[2-(1H-indazol-5-yloxy)phenyl]-N,N-dimethylmethanamine Monohydrochloride 1-[2-(1H-indazol-5-yloxy)phenyl]-N,N-dimethylmethanamine was dissolved in diethyl ether (2 ml), and a 1N-hydrochloric acid/diethyl ether solution (0.3 ml) was added dropwise thereto at 0° C. The resulting suspension was concentrated to obtain 1-[2-(1H-indazol-5-yloxy)phenyl]-N,N-dimethylmethanamine monohydrochloride (20 mg).

MS: m/z=268 (M+1)

EXAMPLE 485

Synthesis of N-[2-(1H-indazol-5-yloxy)benzyl]-2-methylpropan-1-amine monohydrochloride N-[2-(1H-indazol-5-yloxy)benzyl]-2-methylpropan-1-amine monohydrochloride was synthesized by carrying out reaction according to the method described in Example 484, except for using the 2-(1H-indazol-5-yloxy)-N-isobutylbenzamide obtained in Example 480, as a starting material.

MS: m/z=296 (M+1)

The following compound of Example 486 was synthesized by carrying out reaction according to the method described in Example 403, (a), except for using the 5-(4-piperidinyloxy)-1H-indazole obtained in Example 42, as a starting material.

EXAMPLE 486

5-[(1-Acetylpiperidin-4-yl)oxy]-1H-indazole

MS: m/z=260 (M+1)

The following compound of Example 487 was synthesized by carrying out reaction according to the method described in Example 140, except for using the 5-(4-piperidinyloxy)-1H-indazole obtained in Example 42, as a starting material.

EXAMPLE 487

Synthesis of 5-[(1-methylpiperidin-4-yl)oxy]-1H-indazole

MS: m/z=232 (M+1)

The following compound of Example 488 was synthesized by carrying out reaction according to the method described in Example 399, except for using the 5-[(1-acetylpiperidin-4-yl)oxy]-1H-indazole obtained in Example 486, as a starting material.

EXAMPLE 488

Synthesis of 5-[(1-ethylpiperidin-4-yl)oxy]-1H-indazole

MS: m/z=246 (M+1)

EXAMPLE 489

Synthesis of 5-{[1-(2-methoxyethyl)piperidin-4-yl]oxy}-1H-indazole

To a solution of the 5-(4-piperidinyloxy)-1H-indazole (100 mg, 0.460 mmol) obtained in Example 42 in N,N-dimethylformamide (3 ml) were added (2-bromoethyl)methyl ether (76.8 mg, 0.552 mmol) and potassium carbonate (159 mg, 1.15 mmol), and the resulting mixture was stirred overnight at room temperature. Then, the reaction solution was cooled to 0° C. and a saturated aqueous sodium hydrogencarbonate solution was added thereto, followed by extraction with ethyl acetate. The organic layer was washed with a saturated aqueous sodium chloride solution and then dried over anhydrous sodium sulfate. The solvent was distilled off under reduced pressure and the resulting residue was purified by a silica gel column chromatography (eluent: chloroform/methanol) to obtain 5-{[1-(2-methoxyethyl)piperidin-4-yl]oxy}-1H-indazole (52 mg, 41%).

MS: m/z=276 (M+1)

The following compounds of Example 490 and Example 491 were synthesized by carrying out reaction according to the method described in Example 489.

EXAMPLE 490

5-{[1-(Cyclohexylmethyl)piperidin-4-yl]oxy}-1H-indazole
MS: m/z=314 (M+1)

EXAMPLE 491

5-{[1-(Cyclobutylmethyl)piperidin-4-yl]oxy}-1H-indazole
MS: m/z=286 (M+1)

The following compounds of Example 492 and Example 493 were synthesized by carrying out reaction according to the method described in Example 489, except for using the 1H-indazol-5-ol obtained in Reference Example 4, as a starting material.

EXAMPLE 492
2-(1H-indazol-5-yloxy)nicotinonitrile

MS: m/z=237 (M+1)

EXAMPLE 493 2-(1H-indazol-5-yloxy)benzonitrile

MS: m/z=236 (M+1)

EXAMPLE 494

Synthesis of 5-(8-azabicyclo[3.2.1]oct-3-yloxy)-1H-indazole (a) Synthesis of 8-benzyl-8-azabicyclo[3.2.1]octan-3-ol In tetrahydrofuran (16 ml) was dissolved 8-benzyl-8-azabicyclo[3.2.1]octan-3-one (1.0 g, 4.64 mmol), and a 1M-diisobutylaluminum hydride/toluene solution (11.6 ml, 11.6 mmol) was added dropwise thereto at −78° C. over a period of 10 minutes and stirred for another 1 hour. Water was added dropwise thereto to quench the excess reactants, and the resulting mixture was separated by the addition of a 2N-aqueous hydrochloric acid solution and ethyl acetate. The aqueous layer was adjusted to pH 10 or lower with a 2N-aqueous sodium hydroxide solution and then extracted with ethyl acetate. The organic layer was washed with a saturated aqueous sodium chloride solution, dried over anhydrous sodium sulfate, and then concentrated to obtain 8-benzyl-8-azabicyclo[3.2.1]octan-3-ol (886 mg, 88%).
$^1$H-NMR (CDCl$_3$) δ; 1.50–1.75 (4H, m), 1.78–1.85 (m), 1.95–2.20 (6H, m), 2.14 (2H, br), 3.23 (br), 3.52 (2H, s), 3.61 (2H, s), 3.94 (1H, m), 7.40 (1H, t, J=4.3 Hz), 7.18–7.40 (5H, m).

(b) tert-Butyl 3-hydroxy-8-azabicyclo[3.2.1]octane-8-carboxylate

In ethanol (20 ml) was dissolved 8-benzyl-8-azabicyclo[3.2.1]octan-3-ol (740 mg, 3.41 mmol), followed by adding thereto ammonium formate (740 mg) and 10%-palladium/carbon (148 mg) at room temperature, and the resulting mixture was refluxed for 2 hours. After the mixture was filtered, the filtrate was concentrated and the resulting residue was dissolved in diethyl ether. A 1N-hydrochloric acid/diethyl ether solution was added dropwise thereto in excess and the resulting mixture was concentrated. The residue was dissolved in methanol (20 ml), and di-tert-butyl dicarbonate (890 mg, 4.09 mmol) and triethylamine (1.0 ml, 6.82 mmol) were added thereto at 0° C. and stirred at room temperature for 2 hours. After the reaction, a saturated aqueous sodium hydrogencarbonate solution was added to the reaction solution, followed by extraction with ethyl acetate. The organic layer was washed with a saturated aqueous sodium chloride solution, dried over anhydrous sodium sulfate, and then concentrated to obtain tert-butyl 3-hydroxy-8-azabicyclo[3.2.1]octane-8-carboxylate (717 mg, two steps 93%).
$^1$H-NMR (CDCl$_3$) δ; 1.46 (9H, s), 1.47 (s), 1.42–1.74 (4H, m), 1.94 (2H, br), 2.14 (2H, br), 4.14 (2H, br), 4.21 (1H, br).

(c) Synthesis of 5-(8-azabicyclo[3.2.1]oct-3-yloxy)-1H-indazole

Except for using tert-butyl 3-hydroxy-8-azabicyclo[3.2.1]octane-8-carboxylate, 5-(8-azabicyclo[3.2.1]oct-3-yloxy)-1H-indazole was synthesized by carrying out reaction according to the method described in Example 4.
MS: m/z=244 (M+1)

EXAMPLE 495

Synthesis of 4-methyl-N-tetrahydro-2H-pyran-4-yl-1H-indazole-5-carboxamide (a) Synthesis of 2,3-dimethyl-4-nitrophenyl trifluoromethanesulfonate Anhydrous trifluoromethanesulfonate (3.17 ml, 18.8 mmol) and triethylamine (2.75 ml, 19.7 mmol) were added dropwise to a solution of 2,3-dimethyl-4-nitrophenol (3.0 g, 17.9 mmol) in methylene chloride (60 ml) at 0° C. and stirred at room temperature for 1 hour. Then, the reaction solution was poured into water and extracted with chloroform. The organic layer was dried over magnesium sulfate and distilled to remove the solvent, and the resulting residue was purified by a silica gel column chromatography (eluent: hexane/ethyl acetate) to obtain 2,3-dimethyl-4-nitrophenyl trifluoromethanesulfonate (5.32 g, 99%).

(b) Synthesis of 2,3-dimethyl-4-nitrobenzonitrile

Potassium cyanide (2.26 g, 34.7 mmol) was added to a solution of 2,3-dimethyl-4-nitrophenyl trifluoromethanesulfonate (5.20 g, 17.4 mmol) in tetrahydrofuran (21 ml) at room temperature, followed by deaeration. After tetrakistriphenylphosphine (1.00 g, 0.865 mmol) was added thereto, deaeration was conducted again and then the reaction was carried out under reflux conditions for 10 hours. A 0.5M-aqueous potassium hydrogensulfate solution and then water were added to the reaction solution, followed by extraction with ethyl acetate. The organic layer was dried over magnesium sulfate and distilled to remove the solvent, and the resulting residue was purified by a silica gel column chromatography (eluent: n-hexane/chloroform) to obtain 2,3-dimethyl-4-nitrobenzonitrile (2.79 g, 90.9%).

$^1$H-NMR (DMSO-d$_6$) δ; 2.26 (3H, s), 2.49 (3H, s), 7.78 (1H, d, J=8.4 Hz), 7.85 (1H, d, J=8.4 Hz).

(c) Synthesis of 4-amino-2,3-dimethylbenzonitrile

Tin dichloride (12.24 g, 54.2 mmol) was added to a solution of 2,3-dimethyl-4-nitrobenzonitrile (2.73 g, 15.5 mmol) in ethanol (94 ml) at room temperature, and the reaction was carried out for 5 hours under reflux conditions. After cooling, the reaction mixture was concentrated, and the resulting residue was diluted with ethyl acetate and then washed with a saturated aqueous sodium hydrogencarbonate solution. After the insoluble material was filtered off, the filtrate was separated and the organic layer was washed with a saturated aqueous sodium chloride solution. The organic layer was dried over magnesium sulfate and distilled to remove the solvent, whereby 4-amino-2,3-dimethylbenzonitrile (2.12 g, 93.6%) was obtained.

$^1$H-NMR (DMSO-d$_6$) δ; 1.97 (3H, s), 2.30 (3H, s), 5.79 (2H, brs), 6.53 (1H, d, J=8.4 Hz), 7.20 (1H, d, J=8.4 Hz).

(e) Synthesis of N-(4-cyano-2,3-dimethylphenyl)acetamide

Acetic anhydride (1.36 ml, 14.4 mmol) was added to a solution of 4-amino-2,3-dimethylbenzonitrile (1.32 g, 9.03 mmol) in ethyl acetate (10 ml) at room temperature, and then the reaction was carried out for 4 hours under reflux conditions. After the reaction mixture was cooled, the precipitate obtained was collected by filtration and dried to obtain N-(4-cyano-2,3-dimethylphenyl)acetamide (1.39 g, 81.8%).

$^1$H-NMR (DMSO-d$_6$) δ; 2.09 (3H, s), 2.14 (3H, s), 2.43 (3H, s), 7.50 (1H, d, J=9.0 Hz), 7.55 (1H, d, J=8.3 Hz), 9.56 (1H, br s).

(f) Synthesis of 4-methyl-1H-indazole-5-carbonitrile

Acetic anhydride (2.1 ml, 22.3 mmol), tetra-n-butylammonium bromide (118 mg, 0.366 mmol), potassium acetate (1.44 g, 14.7 mmol) and isoamyl nitrite (1.3 ml, 9.68 mmol) were added to an ethyl acetate suspension (15 ml) of N-(4-cyano-2,3-dimethylphenyl)acetamide (1.38 g, 7.33 mmol) at room temperature, and then the reaction was carried out for 7 hours under reflux conditions. The reaction mixture was cooled, diluted with ethyl acetate, and then washed with a saturated aqueous sodium hydrogencarbonate solution. The organic layer was washed with a saturated aqueous sodium chloride solution, dried over magnesium sulfate, and then distilled to remove the solvent, and the resulting residue was purified by a silica gel column chromatography (eluent: n-hexane/chloroform) to obtain 4-methyl-1H-indazole-5-carbonitrile (1.24 g, 84.9%).

$^1$H-NMR (DMSO-d$_6$) δ; 2.81 (3H, s), 2.84 (3H, s), 7.72 (1H, d, J=8.8 Hz), 8.23 (1H, d, J=0.7 Hz), 8.37 (1H, d, J=8.8 Hz).

(g) Synthesis of 4-methyl-1H-indazole-5-carboxylic acid

Water (2 ml) and concentrated sulfuric acid (2 ml) were added to a acetic acid suspension (2 ml) of 4-methyl-1H-indazole-5-carbonitrile (399 mg, 2.00 mmol) at room temperature, and then the reaction was carried out for 18 hours under reflux conditions. The reaction mixture was poured onto ice (20 g) and the precipitate was collected by filtration and dried to obtain 4-methyl-1H-indazole-5-carboxylic acid (247 mg, 70.1%).

$^1$H-NMR (DMSO-d$_6$) δ; 2.82 (s, 3H), 7.37 (d, J=8.8 Hz, 1H), 7.84 (d, J=8.8 Hz, 1H), 8.31 (d, J=1.1 Hz, 1H).

(h) Synthesis of 4-methyl-N-tetrahydro-2H-pyran-4-yl-1H-indazole-5-carboxamide

Tetrahydro-2H-pyran-4-ylamine monohydrochloride (228 mg, 1.66 mmol), triethylamine (0.5 ml, 3.59 mmol), 1-ethyl-3-(3'-dimethylaminopropyl)carbodiimide monohydrochloride (367 mg, 1.91 mmol) and hydroxybenzotriazole (190 mg, 1.41 mmol) were added to a solution of 4-methyl-1H-indazole-5-carboxylic acid (225 mg, 1.28 mmol) in N,N-dimethylformamide (5.5 ml), and the resulting mixture was stirred at room temperature for 4 hours. After completion of the reaction, the reaction mixture was diluted with ethyl acetate and washed with a saturated aqueous sodium hydrogencarbonate solution. A small amount of the insoluble material was collected by filtration and then dried to obtain 4-methyl-N-tetrahydro-2H-pyran-4-yl-1H-indazole-5-carboxamide (41 mg). The filtrate was extracted with ethyl acetate and chloroform, and the combined organic layer was dehydrated over magnesium sulfate and then filtered. The filtrate was concentrated and the resulting residue was suspended in chloroform. The resulting suspension was filtered and the precipitate was dried to obtain 4-methyl-N-tetrahydro-2H-pyran-4-yl-1H-indazole-5-carboxamide (134 mg, 52.7%).

$^1$H-NMR (DMSO-d$_6$) δ; 1.45–1.58 (m, 2H), 1.76–1.80 (m, 2H), 2.58 (s, 3H), 3.33–3.42 (m, 2H), 3.84–4.03 (m, 3H), 7.29 (d, J=8.6 Hz, 1H), 7.35 (d, J=8.6 Hz, 1H), 8.13 (d, J=7.9 Hz, 1H), 8.19 (d, J=0.9 Hz, 1H), 13.11 (br, 1H).

The following compound of Example 496 was synthesized by carrying out reaction according to the method described in Example 495.

EXAMPLE 496 tert-Butyl 3-{[(4-methyl-1H-indazol-5-yl)carbonyl]amino}cyclohexylcarbamate

MS: m/z=373 (M+1)

The following compound of Example 497 was synthesized by carrying out reaction according to the method described in Example 42, (b), except for using the tert-butyl 3-{[(4-methyl-1H-indazol-5-yl)carbonyl]amino}cyclohexylcarbamate obtained in Example 496, as a starting material.

EXAMPLE 497

N-(3-aminocyclohexyl)-4-methyl-1H-indazole-5-carboxamide

MS: m/z=273 (M+1)

EXAMPLE 498

Synthesis of 6-methyl-N-tetrahydro-2H-pyran-4-yl-1H-indazole-5-carboxamide (a) Synthesis of dimethyl 2,5-dimethylterephthalate A suspension of 2,5-dimethylterephthalic acid (3.67 g, 18.9 mmol) in methanol (70 ml) was cooled with ice water, followed by adding dropwise thereto thionyl chloride (7.0 ml, 96 mmol), and the resulting mixture was stirred for 3 hours with heating under reflux. The resulting solution was cooled to room temperature to precipitate a solid. The solid was collected by filtration and the precipitate on a filter was washed with methanol (once) and hexane (twice) and dried under reduced pressure to obtain dimethyl 2,5-dimethyl-terephthalate (3.29 g, 78%). The solvent was distilled off from the filtrate under reduced pressure, and a saturated aqueous sodium hydrogencarbonate solution was added to the residue, followed by extraction with ethyl acetate (twice). The extract solution was dried over anhydrous magnesium sulfate. The solvent was distilled off to obtain dimethyl 2,5-dimethylterephthalate (0.916 g, 22%, total: >99%) additionally.

(b) Synthesis of 4-(methoxycarbonyl)-2,5-dimethylbenzoic acid

Methanol (20 ml) was added to a solution of dimethyl 2,5-dimethylterephthalate (3.95 g, 17.8 mmol) in tetrahydrofuran (40 ml) and the resulting mixture was cooled on a water bath. A 2N-aqueous lithium hydroxide solution (9.8 ml, 19.6 mmol) was slowly added thereto and stirred for 3 hours. The solvent was distilled off under reduced pressure and the residue was adjusted to pH 1 to 2 with a 1N-hydrochloric acid and extracted with ethyl acetate (×3). The extract solution was dried over anhydrous magnesium sulfate. The solvent was distilled off under reduced pressure and the residue was purified by a silica gel chromatography (eluent: chloroform/methanol=30/1) to obtain 4-(methoxycarbonyl)-2,5-dimethylbenzoic acid (2.77 g, 75%).

(c) Synthesis of methyl 4-[(tert-butoxycarbonyl)amino]-2,5-dimethybenzoate

The title compound was synthesized by carrying out reaction according to the method described in Example 4, (a), except for using 4-(methoxycarbonyl)-2,5-dimethylbenzoic acid as a starting material.

(d) Synthesis of methyl 4-amino-2,5-dimethylbenzoate monohydrochloride

The title compound was synthesized by carrying out reaction according to the method described in Example 4, (b), except for using 4-(methoxycarbonyl)-2,5-dimethylbenzoic acid as a starting material.

(e) Synthesis of methyl 4-(acetylamino)-2,5-dimethylbenzoate

Triethylamine (1.16 ml, 8.32 mmol) was added to a suspension of methyl 4-amino-2,5-dimethylbenzoate monohydrochloride (0.600 g, 2.78 mmol) in dichloromethane (8 ml), and the resulting mixture was cooled with ice water, followed by adding dropwise thereto a solution of acetyl chloride (0.263 g, 3.35 mmol) in dichloromethane (2 ml). The resulting mixture was heated to room temperature and stirred for 3 hours, and then acetyl chloride (0.262 g, 3.34 mmol) was further added thereto and stirred for 1.5 hours. The resulting mixture was added to a saturated aqueous sodium hydrogencarbonate solution and extracted three times with ethyl acetate, and the organic layer was washed with a saturated aqueous sodium chloride solution and dried over anhydrous magnesium sulfate. The solvent was distilled off to obtain methyl 4-(acetylamino)-2,5-dimethylbenzoate (0.685 g, 99%).

(f) Synthesis of methyl 1-acetyl-6-methyl-1H-indazole-5-carboxylate

Acetic anhydride (0.85 ml, 9.01 mmol), n-butylammonium bromide (0.0502 g, 0.156 mmol) and potassium acetate (0.587 g, 5.98 mmol) were added to a solution of methyl 4-(acetylamino)-2,5-dimethylbenzoate (0.661 g, 2.99 mmol) in ethyl acetate (5 ml), followed by adding thereto a solution of isoamyl nitrite (0.0458 g, 3.91 mmol) in ethyl acetate (2 ml), and the resulting mixture was stirred for 8 hours with heating under reflux. Water was added thereto, followed by extraction with ethyl acetate (three times), and the extract solution was dried over anhydrous magnesium sulfate. The solvent was distilled off under reduced pressure and the resulting residue was purified by a silica gel column chromatography (hexane/ethyl acetate=5/1 to 1/1). The solid thus obtained was suspended in hexane and stirred to be washed, and then it was collected by filtration and dried under reduced pressure to obtain methyl 1-acetyl-6-methyl-1H-indazole-5-carboxylate (0.0731 g, 11%).

(g) Synthesis of 6-methyl-1H-indazole-5-carboxylic acid

A 2N-aqueous sodium hydroxide solution (0.63 ml, 1.3 mmol) was added to a solution of methyl 1-acetyl-6-methyl-1H-indazole-5-carboxylate (0.0731 g, 0.315 mmol) in tetrahydrofuran (1 ml), and the resulting mixture was stirred for 3 hours with heating under reflux. Then, a 2N-aqueous lithium hydroxide solution (0.63 ml, 1.3 mmol) was added thereto and stirred for another 3 hours. The resulting solution was diluted with water and washed with diethyl ether, and the aqueous layer was adjusted to pH 1 to 2 with 1N-hydrochloric acid to precipitate a solid. The solid precipitated was collected by filtration and the precipitate on a filter was washed with water and dried under reduced pressure to obtain 6-methyl-1H-indazole-5-carboxylic acid (0.0514 g, 93%).

(h) Synthesis of 6-methyl-N-tetrahydro-2H-pyran-4-yl-1H-indazole-5-carboxamide Tetrahydro-2H-pyran-4-ylamine monohydrochloride (0.0402 g, 0.292 mmol), triethylamine (0.07 ml, 0.5 mmol), 1-hydroxybenztriazole (0.0460 g, 0.340 mmol) and 1-ethyl-3-(3'-dimethylaminopropyl)carbodiimide monohydrochloride (0.0606 g, 0.316 mmol) were added to a solution of 6-methyl-1H-indazole-5-carboxylic acid (0.0437 g, 0.248 mmol) in N,N-dimethylformamide (2 ml) and stirred overnight. A saturated aqueous sodium hydrogencarbonate solution was added thereto, followed by extraction with chloroform (×3), and the extract solution was dried over anhydrous sodium sulfate. The solvent was distilled off under reduced pressure, followed by replacement with toluene (three times), whereby a solid was precipitated. The solid obtained was suspended in ethyl acetate and stirred to be washed, and then it was collected by filtration and dried under reduced pressure to obtain 6-methyl-N-tetrahydro-2H-pyran-4-yl-1H-indazole-5-carboxamide (0.0587 g, 91%).

$^1$H-NMR (DMSO-d$_6$) δ; 1.46–1.58 (2H, m), 1.75–1.82 (2H, m), 2.44 (3H, s), 3.39 (2H, td, J=1.9, 11.6 Hz), 3.83–3.90 (2H, m), 3.91–4.02 (1H, m), 7.35 (1H, m), 7.73 (1H, s), 8.06 (1H, s), 8.23 (1H, d, J=7.7 Hz), 13.01 (1H, br).

EXAMPLE 499

Synthesis of N-(8-benzyl-8-azabicyclo[3.2.1]oct-3-yl)-4-methyl-1-tetrahydro-2H-pyran-2-yl-1H-indazol-5-amine (a) Synthesis of ethyl(5-nitro-1-tetrahydro-2H-pyran-2-yl-1H-indazol-4-yl)acetate A solution of potassium tert-butoxide (2.02 g, 18.0 mmol) in tetrahydrofuran (20 ml) was added dropwise to a solution of the 5-nitro-1-tetrahydro-2H-pyran-2-yl-1H-indazole (1.85 g, 7.48 mmol) obtained in Example 317, (d) and ethyl chloroacetate (960 µl, 9.01 mmol) in tetrahydrofuran (10 ml) at −40° C. over a period of 15 minutes, and stirred at −40° C. for 1 hour. The reaction was terminated by pouring 1N-hydrochloric acid, and the reaction solution was extracted with ethyl acetate. The extract solution was washed with a saturated aqueous sodium chloride solution, dried over sodium sulfate, and then distilled under reduced pressure to remove the solvent, whereby a crude product was obtained. The crude product was purified by a silica gel column chromatography (eluent: hexane/ethyl acetate=4/1) to obtain ethyl(5-nitro-1-tetrahydro-2H-pyran-2-yl-1H-indazol-4-yl)acetate (1.93 g, 78%).

$^1$H-NMR (DMSO-$d_6$) δ; 1.26 (3H, t, J=7.1 Hz), 1.74 (3H, m), 2.13 (2H, m), 2.51 (1H, m), 3.77 (1H, m), 4.01 (1H, m), 4.19 (2H, q, J=7.1 Hz), 4.35 (2H, s), 5.76 (1H, dd, J=2.6, 8.8 Hz), 7.63 (1H, d, J=9.2 Hz), 8.21 (1H, d, J=8.0 Hz), 8.22 (1H, s).

(b) Synthesis of 4-methyl-5-nitro-1-tetrahydro-2H-pyran-2-yl-1H-indazole

A 1N-aqueous sodium hydroxide solution (8.64 ml, 8.64 mmol) was added to a solution of ethyl (5-nitro-1-tetrahydro-2H-pyran-2-yl-1H-indazol-4-yl)acetate (1.92 g, 5.76 mmol) in dioxane (20 ml), and the resulting mixture was stirred at room temperature for 3 hours. The solvent was distilled off under reduced pressure, and water, ethyl acetate and 1N-hydrochloric acid were added to the residue. The resulting mixture was extracted with ethyl acetate, and the extract solution was washed with a saturated aqueous sodium chloride solution, dried over sodium sulfate, and then distilled under reduced pressure to remove the solvent, whereby (5-nitro-1-tetrahydro-2H-pyran-2-yl-1H-indazol-4-yl)acetic acid was obtained. N,N-dimethyl-formamide (20 ml) and then potassium carbonate (800 mg, 5.79 mmol) were added thereto, and the resulting mixture was stirred at 50° C. for 30 minutes. Water, ethyl acetate, toluene and 1N-hydrochloric acid were added thereto, followed by extraction with ethyl acetate/toluene=1/1, and the extract solution was washed with a saturated aqueous sodium chloride solution, dried over sodium sulfate, and then distilled under reduced pressure to remove the solvent, whereby 4-methyl-5-nitro-1-tetrahydro-2H-pyran-2-yl-1H-indazole (1.39 g, 93%) was obtained.

$^1$H-NMR (CDCl$_3$) δ; 1.74 (3H, m), 2.13 (2H, m), 2.51 (1H, m), 2.90 (3H, s), 3.78 (1H, m), 4.02 (1H, m), 5.74 (1H, dd, J=2.7, 9.1 Hz), 7.50 (1H, d, J=9.2 Hz), 8.10 (1H, d, J=9.2 Hz), 8.23 (1H, s).

(c) Synthesis of 4-methyl-1-tetrahydro-2H-pyran-2-yl-1H-indazol-5-amine

To a solution of 4-methyl-5-nitro-1-tetrahydro-2H-pyran-2-yl-1H-indazole (1.06 g, 4.06 mmol) in ethanol (20 ml) were added 10% Pd—C (200 mg) and ammonium formate (1.28 g, 20.3 mmol), and the resulting mixture was heated under reflux for 1 hour. After the solid was removed by filtration using Celite, water, ethyl acetate and a saturated aqueous sodium hydrogencarbonate solution were added to the residue. The resulting mixture was extracted with ethyl acetate, and the extract solution was washed with a saturated aqueous sodium chloride solution, dried over sodium sulfate, and then distilled under reduced pressure to remove the solvent, whereby 4-methyl-1-tetrahydro-2H-pyran-2-yl-1H-indazol-5-amine (955 mg, 100%) was obtained.

$^1$H-NMR (CDCl$_3$) δ; 1.74 (3H, m), 2.11 (2H, m), 2.36 (3H, s), 2.53 (1H, m), 3.51 (2H, br), 3.72 (1H, m), 4.01 (1H, m), 5.63 (1H, dd, J=2.7, 9.4 Hz), 6.86 (1H, d, J=8.8 Hz), 7.27 (1H, d, J=7.5 Hz), 7.90 (1H, s).

(d) Synthesis of N-(8-benzyl-8-azabicyclo[3.2.1]oct-3-yl)-4-methyl-1-tetrahydro-2H-pyran-2-yl-1H-indazol-5-amine Sodium triacetoxyborohydride (477 mg, 2.25 mmol) and then acetic acid (99 µl, 1.73 mmol) were added to a suspension of 4-methyl-1-tetrahydro-2H-pyran-2-yl-1H-indazol-5-amine (400 mg, 1.73 mmol) and 8-benzyl-8-azabicyclo[3.2.1]octan-3-one (410 mg, 1.90 mmol) in 1,2-dichloroethane (5 ml), and the resulting mixture was stirred at room temperature for 1 day. The reaction mixture was poured into a saturated aqueous sodium hydrogencarbonate solution and then extracted with ethyl acetate. The extract solution was washed with a saturated aqueous sodium chloride solution, dried over sodium sulfate, and then distilled under reduced pressure to remove the solvent. The residue was purified by a silica gel column chromatography (eluent: chloroform/methanol=100/2) to obtain N-(8-benzyl-8-azabicyclo[3.2.1]oct-3-yl)-4-methyl-1-tetrahydro-2H-pyran-2-yl-1H-indazol-5-amine (283 mg, 38%).

$^1$H-NMR (CDCl$_3$) δ; 1.62–1.85 (7H, m), 1.99–2.23 (4H, m), 2.34 (2H, m), 2.36 (3H, s), 3.23 (2H, m), 3.58 (2H, s), 3.73 (1H, m), 3.79 (1H, m), 4.02 (1H, m), 5.63 (1H, dd, J=2.6, 9.6 Hz), 6.83 (1H, d, J=9.0 Hz), 7.25–7.45 (6H, m), 7.91 (1H, s).

EXAMPLE 500

Synthesis of N-(8-benzyl-8-azabicyclo[3.2.1]oct-3-yl)-4-methyl-1H-indazol-5-amine Trifluoroacetic acid (1 ml) was added to a solution of the N-(8-benzyl-8-azabicyclo[3.2.1]oct-3-yl)-4-methyl-1-tetrahydro-2H-pyran-2-yl-1H-indazol-5-amine (273 mg, 0.634 mmol) obtained in Example 499 in dichloromethane (9 ml), and the resulting mixture was stirred at room temperature for 30 minutes. Then, trifluoroacetic acid (1 ml) was added thereto and stirred for another 30 minutes, and the resulting mixture was poured into a saturated aqueous sodium hydrogencarbonate solution and extracted with chloroform. The extract solution was washed with a saturated aqueous sodium chloride solution, dried over sodium sulfate, and then distilled under reduced pressure to remove the solvent. The residue was purified by a preparative thin-layer chromatography (200×200×0.5 mm, 6 plates, eluent: chloroform/methanol=6/1) to obtain N-(8-benzyl-8-azabicyclo[3.2.1]oct-3-yl)-4-methyl-1H-indazol-5-amine (142 mg, 65%).

$^1$H-NMR (DMSO-$d_6$) δ; 1.72 (2H, m), 1.99–2.23 (6H, m), 2.33 (3H, s), 3.08 (2H, m), 3.51 (2H, m), 3.69 (1H, s), 4.06 (1H, m), 6.76 (1H, d, J=9.2 Hz), 7.17–7.40 (6H, m), 7.90 (1H, s), 12.57 (1H, s).

EXAMPLE 501

Synthesis of N-(8-azabicyclo[3.2.1]oct-3-yl)-4-methyl-1H-indazol-5-amine

To a solution of the N-(8-benzyl-8-azabicyclo[3.2.1]oct-3-yl)-4-methyl-1H-indazol-5-amine (130 mg, 0.375 mmol) obtained in Example 500 in ethanol (10 ml) were added 10% Pd-C (26 mg) and then ammonium formate (118 mg, 1.87 mmol), and the resulting mixture was heated under reflux for 1 hour. The solid was removed by filtration using Celite, and the solvent was distilled off under reduced pressure. Ethyl acetate/aqueous ammonia was added to the residue, followed by extraction with ethyl acetate, and the extract solution was washed with a saturated aqueous sodium chloride solution, dried over sodium sulfate, and then distilled under reduced pressure to remove the solvent, whereby N-(8-azabicyclo[3.2.1]oct-3-yl)-4-methyl-1H-indazol-5-amine (84 mg, 88%) was obtained.

MS: m/z=25 (M+1)

EXAMPLE 502

Synthesis of N-(8-propyl-8-azabicyclo[3.2.1]oct-3-yl)-4-methyl-1H-indazol-5-amine Potassium carbonate (122 mg, 0.883 mmol) and then n-propyl bromide (40 μl, 0.440 mmol) were added to a solution of the N-(8-azabicyclo[3.2.1]oct-3-yl)-4-methyl-1H-indazol-5-amine (74 mg, 0.289 mmol) obtained in Example 501 in N,N-dimethylformamide (2 ml), and the resulting mixture was stirred at room temperature for 15 hours. After the solid was removed by filtration, the solvent was distilled off under reduced pressure as an azeotrope with toluene. The residue was purified by a silica gel column chromatography (chloroform/methanol/triethylamine=100/1/5) and then a preparative thin-layer chromatography (200×200×0.5 mm, 2 plates, eluent: chloroform/methanol/triethylamine=100/5/5) to obtain N-(8-propyl-8-azabicyclo[3.2.1]oct-3-yl)-4-methyl-1H-indazol-5-amine (36 mg, 42%).

MS: m/z=299 (M+1)

EXAMPLE 503

Synthesis of 1-(methylsulfonyl)-N-(8-propyl-8-azabicyclo[3.2.1]oct-3-yl)-1H-indazol-5-amine (a) Synthesis of 1-(methylsulfonyl)-5-nitro-1H-indazole Methanesulfonyl chloride (887 μl, 7.20 mmol) was added to a suspension of 5-nitroindazole (979 mg, 6.00 mmol) and triethylamine (2.0 ml, 14.3 mmol) in dichloromethane (20 ml) at 0° C., and the resulting mixture was stirred at room temperature for 3 hours. Methanesulfonyl chloride (222 μl, 1.80 mmol) was further added thereto, followed by stirring for another 1 hour. The reaction mixture was poured into a saturated aqueous sodium hydrogencarbonate solution to terminate the reaction, followed by extraction with chloroform. The extract solution was washed with a saturated aqueous sodium chloride solution, dried over sodium sulfate, and then distilled under reduced pressure to remove the solvent. The residue was purified by washing with methanol to obtain 1-(methylsulfonyl)-5-nitro-1H-indazole (1.16 g, 80%).

$^1$H-NMR (CDCl$_3$) δ; 3.41 (3H, s), 8.23 (1H, d, J=9.4 Hz), 8.45 (1H, dd, J=2.2, 9.4 Hz), 8.47 (1H, s), 8.75 (1H, d, J=2.2 Hz).

(b) Synthesis of 1-(methylsulfonyl)-1H-indazol-5-amine

To a solution of 1-(methylsulfonyl)-5-nitro-1H-indazole (1.00 g, 4.15 mmol) in ethanol (20 ml) were added 10% Pd-C (100 mg) and then ammonium formate (1.57 g, 24.9 mmol), and the resulting mixture was heated under reflux for 1 hour. The solid was removed by filtration using Celite, and the solvent was distilled off under reduced pressure. Ethyl acetate/water was added to the residue, followed by extraction with ethyl acetate, and the extract solution was washed with a saturated aqueous sodium chloride solution, dried over sodium sulfate, and then distilled under reduced pressure to remove the solvent, whereby 1-(methylsulfonyl)-1H-indazol-5-amine (425 mg, 49%) was obtained.

$^1$H-NMR (CDCl$_3$) δ; 3.27 (3H, s), 5.26 (2H, br), 6.86 (1H, d, J=2.0 Hz), 6.94 (1H, dd, J=2.0, 9.0 Hz), 7.61 (1H, d, J=9.0 Hz), 8.32 (1H, s).

(c) Synthesis of 1-(methylsulfonyl)-N-(8-propyl-8-azabicyclo[3.2.1]oct-3-yl)-1H-indazol-5-amine Sodium cyanoborohydride (242 mg, 3.85 mmol) and then acetic acid (220 μl, 3.84 mmol) were added to a solution of 1-(methylsulfonyl)-1H-indazol-5-amine (163 mg, 0.772 mmol) and 8-propyl-8-azabicyclo[3.2.1]octan-3-one (150 mg, 0.924 mmol) in methanol (3 ml), and the resulting mixture was stirred at room temperature for 4 days. A 1N-aqueous sodium hydroxide solution was added thereto, followed by extraction with ethyl acetate. The extract solution was washed with a saturated aqueous sodium chloride solution, dried over sodium sulfate, and then distilled under reduced pressure to remove the solvent. The residue was purified successively by a silica gel column chromatography (chloroform/methanol=4/1), a preparative thin-layer chromatography (200×200×0.5 mm, 2 plates, eluent: chloroform/methanol=4/1) and partition by LC/MS (water containing 0.05% trifluoroacetic acid-acetonitrile containing 0.035% trifluoroacetic acid, 10%–100% gradient, the extraction of the organic layer with aqueous ammonia/ethyl acetate after the partition) to obtain 1-(methylsulfonyl)-N-(8-propyl-8-azabicyclo[3.2.1]oct-3-yl)-1H-indazol-5-amine (8 mg, 3%).

MS: m/z=363 (M+1)

EXAMPLE 504

Synthesis of 3-bromo-N-(8-propyl-8-azabicyclo[3.2.1]oct-3-yl)-1H-indazol-5-amine (a) Synthesis of 3-bromo-5-nitro-1H-indazole A solution of bromine (0.75 ml, 14.6 mmol) in a 2N-aqueous sodium hydroxide solution (20 ml) was added dropwise to a mixed solution of 5-nitro-1H-indazole (3.26 g, 20.0 mmol), dioxane (60 ml) and a 2N-aqueous sodium hydroxide solution (30 ml) at 0° C. and stirred at 0° C. for 30 minutes and then at room temperature for 3.5 hours. An aqueous sodium hydrogensulfite solution was added thereto until a solid was precipitated, to terminate the reaction, followed by extraction with ethyl acetate. The extract solution was washed with an aqueous sodium thiosulfate solution and a saturated aqueous sodium chloride solution, dried over sodium sulfate, and then distilled under reduced pressure to remove the solvent. The residue was suspended in ethyl acetate and extracted with a 0.1N-aqueous sodium hydroxide solution. After 6 times of the extraction, the combined aqueous layer was acidified with hydrochloric acid and then re-extracted with ethyl acetate. The extract solution was washed with a saturated aqueous sodium chloride solution, dried over sodium sulfate, and then distilled under reduced pressure to remove the solvent, whereby 3-bromo-5-nitro-1H-indazole (0.93 g, 19%) was obtained.

$^1$H-NMR (DMSO-$d_6$) δ; 7.79 (1H, d, J=9.2 Hz), 8.26 (1H, dd, J=2.2, 9.4 Hz), 8.48 (1H, d, J=2.2 Hz), 14.03 (1H, br).

(b) Synthesis of 3-bromo-1H-indazol-5-amine

Tin dichloride dihydrate (846 mg, 3.75 mmol) was added to a solution of 3-bromo-5-nitro-1H-indazole (181 mg, 0.748 mmol) in N,N-dimethylformamide (3 ml), and the resulting mixture was stirred at 70° C. for 1.5 hours. After an aqueous sodium hydrogensulfite solution was added thereto to terminate the reaction, ethyl acetate was added to the reaction mixture and the insoluble material was removed by filtration using Celite. The residue was extracted with ethyl acetate/toluene, and the extract solution was washed with a saturated aqueous sodium chloride solution, dried over sodium sulfate, and then distilled under reduced pressure to remove the solvent, whereby 3-bromo-1H-indazol-5-amine (110 mg, 69%) was obtained.

$^1$H-NMR (DMSO-$d_6$) δ; 5.01 (2H, br), 6.53 (1H, d, J=1.7 Hz), 6.84 (1H, dd, J=2.1, 8.9 Hz), 12.90 (1H, br).

(c) Synthesis of 3-bromo-N-(8-propyl-8-azabicyclo [3.2.1]oct-3-yl)-1H-indazol-5-amine Sodium triacetoxyborohydride (159 mg, 0.750 mmol) and then acetic acid (29 μl, 0.507 mmol) were added to a suspension of 3-bromo-1H-indazol-5-amine (106 mg, 0.500 mmol) and 8-propyl-8-azabicyclo[3.2.1]octan-3-one (100 mg, 0.598 mmol) in dichloroethane (3 ml), and the resulting mixture was stirred at room temperature for 1 day. Aqueous ammonia was added thereto, followed by extraction with ethyl acetate. The extract solution was washed with a saturated aqueous sodium chloride solution, dried over sodium sulfate, and then distilled under reduced pressure to remove the solvent. The residue was purified by a silica gel column chromatography (chloroform/methanol/triethylamine=100/10/5) and a preparative thin-layer chromatography (200×200×0.5 mm, eluent: chloroform/methanol/triethylamine=100/5/5) to obtain 3-bromo-N-(8-propyl-8-azabicyclo[3.2.1]oct-3-yl)-1H-indazol-5-amine (2 mg, 1%).

$^1$H-NMR (CD$_3$OD) δ; 0.88 (3H, t, J=7.4 Hz), 1.53 (2H, m), 1.85 (2H, m), 1.98 (2H, m), 2.09–2.22 (4H, m), 2.49 (2H, m), 3.38 (2H, m), 3.51 (2H, m), 6.28 (1H, d, J=1.9 Hz), 6.87 (1H, dd, J=2.2, 8.9 Hz), 7.21 (1H, d, J=9.1 Hz).

EXAMPLE 505

Synthesis of N-(1H-indazol-5-yl)-N-(8-propyl-8-azabicyclo[3.2.1]oct-3-yl)methanesulfonamide (a) Synthesis of N-(8-propyl-8-azabicyclo[3.2.1]oct-3-yl)-1-tetrahydro-2H-pyran-2-yl-1H-indazol-5-amine Sodium cyanoborohydride (484 mg, 7.70 mmol) and then acetic acid (440 μl, 7.68 mmol) were added to a solution of the 1-tetrahydro-2H-pyran-2-yl-1H-indazol-5-amine (335 mg, 1.54 mmol) obtained in Example 317, (e) and 8-propyl-8-azabicyclo[3.2.1]octan-3-one (300 mg, 1.85 mmol) in methanol (6 ml), and the resulting mixture was stirred at room temperature for 1 day. Aqueous ammonia was added thereto, followed by extraction with ethyl acetate. The extract solution was washed with a saturated aqueous sodium chloride solution, dried over sodium sulfate, and then distilled under reduced pressure to remove the solvent. The residue was purified by a silica gel column chromatography (chloroform/methanol/triethylamine=100/1/5) to obtain N-(8-propyl-8-azabicyclo[3.2.1]oct-3-yl)-1-tetrahydro-2H-pyran-2-yl-1H-indazol-5-amine (413 mg, 73%).

$^1$H-NMR (CDCl$_3$) δ; 1.03 (3H, t, J=7.4 Hz), 1.56–1.89 (6H, m), 2.02–2.63 (8H, m), 2.70–2.85 (4H, m), 3.70–3.83 (4H, m), 4.01 (1H, m), 5.65 (1H, dd, J=2.3, 9.2 Hz), 6.78 (1H, s), 6.83 (1H, dd, J=2.1, 8.9 Hz), 7.47 (1H, d, J=8.8 Hz), 7.88 (1H, s).

(b) Synthesis of N-(8-propyl-8-azabicyclo[3.2.1]oct-3-yl)-N-(1-tetrahydro-2H-pyran-2-yl-1H-indazol-5-yl)-methanesulfonamide Methanesulfonyl chloride (0.10 ml, 1.29 mmol) was added to a solution of N-(8-propyl-8-azabicyclo[3.2.1]oct-3-yl)-1-tetrahydro-2H-pyran-2-yl-1H-indazol-5-amine (37 mg, 0.100 mmol) in pyridine (1 ml), and the resulting mixture was stirred at room temperature for 3 days. The reaction solution was poured into a saturated aqueous sodium hydrogencarbonate solution, followed by extraction with ethyl acetate, and the extract solution was washed with a saturated aqueous sodium chloride solution, dried over sodium sulfate, and then distilled under reduced pressure to remove the solvent. The residue was purified by a preparative thin-layer chromatography (200×200×0.5 mm, 2 plates, eluent: chloroform/methanol=20/1) to obtain N-(8-propyl-8-azabicyclo[3.2.1]oct-3-yl)-N-(1-tetrahydro-2H-pyran-2-yl-1H-indazol-5-yl)-methanesulfonamide (20 mg, 44%).

MS: m/z=447 (M+1)

(c) Synthesis of N-(1H-indazol-5-yl)-N-(8-propyl-8-azabicyclo[3.2.1]oct-3-yl)methanesulfonamide Trifluoroacetic acid (0.2 ml) was added to a solution of N-(8-propyl-8-azabicyclo[3.2.1]oct-3-yl)-N-(1-tetrahydro-2H-pyran-2-yl-1H-indazol-5-yl)-methanesulfonamide (19 mg, 0.0425 mmol) in dichloromethane (0.8 ml), and the resulting mixture was stirred at room temperature for 1.5 hours. The reaction solution was poured into a saturated aqueous sodium hydrogencarbonate solution and extracted with ethyl acetate, and the extract solution was washed with a saturated aqueous sodium chloride solution, dried over sodium sulfate, and then distilled under reduced pressure to remove the solvent. The residue was purified by a preparative thin-layer chromatography (200×200×0.5 mm, eluent: chloroform/methanol=9/1) to obtain N-(1H-indazol-5-yl)-N-(8-propyl-8-azabicyclo[3.2.1]oct-3-yl)methanesulfonamide (6 mg, 40%).

MS: m/z=363 (M+1)

EXAMPLE 506

Synthesis of N-(1H-indazol-5-yl)-N-(8-propyl-8-azabicyclo[3.2.1]oct-3-yl)acetamide (a) Synthesis of N-(8-propyl-8-azabicyclo[3.2.1]oct-3-yl)-N-(1-tetrahydro-2H-pyran-2-yl-1H-indazol-5-yl)-acetamide Acetic anhydride (0.50 m) was added to a solution of the N-(8-propyl-8-azabicyclo[3.2.1]oct-3-yl)-1-tetrahydro-2H- pyran-2-yl-1H-indazol-5-amine (37 mg, 0.100 mmol) obtained in Example 505, (a) in pyridine (1 ml), and the resulting mixture was stirred at room temperature for 17 hours. The reaction solution was poured into a saturated aqueous sodium hydrogencarbonate solution and extracted with ethyl acetate. The extract solution was washed with a saturated aqueous sodium chloride solution, dried over sodium sulfate, and then distilled under reduced pressure to remove the solvent. The residue was purified by a preparative thin-layer chromatography (200×200×0.5 mm, 2 plates, eluent: chloroform/methanol=6/1) to obtain N-(8-propyl-8-azabicyclo[3.2.1]oct-3-yl)-N-(1-tetrahydro-2H-pyran-2-yl-1H-indazol-5-yl)-acetamide (35 mg, 85%).

MS: m/z=411 (M+1)

(b) Synthesis of N-(1H-indazol-5-yl)-N-(8-propyl-8-azabicyclo[3.2.1]oct-3-yl)acetamide Trifluoroacetic acid (0.2 ml) was added to a solution of N-(8-propyl-8-azabicyclo[3.2.1]oct-3-yl)-N-(1-tetrahydro-2H-pyran-2-yl-1H-indazol-5-yl)-acetamide (35 mg, 0.0853 mmol) in dichloromethane (0.8 ml), and the resulting mixture was stirred at room temperature for 1.5 hours. The reaction solution was poured into a saturated aqueous sodium hydrogencarbonate solution and extracted with ethyl acetate. The extract solution was washed with a saturated aqueous sodium chloride solution, dried over sodium sulfate, and then distilled under reduced pressure to remove the solvent, whereby N-(1H-indazol-5-yl)-N-(8-propyl-8-azabicyclo[3.2.1]oct-3-yl)acetamide (18 g, 64%) was obtained.

MS: m/z=327 (M+1)

EXAMPLE 507

Synthesis of 2-(1H-indazol-5-ylamino)benzamide

A 28%-aqueous ammonia solution (57.6 mg, 0.948 mmol), 1-hydroxybenzotriazole (58 mg, 0.379 mmol) and 1-[3-(dimethylamino)propyl]-3-ethylcarbodiimide hydrochloride (73 mg, 0.379 mmol) were added in that order to a solution of 2-(1H-indazol-5-ylamino)benzoic acid (80.0 mg, 0.316 mmol) in N,N-dimethylformamide (0.5 ml), and the resulting mixture was stirred at room temperature for 20 hours. A 5% aqueous sodium hydrogencarbonate solution was added to the reaction solution and stirred, followed by extraction with ethyl acetate/toluene/tetrahydrofuran (2/2/1). The organic phase was washed with a 5% aqueous sodium hydrogencarbonate solution and then a 5%-aqueous sodium chloride solution and dried over anhydrous sodium sulfate. The organic phase dried was concentrated under reduced pressure and the resulting crude product was purified by a silica gel column chromatography (eluent: chloroform/methanol=50/1 to 20/1) to obtain 2-(1H-indazol-5-ylamino)benzamide (66 mg, 83%).

$^1$H-NMR (CDCl$_3$) δ; 6.71 (1H, t-like, J=7.5 Hz), 7.10 (1H, d, J=8.6 Hz), 7.23–7.31 (2H, m), 7.47–7.50 (2H, m), 7.60 (1H, s), 8.02 (1H, s), 9.60 (1H, brs).

The following compounds of Example 508 to Example 513 were synthesized by carrying out reaction according to the method described in Example 507.

EXAMPLE 508

2-(1H-indazol-5-ylamino)-N-methylbenzamide $^1$H-NMR (CDCl$_3$) δ; 3.01 (3H, d, J=5.0 Hz), 6.17 (1H, brs), 6.72 (1H, dt-like, J=1.3, 8.1 Hz), 7.14 (1H, dd, J=1.1, 8.4 Hz), 7.22 (1H, dt-like, J=1.3, 8.4 Hz), 7.28 (1H, dd, J=1.8, 8.8 Hz), 7.40 (1H, dd, J=1.5, 7.9 Hz), 7.46 (1H, d, J=8.8 Hz), 7.58 (1H, d, J=1.8 Hz), 8.00 (1H, d, J=0.92 Hz), 9.38 (1H, brs), 10.08 (1H, brs).

EXAMPLE 509

2-(1H-indazol-5-ylamino)-N-isobutylbenzamide $^1$H-NMR (CDCl$_3$) δ; 0.99 (6H, d, J=6.6 Hz), 1.92 (1H, m), 3.28 (2H, t-like, J=6.4 Hz), 6.33 (1H, br t), 6.72 (1H, dt-like, J=1.3, 8.3 Hz), 7.14 (1H, dd, J=1.1, 8.4 Hz), 7.20–7.27 (2H, m), 7.41–7.47 (2H, m), 7.56 (1H, d, J=1.8 Hz), 8.01 (1H, d, J=0.7 Hz), 9.33 (1H, brs), 10.73 (1H, brs).

EXAMPLE 510

2-(1H-indazol-5-ylamino)-N-(2,2,2-trifluoroethyl)benzamide $^1$H-NMR (CDCl$_3$) 67 ; 4.07–4.18 (2H, m), 6.44 (1H, m), 6.75 (1H, t-like, J=7.5 Hz), 7.11 (1H, d, J=8.4 Hz), 7.25–7.30 (2H, m), 7.45–7.50 (2H, m), 7.58 (1H, d, J=1.3 Hz), 8.02 (1H, s), 9.27 (1H, brs), 10.13 (1H, brs).

EXAMPLE 511

N-[2-(dimethylamino)ethyl]-2-(1H-indazol-5-ylamino)benzamide $^1$H-NMR (CDCl$_3$) δ; 2.29 (6H, s), 2.54 (2H, t, J=5.9 Hz), 3.51 (2H, m), 6.73 (1H, t-like, J=7.5 Hz), 6.88 (1H, bm), 7.13 (1H, d, J=7.3 Hz), 7.22 (1H, d, J=6.9 Hz), 7.29 (1H, dd, J=2.0, 8.9 Hz), 7.44–7.47 (2H, m), 7.57 (1H, d, J=2.0 Hz), 8.00 (1H, s), 9.48 (1H, brs).

EXAMPLE 512

N-[2-(morpholin-4-ylcarbonyl)phenyl]-1H-indazol-5-amine $^1$H-NMR (CDCl$_3$) δ; 3.70 (8H, m), 6.82 (1H, dt-like, J=7.7 Hz), 7.15–7.21 (4H, m), 7.42 (1H, d, J=8.4 Hz), 7.47 (1H, d, J=1.8 Hz), 7.99 (1H, s), 10.94 (1H, brs).

EXAMPLE 513

N-(1-benzylpiperidin-4-yl)-2-(1H-indazol-5-ylamino)benzamide $^1$H-NMR (CDCl$_3$) δ; 1.57–1.61 (2H, m), 2.01–2.05 (2H, m), 2.16–2.23 (2H, m), 2.85–2.89 (2H, m), 3.53 (2H, s), 3.97 (1H, m), 6.04 (1H, bd, J=7.7 Hz), 6.73 (1H, dt-like, J=1.1, 8.1 Hz), 7.14 (1H, dd, J=1.1, 8.4 Hz), 7.21–7.33 (7H, m), 7.39 (1H, dd, J=1.3, 7.9 Hz), 7.45 (1H, d, J=8.8 Hz), 7.56 (1H, d, J=2.0 Hz), 8.00 (1H, d, J=0.92 Hz), 9.35 1H, brs).

The following compound of Example 514 was synthesized by carrying out reaction according to the method described in Example 148, except for using the N-(1-benzylpiperidin-4-yl)-2-(1H-indazol-5-ylamino)benzamide synthesized in Example 513, as a starting material.

EXAMPLE 514

2-(1H-indazol-5-ylamino)-N-piperidin-4-ylbenzamide $^1$H-NMR (CDCl$_3$) δ; 1.39–1.52 (2H, m), 2.05–2.09 (2H, m), 2.73–2.81 (2H, m), 3.12–3.16 (2H, m), 4.01–4.11 (1H, m), 6.08 (1H, bd, J=7.7 Hz), 6.73 (1H, t-like, J=7.4 Hz), 7.15

(1H, d, J=8.4 Hz), 7.22–7.29 (2H, m), 7.41 (1H, d, J=7.9 Hz), 7.46 (1H, d, J=9.0 Hz), 7.57 (1H, s), 8.00 (1H, s), 9.36 (1H, brs).

EXAMPLE 515

Synthesis of N-{2-[(4-benzylpiperazin-1-yl)carbonyl]phenyl}-1H-indazol-5-amine

To a solution of 2-(1H-indazol-5-ylamino)benzoic acid (102 mg, 0.402 mmol) in N,N-dimethylformamide (0.5 ml) were added 1-benzylpiperazine (210 μl, 1.21 mmol), 1-hydroxybenzotriazole (74 mg, 0.484 mmol) and 1-ethyl-3-(3-dimethylaminopropyl)-carbodiimide hydrochloride (94 mg, 0.490 mmol) in that order, and the resulting mixture was stirred at room temperature for 21 hours. The mixture was dissolved in a 2N-aqueous sodium hydroxide solution (10 ml) and then extracted twice with ethyl acetate/toluene/tetrahydrofuran (2/2/1, 10 ml). The extract solution was washed with a saturated aqueous sodium chloride solution, dried over sodium sulfate, and then distilled under reduced pressure to remove the solvent, whereby a crude product was obtained. The crude product was purified by a silica gel column chromatography (eluent: chloroform/methanol=100/3) to obtain N-{2-[(4-benzylpiperazin-1-yl)carbonyl]phenyl}-1H-indazol-5-amine (162 mg, 100%).

MS: m/z=412 (M+1)

The following compounds of Example 516 to Example 519 were synthesized by carrying out reaction according to the method described in Example 515.

EXAMPLE 516

N-(2-hydroxyethyl)-2-(1H-indazol-5-ylamino)benzamide $^1$H-NMR (DMSO-$d_6$) 67 ; 3.31 (2H, m), 3.51 (2H, m), 4.72 (1H, m), 6.72 (1H, t, J=7.4 Hz), 7.05 (1H, d, J=8.4 Hz), 7.16 (1H, d, J=9.0 Hz), 7.24 (1H, t, J=7.7 Hz), 7.51 (2H, m), 7.65 (1H, d, J=7.9 Hz), 7.96 (1H, s), 8.44 (1H, br), 9.67 (1H, s), 12.98 (1H, s).

EXAMPLE 517

1-[2-(1H-indazol-5-ylamino)benzoyl]piperidin-4-ol

MS: m/z=337 (M+1)

EXAMPLE 518

N,N-bis(2-hydroxyethyl)-2-(1H-indazol-5-ylamino)benzamide $^1$H-NMR (CD$_3$OD) δ; 3.50–3.86 (8H, m), 6.87 (1H, t, J=7.4 Hz), 7.11 (1H, d, J=7.9 Hz), 7.19–7.27 (3H, m), 7.43–7.48 (2H, m), 7.91 (1H, s).

EXAMPLE 519 trans-N-(4-hydroxycyclohexyl)-2-(1H-indazol-5-ylamino)benzamide $^1$H-NMR (DMSO-$d_6$) δ; 1.18–1.46 (4H, m), 2.26 (4H, m), 3.39 (1H, m), 3.72 (1H, m), 4.55 (1H, d, J=4.4 Hz), 6.72 (1H, t, J=7.2 Hz), 7.06 (1H, d, J=8.4 Hz), 7.15 (1H, d, J=8.5 Hz), 7.24 (1H, t, J=7.9 Hz), 7.49 (1H, s), 7.51 (1H, d, J=9.0 Hz), 7.61 (1H, d, J=7.7 Hz), 7.96 (1H, s), 8.24 (1H, d, J=7.7 Hz), 9.60 (1H, s), 12.98 (1H, s).

EXAMPLE 520

Synthesis of N-[2-(piperazin-1-ylcarbonyl)phenyl]-1H-indazol-5-amine

To a solution of the N-{2-[(4-benzylpiperazin-1-yl)carbonyl]phenyl}-1H-indazol-5-amine (127 mg, 0.309 mmol) obtained in Example 515 in ethanol (5 ml) were added 10% Pd-C (20 mg) and ammonium formate (98 mg, 1.55 mmol), and the resulting mixture was heated under reflux for 2 hours. The solid was removed by filtration using Celite, and the solvent was distilled off under reduced pressure. The residue was extracted with ethyl acetate, and the extract solution was washed with a saturated aqueous sodium hydrogencarbonate solution and then a saturated aqueous sodium chloride solution, dried over sodium sulfate, and then distilled under reduced pressure to remove the solvent, whereby N-[2-(piperazin-1-ylcarbonyl)phenyl]-1H-indazol-5-amine (56 mg, 57%) was obtained.

$^1$H-NMR (DMSO-$d_6$) δ; 2.61 (4H, m), 3.46 (4H, m), 6.84 (1H, t, J=7.3 Hz), 7.05 (1H, d, J=8.3 Hz), 7.10–7.17 (2H, m), 7.21 (1H, t, J=7.7 Hz), 7.36 (1H, s), 7.43 (1H, s), 7.44 (1H, d, J=8.8 Hz), 7.90 (1H, s), 12.89 (1H, s).

EXAMPLE 521

Synthesis of 4-(1H-indazole-5-ylamino)benzoic acid (a) tert-butyl 4-{1-(2-tetrahydropyranyl)-1H-indazol-5-ylamino}benzoate In a two-necked flask the inner atmosphere of which had been replaced with nitrogen were placed tert-butyl 4-bromobenzoate (2.57 mg, 1.00 mmol), toluene (2 ml), 18-crown-6 (380 mg, 1.40 mmol), the 1-(2-tetrahydropyranyl)-1H-indazol-5-amine (261 mg, 1.23 mmol) obtained in Example 317, (e) and sodium tert-butoxide (135 mg, 1.40 mmol) in that order. After the inner atmosphere of the flask was replaced with nitrogen again, tris(dibenzylideneacetone)(chloroform) dipalladium(0) (52 mg, 0.050 mmol) and (S)-2,2'-bis(diphenylphophino)-1,1'-binaphthyl (94 mg, 0.151 mmol) were added. After the third replacement of the inner atmosphere of the flask with nitrogen, stirring was conducted at 80° C. for 8 hours. The resulting mixture was diluted with diethyl ether and the solid was removed by filtration using Celite. Then, the solvent was distilled off under reduced pressure to obtain a crude product. The crude product was purified by a silica gel column chromatography (eluent: hexane/ethyl acetate=3/1) to obtain tert-butyl 4-{1-(2-tetrahydropyranyl)-1H-indazol-5-ylamino}benzoate (218 mg, 56%).

$^1$H-NMR (CDCl$_3$) δ; 1.57 (9H, s), 1.73 (3H, m), 2.11 (2H, m), 2.56 (1H, m), 3.77 (1H, m), 4.03 (1H, m), 5.72 (1H, dd, J=2.5, 9.5 Hz), 5.97 (1H, s), 6.86 (2H, d, J=8.8 Hz), 7.25 (1H, m), 7.51 (1H, s), 7.59 (1H, d, J=8.8 Hz), 7.85 (2H, d, J=8.8 Hz), 7.96 (1H, s).

(b) Synthesis of 4-(1H-indazole-5-ylamino)benzoic acid

Trifluoroacetic acid (5 ml) was added to a dichloromethane solution (5 ml) of tert-butyl 4-{1-(2-tetrahydropyranyl)-1H-indazol-5-ylamino}benzoate (205 mg, 0.521 mmol), and the resulting mixture was stirred at room temperature for 3 hours. The mixture was added dropwise to saturated aqueous sodium hydrogencarbonate solution/ethyl acetate and then extracted with ethyl acetate. The extract solution was washed with a saturated aqueous sodium chloride solution, dried over sodium sulfate, and then distilled under reduced pressure to remove the solvent, whereby a crude product was obtained. The crude product was washed by the addition of chloroform containing a small amount of methanol, and then was collected by filtration to obtain 4-(1H-indazole-5-ylamino)benzoic acid (46 mg, 35%).

$^1$H-NMR (DMSO-$d_6$) δ; 6.92 (2H, d, J=8.6 Hz), 7.19 (1H, d, J=9.0 Hz), 7.52 (2H, m), 7.73 (2H, d, J=8.6 Hz), 7.98 (1H, s), 8.59 (1H, s).

The following compound of Example 522 was synthesized by carrying out reaction according to the method described in Example 521.

EXAMPLE 522

3-(1H-indazole-5-ylamino)benzoic acid $^1$H-NMR (DMSO-$d_6$) δ; 7.14–7.18 (2H, m), 7.28 (2H, m), 7.44 (1H, s), 7.48–7.53 (2H, m), 7.95 (1H, s), 8.19 (1H, s).

EXAMPLE 523

Synthesis of N-(1,1-dioxidetetrahydro-2H-thiopyran-4-yl)-1H-indazol-5-amine (a) Synthesis of 1,1-dioxidetetrahydro-2H-thiopyran-4-one (CVA-3878)

A solution of m-chloroperbenzoic acid (1.859 g, 10.8 mmol) in ethyl acetate (13 ml) was added dropwise to a solution of tetrahydrothiopyran-4-one (0.500 g, 4.30 mmol) in ethyl acetate (5 ml) at such a rate that no reflux was caused by heat generation. The resulting mixture was stirred overnight. The solution thus obtained was cooled on an ice bath and the solid precipitated was collected by filtration. The precipitate on a filter was washed with cold ethyl acetate and then dried under reduced pressure to obtain 1,1-dioxidetetrahydro-2H-thiopyran-4-one (0.430 g, 67%).

(b) Synthesis of N-(1,1-dioxidetetrahydro-2H-thiopyran-4-yl)-1H-indazol-5-amine (CVA-3879)

To a solution of 1,1-dioxidetetrahydro-2H-thiopyran-4-one (0.400 g, 2.70 mmol) in 1,2-dichloroethane (10 ml) were added 5-aminoindazole (0.360 g, 2.70 mmol) and sodium triacetoxyborohydride (0.801 g, 3.78 mmol), and the resulting mixture was cooled on a water bath. Acetic acid (0.16 ml, 2.8 mmol) was added thereto and stirred overnight. A saturated aqueous sodium hydrogencarbonate solution was added thereto, and the solid precipitated was collected by filtration and the precipitate on a filter was washed with water. The precipitate on the filter was suspended in methanol and washed by stirring at 50° C. The suspension was cooled to room temperature and the precipitate was collected by filtration. The precipitate on the filter was washed twice with diethyl ether and then dried under reduced pressure to obtain N-(1,1-dioxidetetrahydro-2H-thiopyran-4-yl)-1H-indazol-5-amine (0.355 g, 50%).

Melting point: 254–256° C.

EXAMPLE 524

Synthesis of N-(1-oxidetetrahydro-2H-thiopyran-4-yl)-1H-indazol-5-amine

The residue obtained by distilling off the solvent under the reduced pressure from the filtrate obtained after the washing with methanol in Example 523 was purified by a silica gel chromatography (eluent: chloroform/methanol=10/1) to obtain N-(1-oxidetetrahydro-2H-thiopyran-4-yl)-1H-indazol-5-amine (0.0648 g, 10%).

Melting point: 220–222° C.

EXAMPLE 525

Synthesis of N-(8-azabicyclo[3.2.1]oct-3-yl)-1H-indazol-5-amine

A solution of iodine (0.488 g, 1.92 mmol) in hexamethyldisilane (0.560 g, 3.83 mmol) was heated at 110° C. and stirred until the purple solution became colorless. The solution was cooled to room temperature, followed by adding thereto a solution of the ethyl 3-(1H-indazol-5-ylamino)-8-azabicyclo[3.2.1]octane-8-carboxylate (0.200 g, 0.637 mmol) obtained in Example 14 in 1,2-dichloroethane (6 ml), and the resulting mixture was heated at 50° C. and stirred for 7 hours. The mixture was cooled to room temperature and methanol was added thereto to quench the mixture. Then, the solvent was distilled off under reduced pressure and a 1N-aqueous sodium hydroxide solution was added to the residue. The solvent was distilled off under reduced pressure and the residue was dried up and then purified by a silica gel chromatography (eluent: chloroform/methanol/30%-aqueous ammonia=100/10/1) to obtain N-(8-azabicyclo[3.2.1] oct-3-yl)-1H-indazol-5-amine (0.0893 g, 58%).

Melting point: 236–238° C.

EXAMPLE 526

Synthesis of N-isopropyl-1H-indazol-5-amine

Acetone (25 μl, 0.340 mmol), sodium triacetoxyborohydride (83 mg, 0.392 mmol) and acetic acid (18 μl, 0.314 mmol) were added in that order to a solution of 5-amino-1H-indazole (40 mg, 0.300 mmol) in 1,2-dichloroethane (1 ml), and the resulting mixture was stirred at room temperature for 20 hours. The reaction was terminated by the use of a saturated aqueous sodium hydrogencarbonate solution (4 ml), followed by extraction with ethyl acetate. The solvent was distilled off under reduced pressure to obtain a crude product. The crude product was purified by a silica gel column chromatography (eluent: chloroform/methanol=100/2) to obtain N-isopropyl-1H-indazol-5-amine (40 mg, 76%).

MS: m/z=176 (M+1)

The following compounds of Example 527 to Example 541 were synthesized by carrying out reaction according to the method described in Example 526.

EXAMPLE 527

N-cyclobutyl-1H-indazol-5-amine

MS: m/z=188 (M+1)

EXAMPLE 528

N-cyclopentyl-1H-indazol-5-amine

MS: m/z=202 (M+1)

EXAMPLE 529

N-cycloheptyl-1H-indazol-5-amine

MS: m/z=230 (M+1)

EXAMPLE 530

N-(2,6-dimethylcyclohexyl)-1H-indazol-5-amine

MS: m/z=244 (M+1)

EXAMPLE 531

N-(2-methoxycyclohexyl)-1H-indazol-5-amine

MS: m/z=246 (M+1)

EXAMPLE 532

N-(2,2-dimethyl-1,3-dioxan-5-yl)-1H-indazol-5-amine

MS: m/z=248 (M+1)

EXAMPLE 533 tert-butyl 4-(1H-indazol-5-ylamino)cyclohexylcarbamate $^1$H-NMR (DMSO-d$_6$) δ; 1.10–1.30 (4H, m), 1.37 (9H, s), 1.77 (2H, m), 1.99 (2H, m), 3.08 (1H, m), 3.23 (1H, m), 5.05 (1H, d, J=8.1 Hz), 6.63 (1H, s), 6.77 (1H, d, J=9.0 Hz), 7.23 (1H, d, J=8.4 Hz), 7.72 (1H, s), 12.54 (1H, s).

EXAMPLE 534

N,N-dicyclopentyl-1H-indazol-5-amine

MS: m/z=270 (M+1)

EXAMPLE 535

N-(1-benzylpiperidin-3-yl)-1H-indazol-5-amine

MS: m/z=307 (M+1)

EXAMPLE 536

N-(1-azabicyclo[2.2.2]oct-3-yl)-1H-indazol-5-amine

MS: m/z=243 (M+1)

EXAMPLE 537

N-(2,2,6,6-tetramethylpiperidin-4-yl)-1H-indazol-5-amine

MS: m/z=273 (M+1)

EXAMPLE 538

N-(9-methyl-9-azabicyclo[3.3.1]non-3-yl)-1H-indazol-5-amine

MS: m/z=271 (M+1)

EXAMPLE 539

N-(8-methyl-8-azabicyclo[3.2.1]oct-3-yl)-1H-indazol-5-amine

MS: m/z=257 (M+1)

EXAMPLE 540

3-(1H-indazol-5-ylamino)-8-methyl-8-azabicyclo[3.2.1]octan-6-ol

MS: m/z=273 (M+1)

EXAMPLE 541

Ethyl 3-[(1H-indazol-5-ylamino)methyl]-8-azabicyclo[3.2.1]octane-8-carbamate

MS: m/z=329 (M+1)

EXAMPLE 542

Synthesis of 2-(1H-indazol-5-ylamino)propane-1,3-diol

To a solution of the N-(2,2-dimethyl-1,3-dioxan-5-yl)-1H-indazol-5-amine (23 mg, 0.0930 mmol) obtained in Example 532 in tetrahydrofuran (1 ml) was added 1N-hydrochloric acid (1 ml), and the resulting mixture was stirred at room temperature for 1.5 hours. The reaction was terminated by the use of a saturated aqueous sodium hydrogencarbonate solution, followed by extraction with ethyl acetate, whereby 2-(1H-indazol-5-ylamino)propane-1,3-diol (16 mg, 84%) was obtained.

MS: m/z=208 (M+1)

EXAMPLE 543

Synthesis of 2-(1H-indazol-5-yl)cyclohexane-1,4-diamine ditrifluoroacetate

Trifluoroacetic acid (1 ml) was added to a solution of the tert-butyl 4-(1H-indazol-5-ylamino)cyclohexylcarbamate (25 mg, 0.0757 mmol) obtained in Example 533 in dichloromethane (1 ml), and the resulting mixture was stirred at room temperature for 4 hours. The solvent was distilled off under reduced pressure and the residue was washed with diethyl ether and filtered to obtain 2-(1H-indazol-5-yl)cyclohexane-1,4-diamine ditrifluoroacetate (32 mg, 91%).

MS: m/z=231 (M+1)

EXAMPLE 544

Synthesis of N-piperidin-3-yl-1H-indazol-5-amine

To a solution of the N-(1-benzylpiperidin-3-yl)-1H-indazol-5-amine (463 mg, 1.51 mmol) obtained in Example 535 in ethanol (10 ml) were added 10% Pd—C (50 mg) and then ammonium formate (952 mg, 15.1 mmol), and the resulting mixture was heated under reflux for 2 hours. The solid was removed by filtration using Celite, and the solvent was distilled off under reduced pressure. Chloroform/aqueous ammonia was added to the residue, followed by extraction with chloroform, and the extract solution was washed with a saturated aqueous sodium chloride solution, dried over sodium sulfate, and then distilled under reduced pressure to remove the solvent, whereby N-piperidin-3-yl-1H-indazol-5-amine (241 mg, 74%) was obtained.

MS: m/z=217 (M+1)

EXAMPLE 545

Synthesis of N-(8-azabicyclo[3.2.1]oct-3-ylmethyl)-1H-indazol-5-amine

Iodine (599 mg, 2.36 mmol) was added to hexamethyldisilane (864 mg, 5.90 mmol) and the resulting mixture was heated to 70° C. with stirring. When the reaction solution became substantially colorless after violent reaction, it was cooled to room temperature. A solution of the ethyl 3-[(1H-indazol-5-ylamino)methyl]-8-azabicyclo[3.2.1]octane-8-carbamate (386 mg, 1.18 mmol) obtained in Example 541 in dichloroethane (8 ml) was added thereto, and the resulting mixture was stirred at 50° C. for 5 hours. The reaction was terminated by adding methanol (4 ml) under ice-cooling, and then the solvent was distilled off under reduced pressure. Chloroform/aqueous ammonia was added to the residue, followed by extraction with chloroform, and the extract solution was washed with a saturated aqueous sodium chloride solution, dried over sodium sulfate, and then distilled under reduced pressure to remove the solvent, whereby N-(8-azabicyclo[3.2.1]oct-3-ylmethyl)-1H-indazol-5-amine (258 mg, 85%) was obtained.

MS: m/z=257 (M+1)

EXAMPLE 546

Synthesis of N-(8-(2-phenoxyethyl)-8-azabicyclo[3.2.1]oct-3-yl)-1H-indazol-5-amine Potassium carbonate (52 mg, 0.376 mmol) and then 2-phenoxyethyl bromide (38 mg, 0.189 mmol) were added to a suspension of the N-(8-azabicyclo[3.2.1]oct-3-yl)-1H-indazol-5-amine (30 mg, 0.124 mmol) obtained in Example 525 in dimethylformamide (1 ml), and the resulting mixture was stirred at room temperature for 20 hours. After the solid was removed by filtration, the dimethylformamide was distilled off under reduced pressure as an azeotrope with toluene to obtain a crude product. The crude product was purified by a silica gel column chromatography (eluent: chloroform/methanol/triethylamine=20/1/1) to obtain N-(8-(2-phenoxyethyl)-8-azabicyclo[3.2.1]oct-3-yl)-1H-indazol-5-amine (40 mg, 89%).

MS: m/z=377 (M+1)

The following compounds of Example 547 to Example 567 were synthesized by carrying out reaction according to the method described in Example 546.

EXAMPLE 547

N-(8-propyl-8-azabicyclo[3.2.1]oct-3-yl)-1H-indazol-5-amine

MS: m/z=285 (M+1)

EXAMPLE 548

N-(8-isopropyl-8-azabicyclo[3.2.1]oct-3-yl)-1H-indazol-5-amine

MS: m/z=285 (M+1)

EXAMPLE 549

N-(8-isobutyl-8-azabicyclo[3.2.1]oct-3-yl)-1H-indazol-5-amine

MS: m/z=299 (M+1)

EXAMPLE 550

N-[8-(cyclobutylmethyl)-8-azabicyclo[3.2.1]oct-3-yl]-1H-indazol-5-amine

MS: m/z=311 (M+1)

EXAMPLE 551

N-[8-(cyclohexylmethyl)-8-azabicyclo[3.2.1]oct-3-yl]-1H-indazol-5-amine

MS: m/z=339 (M+1)

EXAMPLE 552

N-[8-(2-phenylethyl)-8-azabicyclo[3.2.1]oct-3-yl]-1H-indazol-5-amine

MS: m/z=347 (M+1)

EXAMPLE 553

2-[3-(1H-indazol-5-ylamino)-8-azabicyclo[3.2.1]oct-8-yl]ethanol

MS: m/z=287 (M+1)

EXAMPLE 554

3-[3-(1H-indazol-5-ylamino)-8-azabicyclo[3.2.1]oct-8-yl]propan-1-ol

MS: m/z=301 (M+1)

EXAMPLE 555

N-[8-(2-methoxyethyl)-8-azabicyclo[3.2.1]oct-3-yl]-1H-indazol-5-amine

MS: m/z=301 (M+1)

EXAMPLE 556

N-[8-(tetrahydro-2H-pyran-2-ylmethyl)-8-azabicyclo[3.2.1]oct-3-yl]-1H-indazol-5-amine MS: m/z=341 (M+1)

EXAMPLE 557

3-[3-(1H-indazol-5-ylamino)-8-azabicyclo[3.2.1]oct-8-yl]propanenitrile

MS: m/z=296 (M+1)

EXAMPLE 558

2-[3-(1H-indazol-5-ylamino)-8-azabicyclo[3.2.1]oct-8-yl]acetamide

MS: m/z=300 (M+1)

EXAMPLE 559

N-(8-ethyl-8-azabicyclo[3.2.1]oct-3-yl)-1H-indazol-5-amine

MS: m/z=271 (M+1)

EXAMPLE 560

N-(8-allyl-8-azabicyclo[3.2.1]oct-3-yl)-1H-indazol-5-amine

MS: m/z=283 (M+1)

EXAMPLE 561

N-(8-but-3-enyl-8-azabicyclo[3.2.1]oct-3-yl)-1H-indazol-5-amine

MS: m/z 297 (M+1)

EXAMPLE 562

N-[8-(3-methylbut-2-enyl)-8-azabicyclo[3.2.1]oct-3-yl]-1H-indazol-5-amine

MS: m/z=311 (M+1)

EXAMPLE 563

N-[8-(cyclopropylmethyl)-8-azabicyclo[3.2.1]oct-3-yl]-1H-indazol-5-amine

MS: m/z=297 (M+1)

EXAMPLE 564

1-[3-(1H-indazol-5-ylamino)-8-azabicyclo[3.2.1]oct-8-yl]propan-2-ol

MS: m/z=301 (M+1)

EXAMPLE 565

[3-(1H-indazol-5-ylamino)-8-azabicyclo[3.2.1]oct-8-yl]acetonitrile

MS: m/z=282 (M+1)

EXAMPLE 566

4-[3-(1H-indazol-5-ylamino)-8-azabicyclo[3.2.1]oct-8-yl]butanenitrile

MS: m/z=310 (M+1)

EXAMPLE 567

N-[8-(2,2,2-trifluoroethyl)-8-azabicyclo[3.2.1]oct-3-yl]-1H-indazol-5-amine

MS: m/z=325 (M+1)

EXAMPLE 568

Synthesis of N-(8-benzyl-8-azabicyclo[3.2.1]oct-3-yl)-1H-indazol-5-amine

Benzaldehyde (37 μl, 0.364 mmol) and sodium triacetoxyborohydride (127 mg, 0.599 mmol) were added to a suspension of the N-(8-azabicyclo[3.2.1]oct-3-yl)-1H-indazol-5-amine (73 mg, 0.301 mmol) obtained in Example 525 in dichloromethane (1 ml), and the resulting mixture was stirred at room temperature for 25 hours. The reaction was terminated by the addition of a saturated aqueous sodium hydrogencarbonate solution, followed by extraction with ethyl acetate. The extract solution was washed with a saturated aqueous sodium chloride solution, dried over sodium sulfate, and then distilled under reduced pressure to remove the solvent, whereby a crude product was obtained. The crude product was washed with cold methanol and collected by filtration to obtain N-(8-benzyl-8-azabicyclo[3.2.1]oct-3-yl)-1H-indazol-5-amine (52 mg, 52%).

$^1$H-NMR (DMSO-$d_6$) δ; 1.68 (2H, m), 2.01 (6H, m), 3.06 (2H, m), 3.48 (1H, m), 3.50 (2H, s), 5.21 (1H, br), 6.47 (1H, s), 6.85 (1H, d, J=9.2 Hz), 7.18–7.40 (6H, m), 7.73 (1H, s), 12.55 (1H, s).

The following compounds of Example 569 to Example 572 were synthesized by carrying out reaction according to the method described in Example 568.

EXAMPLE 569

N-(8-cyclobutyl-8-azabicyclo[3.2.1]oct-3-yl)-1H-indazol-5-amine

MS: m/z=297 (M+1)

EXAMPLE 570

N-(8-cyclopentyl-8-azabicyclo[3.2.1]oct-3-yl)-1H-indazol-5-amine

MS: m/z=311 (M+1)

EXAMPLE 571

N-(8-cyclohexyl-8-azabicyclo[3.2.1]oct-3-yl)-1H-indazol-5-amine

MS: m/z=325 (M+1)

EXAMPLE 572

N-(8-tetrahydro-2H-pyran-4-yl-8-azabicyclo[3.2.1]oct-3-yl)-1H-indazol-5-amine

MS: m/z=327 (M+1)

EXAMPLE 573

Synthesis of 2-[3-(1H-indazol-5-ylamino)-8-azabicyclo[3.2.1]oct-8-yl]-2-oxoethanol Hydroxyacetic acid (32 mg, 0.421 mmol), 1-hydroxybenzotriazole (76 mg, 0.496 mmol) and 1-ethyl-3-(3-dimethylaminopropyl)-carbodiimide hydrochloride (95 mg, 0.496 mmol) were added in that order to a suspension of the N-(8-azabicyclo[3.2.1]oct-3-yl)-1H-indazol-5-amine (100 mg, 0.413 mmol) obtained in Example 525 in dimethylformamide (1 ml), and the resulting mixture was stirred at room temperature for 23 hours. The reaction mixture was poured into a saturated aqueous sodium hydrogencarbonate solution to terminate the reaction, and was extracted twice with ethyl acetate. The extract solution was washed with a saturated aqueous sodium chloride solution, dried over sodium sulfate, and then distilled under reduced pressure to remove the solvent, whereby a crude product was obtained. The crude product was purified by a preparative thin-layer chromatography (200×200×0.5 mm, 4 plates, eluent: chloroform/methanol=15/1) to obtain 2-[3-(1H-indazol-5-ylamino)-8-azabicyclo[3.2.1]oct-8-yl]-2-oxoethanol (13 mg, 11%).

MS: m/z=301 (M+1)

The following compounds of Example 574 and Example 575 were synthesized by carrying out reaction according to the method described in Example 573.

EXAMPLE 574

N-[8-(2-methoxyacetyl)-8-azabicyclo[3.2.1]oct-3-yl]-1H-indazol-5-amine

MS: m/z=315 (M+1)

EXAMPLE 575

N-[8-(2-phenoxyacetyl)-8-azabicyclo[3.2.1]oct-3-yl]-1H-indazol-5-amine

MS: m/z=377 (M+1)

EXAMPLE 576

Synthesis of N-(1-azabicyclo[2.2.2]oct-3-yl)-1H-indazol-5-amine dihydrochloride

To a solution of the N-(1-azabicyclo[2.2.2]oct-3-yl)-1H-indazol-5-amine (178 mg, 0.75 mmol) obtained in Example 536 in methanol (5 ml) was added 1N-hydrochloric acid/diethyl ether (3 ml), and the resulting mixture was stirred at room temperature for 1 hour. After diethyl ether (15 ml) was added thereto, the solid formed was collected by filtration, washed with diethyl ether and then dried to obtain N-(1-azabicyclo[2.2.2]oct-3-yl)-1H-indazol-5-amine dihydrochloride (210 mg, 91%).

Melting point: 184–188° C.

The following compound of Example 577 was synthesized by carrying out reaction according to the method described in Example 576, except for using the 2-[3-(1H-indazol-5-ylamino)-8-azabicyclo[3.2.1]oct-8-yl]ethanol obtained in Example 553, as a starting material.

EXAMPLE 577

2-[3-(1H-indazol-5-ylamino)-8-azabicyclo[3.2.1]oct-8-yl]ethanol dihydrochloride

Melting point: 154–157° C.

The following compound of Example 578 was synthesized by carrying out reaction according to the method described in Example 576, except for using the N-(8-propyl-8-azabicyclo[3.2.1]oct-3-yl)-1H-indazol-5-amine obtained in Example 547, as a starting material.

EXAMPLE 578

N-(8-propyl-8-azabicyclo[3.2.1]oct-3-yl)-1H-indazol-5-amine dihydrochloride

Melting point: 198–203° C.

The following compounds of Examples 579 and 580 were synthesized by carrying out reactions according to the methods described in Example 372, (b) and Example 377, except for using the 4-methoxy-1H-indazol-5-ol obtained in Example 469, as a starting material.

EXAMPLE 579

5-(4-Azepanyloxy)-4-methoxy-1H-indazole $^1$H-NMR (DMSO-$d_6$) δ; 1.57 (1H, m), 1.83–2.02 (5H, m), 2.85–3.00 (3H, m), 3.14 (1H, m), 4.04 (3H, s), 4.33 (1H, m), 7.10 (2H, s), 8.15 (1H, s), 13.00 (1H, brs)

EXAMPLE 580

4-Methoxy-5-(4-piperidinyloxy)-1H-indazole monohydrochloride $^1$H-NMR (DMSO-$d_6$) δ; 1.85 (2H, m), 1.98 (2H, m), 3.03 (2H, m), 3.24 (2H, m), 4.08 (3H, s), 4.33 (1H, m), 7.12 (1H, d, J=8.8 Hz), 7.14 (1H, d, J=8.8 Hz), 8.19 (1H, s), 8.82 (2H, brs).

The following compound of Example 581 was synthesized by carrying out reactions according to the methods described in Example 372, (b), Example 377 and Example 327, except for using the 4-methoxy-1H-indazol-5-ol obtained in Example 469, as a starting material.

EXAMPLE 581

4-Methoxy-5-(3-piperidinyloxy)-1H-indazole monohydrochloride $^1$H-NMR (DMSO-$d_6$) δ; 1.64 (1H, m), 1.80 (2H, m), 1.98 (1H, m), 3.04 (2H, m), 3.25 (2H, m), 4.12 (3H, s), 4.30 (1H, m), 7.12 (1H, d, J=8.8 Hz), 7.18 (1H, d, J=8.8 Hz), 8.24 (1H, s), 8.60 (1H, brs), 9.02 (1H, brs).

The following compounds of Example 582 and Example 583 were synthesized by carrying out reaction according to the method described in Example 385, except for using the 4-methoxy-1H-indazol-5-ol obtained in Example 469, as a starting material.

EXAMPLE 582 trans-3-[(4-Methoxy-1H-indazol-5-yl)oxy]cyclohexanamine $^1$H-NMR (DMSO-$d_6$) δ; 1.11 (1H, m), 1.30–1.56 (5H, m), 1.65 (3H, m), 1.96 (1H, m), 3.04 (1H, m), 4.02 (3H, s), 4.46 (1H, m), 7.09 (2H, s), 8.10 (1H, s), 12.95 (1H, brs).

EXAMPLE 583 cis-3-[(4-Methoxy-1H-indazol-5-yl)oxy]cyclohexanamine $^1$H-NMR (DMSO-$d_6$) δ; 0.89 (1H, m), 1.04–1.23 (3H, m), 1.45 (2H, brs), 1.68 (2H, m), 1.93 (1H, m), 2.08 (1H, m), 2.51 (1H, m), 3.97 (1H, m), 4.03 (3H, s), 7.08 (2H, s), 8.11 (1H, s), 12.96 (1H, brs).

The following compounds of Example 584 and Example 585 were synthesized by carrying out reactions according to the methods described in Example 385 and Example 327, except for using the 4-methoxy-1H-indazol-5-ol obtained in Example 469, as a starting material.

EXAMPLE 584 trans-4-[(4-Methoxy-1H-indazol-5-yl)oxy]cyclohexanamine monohydrochloride $^1$H-NMR (DMSO-$d_6$) δ; 1.30–1.53 (4H, m), 1.94–2.06 (4H, m), 3.04 (1H, m), 3.97 (1H, m), 4.04 (3H, s), 7.09 (1H, d, J=8.8 Hz), 7.10 (1H, d, J=8.8 Hz), 7.92 (3H, brs), 8.13 (1H, s).

EXAMPLE 585 cis-4-[(4-Methoxy-1H-indazol-5-yl)oxy]cyclohexanamine monohydrochloride $^1$H-NMR (DMSO-$d_6$) δ; 1.55 (2H, m), 1.76–1.84 (4H, m), 1.90–1.95 (2H, m), 3.07 (1H, m), 4.07 (3H, s), 4.30 (1H, m), 7.11 (2H, s), 7.92 (3H, brs), 8.15 (1H, s).

The following compounds of Example 586 to Example 588 were synthesized by carrying out reactions according to the methods described in Example 365 and Example 381, except for using the 4-(trifluoromethyl)-1H-indazol-5-ol obtained in Example 474, as a starting material.

EXAMPLE 586 trans-4-{[4-(Trifluoromethyl)-1H-indazol-5-yl]oxy}cyclohexanamine

MS: m/z=300 (M+1)

EXAMPLE 587 cis-3-{[4-(Trifluoromethyl)-1H-indazol-5-yl]oxy}cyclohexanamine

MS: m/z=300 (M+1)

EXAMPLE 588 cis-4-{[4-(Trifluoromethyl)-1H-indazol-5-yl]oxy}cyclohexanamine

MS: m/z=300 (M+1)

EXAMPLE 589

Synthesis of 5-(azepan-3-yloxy)-4-methyl-1H-indazole (a) Synthesis of Ethyl 5-[benzyl(2-ethoxy-2-oxoethyl)amino]pentanoate Under a nitrogen atmosphere, triethylamine (1.73 ml, 0.01243 mol) and ethyl 5-bromovalerate (1.72 ml, 0.0109 mol) were added to a solution of N-benzylglycine ethyl ester (2.0 g, 0.0103 mol) in acetonitrile (40 ml) at room temperature, and the resulting mixture was heated at 60° C. After 1 hour, the mixture was refluxed. After 9 hours, the mixture was concentrated under reduced pressure, and the resulting residue was extracted with water (200 ml) and ethyl acetate (200 ml×2) and the organic layer was dried over anhydrous magnesium sulfate. The organic layer dried was concentrated under reduced pressure and the resulting residue was purified by a silica gel column chromatography (eluent: hexane/ethyl acetate) to obtain ethyl 5-[benzyl(2-ethoxy-2-oxoethyl)amino]pentanoate (1.2473 g, 37%).

(b) Synthesis of ethyl 1-benzyl-3-oxoazepane-2-carboxylate and ethyl 1-benzyl-3-oxoazepane-4-carboxylate Under a nitrogen atmosphere, a 21% wt. sodium ethoxide-ethanol solution (1.23 ml, 3.31 mmol) was added to toluene (100 ml) at room temperature, and the resulting mixture was refluxed by the use of a Dean-Stark trap. A solution of ethyl 5-[benzyl(2-ethoxy-2-oxoethyl)amino]pentanoate (965.9 mg, 3.01 mmol) in toluene (50 ml) was added dropwise thereto over a period of 1.5 hours. After 3 hours, a 21% wt. sodium ethoxide-ethanol solution (1.23 ml, 3.31 mmol) was further added thereto. After another 1 hour, the toluene (30 ml) was distilled off with heating. After 5 hours, the reaction solution was poured into water (200 ml) and extracted with ethyl acetate (100 ml×2), and the organic layer was dried over anhydrous magnesium sulfate. The organic layer dried was concentrated under reduced pressure and the resulting residue was purified by a silica gel column chromatography (eluent: hexane/ethyl acetate) to obtain ethyl 1-benzyl-3-oxoazepane-4-carboxylate (158.5 mg, 19%) and ethyl 1-benzyl-3-oxoazepane-2-carboxylate (213.8 mg, content=about 75%).

(c) Synthesis of 1-benzylazepan-3-one

Under a nitrogen atmosphere, a 75%-aqueous sulfuric acid solution (2 ml) was added to a solution of ethyl 1-benzyl-3-oxoazepane-4-carboxylate (150 mg, 0.545 mmol) in ethanol (1 ml) at room temperature, and the resulting mixture was heated to 120° C. After 3 hours, completion of the reaction was confirmed and the resulting mixture was cooled. On the other hand, under a nitrogen atmosphere, a 75%-aqueous sulfuric acid solution (2 ml) was added to a solution of the mixture containing ethyl 1-benzyl-3-oxoazepane-2-carboxylate (200 mg, content=about 75%) in ethanol (1 ml) at room temperature, and the resulting mixture was heated to 120° C. After 12 hours, completion of the reaction was confirmed and the temperature was lowered. The reaction solution was combined with that obtained above, and the combined reaction solution was poured onto ice and adjusted to pH 8 with a 2M-aqueous sodium hydroxide solution. The combined reaction solution thus treated was extracted with ethyl acetate (50 ml×2) and the organic layer was dried over anhydrous magnesium sulfate. The organic layer dried was concentrated under reduced pressure and the resulting residue was purified by a silica gel column chromatography (eluent: hexane/ethyl acetate) to obtain 1-benzylazepan-3-one (118.1 mg, 53%).

(d) Synthesis of 1-benzylazepan-3-ol

Under a nitrogen atmosphere, lithium aluminum hydride (1.4 mg, 0.0369 mmol) was added to a solution of 1-benzylazepan-3-one (15 mg, 0.0738 mmol) in diethyl ether (1 ml) at 0° C., and the resulting mixture was heated to room temperature. After 30 minutes, water, a 2M-aqueous sodium hydroxide solution and water were added in that order to the reaction solution. The resulting mixture was filtered by the use of Celite, and the filtrate was concentrated under reduced pressure and the resulting residue was purified by a silica gel column chromatography (eluent: chloroform/methanol) to obtain 1-benzylazepan-3-ol (16.2 mg, 100%).

(e) Synthesis of tert-butyl 3-hydroxyazepane-1-carboxylate

Under a nitrogen atmosphere, 10%-Pd/C 50% wet (500 mg) and ammonium formate (2.0 g) were added to a solution of 1-benzylazepan-3-ol (1.072 g, 5.22 mmol) in ethanol (40 ml) at room temperature, and the resulting mixture was refluxed. After 1 hour, the reaction solution was filtered by the use of Celite and the resulting filtrate was concentrated under reduced pressure. The concentrate was dried under reduced pressure and to a solution of the resulting residue in dichloromethane (25 ml) was added di-t-butyl dicarbonate (1.32 ml, 5.74 mmol) at 0° C. After 30 minutes, the mixture thus obtained was warmed up to room temperature. After 2.5 hours, the mixture was poured into water (100 ml) and extracted with chloroform (50 ml×2), and then the organic layer was dried over anhydrous magnesium sulfate. The organic layer dried was concentrated under reduced pressure and the resulting residue was purified by a silica gel column chromatography (eluent: hexane/ethyl acetate) to obtain tert-butyl 3-hydroxyazepane-1-carboxylate (946.7 mg, 84%).

(f) Synthesis of 5-(azepan-3-yloxy)-4-methyl-1H-indazole

Under a nitrogen atmosphere, triphenylphosphine (146 mg, 0.559 mmol), tert-butyl 3-hydroxyazepane-1-carboxylate (100 mg, 0.466 mmol) and diisopropyl azodicarboxylate (101 μl, 0.512 mmol) were added at 0° C. to a solution of the 4-methyl-1H-indazol-5-ol (69 mg, 0.466 mmol) obtained in Example 402 in tetrahydrofuran (4 ml). After 30 minutes, the mixture thus obtained was warmed up to room temperature and stirred overnight. The reaction solution was concentrated under reduced pressure, and the resulting residue was diluted with chloroform and washed with a 1M-aqueous sodium hydroxide solution. After the aqueous layer was re-extracted with chloroform, the organic layer was dried over anhydrous magnesium sulfate. The organic layer dried was concentrated under reduced pressure and the resulting residue was purified by a silica gel column chromatography (eluent: hexane/ethyl acetate). The oil thus obtained was dissolved in methanol (2 ml) at room temperature, and 4N-hydrochloric acid-dioxane (2 ml) was added thereto. After 1 hour, the mixture thus obtained was concentrated under reduced pressure and the resulting residue was dissolved in methanol (5 ml). The resulting solution was adjusted to pH 10 by dropwise addition of a 2M-aqueous sodium hydroxide solution. The solution adjusted was concentrated under reduced pressure and the resulting residue was re-dissolved in methanol (5 ml). Silica gel (1 g) was added thereto and the resulting mixture was concentrated under reduced pressure and then dried. The resulting solid was purified by a silica gel column chromatography (eluent: chloroform/methanol→chloroform/methanol (1%-aqueous ammonia)) to obtain 5-(azepan-3-yloxy)-4-methyl-1H-indazole (45.1 mg, 39%).

IR (neat) cm$^{-1}$; 3220, 2941, 1512, 1217, 715.

EXAMPLE 590

Synthesis of trans-2,2-dimethyl-5-[(4-methyl-1H-indazol-5-yl)oxy]cyclohexanamine (a) Synthesis of cis-3-amino-4,4-dimethylcyclohexanol hydrochloride Sodium borohydride (4.2 mmol, 160 mg) was added in small portions to a solution of 3-azide-4,4-dimethylcyclohexanone (700 mg, 4.2 mmol) in methanol (10 ml) at room temperature, and the resulting mixture was stirred for 20 minutes. The reaction mixture was diluted with ethyl acetate (100 ml) and washed with a saturated aqueous sodium chloride solution (100 ml×2). The organic layer was dried over anhydrous magnesium sulfate and the insoluble material was filtered off. Then, the filtrate was concentrated under reduced pressure to a total volume of about 10 ml. After the rsulting residue was diluted with methanol (30 ml), 10% palladium carbon (50% wet, 200 mg) was added thereto and the resulting mixture was stirred at room temperature for 1 hour under a hydrogen atmosphere. After the insoluble material was removed by filtration using Celite, the filtrate was concentrated under reduced pressure and the resulting residue was converted to its hydrochloride with a 1N-HCl ether solution to obtain cis-3-amino-4,4-dimethylcyclohexanol hydrochloride (720 mg, 95%, containing about 15% of trans isomer) as white powder.

$^1$H-NMR (DMSO-d$_6$) δ; 0.85 (3H, s), 0.98 (3H, s), 1.05–1.80 (5H, m), 1.90–2.00 (1H, m), 2.79 (1H, m), 3.40 (1H, m), 4.80 (1H, brs), 7.99 (3H, m).

(b) Synthesis of cis-2-(5-hydroxy-2,2-dimethylcyclohexyl)-1H-isoindole-1,3(2H)-dione Acetonitrile (5 ml), potassium carbonate (3.1 mmol, 423 mg) and N-carboethoxyphthalimide (3.1 mmol, 670 mg) were added to a solution of cis-3-amino-4,4-dimethylcyclohexanol hydrochloride (500 mg, 2.8 mmol) in water (10 ml), and the resulting mixture was stirred as it was for 2 hours. The crystals precipitated were collected by filtration and then recrystallized from chloroform-diethyl ether to obtain cis-2-(5-hydroxy-2,2-dimethylcyclohexyl)-1H-isoindole-1,3(2H)-dione (400 mg, 53%, containing about 10% of trans isomer) as white powder.

¹H-NMR (DMSO-d₆) δ; 0.90 (3H, s), 1.05 (3H, s), 1.30–1.75 (5H, m), 1.80–1.95 (2H, m), 2.84 (1H, q, J=12.5 Hz), 3.69 (1H, m), 4.04 (1H, dd, J=3.1, 13.0 Hz), 7.65–7.90 (4H, m).

(c) Synthesis of trans-2-{2,2-dimethyl-5-[(4-methyl-1H-indazol-5-yl)oxy]cyclohexyl}-1H-isoindole-1,3 (2H)-dione To a solution of the 4-methyl-1H-indazol-5-ol (500 mg, 1.83 mmol) obtained in Example 402 in toluene (8 ml) were added cis-2-(5-hydroxy-2,2-dimethylcyclohexyl)-1H-isoindole-1,3(2H)-dione (400 mg, 1.5 mmol) and cyanomethylenetri-n-butylphosphorane (494 mg, 2.1 mmol) at room temperature, and the resulting mixture was heated to 100° C. After stirring for 7 hours, the reaction solution was concentrated under reduced pressure and the resulting residue was dissolved in chloroform and washed with a 1M-aqueous sodium hydroxide solution. Extraction with chloroform was carried out again and the organic layer was dried over anhydrous magnesium sulfate. The organic layer dried was concentrated under reduced pressure and the resulting residue was purified by a silica gel column chromatography (eluent: hexane/ethyl acetate) to obtain trans-2-{2,2-dimethyl-5-[(4-methyl-1H-indazol-5-yl)oxy]cyclohexyl}-1H-isoindole-1,3(2H)-dione (360 mg, 61%, containing about 10% of cis isomer).

¹H-NMR (CDCl₃) δ; 1.00 (3H, s), 1.08 (3H, s), 1.35–1.50 (1H, m), 1.70–2.20 (4H, m), 2.59 (3H, s), 3.05 (1H, dt, J=2.6, 13.5 Hz), 4.65–4.78 (2H, m), 7.09 (1H, d, J=9.0 Hz), 7.24 (1H, d, J=9.0 Hz), 7.67–7.75 (2H, m), 7.76–7.85 (2H, m), 8.03 (1H, d, J=1.1 Hz), 10.04 (1H, brs)

(d) Synthesis of trans-2,2-dimethyl-5-[(4-methyl-1H-indazol-5-yl)oxy]cyclohexanamine To trans-2-{2,2-dimethyl-5-[(4-methyl-1H-indazol-5-yl)oxy]cyclohexyl}-1H-isoindole-1,3(2H)-dione was added 30%-methylamine/ethanol (10 ml) at room temperature, and the resulting mixture was refluxed for 8 hours. The reaction solution was concentrated under reduced pressure at room temperature and the resulting residue was purified by a silica gel column chromatography (eluent: chloroform→chloroform/methanol/(1%-aqueous ammonia) =20/1) to obtain trans-2,2-dimethyl-5-[(4-methyl-1H-indazol-5-yl)oxy]cyclohexanamine (143 mg, 60%, containing about 10% of cis isomer).

¹H-NMR (DMSO-d₆) δ; 0.79 (3H, s), 0.94 (3H, s), 1.10–1.90 (6H, m), 2.39 (3H, s), 2.74 (1H, dd, J=4.1, 10.4 Hz), 4.49 (1H, m), 7.09 (1H, d, J=8.8 Hz), 7.27 (1H, d, J=8.8 Hz), 7.99 (1H, d, J=0.9 Hz), 12.85 (1H, brs).

EXAMPLE 591

Synthesis of cis-2,2-dimethyl-5-[(4-methyl-1H-indazol-5-yl)oxy]cyclohexanamine (a) trans-3-(1,3-dioxo-1,3-dihydro-2H-isoindol-2-yl)-4,4-dimethylcyclohexyl 4-nitrobenzoate To a solution of the cis-2-(5-hydroxy-2,2-dimethylcyclohexyl)-1H-isoindole-1,3(2H)-dione (500 mg, 1.83 mmol) obtained in Example 590 in tetrahydrofuran (10 ml) were added 4-nitrobenzoic acid (321 mg, 1.05 mmol), triphenylphosphine (576 mg, 2.20 mmol) and a 40%-diethyl azodicarboxylate/toluene solution (1.00 ml, 2.20 mmol) at 3° C., and stirred overnight at room temperature. The reaction solution was concentrated and the resulting residue was purified by a silica gel column chromatography (eluent: hexane/ethyl acetate) to obtain trans-3-(1,3-dioxo-1,3-dihydro-2H-isoindol-2-yl)-4,4-dimethylcyclohexyl 4-nitrobenzoate (509 mg, 66%).

¹H-NMR (CDCl₃) δ; 0.90 (3H, s), 1.05 (3H, s), 1.30–2.00 (6H, m), 2.85 (1H, q, J=13.4 Hz), 3.69 (1H, m), 4.05 (1H, dd, J=3.5, 13.4 Hz), 7.66–7.75 (2H, m), 7.78–7.87 (2H, m).

(b) Synthesis of trans-2-(5-hydroxy-2,2-dimethylcyclohexyl)-1H-isoindole-1,3(2H)-dione To a suspension of trans-3-(1,3-dioxo-1,3-dihydro-2H-isoindol-2-yl)-4,4-dimethylcyclohexyl 4-nitrobenzoate (420 mg, 1.00 mmol) in a mixture of methanol (0.10 ml) and tetrahydrofuran (10 ml) was added 28%-sodium methoxide (0.24 ml, 1.00 mmol) at 3° C., and stirred at 0° C. for 30 minutes and then at room temperature for 35 minutes. The reaction solution was adjusted to pH 4 with a 0.5M-aqueous potassium hydrogensulfate solution and then distilled under reduced pressure to remove the solvent. The residue was added to water and extracted with ethyl acetate. The organic layer was dried over anhydrous magnesium sulfate and distilled under reduced pressure to remove the solvent, and the resulting residue was purified by a silica gel column chromatography (hexane/ethyl acetate=2/1) to obtain trans-2-(5-hydroxy-2,2-dimethylcyclohexyl)-1H-isoindole-1,3 (2H)-dione (231 mg, 85%).

¹H-NMR (CDCl₃) δ; 0.93 (3H, s), 1.02 (3H, s), 1.25–1.40 (2H, m), 1.55–2.00 (4H, m), 3.04 (1H, dt, J=2.9, 13.7 Hz), 4.31 (1H, m), 4.55 (1H, dd, J=3.5, 13.4 Hz), 7.67–7.75 (2H, m), 7.76–7.87 (2H, m).

(c) cis-2-{2,2-Dimethyl-5-[(4-methyl-1H-indazol-5-yl)oxy]cyclohexyl}-1H-isoindole-1,3(2H)-dione The title compound was synthesized by carrying out reaction according to the method described in Example 590, (c)

¹H-NMR (CDCl₃) δ; 0.92 (3H, s), 1.12 (3H, s), 1.20–2.20 (5H, m), 2.51 (3H, s), 3.04 (1H, m), 4.00–4.15 (2H, m), 7.11 (1H, d, J=8.8 Hz), 7.24 (1H, d, J=8.8 Hz), 7.67–7.75 (2H, m), 7.76–7.85 (2H, m), 8.02 (1H, d, J=0.9 Hz).

(d) Synthesis of trans-2,2-dimethyl-5-[(4-methyl-1H-indazol-5-yl)oxy]cyclohexanamine The title compound was synthesized by carrying out reaction according to the method described in Example 590, (d).

Melting point: 170–171° C.

¹H-NMR (DMSO-d₆) δ; 0.79 (3H, s), 0.87 (3H, s), 1.00–1.60 (6H, m), 1.70–1.95 (2H, m), 2.30 (1H, dd, J=3.7, 11.9 Hz), 2.37 (3H, s), 3.98 (1H, m), 7.10 (1H, d, J=8.8 Hz), 7.27 (1H, d, J=8.8 Hz), 7.99 (1H, d, J=0.6 Hz), 12.87 (1H, brs).

EXAMPLE 592

Synthesis of 1-{4-[(4-methyl-1H-indazol-5-yl)oxy]cyclohexyl}-methanamine hydrochloride (a) Synthesis of methyl 4-{[tert-butyl(dimethyl)silyl]oxy}cyclohexanecarboxylate To a solution of methyl 4-hydroxycyclohexane-carboxylate (a cis/trans mixture, 5.00 g, 31.6 mmol) and imidazole (4.30 g, 63.2 mmol) in dimethylformamide (20 ml) was added t-butyldimethylsilyl chloride (5.72 g, 37.9 mmol) at room temperature, and stirred at the same temperature for 5 hours. After completion of the reaction, an ethyl acetate/toluene (1/1) solution and water were added thereto, and the organic layer was collected, dried over sodium sulfate and distilled under reduced pressure to remove the solvent, whereby methyl 4-{[tert-butyl(dimethyl)silyl]oxy}cyclohexane-carboxylate (8.66 g, 100%) was obtained.

(b) Synthesis of (4-{[tert-butyl(dimethyl)silyl]-oxy}cyclohexyl)methanol

Lithium aluminum hydride (696 mg, 18.4 mmol) was added to a tetrahydrofuran solution (25 ml) of methyl 4-{[tert-butyl(dimethyl)silyl]oxy}cyclohexanecarboxylate (2.50 g, 9.18 mmol) under ice-cooling. The resulting mixture was warmed up to room temperature and then stirred overnight. After completion of the reaction, water and a 15% aqueous sodium hydroxide solution were added thereto and stirred. The solid formed was removed by filtration, and the solvent was distilled off under reduced pressure to obtain a crude product. The crude product was purified by a silica gel column chromatography (hexane-ethyl acetate=1:1) to obtain (4-{[tert-butyl(dimethyl)silyl]oxy}cyclohexyl)methanol (2.08 g, 93%).

(c) Synthesis of 2-[(4-{[tert-butyl(dimethyl)silyl]oxy}cyclohexyl)methyl]-1H-isoindazole-1,3(2H)-dione At room temperature, a solution of (4-{[tert-butyl(dimethyl)silyl]oxy}cyclohexyl)methanol (1.00 g, 4.09 mmol), triphenylphosphine (1.18 g, 4.50 mmol) and phthalimide (722 mg, 4.91 mmol) in tetrahydrofuran (15 ml) were stirred for 30 minutes. Diethyl diazodicarboxylate (a 40% toluene solution, 2.20 g, 4.91 mmol) was slowly added to the reaction solution, and the resulting mixture was stirred at room temperature for 5 hours. The solvent was distilled off under reduced pressure and the residue was purified by a silica gel column chromatography (hexane/ethyl acetate=4:1) to obtain 2-[(4-{[tert-butyl(dimethyl)silyl]oxy}cyclohexyl)methyl]-1H-isoindazole-1,3(2H)-dione (1.60 g, 100%).

(d) Synthesis of 2-[4-(hydroxycyclohexyl)methyl]-1H-isoindazole-1,3(2H)-dione

Trifluoroacetic acid (1 ml) was added to a solution of 2-[(4-{[tert-butyl(dimethyl)silyl]oxy}cyclohexyl)methyl]-1H-isoindazole-1,3(2H)-dione (1.60 g, 4.09 mmol) in tetrahydrofuran/water (1:1, 10 ml), and the resulting mixture was stirred at room temperature for 6 hours. Ethyl acetate/5% aqueous sodium chloride solution was added to the reaction solution, followed by extraction with ethyl acetate, and the extract solution was dried over sodium sulfate and distilled under reduced pressure to remove the solvent. The residue was purified by a silica gel column chromatography (hexane/ethyl acetate=2:1-1:1) to obtain 2-[4-(hydroxycyclohexyl)methyl]-1H-isoindazole-1,3(2H)-dione (0.70 g, 61%).

(e) Synthesis of 2-({4-[(4-methyl-1H-indazol-5-yl)oxy]cyclohexyl}methyl)-1H-isoindazole-1,3(2H)-dione Cyanomethylenetri-n-butylphosphorane (500 mg, 2.07 mmol) and the 4-methyl-1H-indazol-5-ol (306 mg, 2.07 mmol) obtained in Example 402 were added to a toluene solution (10 ml) of 2-[4-(hydroxycyclohexyl)methyl]-1H-isoindazole-1,3(2H)-dione (358 mg, 1.38 mmol) at room temperature, and the resulting mixture was heated under reflux for 2 hours. The reaction solution was cooled to room temperature and distilled under reduced pressure to remove the solvent. Chloroform and a 5% aqueous sodium hydroxide solution were added to the residue, and the organic layer was collected and then dried over sodium sulfate. The solvent was distilled off under reduced pressure to obtain a crude product 2-({4-[(4-methyl-1H-indazol-5-yl)oxy]cyclohexyl}methyl)-1H-isoindazole-1,3(2H)-dione (1.43 g).

(f) Synthesis of 1-{4-[(4-methyl-1H-indazol-5-yl)oxy]cyclohexyl}-methanamine

A 30% methylamine-ethanol solution (10 g) was added to 2-({4-[(4-methyl-1H-indazol-5-yl)oxy]cyclohexyl}methyl)-1H-isoindazole-1,3(2H)-dione (358 mg, 1.38 mmol) at room temperature, and the resulting mixture was heated under reflux for 2 hours. The reaction solution was cooled to room temperature and distilled under reduced pressure to remove the solvent. The residue was purified by a silica gel column chromatography (chloroform/methanol/triethylamine=10:1:1) to obtain 1-{4-[(4-methyl-1H-indazol-5-yl)oxy]cyclohexyl}-methanamine (1.50 mg, 42%).

(g) Synthesis of 1-{4-[(4-methyl-1H-indazol-5-yl)oxy]cyclohexyl}-methanamine hydrochloride A 1N-hydrochloric acid-diethyl ether solution (0.70 ml, 0.70 mmol) was added to a solution of 1-{4-[(4-methyl-1H-indazol-5-yl)oxy]cyclohexyl}-methanamine (150 mg, 0.578 mmol) in methanol (2 ml) at room temperature and stirred at the same temperature for 30 minutes. The solvent was distilled off under reduced pressure, and the residue was solidified with isopropyl alcohol-diisopropyl ether, filtered and then dried to obtain 1-{4-[(4-methyl-1H-indazol-5-yl)oxy]cyclohexyl}-methanamine hydrochloride (148 mg, 87%).

IR (neat) cm$^{-1}$; 2927, 1508, 1267, 1227, 1084, 945.

EXAMPLE 593

Synthesis of cis-4-[(4-chloro-1H-indazol-5-yl)oxy]cyclohexanamine hydrochloride (a) Synthesis of cis-4-[(4-chloro-1H-indazol-5-yl)oxy]cyclohexanamine Under a nitrogen atmosphere, triphenylphosphine (280 mg, 1.07 mmol), the trans-2-(4-hydroxycyclohexyl)-1H-isoindole-1,3(2H)-dione (218 mg, 0.890 mmol) obtained in Example 323, (a) and diisopropyl azodicarboxylate (193 μl, 0.979 mmol) were added to a solution of the 4-chloro-1H-indazol-5-ol (150 mg, 0.890 mmol) obtained in Example 468 in tetrahydrofuran (6 ml) at 0° C. After 30 minutes, the mixture thus obtained was warmed up to room temperature and stirred overnight. The reaction solution was concentrated under reduced pressure, and the resulting residue was diluted with chloroform (20 ml) and then washed with a 1M-aqueous sodium hydroxide solution (10 ml). After the aqueous layer was re-extracted with chloroform (10 ml), the organic layer was dried over anhydrous magnesium sulfate. The organic layer dried was concentrated under reduced pressure and the resulting residue was purified by a silica gel column chromatography (eluent: hexane/ethyl acetate). To the resulting oil was added a 30%-methylamine-ethanol solution at room temperature, and the resulting mixture was refluxed. After 4 hours, the mixture was concentrated under reduced pressure at room temperature, and the resulting residue was purified by a silica gel column chromatography (eluent: chloroform/methanol→chloroform/methanol (1%-aqueous ammonia)) to obtain cis-4-[(4-chloro-1H-indazol-5-yl)oxy]cyclohexanamine (83.6 mg, 35%).

(b) Synthesis of cis-4-[(4-chloro-1H-indazol-5-yl) oxy]cyclohexanamine hydrochloride Under a nitrogen atmosphere, methanol (1 drop) was added to a suspension of cis-4-[(4-chloro-1H-indazol-5-yl)oxy]cyclohexanamine (54.2 mg, 0.204 mmol) in acetonitrile (4 ml) at room temperature to effect dissolution, and 1M-hydrochloric acid-diethyl ether (224 µl, 0.224 mmol) was added dropwise thereto. After 1 hour, diethyl ether (10 ml) was added to the reaction suspension and the resulting mixture was filtered. Then, the precipitate was dried under pressure to obtain cis-4-[(4-chloro-1H-indazol-5-yl)oxy]cyclohexanamine hydrochloride (57.8 mg, 94%).

IR (neat) cm$^{-1}$; 2939, 1504, 1240, 939, 796.

EXAMPLE 594

Synthesis of 5-(azepin-4-yloxy)-4-chloro-1H-indazole

Under a nitrogen atmosphere, triphenylphosphine (280 mg, 1.07 mmol), the tert-butyl 4-hydroxyazepane-1-carboxylate (192 mg, 0.890 mmol) obtained in Example 322, (c) and diisopropyl azodicarboxylate (193 µl, 0.979 mmol) were added at 0° C. to a solution of the 4-chloro-1H-indazol-5-ol (150 mg, 0.890 mmol) obtained in Example 468 in tetrahydrofuran (6 ml). After 30 minutes, the mixture thus obtained was warmed up to room temperature and stirred overnight. The reaction solution was concentrated under reduced pressure, and the resulting residue was diluted with chloroform (20 ml) and washed with a 1M-aqueous sodium hydroxide solution (10 ml). After the aqueous layer was re-extracted with chloroform (10 ml), the organic layer was dried over anhydrous magnesium sulfate. The organic layer dried was concentrated under reduced pressure and the resulting residue was purified by a silica gel column chromatography (eluent: hexane/ethyl acetate). The oil thus obtained was dissolved in methanol (3 ml) at room temperature and 4N-hydrochloric acid-dioxane (3 ml) was added thereto. After 1 hour, the mixture thus obtained was concentrated under reduced pressure, and the resulting residue was dissolved in methanol (5 ml) and the resulting solution was adjusted to pH 10 by dropwise addition of a 2M-aqueous sodium hydroxide solution. The solution adjusted was concentrated under reduced pressure and the resulting residue was re-dissolved in methanol (5 ml). Silica gel (1 g) was added thereto and the resulting mixture was concentrated under reduced pressure and then dried. The resulting solid was purified by a silica gel column chromatography (eluent: chloroform/methanol→chloroform/methanol (1%-aqueous ammonia)) to obtain 5-(azepin-4-yloxy)-4-chloro-1H-indazole (128.1 mg, 54%).

IR (neat) cm$^{-1}$; 3081, 2923, 1497, 1184, 729.

The following compound of Example 595 was synthesized by carrying out reaction according to the method described in Example 594, except for using tert-butyl 3-hydroxypiperidine-1-carboxylate as a starting material.

EXAMPLE 595

5-(Piperidin-3-yloxy)-4-chloro-1H-indazole $^1$H-NMR (DMSO-d$_6$) δ; 1.60 (1H, m), 1.73 (1H, m), 1.92 (2H, m), 2.93 (2H, m), 3.06 (1H, m), 3.24 (1H, m), 4.40 (1H, m), 7.36 (1H, d, J=9.0 Hz), 7.49 (1H, d, J=9.0 Hz), 8.05 (1H, s), 13.37 (1H, s)

EXAMPLE 596

Synthesis of 5-(piperidin-4-yloxy)-4-chloro-1H-indazole hydrochloride

Under a nitrogen atmosphere, triphenylphosphine (280 mg, 1.07 mmol), tert-butyl 4-hydroxypiperidine-1-carboxylate (179 mg, 0.890 mmol) and diisopropyl azodicarboxylate (193 µl, 0.979 mmol) were added at 0° C. to a solution of the 4-chloro-1H-indazol-5-ol (150 mg, 0.890 mmol) obtained in Example 468 in tetrahydrofuran (6 ml). After 30 minutes, the mixture thus obtained was heated to room temperature and stirred overnight. The reaction solution was concentrated under reduced pressure, and the resulting residue was diluted with chloroform and then washed with a 1M-aqueous sodium hydroxide solution. After the aqueous layer was re-extracted with chloroform, the organic layer was dried over anhydrous magnesium sulfate. The organic layer dried was concentrated under reduced pressure and the resulting residue was purified by a silica gel column chromatography (eluent: hexane/ethyl acetate). The oil thus obtained was dissolved in methanol (3 ml) at room temperature and 4N-hydrochloric acid-dioxane (3 ml) was added thereto. After 1 hour, the mixture thus obtained was concentrated under reduced pressure and the resulting residue was washed with ethyl acetate by repulping to obtain 5-(piperidin-4-yloxy)-4-chloro-1H-indazole hydrochloride (219.7 mg, 86%).

$^1$H-NMR (DMSO-d$_6$) δ; 1.93 (2H, m), 2.05 (2H, m), 3.06 (2H, m), 3.24 (2H, m), 4.61 (1H, m), 7.36 (1H, d, J=9.0 Hz), 7.49 (1H, dd, J=9.0, 1.0 Hz), 8.03 (1H, d, J=1.0 Hz), 8.99 (2H, brs.).

The following compound of Example 597 was synthesized by carrying out reaction according to the method described in Example 589, except for using the 4-methoxy-1H-indazol-5-ol obtained in Example 469, as a starting material.

EXAMPLE 597

5-(Azepan-3-yloxy)-4-methoxy-1H-indazole

IR (neat) cm$^{-1}$; 3174, 2929, 1510, 1230, 928, 723.

EXAMPLE 598

Synthesis of 4-bromo-1H-indazol-5-ol

N-bromosuccinimide (1.06 g, 5.96 mmol) was added to a solution of the 1H-indazol-5-ol (800 mg, 5.96 mmol) obtained in Reference Example 4 in tetrahydrofuran (20 ml) at room temperature. The resulting mixture was stirred for 14 hours while being maintained at room temperature. The mixture was concentrated under reduced pressure and the resulting residue was purified by a silica gel column chromatography (eluent: hexane/ethyl acetate) to obtain 4-bromo-1H-indazol-5-ol (1.15 g, 91%).

$^1$H-NMR (DMSO-d$_6$) δ; 7.37 (1H, d, J=0.92 Hz), 7.40 (1H, d, J=0.92 Hz), 7.82 (1H, s), 9.77 (1H, brs), 13.12 (1H, brs).

The following compound of Example 599 was synthesized by carrying out reaction according to the method described in Example 407, except for using the 4-bromo-1H-indazol-5-ol obtained in Example 598, as a starting material.

EXAMPLE 599

5-(Azepan-4-yloxy)-4-bromo-1H-indazole

MS: m/z=310 (M+1)

The following compounds of Examples 600 to Example 603 were synthesized by carrying out reaction according to the method described in Example 470, except for using the 4-bromo-1H-indazol-5-ol obtained in Example 598, as a starting material.

EXAMPLE 600 trans-3-[(4-Bromo-1H-indazol-5-yl)oxy]cyclohexanamine

MS: m/z=310 (M+1)

EXAMPLE 601 cis-3-[(4-Bromo-1H-indazol-5-yl)oxy]cyclohexanamine

MS m/z=310 (M+1)

EXAMPLE 602 trans-4-[(4-Bromo-1H-indazol-5-yl)oxy]cyclohexanamine

MS: m/z=310 (M+1)

EXAMPLE 603 cis-4-[(4-Bromo-1H-indazol-5-yl)oxy]cyclohexanamine

MS: m/z=310 (M+1)

EXAMPLE 604

Synthesis of 4-fluoro-1H-indazol-5-ol (a) Synthesis of 6-chloro-2-fluoro-3-methyl-4-nitrophenol A solution of 6-chloro-2-fluoro-3-methylphenol (9.00 g, 56.1 mmol) in dichloromethane (100 ml) was added dropwise to a suspension of 85% nitronium•tetrafluoroborate (9.50 g, 60.8 mmol) in dichloromethane (150 ml) at 0 to 5° C. under ice-cooling. The resulting mixture was warmed up to room temperature and stirred for 2 hours while maintaining the temperature. The mixture was poured into ice water and then partitioned and extracted with chloroform, and the organic layer was washed with water, dried over anhydrous magnesium sulfate and then filtered. The filtrate was concentrated under reduced pressure to obtain a crude product. After the crude product was dissolved in toluene (57 ml) by heating to 80° C., the solution was allowed to cool to 60° C. and maintained at this temperature. Hexane (171 ml) was added dropwise thereto and the resulting mixture was allowed to cool to room temperature and then it was ice-cooled while maintaining temperature. Thereafter, the crystals formed were collected by filtration and dried to obtain 6-chloro-2-fluoro-3-methyl-4-nitrophenol (7.05 g, 61%).

(b) Synthesis of 4-amino-2-fluoro-3-methylphenol

To a solution of 6-chloro-2-fluoro-3-methyl-4-nitrophenol (4.11 g, 19.9 mmol) in ethanol (200 ml) were added 10%-palladium/carbon (containing 50% water, 410 mg) and ammonium formate (15.1 g, 240 mmol), and the resulting mixture was stirred for 3 hours with heating under reflux while maintaining the temperature. The mixture was filtered by the use of Celite and the filtrate was concentrated under reduced pressure to obtain a crude product. The crude product was partitioned by the use of water and ethyl acetate (the aqueous layer was adjusted to pH 6 to 7 with a 5% aqueous sodium hydrogencarbonate solution and re-extracted), and the organic phase was washed with a 5% aqueous sodium chloride solution, dried over anhydrous magnesium sulfate, and then filtered. The filtrate was concentrated under reduced pressure to obtain 4-amino-2-fluoro-3-methylphenol (2.89 g, 100%).

(c) Synthesis of 4-(acetylamino)-2-fluoro-3-methylphenyl acetate

Acetic anhydride (4.49 ml, 47.6 mmol) was added dropwise to a solution of 4-amino-2-fluoro-3-methylphenol (2.80 g, 1.91 mmol) and pyridine (3.53 ml, 43.6 mmol) in ethyl acetate (60 ml) at room temperature, and the resulting mixture was slowly heated to 65° C. and stirred for 45 minutes while being maintained at this temperature. The resulting reaction solution was cooled to room temperature and partitioned by the use of water and ethyl acetate to find that an insoluble material was present. The insoluble material was collected by filtration and dried to obtain 4-(acetylamino)-2-fluoro-3-methylphenyl acetate (679 mg, 15%). The filtrate was concentrated and then extracted with chloroform to obtain a crude product, and the crude product was washed with ethyl acetate (8 ml)-hexane (24 ml) by repulping, collected by filtration and then dried to obtain 4-(acetylamino)-2-fluoro-3-methylphenyl acetate (3.54 g, 79%).

(d) Synthesis of 1-acetyl-4-fluoro-1H-indazol-5-yl acetate

Acetic anhydride (2.83 ml, 30.0 mmol), tetrabutylammonium bromide (161 mg, 0.500 mmol), potassium acetate (1.96 g, 20.0 mmol) and isoamyl nitrite (1.75 ml, 13.0 mmol) were added in that order to a solution of 4-(acetylamino)-2-fluoro-3-methylphenyl acetate (2.25 g, 9.99 mmol) in ethyl acetate (30 ml) at room temperature. The resulting mixture was slowly heated until heating under reflux was caused. Then, the mixture was stirred for 11 hours while maintaining the temperature. After cooling, the mixture was partitioned and extracted with water and ethyl acetate, and the organic phase was washed with an aqueous sodium chloride solution, dried over anhydrous magnesium sulfate and then filtered. The filtrate was concentrated under reduced pressure to obtain a crude product. The crude product was purified by a silica gel column chromatography (eluent: hexane/ethyl acetate) to obtain 1-acetyl-4-fluoro-1H-indazol-5-yl acetate (1.00 g, 38%).

(e) Synthesis of 4-fluoro-1H-indazol-5-ol

A 6N aqueous sodium hydroxide solution (5 ml, 30 mmol) was added dropwise to a solution of 1-acetyl-4-fluoro-1H-indazol-5-yl acetate (995 mg, 3.78 mmol) in methanol (5 ml)-tetrahydrofuran (5 ml) at room temperature, and the resulting mixture was stirred for 3.5 hours while being maintained at room temperature. The resulting reaction solution was adjusted to pH 5 to 6 by dropwise addition of a 1N aqueous hydrochloric acid solution (about 25 ml) and extracted with ethyl acetate, and the organic layer was washed with an aqueous sodium chloride solution, dried over anhydrous magnesium sulfate and then filtered. The filtrate was concentrated under reduced pressure to obtain a crude product. The crude product was purified by a silica gel column chromatography (eluent: chloroform/ethyl acetate) to obtain 4-fluoro-1H-indazol-5-ol (219 mg, 38%).

$^1$H-NMR (DMSO-$d_6$) δ; 7.05 (1H, t-like, J=8.4 Hz), 7.18 (1H, d, J=8.8 Hz), 7.99 (1H, s), 9.29 (1H, s), 13.07 (1H, brs).

The following compound of Example 605 was synthesized by carrying out reaction according to the method described in Example 407, except for using the 4-fluoro-1H-indazol-5-ol obtained in Example 604, as a starting material.

EXAMPLE 605

5-(Azepan-4-yloxy)-4-fluoro-1H-indazole

MS: m/z=250 (M+1)

The following compound of Example 606 was synthesized by carrying out reaction according to the method described in Example 470, except for using the 4-fluoro-1H-indazol-5-ol obtained in Example 604, as a starting material.

EXAMPLE 606 cis-3-[(4-Fluoro-1H-indazol-5-yl)oxy]cyclohexanamine

MS: m/z=250 (M+1)

EXAMPLE 607

Synthesis of 4-(methylthio)-1H-indazol-5-ol (a) Synthesis of 4-bromo-1-tetrahydro-2H-pyran-2-yl-5-(tetrahydro-2H-pyran-2-yloxy)-1H-indazole To a solution of the 4-bromo-1H-indazol-5-ol (13.08 g, 61.4 mmol) obtained in Example 598 in dichloromethane (200 ml) were added 3,4-dihydro-2H-pyran (16.8 ml, 184 mmol) and p-toluenesulfonic acid pyridine salt (4.64 g, 18.4 mmol), and stirred overnight. The reaction solution was added to a saturated aqueous sodium hydrogencarbonate solution and extracted twice with chloroform, and the extract solution was dried over anhydrous magnesium sulfate. The solvent was distilled off and the residue was purified by a silica gel chromatography (hexane/ethyl acetate=10/1 to 5/1) to obtain 4-bromo-1-tetrahydro-2H-pyran-2-yl-5-(tetrahydro-2H-pyran-2-yloxy)-1H-indazole (18.14 g, 77%).

(b) Synthesis of 4-(methylthio)-1-tetrahydro-2H-pyran-2-yl-5-(tetrahydro-2H-pyran-2-yloxy)-1H-indazole Sodium thiomethoxide (0.0265 g, 0.38 mmol) was added to a solution of 4-bromo-1-tetrahydro-2H-pyran-2-yl-5-(tetrahydro-2H-pyran-2-yloxy)-1H-indazole (0.100 g, 0.26 mmol) in N,N-dimethylformamide (1 ml), and the resulting mixture was heated at 70° C. and stirred for 11 hours. The reaction solution was added to water and extracted three times with toluene/ethyl acetate=1/1, and the extract solution was dried over anhydrous magnesium sulfate. The solvent was distilled off and the residue was purified by a silica gel chromatography (hexane/ethyl acetate=10/1) to obtain 4-(methylthio)-1-tetrahydro-2H-pyran-2-yl-5-(tetrahydro-2H-pyran-2-yloxy)-1H-indazole (0.0737 g, 80%).

(c) Synthesis of 4-(methylthio)-1H-indazol-5-ol

Trifluoroacetic acid (1 ml) was added to a solution of 4-(methylthio)-1-tetrahydro-2H-pyran-2-yl-5-(tetrahydro-2H-pyran-2-yloxy)-1H-indazole (0.0730 g, 0.21 mmol) in dichloromethane (1 ml) and stirred for 1 hour. The reaction solution was added to water and extracted three times with ethyl acetate and the extract solution was dried over anhydrous magnesium sulfate. The solvent was distilled off and the residue was purified by a silica gel chromatography (hexane/ethyl acetate=2/1), crystallized from hexane/ethyl acetate and then dried up to obtain 4-(methylthio)-1H-indazol-5-ol (0.0481 g, >99%).

Melting point: 126–128° C.

EXAMPLE 608

Synthesis of 5-(azepan-4-yloxy)-4-(methylthio)-1H-indazole monohydrochloride (a) Synthesis of tert-butyl 4-{[4-(methylthio)-1H-indazol-5-yl]oxy}azepane-1-carboxylate The tert-butyl 4-hydroxyazepane-1-carboxylate (0.0504 g, 0.23 mmol) obtained in Example 322, (c) and triphenylphosphine (0.0723 g, 0.28 mmol) were added to a solution of the 4-(methylthio)-1H-indazol-5-ol (0.0377 g, 0.21 mmol) obtained in Example 607 in tetrahydrofuran (2 ml), and the resulting mixture was ice-cooled. A solution of diisopropyl azodicarboxylate (0.0557 g, 0.28 mmol) in tetrahydrofuran (1 ml) was added dropwise thereto, and the resulting mixture was slowly heated to room temperature and stirred overnight. The reaction solution was concentrated and then diluted with chloroform, and a 1N-aqueous sodium hydroxide solution was added thereto, followed by extraction with chloroform (twice). The extract solution was dried over anhydrous magnesium sulfate. The solvent was distilled off and the residue was purified by a silica gel chromatography (hexane/ethyl acetate=3/1~2/1~3/2) to obtain tert-butyl 4-{[4-(methylthio)-1H-indazol-5-yl]oxy}azepane-1-carboxylate (0.0318 g, 40%).

(b) Synthesis of 5-(azepan-4-yloxy)-4-(methylthio)-1H-indazole

The title compound was synthesized by carrying out reaction according to the method described in Example 377, except for using tert-butyl 4-{[4-(methylthio)-1H-indazol-5-yl]oxy}azepane-1-carboxylate as a starting material.

(c) Synthesis of 5-(azepan-4-yloxy)-4-(methylthio)-1H-indazole monohydrochloride The title compound was synthesized by carrying out reaction according to the method described in Example 327, except for using 5-(azepan-4-yloxy)-4-(methylthio)-1H-indazole as a starting material.

IR (neat) cm$^{-1}$; 2769, 1255, 1245, 1087, 958.

EXAMPLE 609

Synthesis of 5-(azepan-4-yloxy)-4-(methylsulfonyl)-1H-indazole monohydrochloride (a) Synthesis of tert-butyl 4-{[4-(methylsulfonyl)-1H-indazol-5-yl]oxy}azepane-1-carboxylate A solution of the tert-butyl 4-{[4-(methylthio)-1H-indazol-5-yl]oxy}azepane-1-carboxylate (0.0212 g, 0.056 mmol) obtained in Example 608, (a) in chloroform (1 ml) was ice-cooled, and m-chloroperbenzoic acid (0.0221 g, 0.13 mmol) was added thereto. Then, the resulting mixture was slowly heated to room temperature and stirred overnight. The reaction solution was added to a saturated aqueous sodium hydrogencarbonate solution and extracted three times with chloroform, and the extract solution was dried over anhydrous magnesium sulfate. The solvent was distilled off and the residue was purified by a silica gel chromatography (chloroform/methanol=30/1) to obtain tert-butyl 4-{[4-(methylsulfonyl)-1H-indazol-5-yl]oxy}azepane-1-carboxylate (0.0199 g, 86%).

(b) Synthesis of 5-(azepan-4-yloxy)-4-(methylsulfonyl)-1H-indazole monohydrochloride The title compound was synthesized by carrying out reactions according to the methods described in Example 377 and Example 327, except for using tert-butyl 4-{[4-(methylsulfonyl)-1H-indazol-5-yl]oxy}azepane-1-carboxylate as a starting material.

Melting point: 185–187° C.

EXAMPLE 610

Synthesis of 2-(cis-4-{[4-(methylthio)-1H-indazol-5-yl]oxy}cyclohexyl)-1H-isoindole-1,3(2H)-dione The 4-(methylthio)-1H-indazol-5-ol (0.166 g, 0.92 mmol) obtained in Example 607 and the trans-2-(4-hydroxycyclohexyl)-1H-isoindole-1,3(2H)-dione (0.151 g, 0.61 mmol) obtained in Example 323, (a) were added to a solution of cyanomethylenetri-n-butylphosphorane (0.247 g, 0.92 mmol) in toluene (6 ml), and the resulting mixture was heated at 100° C. and stirred for 7 hours. The reaction solution was concentrated and then diluted with chloroform, and a 1N-aqueous sodium hydroxide solution was added thereto, followed by extraction with chloroform (three times). The extract solution was dried over anhydrous magnesium sulfate. The solvent was distilled off and the residue was purified by a silica gel chromatography (hexane/ethyl acetate=2/1~1/1) to obtain 2-(cis-4-{[4-(methylthio)-1H-indazol-5-yl]oxy}cyclohexyl)-1H-isoindole-1,3(2H)-dione (0.144 g: 58%).

Melting point: 211–212° C.

EXAMPLE 611

Synthesis of cis-4-{[4-(methylthio)-1H-indazol-5-yl]oxy}cyclohexanamine monohydrochloride (a) Synthesis of cis-4-{[4-(methylthio)-1H-indazol-5-yl]oxy}cyclohexanamine The title compound was synthesized by carrying out reaction according to the method described in Example 381, except for using the 2-(cis-4-{[4-(methylthio)-1H-indazol-5-yl]oxy}cyclohexyl)-1H-isoindole-1,3(2H)-dione obtained in Example 610, as a starting material.

(b) Synthesis of cis-4-{[4-(methylthio)-1H-indazol-5-yl]oxy}cyclohexanamine monohydrochloride The title compound was synthesized by carrying out reaction according to the method described in Example 327, except for using cis-4-{[4-(methylthio)-1H-indazol-5-yl]oxy}cyclohexanamine as a starting material.

Melting point: 199–201° C.

EXAMPLE 612

Synthesis of cis-4-{[4-(methylsulfonyl)-1H-indazol-5-yl]oxy}cyclohexanamine (a) Synthesis of 2-(cis-4-{[4-(methylsulfonyl)-1H-indazol-5-yl]oxy}cyclohexyl)-1H-isoindole-1,3(2H)-dione and 2-(cis-4-{[4-(methylsulfinyl)-1H-indazol-5-yl]oxy}cyclohexyl)-1H-isoindole-1,3(2H)-dione The title compounds were synthesized by carrying out reaction according to the method described in Example 609, (a), except for using the 2-(cis-4-{[4-(methylthio)-1H-indazol-5-yl]oxy}cyclohexyl)-1H-isoindole-1,3(2H)-dione obtained in Example 610, as a starting material.

(b) Synthesis of cis-4-{[4-(methylsulfonyl)-1H-indazol-5-yl]oxy}cyclohexanamine

The title compound was synthesized by carrying out reaction according to the method described in Example 381, except for using 2-(cis-4-{[4-(methylsulfonyl)-1H-indazol-5-yl]oxy}cyclohexyl)-1H-isoindole-1,3(2H)-dione as a starting material.

IR (neat) cm$^{-1}$; 1300, 1228, 1128, 978, 931.

EXAMPLE 613

Synthesis of cis-4-{[4-(methylsulfinyl)-1H-indazol-5-yl]oxy}cyclohexanamine

The title compound was synthesized by carrying out reaction according to the method described in Example 381, except for using the 2-(cis-4-{[4-(methylsulfinyl)-1H-indazol-5-yl]oxy}cyclohexyl)-1H-isoindole-1,3(2H)-dione obtained in Example 612, (a), as a starting material.

IR (neat) cm$^{-1}$; 3168, 1284, 1228, 1018, 931.

EXAMPLE 614

Synthesis of 2-(cis-3-{[4-(methylthio)-1H-indazol-5-yl]oxy}cyclohexyl)-1H-isoindole-1,3(2H)-dione The title compound was synthesized by carrying out reaction according to the method described in Example 608, (a), except for using the trans-2-(3-hydroxycyclohexyl)-1H-isoindole-1,3(2H)-dione obtained in Example 385, (b), as a starting material.
Melting point: 156–157° C.

EXAMPLE 615

Synthesis of cis-3-{[4-(methylthio)-1H-indazol-5-yl]oxy}cyclohexanamine

The title compound was synthesized by carrying out reaction according to the method described in Example 381, except for using the 2-(cis-3-{[4-(methylthio)-1H-indazol-5-yl]oxy}cyclohexyl)-1H-isoindole-1,3(2H)-dione obtained in Example 614, as a starting material.
Melting point: 140° C.

EXAMPLE 616

Synthesis of trans-4-{[4-(methylthio)-1H-indazol-5-yl]oxy}cyclohexanamine (a) Synthesis of 2-(trans-4-{[4-(methylthio)-1H-indazol-5-yl]oxy}cyclohexyl)-1H-isoindole-1,3(2H)-dione The title compound was synthesized by carrying out reaction according to the method described in Example 610, except for using the cis-2-(4-hydroxycyclohexyl)-1H-isoindole-1,3(2H)-dione obtained in Example 323, (c), as a starting material.

(b) Synthesis of trans-4-{[4-(methylthio)-1H-indazol-5-yl]oxy}cyclohexanamine

The title compound was synthesized by carrying out reaction according to the method described in Example 381, except for using 2-(trans-4-{[4-(methylthio)-1H-indazol-5-yl]oxy}cyclohexyl)-1H-isoindole-1,3(2H)-dione as a starting material.
Melting point: 138–140° C.

EXAMPLE 617

Synthesis of 2-(trans-3-{[4-(methylthio)-1H-indazol-5-yl]oxy}cyclohexyl)-1H-isoindole-1,3(2H)-dione The title compound was synthesized by carrying out reaction according to the method described in Example 610, except for using the cis-2-(3-hydroxycyclohexyl)-1H-isoindole-1,3(2H)-dione obtained in Example 326, (d), as a starting material.
IR (neat) cm$^{-1}$; 3172, 1697, 1232, 1134, 945.

EXAMPLE 618

Synthesis of trans-3-{[4-(methylthio)-1H-indazol-5-yl]oxy}cyclohexanamine

The title compound was synthesized by carrying out reaction according to the method described in Example 381, except for using the 2-(trans-3-{[4-(methylthio)-1H-indazol-5-yl]oxy}cyclohexyl)-1H-isoindole-1,3(2H)-dione obtained in Example 617, as a starting material.
Melting point: 112–113° C.

EXAMPLE 619

Synthesis of cis-N,N-dimethyl-4-{[4-(methylthio)-1H-indazol-5-yl]oxy}cyclohexanamine The title compound was synthesized by carrying out reaction according to the method described in Example 140, except for using the cis-4-{[4-(methylthio)-1H-indazol-5-yl]oxy}cyclohexanamine obtained in Example 611, (a), as a starting material.
Melting point: 157–159° C.

EXAMPLE 620

Synthesis of trans-N,N-dimethyl-4-{[4-(methylthio)-1H-indazol-5-yl]oxy}cyclohexanamine The title compound was synthesized by carrying out reaction according to the method described in Example 140, except for using the trans-4-{[4-(methylthio)-1H-indazol-5-yl]oxy}cyclohexanamine obtained in Example 616, as a starting material.
Melting point: 139–140° C.

The following compounds of Example 621 and Example 622 were synthesized by carrying out reaction according to the method described in Example 391, except for using the cis-4-{[4-(methylthio)-1H-indazol-5-yl]oxy}cyclohexanamine obtained in Example 611, (a), as a starting material.

EXAMPLE 621

N-(cis-4-{[4-(methylthio)-1H-indazol-5-yl]oxy}cyclohexyl)propanamide

Melting point: 155–156° C.

EXAMPLE 622

N-(cis-4-{[4-(methylthio)-1H-indazol-5-yl]oxy}cyclohexyl)benzamide

Melting point: 146–148° C.

EXAMPLE 623

Synthesis of cis-4-{[4-(methylthio)-1H-indazol-5-yl]oxy}-N-propylcyclohexanamine monohydrochloride (a) Synthesis of cis-4-{[4-(methylthio)-1H-indazol-5-yl]oxy}-N-propylcyclohexanamine The title compound was synthesized by carrying out reaction according to the method described in Example 399, except for using the N-(cis-4-{[4-(methylthio)-1H-indazol-5-yl]oxy}cyclohexyl)propanamide obtained in Example 621, as a starting material.

(b) Synthesis of cis-4-{[4-(methylthio)-1H-indazol-5-yl]oxy}-N-propylcyclohexanamine monohydrochloride The title compound was synthesized by carrying out reaction according to the method described in Example 327, except for using cis-4-{[4-(methylthio)-1H-indazol-5-yl]oxy}-N-propylcyclohexanamine as a starting material.
Melting point: 178–179° C.

EXAMPLE 624

Synthesis of cis-N-benzyl-4-{[4-(methylthio)-1H-indazol-5-yl]oxy}cyclohexanamine monohydrochloride (a) Synthesis of cis-N-benzyl-4-{[4-(methylthio)-1H-indazol-5-yl]oxy}cyclohexanamine The title compound was synthesized by carrying out reaction according to the method described in Example 399, except for using the N-(cis-4-{[4-(methylthio)-1H-indazol-5-yl]oxy}cyclohexyl)benzamide obtained in Example 622, as a starting material.

(b) Synthesis of cis-N-benzyl-4-{[4-(methylthio)-1H-indazol-5-yl]oxy}cyclohexanamine monohydrochloride The title compound was synthesized by carrying out reaction according to the method described in Example 327, except for using cis-N-benzyl-4-{[4-(methylthio)-1H-indazol-5-yl]oxy}cyclohexanamine as a starting material.
Melting point: 232° C. (decomp.)

EXAMPLE 625

Synthesis of N-(trans-4-{[4-(methylthio)-1H-indazol-5-yl]oxy}cyclohexyl)propanamide The title compound was synthesized by carrying out reaction according to the method described in Example 391, except for using the trans-4-{[4-(methylthio)-1H-indazol-5-yl]oxy}cyclohexanamine obtained in Example 616, as a starting material.
Melting point: 201–202° C.

EXAMPLE 626

Synthesis of trans-4-{[4-(methylthio)-1H-indazol-5-yl]oxy}-N-propylcyclohexanamine The title compound was synthesized by carrying out reaction according to the method described in Example 399, except for using the N-(trans-4-{[4-(methylthio)-1H-indazol-5-yl]oxy}cyclohexyl)propanamide obtained in Example 625, as a starting material.
Melting point: 168–169° C.

EXAMPLE 627

Synthesis of trans-N-benzyl-4-{[4-(methylthio)-1H-indazol-5-yl]oxy}cyclohexanamine (a) Synthesis of N-(trans-4-{[4-(methylthio)-1H-indazol-5-yl]oxy}cyclohexyl)benzamide The title compound was synthesized by carrying out reaction according to the method described in Example 391, except for using the trans-4-{[4-(methylthio)-1H-indazol-5-yl]oxy}cyclohexanamine obtained in Example 616, as a starting material.

(b) Synthesis of trans-N-benzyl-4-{[4-(methylthio)-1H-indazol-5-yl]oxy}cyclohexanamine The title compound was synthesized by carrying out reaction according to the method described in Example 399, except for using N-(trans-4-{[4-(methylthio)-1H-indazol-5-yl]oxy}cyclohexyl)benzamide as a starting material.
Melting point: 135.5–136° C.

EXAMPLE 628

Synthesis of 4-(ethylthio)-1H-indazol-5-ol (a) Synthesis of 4-(ethylthio)-1-tetrahydro-2H-pyran-2-yl-5-(tetrahydro-2H-pyran-2-yloxy)-1H-indazole The title compound was synthesized by carrying out reaction according to the method described in Example 607, (b), except for using sodium thioethoxide as a starting material.

(b) Synthesis of 4-(ethylthio)-1H-indazol-5-ol

The title compound was synthesized by carrying out reaction according to the method described in Example 607, (c), except for using 4-(ethylthio)-1-tetrahydro-2H-pyran-2-yl-5-(tetrahydro-2H-pyran-2-yloxy)-1H-indazole as a starting material.
Melting point: 116° C.

EXAMPLE 629

Synthesis of 2-(cis-4-{[4-(ethylthio)-1H-indazol-5-yl]oxy}cyclohexyl)-1H-isoindole-1,3(2H)-dione The title compound was synthesized by carrying out reaction according to the method described in Example 610, except for using the 4-(ethylthio)-1H-indazol-5-ol obtained in Example 628, as a starting material.
$^1$H-NMR (CDCl$_3$) δ; 1.26 (3H, t, J=7.3 Hz), 1.73–1.61 (2H, m), 2.29–2.21 (2H, m), 2.98–2.86 (2H, m), 3.18 (2H, q, J=7.3 Hz), 4.28–4.18 (1H, m), 4.67–4.63 (1H, m), 7.19 (1H, d, J=9.0 Hz), 7.38 (1H, d, J=9.0 Hz), 7.74–7.68 (2H, m), 7.87–7.81 (2H, m), 8.23 (1H, s).

EXAMPLE 630

Synthesis of cis-4-{[4-(ethylthio)-1H-indazol-5-yl]oxy}cyclohexanamine monohydrochloride (a) Synthesis of cis-4-{[4-(ethylthio)-1H-indazol-5-yl]oxy}cyclohexanamine The title compound was synthesized by carrying out reaction according to the method described in Example 381, except for using the 2-(cis-4-{[4-(ethylthio)-1H-indazol-5-yl]oxy}cyclohexyl)-1H-isoindole-1,3(2H)-dione obtained in Example 629, as a starting material.

(b) Synthesis of cis-4-{[4-(ethylthio)-1H-indazol-5-yl]oxy}cyclohexanamine monohydrochloride The title compound was synthesized by carrying out reaction according to the method described in Example 327, except for using cis-4-{[4-(ethylthio)-1H-indazol-5-yl]oxy}cyclohexanamine as a starting material.
Melting point: 190° C. (decomp.)

EXAMPLE 631

Synthesis of cis-3-{[4-(ethylthio)-1H-indazol-5-yl]oxy}cyclohexanamine (a) Synthesis of 2-(cis-3-{[4-(ethylthio)-1H-indazol-5-yl]oxy}cyclohexyl)-1H-isoindole-1,3(2H)-dione The title compound was synthesized by carrying out reaction according to the method described in Example 610, except for using the trans-2-(3-hydroxycyclohexyl)-1H-isoindole-1,3(2H)-dione obtained in Example 385, (b) and the 4-(ethylthio)-1H-indazol-5-ol obtained in Example 628, as starting materials.

(b) Synthesis of cis-3-{[4-(ethylthio)-1H-indazol-5-yl]oxy}cyclohexanamine

The title compound was synthesized by carrying out reaction according to the method described in Example 381, except for using 2-(cis-3-{[4-(ethylthio)-1H-indazol-5-yl]oxy}cyclohexyl)-1H-isoindole-1,3(2H)-dione as a starting material.
Melting point: 109.5–110.5° C.

EXAMPLE 632

Synthesis of trans-4-{[4-(ethylthio)-1H-indazol-5-yl]oxy}cyclohexanamine (a) Synthesis of 2-(trans-4-{[4-(ethylthio)-1H-indazol-5-yl]oxy}cyclohexyl)-1H-isoindole-1,3(2H)-dione The title compound was synthesized by carrying out reaction according to the method described in Example 610, except for using the cis-2-(4-hydroxycyclohexyl)-1H-isoindole-1,3(2H)-dione obtained in Example 323, (c) and the 4-(ethylthio)-1H-indazol-5-ol obtained in Example 628, as starting materials.

(b) Synthesis of trans-4-{[4-(ethylthio)-1H-indazol-5-yl]oxy}cyclohexanamine

The title compound was synthesized by carrying out reaction according to the method described in Example 381, except for using 2-(trans-4-{[4-(ethylthio)-1H-indazol-5-yl]oxy}cyclohexyl)-1H-isoindole-1,3(2H)-dione as a starting material.
Melting point: 157–158° C.

EXAMPLE 633

Synthesis of trans-3-{[4-(ethylthio)-1H-indazol-5-yl]oxy}cyclohexanamine (a) Synthesis of 2-(trans-3-{[4-(ethylthio)-1H-indazol-5-yl]oxy}cyclohexyl)-1H-isoindole-1,3(2H)-dione The title compound was synthesized by carrying out reaction according to the method described in Example 610, except for using the cis-2-(3-hydroxycyclohexyl)-1H-isoindole-1,3(2H)-dione obtained in Example 326, (d) and the 4-(ethylthio)-1H-indazol-5-ol obtained in Example 628, as starting materials.

(b) Synthesis of trans-3-{[4-(ethylthio)-1H-indazol-5-yl]oxy}cyclohexanamine

The title compound was synthesized by carrying out reaction according to the method described in Example 381, except for using 2-(trans-3-{[4-(ethylthio)-1H-indazol-5-yl]oxy}cyclohexyl)-1H-isoindole-1,3(2H)-dione as a starting material.
Melting point: 111–112° C.

EXAMPLE 634

Synthesis of 4-propoxy-1H-indazol-5-ol (a) Synthesis of 1-tetrahydro-2H-pyran-2-yl-5-(tetrahydro-2H-pyran-2-yloxy)-1H-indazol-4-ol Under a nitrogen atmosphere, a 1.57M-n-butyllithium/hexane solution (12.00 ml, 0.0189 mol) was added dropwise to a solution of the 4-bromo-1-tetrahydro-2H-pyran-2-yl-5-(tetrahydro-2H-pyran-2-yloxy)-1H-indazole (6.0 g, 0.0157 mol) obtained in Example 607 in tetrahydrofuran (120 ml) at −78° C. over a period of 15 minutes. After 30 minutes, a solution of trimethoxyborane (2.65 ml, 0.0236 mol) in tetrahydrofuran (30 ml) was added dropwise thereto over a period of 5 minutes and the resulting mixture was slowly heated. After 15 hours, acetic acid (1.98 ml, 0.0346 mol) was added thereto. After 15 minutes, a solution of 30%-aqueous hydrogen peroxide solution (4.46 ml, 0.0393 mol) in tetrahydrofuran (20 ml) was added dropwise thereto over a period of 10 minutes, and the resulting mixture was slowly heated to room temperature. After 8.5 hours, a 30%-aqueous hydrogen peroxide solution (4.72 mmol) was further added thereto. After 15 hours, a 10%-aqueous sodium hydrogensulfite solution and a saturated aqueous sodium hydrogencarbonate solution were added thereto, and the resulting mixture was poured into water and extracted with ethyl acetate. The extract solution was concentrated under reduced pressure and the resulting residue was purified by a silica gel column chromatography (eluent: hexane/ethyl acetate). The residue purified was concentrated under reduced pressure and the resulting residue was washed with hexane by repulping to obtain 1-tetrahydro-2H-pyran-2-yl-5-(tetrahydro-2H-pyran-2-yloxy)-1H-indazol-4-ol (2.9892 g, 42%).

(b) Synthesis of 4-propoxy-1-tetrahydro-2H-pyran-2-yl-5-(tetrahydro-2H-pyran-2-yloxy)-1H-indazole Under a nitrogen atmosphere, n-propyl iodide (257 μl, 2.64 mmol) and cesium carbonate (860 mg, 2.64 mmol) were added to a solution of 1-tetrahydro-2H-pyran-2-yl-5-(tetrahydro-2H-pyran-2-yloxy)-1H-indazol-4-ol (700 mg, 2.20 mmol) in N,N-dimethylformamide (7 ml) at room temperature. After 2 hours, the reaction solution was poured into water and extracted with ethyl acetate. The extract solution was concentrated under reduced pressure and the resulting residue was purified by a silica gel column chromatography (eluent: hexane/ethyl acetate) to obtain 4-propoxy-1-tetrahydro-2H-pyran-2-yl-5-(tetrahydro-2H-pyran-2-yloxy)-1H-indazole (852.6 mg).

(c) Synthesis of 4-propoxy-1H-indazol-5-ol

Under a nitrogen atmosphere, trifluoroacetic acid (5.5 ml) was added to a solution of 4-propoxy-1-tetrahydro-2H-pyran-2-yl-5-(tetrahydro-2H-pyran-2-yloxy)-1H-indazole (852.6 mg) in dichloromethane (16.5 ml) at room temperature. After 2.5 hours, the reaction solution was poured onto ice, adjusted to pH 7 with an aqueous sodium hydroxide solution, and then extracted with ethyl acetate. The extract solution was concentrated under reduced pressure and the resulting residue was purified by a silica gel column chromatography (eluent: hexane/ethyl acetate). The residue purified was concentrated under reduced pressure and the resulting residue was washed with diethyl ether/hexane by repulping to obtain 4-propoxy-1H-indazol-5-ol (338.2 g, 80%, two steps).

IR (neat) cm$^{-1}$; 3282, 2931, 1305, 1081, 800.

EXAMPLE 635

Synthesis of 4-nitro-1H-indazol-5-ol

Under a nitrogen atmosphere, a solution of tetrafluoroborate nitrite (110 mg, 0.783 mmol) in acetonitrile (3 ml) was added dropwise to a suspension of the 1H-indazol-5-ol (100 mg, 0.745 mmol) obtained in Reference Example 4 in acetonitrile (4.0 ml) at −35° C. over a period of 10 minutes, and the resulting mixture was slowly heated to 0° C. After 2 hours, the reaction solution was poured into water and extracted with ethyl acetate. The extract solution was concentrated under reduced pressure and the resulting residue was purified by a silica gel column chromatography (eluent: hexane/ethyl acetate). The residue purified was concentrated under reduced pressure and the resulting residue was washed with ethanol/diisopropyl ether by repulping to obtain 4-nitro-1H-indazol-5-ol (59.8 mg, 45%).

IR (neat) cm$^{-1}$; 3091, 1629, 1500, 1147, 933, 702.

EXAMPLE 636

Synthesis of cis-3-[(4-propoxy-1H-indazol-5-yl) oxy]cyclohexanamine hydrochloride (a) cis-3-[(4-Propoxy-1H-indazol-5-yl)oxy]cyclohexanamine Under a nitrogen atmosphere, triphenylphosphine (164 mg, 0.624 mmol), the trans-2-(3-hydroxycyclohexyl)-1H-isoindole-1,3(2H)-dione (128 mg, 0.520 mmol) obtained in Example 385, (b) and diisopropyl azodicarboxylate (113 μl, 0.572 mmol) were added at 0° C. to a solution of the 4-propoxy-1H-indazol-5-ol (100 mg, 0.520 mmol) obtained in Example 634 in tetrahydrofuran (4 ml). After 30 minutes, the resulting mixture was heated to room temperature and stirred overnight. The reaction solution was concentrated under reduced pressure, and the resulting residue was diluted with chloroform and washed with a 1M-aqueous sodium hydroxide solution. The aqueous layer was re-extracted with chloroform and then the organic layer was dried over anhydrous magnesium sulfate. The organic layer dried was concentrated under reduced pressure and the resulting residue was purified by a silica gel column chromatography (eluent: hexane/ethyl acetate). To the oil thus obtained was added a 30%-methylamine-ethanol solution at room temperature, and the resulting mixture was refluxed. After 2 hours, the mixture was concentrated under reduced pressure at room temperature, and the resulting residue was purified by a silica gel column chromatography (eluent: chloroform/methanol→chloroform/methanol (1%-aqueous ammonia)) to obtain cis-3-[(4-propoxy-1H-indazol-5-yl)oxy]cyclohexanamine (82.3 mg, 55%).

(b) Synthesis of cis-3-[(4-propoxy-1H-indazol-5-yl) oxy]cyclohexanamine hydrochloride Under a nitrogen atmosphere, 1M-hydrochloric acid-diethyl ether (341 μl, 0.341 mmol) was added dropwise to a solution of cis-3-[(4-propoxy-1H-indazol-5-yl)oxy]cyclohexanamine (82.3 mg, 0.284 mmol) in methanol (2 ml) at room temperature. After 1 hour, the mixture thus obtained was concentrated under reduced pressure and the resulting residue was crystallized from ethyl acetate, followed by filtration under reduced pressure, and then drying. The solid thus obtained was washed with hexane by repulping to obtain cis-3-[(4-propoxy-1H-indazol-5-yl)oxy]cyclohexanamine hydrochloride (76.8 mg, 83%).

IR (neat) cm$^{-1}$; 2939, 1508, 1228, 1147, 939.

The following compound of Example 637 was synthesized by carrying out reaction according to the method described in Example 636, except for using the trans-2-(4-hydroxycyclohexyl)-1H-isoindole-1,3(2H)-dione obtained in Example 323, (a), as a starting material.

EXAMPLE 637

Synthesis of cis-4-[(4-propoxy-1H-indazol-5-yl) oxy]cyclohexanamine hydrochloride $^{1}$H-NMR (DMSO-d$_{6}$) δ; 1.01 (3H, t, J=7.4 Hz), 1.60 (2H, m), 1.70–1.86 (6H, m), 1.91 (2H, m), 3.08 (1H, brs), 4.24 (2H, t, J=6.5 Hz), 4.29 (1H, m), 7.09 (2H, s), 7.90 (3H, brs), 8.09 (1H, s), 13.00 (1H, brs).

The following compound of Example 638 was synthesized by carrying out reaction according to the method described in Example 634.

EXAMPLE 638

4-Isopropoxy-1H-indazol-5-ol $^{1}$H-NMR (DMSO-d$_{6}$) δ; 1.25 (6H, d, J=6.2 Hz), 4.63 (1H, qq, J=6.2, 6.2 Hz), 6.97 (1H, d, J=8.8 Hz), 7.01 (1H, d, J=8.8 Hz), 7.89 (1H, s), 8.49 (1H, s), 12.78 (1H, brs).

EXAMPLE 639

Synthesis of cis-N-{4-[(4-methyl-1H-indazol-5-yl) oxy]cyclohexyl}methanesulfonamide Under a nitrogen atmosphere, triethylamine (49.5 μl, 0.355 mmol) was added at 0° C. to a solution of the cis-4-[(4-methyl-1H-indazol-5-yl)oxy]cyclohexanamine hydrochloride (100 mg, 0.355 mmol) obtained in Example 410 in tetrahydrofuran (4 ml), followed by adding dropwise thereto a solution of methanesulfonyl chloride (28 μl, 0.362 mmol) in dichloromethane (2 ml). After 30 minutes, the resulting mixture was heated to room temperature and triethylamine (0.355 mmol) was further added thereto. After 2 hours, triethylamine (0.355 mmol) and methanesulfonyl chloride (0.355 mmol) were further added thereto. After 2 hours, the reaction solution was poured into water and extracted with ethyl acetate. The extract solution was concentrated under reduced pressure and the resulting residue was purified by a silica gel column chromatography (eluent: chloroform/ethyl acetate) to obtain cis-N-{4-[(4-methyl-1H-indazol-5-yl)oxy]cyclohexyl}methanesulfonamide (31.7 mg, 28%).

IR (neat) cm$^{-1}$; 3249, 2933, 1508, 1298, 1155, 945.

EXAMPLE 640

Synthesis of cis-3-[(4-isopropoxy-1H-indazol-5-yl)oxy]cyclohexanamine hydrochloride (a) Synthesis of cis-3-[(4-isopropoxy-1H-indazol-5-yl)oxy]cyclohexanamine Under a nitrogen atmosphere, the 4-isopropoxy-1H-indazol-5-ol (118 mg, 0.614 mmol) obtained in Example 638 and the trans-2-(3-hydroxycyclohexyl)-1H-isoindole-1,3(2H)-dione (100 mg, 0.408 mmol) obtained in Example 385, (b) were added to a solution of 90%-cyanomethylenetri-n-butylphosphorane (155 mg, 0.614 mmol) in toluene (4 ml) at room temperature, and the resulting mixture was heated to 100° C. After 4.5 hours, the reaction solution was concentrated under reduced pressure and the resulting residue was diluted with chloroform and washed with a 1M-aqueous sodium hydroxide solution. The aqueous layer was re-extracted with chloroform and then the organic layer was dried over anhydrous magnesium sulfate. The organic layer dried was concentrated under reduced pressure and the resulting residue was purified by a silica gel column chromatography (eluent: hexane/ethyl acetate). To the resulting oil was added a 30%-methylamine-ethanol solution at room temperature, and the resulting mixture was refluxed. After 4 hours, the mixture was concentrated under reduced pressure at room temperature, and the resulting residue was purified by a silica gel column chromatography (eluent: chloroform/methanol→chloroform/methanol (1%-aqueous ammonia)) to obtain cis-3-[(4-isopropoxy-1H-indazol-5-yl)oxy]cyclohexanamine (71.0 mg, 60%).

(b) Synthesis of cis-3-[(4-isopropoxy-1H-indazol-5-yl)oxy]cyclohexanamine hydrochloride Under a nitrogen atmosphere, 1M-hydrochloric acid-diethyl ether (350 µl, 0.341 mmol) was added dropwise to a solution of cis-3-[(4-isopropoxy-1H-indazol-5-yl)oxy]cyclohexanamine (84.3 mg, 0.284 mmol) in isopropanol (2 ml) at room temperature. After 1 hour, the mixture thus obtained was concentrated under reduced pressure and the resulting residue was crystallized from ethyl acetate, followed by filtration under reduced pressure, and then drying. The solid thus obtained was washed with hexane by repulping to obtain cis-3-[(4-isopropoxy-1H-indazol-5-yl)oxy]cyclohexanamine hydrochloride (70.1 mg, 74%).

IR (neat) cm$^{-1}$; 2937, 1508, 1227, 1087, 928.

The following compound of Example 641 was synthesized by carrying out reaction according to the method described in Example 640, except for using the trans-2-(4-hydroxycyclohexyl)-1H-isoindole-1,3(2H)-dione obtained in Example 323, (a), as a starting material.

EXAMPLE 641 cis-4-[(4-Isopropoxy-1H-indazol-5-yl)oxy]cyclohexanamine hydrochloride

IR (neat) cm$^{-1}$; 2935, 1506, 1228, 1083, 939.

EXAMPLE 642

Synthesis of cis-4-methyl-5-[(4-pyrrolidin-1-ylcyclohexyl)oxy]-1H-indazole and cis-4-({4-methyl-1H-indazol-5-yl}oxy)cyclohexyl}amino)butan-1-ol (a) Synthesis of cis-1-{4-[(1-acetyl-4-methyl-1H-indazol-5-yl)oxy]cyclohexyl}pyrrolidine-2,5-dione Under a nitrogen atmosphere, succinic anhydride (105 mg, 1.05 mmol) and triethylamine (279 µl, 2.00 mmol) were added to a solution of the cis-4-[(4-methyl-1H-indazol-5-yl)oxy]cyclohexanamine hydrochloride (282 mg, 1.00 mmol) obtained in Example 410 in toluene (6 ml) at room temperature, and the resulting mixture was refluxed. After 5.5 hours, the reaction solution was poured into water and extracted with ethyl acetate. The extract solution was concentrated under reduced pressure, and to a solution of the resulting residue in ethyl acetate (4 ml) was added acetyl chloride (214 µl, 3.00 mmol), and the resulting mixture was heated to 100° C. Dimethylformamide (2 ml) was added thereto because a solid was precipitated. After 2 hours, the reaction solution was poured into water and extracted with ethyl acetate. The extract solution was concentrated under reduced pressure and the resulting residue was purified by a silica gel column chromatography (eluent: hexane/ethyl acetate) to obtain cis-1-{4-[(1-acetyl-4-methyl-1H-indazol-5-yl)oxy]cyclohexyl}pyrrolidine-2,5-dione (123.7 mg, 33%).

(b) Synthesis of cis-4-methyl-5-[(4-pyrrolidin-1-ylcyclohexyl)oxy]-1H-indazole and cis-4-({4-methyl-1H-indazol-5-yl}oxy)cyclohexyl}amino)butan-1-ol Under a nitrogen atmosphere, 28%-sodium methoxide (64 µl, 0.311 mmol) was added at 0° C. to a suspension of cis-1-{4-[(1-acetyl-4-methyl-1H-indazol-5-yl)oxy]cyclohexyl}pyrrolidine-2,5-dione (500 mg, 0.311 mmol) in a mixture of methanol (3 ml) and tetrahydrofuran (3 ml). After 10 minutes, a saturated aqueous ammonium chloride solution was added to the reaction solution and the resulting mixture was poured into water and extracted with ethyl acetate. The extract solution was concentrated under reduced pressure, and to a solution of the resulting residue in tetrahydrofuran (4 ml) was added lithium aluminum hydride (47 mg, 1.25 mmol) and the resulting mixture was refluxed. After 4 hours, water, a 2M-aqueous sodium hydroxide solution and water were added thereto in that order, and the resulting mixture was filtered by the use of Celite. The filtrate was concentrated under reduced pressure and the resulting residue was purified by a silica gel column chromatography (eluent: chloroform/methanol→chloroform/methanol (1%-aqueous ammonia)) to obtain cis-4-methyl-5-[(4-pyrrolidin-1-ylcyclohexyl)oxy]-1H-indazole (59.6 mg, 64%) and cis-4-({4-methyl-1H-indazol-5-yl}oxy)cyclohexyl}amino)butan-1-ol (15.4 mg, 16%).

IR (neat) cm$^{-1}$; 3156, 2943, 1514, 1222, 1095, 951.

EXAMPLE 643

Synthesis of 4-morpholin-4-yl-1H-indazol-5-ol (a) Synthesis of 4-morpholine-1-tetrahydro-2H-pyran-2-yl-5-(tetrahydro-2H-pyran-2-yloxy)-1H-indazole Under a nitrogen atmosphere, morpholine (1.10 ml, 0.0126 mol), (oxydi-2,1-phenylene)bis(diphenylphosphine) (226 mg, 0.420 mmol), sodium t-butoxide (1.41 g, 0.0147 mol) and tris(dibenzylideneacetone)dipalladium(0)-chloroform (217 mg, 0.210 mmol) were added to a solution of the 4-bromo-1-tetrahydro-2H-pyran-2-yl-5-(tetrahydro-2H-pyran-2-yloxy)-1H-indazole (395 mg, 0.0105 mol) obtained in Example 607 in dioxane (80 ml) at room temperature, and the resulting mixture was refluxed. After 2 hours, the reaction solution was concentrated under reduced pressure and the resulting residue was poured into water and extracted with ethyl acetate. The extract solution was concentrated under reduced pressure and the resulting residue was purified by a silica gel column chromatography (hexane/ethyl acetate) to obtain 4-morpholine-1-tetrahydro-2H-pyran-2-yl-5-(tetrahydro-2H-pyran-2-yloxy)-1H-indazole (2.4267 g, 61%).

(b) Synthesis of 4-morpholin-4-yl-1H-indazol-5-ol

Under a nitrogen atmosphere, trifluoroacetic acid (12.5 ml) was added to a solution of 4-morpholine-1-tetrahydro-2H-pyran-2-yl-5-(tetrahydro-2H-pyran-2-yloxy)-1H-indazole (2.4267 g, 6.43 mol) in dichloromethane (50 ml) at room temperature. After 3 hours, the reaction solution was poured onto ice and adjusted to pH 6 with an aqueous sodium hydroxide solution to separate a dichloromethane layer, and then the aqueous layer was extracted with ethyl acetate. The extract solution was concentrated under reduced pressure and the resulting residue was purified by a silica gel column chromatography (eluent: hexane/ethyl acetate). The residue purified was concentrated under reduced pressure and the resulting residue was washed with diethyl ether/hexane by repulping to obtain 4-morpholin-4-yl-1H-indazol-5-ol (882.4 mg, 63%).

$^1$H-NMR (DMSO-$d_6$) δ; 3.15 (4H, m), 3.77 (4H, m), 6.95 (1H, d, J=8.8 Hz), 7.08 (1H, d, J=8.8 Hz), 8.06 (1H, s), 8.24 (1H, s), 12.79 (1H, s).

The following compounds of Examples 644 and 645 were synthesized by carrying out reaction according to the method described in Example 640, (a), except for using the 4-morpholin-4-yl-1H-indazol-5-ol obtained in Example 643, as a starting material.

EXAMPLE 644 cis-4-[(4-morpholine-1H-indazol-5-yl)oxy]cyclohexanamine

IR (neat) cm$^{-1}$; 2941, 1495, 1219, 1113, 937.

EXAMPLE 645

Synthesis of cis-3-[(4-morpholine-1H-indazol-5-yl)oxy]cyclohexanamine

IR (neat) cm$^{-1}$; 2931, 1506, 1220, 1111, 930.

EXAMPLE 646

Synthesis of {cis-2-[(4-methyl-1H-indazol-5-yl)oxy]cyclohexyl}methylamine (a) Synthesis of trans-2-[(2-hydroxycyclohexyl)methyl]-1H-isoindole-1,3(2H)-dione Under a nitrogen atmosphere, a solution of trans-2-cyanohexanol (1.0 g, 7.99 mmol) in tetrahydrofuran (10 ml) was added dropwise to a solution of lithium aluminum hydride (1.21 g, 0.0320 mol) in tetrahydrofuran (15 ml) at 0° C., and the resulting mixture was refluxed. After 2 hours, water, a 2M-aqueous sodium hydroxide solution and water were added in that order to the reaction solution, and the resulting mixture was filtered by the use of Celite. To the filtrate was added 1M-hydrochloric acid-diethyl ether (9.59 ml, 9.59 mmol), and the resulting mixture was concentrated under reduced pressure. Potassium carbonate (1.99 g, 0.0144 mol) and ethoxycarbonylphthalimide (1.93 g, 8.79 mmol) were added to an aqueous solution (30 ml) of the concentration residue at room temperature. After 15 hours, the reaction solution was poured into water and extracted with ethyl acetate, and the organic layer was dried over anhydrous magnesium sulfate. The organic layer dried was concentrated under reduced pressure and the resulting residue was purified by a silica gel column chromatography (eluent: hexane/ethyl acetate) to obtain trans-2-[(2-hydroxycyclohexyl)methyl]-1H-isoindole-1,3(2H)-dione (1.1736 g, 57%).

(b) Synthesis of {cis-2-[(4-methyl-1H-indazol-5-yl)oxy]cyclohexyl}methylamine

Reaction was carried out according to the method described in Example 640, (a), except for using the 4-methyl-1H-indazol-5-ol obtained in Example 402, as a staring material.

$^1$H-NMR (DMSO-$d_6$) δ; 1.24–1.85 (11H, m), 2.40 (3H, s), 2.69 (2H, m), 2.03 (1H, m), 2.27 (1H, m), 2.70 (2H, m), 4.59 (1H, m), 7.21 (1H, d, J=9.0 Hz), 7.25 (1H, d, J=9.0 Hz), 7.98 (1H, s), 12.81 (1H, s).

EXAMPLE 647

Synthesis of trans-2-[(4-methyl-1H-indazol-5-yl)oxy]cyclohexanamine (a) Synthesis of cis-2-(2-hydroxycyclohexyl)-1H-isoindole-1,3(2H)-dione Under a nitrogen atmosphere, a solution of monomethyl phthalate (1.31 g, 7.31 mmol) and N,N-diisopropylamine (1.72 ml, 7.31 mmol) in tetrahydrofuran (10 ml) was added dropwise to a solution of benzotriazol-1-yloxy-trispyrrolidinophosphonium hexafluorophosphate (3.77 g, 7.31 mmol) in tetrahydrofuran (10 ml) over a period of 15 minutes at room temperature. After 40 minutes, the solution thus prepared was slowly dropped into a solution of cis-2-aminocyclohexanol hydrochloride (1.0 g, 6.65 mmol) and triethylamine (1.01 ml, 7.31 mmol) in tetrahydrofuran (10 ml). After 3 hours, p-toluenesulfonic acid (35 mg) was added thereto, and the resulting mixture was refluxed. After 5 hours, water was added thereto and the resulting mixture was poured into a saturated aqueous sodium hydroxide solution and extracted with ethyl acetate. The organic layer was dried over anhydrous magnesium sulfate. The organic layer dried was concentrated under reduced pressure and the resulting residue was purified by a silica gel column chromatography (eluent: hexane/ethyl acetate) and purified again by a silica gel column chromatography (eluent: chloroform/ethyl acetate) to obtain cis-2-(2-hydroxycyclohexyl)-1H-isoindole-1,3(2H)-dione (1.5746 g, 97%).

(b) Synthesis of trans-2-[(4-methyl-1H-indazol-5-yl) oxy]cyclohexanamine

Reaction was carried out according to the method described in Example 640, (a), except for using the 4-methyl-1H-indazol-5-ol obtained in Example 402, as a staring material.
IR (neat) cm$^{-1}$; 3161, 1508, 1219, 1092, 941.

EXAMPLE 648

Synthesis of {trans-2-[(4-methyl-1H-indazol-5-yl) oxy]cyclohexyl}methylamine hydrochloride (a) Synthesis of cis-2-[(2-hydroxycyclohexyl)methyl]-1H-isoindole-1,3(2H)-dione Under a nitrogen atmosphere, potassium carbonate (375 mg, 2.72 mmol) and ethoxycarbonylphthalimide (364 mg, 1.66 mmol) were added to an aqueous solution (4 ml) of 2-aminomethylcyclohexanol hydrochloride (250 mg, 1.51 mmol) at room temperature. After 3 hours, the reaction solution was poured into water and extracted with ethyl acetate, and the organic layer was dried over anhydrous magnesium sulfate. The organic layer dried was concentrated under reduced pressure and the resulting residue was purified by a silica gel column chromatography (eluent: hexane/ethyl acetate) to obtain cis-2-[(2-hydroxycyclohexyl)methyl]-1H-isoindole-1,3(2H)-dione (291.6 mg, 75%).

(b) Synthesis of {trans-2-[(4-methyl-1H-indazol-5-yl)oxy]cyclohexyl}methylamine

Reaction was carried out according to the method described in Example 640, (a), except for using the 4-methyl-1H-indazol-5-ol obtained in Example 402, as a staring material.

(c) Synthesis of {trans-2-[(4-methyl-1H-indazol-5-yl)oxy]cyclohexyl}methylamine hydrochloride Under a nitrogen atmosphere, 1M-hydrochloric acid-diethyl ether (249 µl, 0.249 mmol) was added to a solution of {trans-2-[(4-methyl-1H-indazol-5-yl)oxy] cyclohexyl}methylamine (53.8 mg, 0.207 mmol) in 2-propanol (1 ml) at room temperature. After 1 hour, the reaction solution was concentrated under reduced pressure and the resulting residue was crystallized from 2-propanol/acetonitrile to obtain {trans-2-[(4-methyl-1H-indazol-5-yl)oxy] cyclohexyl}methylamine hydrochloride (49.4 mg, 81%).
IR (neat) cm$^{-1}$; 2929, 1508, 1259, 1080, 810.

EXAMPLE 649

Synthesis of {trans-3-[(4-methyl-1H-indazol-5-yl) oxy]cyclohexyl}methylamine (a) Synthesis of 1-cyanocyclohexan-3-one Under a nitrogen atmosphere, ammonium chloride (4.17 g, 0.078 mol) and potassium cyanide (6.77 g, 0.104 mol) were added to a solution of 2-cyclohexen-1-one (5.0 g, 0.052 mol) in a 15%-aqueous N,N-dimethylformamide solution (60 ml) at room temperature, and the resulting mixture was heated to 100° C. After 3 hours, the reaction solution was poured into water and extracted with chloroform, and the organic layer was dried over anhydrous magnesium sulfate. The organic layer dried was concentrated under reduced pressure and the resulting residue was purified by a silica gel column chromatography (eluent: hexane/ethyl acetate) to obtain 1-cyanocyclohexan-3-one (345.4 mg, 5.4%).

(b) Synthesis of cis-2-[(3-hydroxycyclohexyl)methyl]-1H-isoindole-1,3(2H)-dione

Under a nitrogen atmosphere, lithium aluminum hydride (92 mg, 2.44 mmol) was added to a solution of 1-cyanocyclohexan-3-one (100 mg, 0.812 mmol) in tetrahydrofuran (2 ml) at room temperature, and the resulting mixture was refluxed. After 5 hours, water, an aqueous sodium hydroxide solution and water were added in that order to the reaction solution, and the resulting mixture was filtered under reduced pressure. Thereafter, 1M-hydrochloric acid-diethyl ether (974 µl, 0.974 mmol) was added to the filtrate. The resulting mixture was concentrated under reduced pressure, and to an aqueous solution (4 ml) of the resulting residue were added potassium carbonate (202 mg, 1.46 mmol), ethoxycarbonylphthalimide (196 mg, 0.893 mmol) and acetonitrile (1 ml) at room temperature. After 21 hours, the reaction solution was poured into water and extracted with ethyl acetate, and the organic layer was dried over anhydrous magnesium sulfate. The organic layer dried was concentrated under reduced pressure and the resulting residue was purified by a silica gel column chromatography (eluent: hexane/ethyl acetate) and purified again by a silica gel column chromatography (eluent: chloroform/ethyl acetate) to obtain cis-2-[(3-hydroxycyclohexyl)methyl]-1H-isoindole-1,3(2H)-dione (83.5 mg, 40%, cis:trans=12:1).

(c) Synthesis of {trans-3-[(4-methyl-1H-indazol-5-yl)oxy]cyclohexyl}methylamine

Reaction was carried out according to the method described in Example 640, (a), except for using the 4-methyl-1H-indazol-5-ol obtained in Example 402, as a staring material.
$^1$H-NMR (CDCl$_3$) δ; 1.04 (1H, m), 1.26 (1H, m), 1.47 (1H, m), 1.59 (1H, m), 1.74–2.10 (5H, m), 2.51 (3H, s), 2.55 (2H, m), 4.54 (1H, m), 7.11 (1H, d, J=9.0 Hz), 7.23 (1H, d, J=9.0 Hz), 8.02 (1H, s).

EXAMPLE 650

Synthesis of {cis-3-[(4-methyl-1H-indazol-5-yl)oxy] cyclohexyl}methylamine hydrochloride (a) Synthesis of cis-3-methoxycyclohexanecarboamide and trans-3-methoxycyclohexanecarboamide Under a nitrogen atmosphere, thionyl chloride (902 mg, 7.59 mmol) was added to a solution of 3-methoxycyclohexylcarboxylic acid (1.0 g, 6.32 mmol, cis:trans=4:3) in toluene (20 ml) at room temperature, and the resulting mixture was heated to 50° C. After 2 hours, N,N-dimethylformamide (4 drops) was added thereto because no reaction had took place. After 1 hour, the mixture thus obtained was concentrated under reduced pressure, and a solution of the resulting residue in chloroform (20 ml) was added dropwise to a saturated ammonia-chloroform solution (15 ml) at room temperature. After 19 hours, the reaction solution was filtered under reduced pressure and the filtrate was concentrated under reduced pressure. Then, the resulting residue was purified by a silica gel column chromatography (eluent: chloroform/methanol) to obtain cis-3-methoxycyclohexanecarboamide (364.1 mg, 37%) and trans-3-methoxycyclohexanecarboamide (261.3 mg, 26%).

(b) Synthesis of trans-2-[(3-methoxycyclohexyl)methyl]-1H-isoindole-1,3(2H)-dione Reaction was carried out according to the method described in Example 649, (b).

(c) Synthesis of trans-2-[(3-hydroxycyclohexyl)methyl]-1H-isoindole-1,3(2H)-dione Under a nitrogen atmosphere, a solution of sodium iodide (247 mg, 1.65 mmol) and 15-crown-5 (327 μl, 1.65 mmol) in dichloromethane (2.7 ml) was slowly dropped into a solution of trans-2-[(3-methoxycyclohexyl)methyl]-1H-isoindole-1,3(2H)-dione (100 mg, 0.366 mmol) in dichloromethane (2 ml) at –40° C. After 10 minutes, a 1M-tribromoborane-dichloromethane solution (1.10 ml, 1.10 mmol) was added dropwise thereto. After 1 hour, the mixture thus obtained was slowly heated to be adjusted to 0° C. 2.5 hours after the start of the heating. After standing at room temperature for 14 hours, the reaction solution was poured onto ice and extracted with chloroform. The extract solution was concentrated under reduced pressure and the resulting residue was purified by a silica gel column chromatography (eluent: hexane/ethyl acetate) to obtain trans-2-[(3-hydroxycyclohexyl)methyl]-1H-isoindole-1,3(2H)-dione (63.2 mg, 67%).

(d) Synthesis of {cis-3-[(4-methyl-1H-indazol-5-yl)oxy]cyclohexyl}methylamine

Reaction was carried out according to the method described in Example 640, (a), except for using the 4-methyl-1H-indazol-5-ol obtained in Example 402, as a starting material.

(e) Synthesis of {cis-3-[(4-methyl-1H-indazol-5-yl)oxy]cyclohexyl}methylamine hydrochloride Under a nitrogen atmosphere, 1M-hydrochloric acid-diethyl ether (119 μl, 0.119 mmol) was added to a solution of {cis-3-[(4-methyl-1H-indazol-5-yl)oxy]cyclohexyl}methylamine (25.8 mg, 0.0995 mmol) in 2-propanol (1 ml) at room temperature. After 1 hour, the reaction solution was concentrated under reduced pressure and the resulting residue was crystallized from 2-propanol/diethyl ether to obtain {cis-3-[(4-methyl-1H-indazol-5-yl)oxy]cyclohexyl}methylamine hydrochloride (21.8 mg, 74%).

$^1$H-NMR (DMSO-d$_6$) δ; 0.93 (1H, m), 1.11 (1H, m), 1.28 (2H, m), 1.67–1.78 (3H, m), 2.02 (1H, m), 2.11 (1H, m), 2.37 (3H, s), 2.69 (2H, m), 4.03 (1H, m), 7.14 (1H, d, J=9.0 Hz), 7.26 (1H, d, J=9.0 Hz), 7.86 (3H, brs.), 8.01 (1H, s)

EXAMPLE 651

Synthesis of trans-N-{4-[(1-acetyl-4-methyl-1H-indazol-5-yl)oxy]cyclohexyl}-N,N-dimethylamine Under a nitrogen atmosphere, triethylamine (112 μl, 0.807 mmol) and acetyl chloride (25.2 μl, 0.355 mmol) were added to a solution of monohydrochloride (100 mg, 0.323 mmol) of the trans-N,N-dimethyl-N-{4-[(4-methyl-1H-indazol-5-yl)oxy]cyclohexyl}amine obtained in Example 412 in N,N-dimethylformamide (2 ml) at room temperature. After 1 hour, triethylamine (0.420 mmol) and acetyl chloride (0.355 mmol) were further added thereto. After 2 hours, the reaction solution was poured into water and extracted with chloroform, and the organic layer was dried over anhydrous magnesium sulfate. The organic layer dried was concentrated under reduced pressure and the resulting residue was purified by a silica gel column chromatography (eluent: chloroform/methanol) to obtain trans-N-{4-[(1-acetyl-4-methyl-1H-indazol-5-yl)oxy]cyclohexyl}-N,N-dimethylamine (20.1 mg, 20%).

IR (neat) cm$^{-1}$; 2937, 1705, 1508, 1252, 935, 814.

EXAMPLE 652

Synthesis of Methyl trans-5-{[4-(dimethylamino)cyclohexyl]oxy}-4-methyl-1H-indazole-1-carboxylate Under a nitrogen atmosphere, triethylamine (135 μl, 0.968 mmol) and methyl chloroformate (37 μl, 0.484 mmol) were added at 0° C. to a solution of monohydrochloride (100 mg, 0.323 mmol) of the trans-N,N-dimethyl-N-{4-[(4-methyl-1H-indazol-5-yl)oxy]cyclohexyl}amine obtained in Example 412 in acetone (2 ml). After 15 minutes, the mixture thus obtained was warmed up to room temperature. After 1 hour, triethylamine (0.646 mmol) and methyl chloroformate (0.484 mmol) were further added thereto. After 1 hour, chloroform (2 ml) was added thereto. After another 3 hours, the reaction solution was poured into a saturated aqueous sodium chloride solution and extracted with chloroform, and the organic layer was dried over anhydrous magnesium sulfate. The organic layer dried was concentrated under reduced pressure and the resulting residue was purified by a silica gel column chromatography (eluent: chloroform/methanol) to obtain methyl trans-5-{[4-(dimethylamino)cyclohexyl]oxy}-4-methyl-1H-indazole-1-carboxylate (38.7 mg, 36%).

$^1$H-NMR (DMSO-d$_6$) δ; 1.22–1.47 (4H, m), 1.84 (2H, m), 2.05 (2H, m), 2.21 (6H, s), 2.26 (1H, m), 2.39 (3H, s), 4.00 (3H, s), 4.17 (1H, m), 7.38 (1H, d, J=9.0 Hz), 7.85 (1H, d, J=9.0 Hz), 8.48 (1H, s).

EXAMPLE 653

Synthesis of {cis-1-methyl-3-[(4-methyl-1H-indazol-5-yl)oxy]cyclohexyl}methylamine (a) Synthesis of methyl cis-3-methoxycyclohexanecarboxylate and methyl trans-3-methoxycyclohexanecarboxylate Under a nitrogen atmosphere, thionyl chloride (11.3 g, 0.0948 mol) was slowly dropped into methanol (30 ml) at –5° C. over a period of 20 minutes. After 15 minutes, a solution of 3-methoxycyclohexylcarboxylic acid (5.0 g, 0.0316 mol, cis:trans=4:3) in methanol (30 ml) was added dropwise thereto over a period of 15 minutes. After 2.5 hours, the reaction solution was concentrated under reduced pressure, and the resulting residue was diluted with ethyl acetate and washed with a saturated aqueous sodium hydrogencarbonate solution. The aqueous layer was re-extracted with ethyl acetate and then the organic layer was dried over anhydrous magnesium sulfate. The organic layer dried was concentrated under reduced pressure and the resulting residue was purified by a silica gel column chromatography (eluent: hexane/ethyl acetate) to obtain methyl cis-3-methoxycyclohexane-carboxylate (3.0673 g, 56%) and methyl trans-3-methoxycyclohexanecarboxylate (1.5859 g, 29%).

(b) Synthesis of methyl 3-methoxy-1-methylcyclohexanecarboxylate

Under a nitrogen atmosphere, a 2M-lithium diisopropylamide solution (7.32 ml, 0.0146 mmol) was added dropwise to a solution of methyl cis-3-methoxycyclohexane-carboxylate (1.80 g, 0.0105 mol) in tetrahydrofuran (36 ml) at −78° C. over a period of 15 minutes. After 3 hours, a solution of methyl iodide (4.45 g, 0.0314 mmol) in tetrahydrofuran (9 ml) was added dropwise thereto over a period of 20 minutes, and the resulting mixture was slowly warmed up to 0° C. After 3 hours, a saturated aqueous ammonium solution was added thereto and the resulting mixture was poured into water and extracted with ethyl acetate, and the organic layer was dried over anhydrous magnesium sulfate. The organic layer dried was concentrated under reduced pressure and the resulting residue was purified by a silica gel column chromatography (eluent: hexane/ethyl acetate) to obtain methyl 3-methoxy-1-methylcyclohexanecarboxylate (1.8985 g, 98%, a 4:1 mixture of isomers).

(c) Synthesis of trans-3-methoxy-1-methylcyclohexanecarboxylic acid

Under a nitrogen atmosphere, a 2M-aqueous lithium hydroxide solution (16.0 ml, 0.0319 mol) was added to a solution of methyl 3-methoxy-1-methylcyclohexanecarboxylate (1.9835 g, 0.0106 mol, a 4:1 mixture) in methanol (16 ml) at room temperature. After 1 hour, the mixture thus obtained was heated to 50° C. After another 3 hours, a 2M-aqueous lithium hydroxide solution (0.0213 mol) was further added thereto. After 1 hour, the reaction solution was adjusted to pH 4 to 5 with an aqueous hydrochloric acid solution and extracted with chloroform, and the organic layer was dried over anhydrous magnesium sulfate. The organic layer dried was concentrated under reduced pressure and the resulting residue was purified by a silica gel column chromatography (eluent: chloroform/methanol). The residue purified was recrystallized from hexane to obtain trans-3-methoxy-1-methylcyclohexanecarboxylic acid (1.178 g, 64%) as a white solid, and cis-3-methoxy-1-methylcyclohexanecarboxylic acid (469.2 mg, 26%, a mixture containing 33% trans-3-methoxy-1-methylcyclohexanecarboxylic acid) was obtained as a filtrate residue.

(d) Synthesis of trans-3-methoxy-1-methylcyclohexanecarboamide

Under a nitrogen atmosphere, thionyl chloride (390 mg, 3.27 mmol) and N,N-dimethylformamide (4 drops) were added to a solution of trans-3-methoxy-1-methylcyclohexanecarboxylic acid (470 mg, 2.73 mmol) in toluene (10 ml) at room temperature, and the resulting mixture was heated to 50° C. After 6 hours, the mixture was heated to 100° C. After another 1 hour, thionyl chloride (1.64 mmol) was further added thereto. After 2 hours, the mixture thus obtained was concentrated under reduced pressure, and a solution of the resulting residue in chloroform (10 ml) was added dropwise to a saturated ammonia-chloroform solution (10 ml) at room temperature. After 2 hours, the mixture thus obtained was heated to 50° C. After 9 hours, the reaction solution was filtered under reduced pressure, and the filtrate was concentrated under reduced pressure and the resulting residue was purified by a silica gel column chromatography (eluent: hexane/ethyl acetate→chloroform/methanol) to obtain trans-3-methoxy-1-methylcyclohexanecarboamide (389.8 mg, 83%).

(e) Synthesis of 2-[(3-methoxy-1-methylcyclohexyl)methyl]-1H-isoindole-1,3(2H)dione Reaction was carried out according to the method described in Example 0.649, (b).

(f) Synthesis of 2-[(3-hydroxy-1-methylcyclohexyl)methyl]-1H-isoindole-1,3(2H)-dione Reaction was carried out according to the method described in Example 650, (c).

(g) Synthesis of {cis-1-methyl-3-[(4-methyl-1H-indazol-5-yl)oxy]cyclohexyl}methylamine Reaction was carried out according to the method described in Example 640, (a), except for using the 4-methyl-1H-indazol-5-ol obtained in Example 402, as a starting material.

IR (neat) cm$^{-1}$; 2921, 1508, 1221, 941, 816.

EXAMPLE 654

Synthesis of trans-2,2-dimethyl-5-[(4-methyl-1H-indazol-5-yl)oxy]cyclohexanecarbonitrile (a) Synthesis of 2,2-dimethyl-5-oxocyclohexanecarbonitrile Under a nitrogen atmosphere, an aqueous solution (10 ml) of ammonium chloride (2.37 g, 0.0443 mol) and an aqueous solution (20 ml) of potassium cyanide (3.15 g, 0.0483 mol) were added dropwise to a solution of 4,4-dimethyl-2-cyclohexen-1-one (5.0 g, 0.0403 mol) in N,N-dimethylformamide (30 ml) at room temperature, and the resulting mixture was heated to 70° C. After 2 hours, the reaction solution was poured into water and extracted with diethyl ether and then dichloromethane. The organic layer was dried over anhydrous magnesium sulfate. The organic layer dried was concentrated under reduced pressure and the resulting residue was purified by a silica gel column chromatography (eluent: hexane/ethyl acetate) to obtain 2,2-dimethyl-5-oxocyclohexanecarbonitrile (4.033 g, 66%).

(b) Synthesis of cis-5-hydroxy-2,2-dimethylcyclohexanecarbonitrile

Under a nitrogen atmosphere, a solution of 2,2-dimethyl-5-oxocyclohexanecarbonitrile (4.0 g, 0.0265 mol) in methanol (30 ml) was added dropwise to a solution of sodium borohydride (1.00 g, 0.0265 mol) in methanol (40 ml) at 0° C. After 1 hour, sodium borohydride (0.0133 mol) was further added thereto and the resulting mixture was warmed up to room temperature. After 45 minutes, a saturated aqueous ammonium chloride solution was added to the reaction solution and then the methanol was concentrated under reduced pressure. The resulting aqueous solution was diluted with water and extracted with chloroform, and the organic layer was dried over anhydrous magnesium sulfate. The organic layer dried was concentrated under reduced pressure and the resulting residue was purified by a silica gel column chromatography (eluent: hexane/ethyl acetate) to obtain cis-5-hydroxy-2,2-dimethylcyclohexanecarbonitrile (3.0550 g, 75%).

(c) Synthesis of trans-2,2-dimethyl-5-[(4-methyl-1H-indazol-5-yl)oxy]cyclohexanecarbonitrile Under a nitrogen atmosphere, a solution of 90%-cyanomethylenetri-n-butylphosphorane (1.05 g, 4.05 mmol) in toluene (5 ml) was added dropwise to a solution of cis-5-hydroxy-2,2-dimethylcyclohexanecarbonitrile (500 mg, 3.37 mmol) in toluene (12 ml) at room temperature, followed by adding thereto the 4-methyl-1H-indazol-5-ol (507 mg, 3.54 mmol) obtained in Example 402, and the resulting mixture was heated to 100° C. After 4 hours, the reaction solution was concentrated under reduced pressure, and the resulting residue was diluted with chloroform and washed with a 1M-aqueous sodium hydroxide solution. The aqueous layer was re-extracted with chloroform and then the organic layer was dried over anhydrous magnesium sulfate. The organic layer dried was concentrated under reduced pressure and the resulting residue was purified by a silica gel column chromatography (eluent: hexane/ethyl acetate) to obtain trans-2,2-dimethyl-5-[(4-methyl-1H-indazol-5-yl)oxy]cyclohexanecarbonitrile (351.1 mg, 46%).

IR (neat) cm$^{-1}$; 3176, 2954, 1508, 1223, 1094, 945.

EXAMPLE 655

Synthesis of trans-4-methyl-5-{[3-(1-methyl-1-nitroethyl)cyclohexyl]oxy}-1H-indazole (a) Synthesis of cis-3-(1-methyl-1-nitroethyl)cyclohexanol and trans-3-(1-methyl-1-nitroethyl)cyclohexanol Under a nitrogen atmosphere, sodium borohydride (343 mg, 9.07 mmol) was added to a solution of 3-(1-methyl-1-nitroethyl)cyclohexanone (1.68 g, 9.07 mmol) known in literature in methanol (17 ml) at 0° C. After 45 minutes, a saturated aqueous ammonium chloride solution was added to the reaction solution and then the methanol was concentrated under reduced pressure. The resulting aqueous solution was diluted with water and extracted with chloroform, and the organic layer was dried over anhydrous magnesium sulfate. The organic layer dried was concentrated under reduced pressure and the resulting residue was purified by a silica gel column chromatography (eluent: hexane/ethyl acetate) to obtain cis-3-(1-methyl-1-nitroethyl)cyclohexanol (499.1 mg, 29%), trans-3-(1-methyl-1-nitroethyl)cyclohexanol (259.6 mg, 15%) and a mixture of the isomers (55%).

(b) Synthesis of trans-4-methyl-5-{[3-(1-methyl-1-nitroethyl)cyclohexyl]oxy}-1H-indazole Reaction was carried out according to the method described in Example 654, (c).

IR (neat) cm$^{-1}$; 3184, 2931, 1533, 1508, 1220, 951, 845.

EXAMPLE 656

Synthesis of cis-4-[(7-methyl-1H-indazol-5-yl)oxy]cyclohexanamine (a) Synthesis of 4-amino-3,5-dimethylphenol An aqueous solution (4 ml) of sodium nitrite (1.90 g, 27.5 mmol) was added to an aqueous solution (20 ml) of sodium sulfanilate dihydrate (5.78 g, 25.0 mmol). The resulting solution was dropped into a beaker containing concentrated hydrochloric acid (5.1 ml) and ice (30 g), and the resulting mixture was kept cold in an ice bath for 20 minutes to prepare solution A. An aqueous solution (30 ml) of sodium hydroxide (5.50 g, 138 mmol) and ice (20 g) were added to 3,5-dimethylphenol (3.05 g, 250 mmol) to effect dissolution, and then solution A was added dropwise thereto in an ice bath. The resulting solution was stirred in the ice bath for 1 hour and then heated to 65° C. to 75° C., and sodium dithionate (16.8 g, 96.5 mmol) was added thereto until the solution lost its color. The solution was cooled to room temperature and stirred for 30 minutes, and the solid formed was collected by filtration and dried to obtain 4-amino-3,5-dimethylphenol (2.46 g, 72%).

(b) Synthesis of [4-(acetylamino)-3,5-dimethylphenyl]acetate

Pyridine (3.30 ml, 40.8 mmol) and acetic anhydride (1.90 ml, 20.1 mmol) were added to a suspension of 4-amino-3,5-dimethylphenol (1.10 g, 8.02 mmol) in ethyl acetate (20 ml), and the resulting mixture was stirred at 70° C. for 1 hour. The mixture was cooled to room temperature and hexane (60 ml) was added thereto to cause crystallization. The crystals were collected by filtration and dried to obtain [4-(acetylamino)-3,5-dimethylphenyl]acetate (1.69 g, 96%).

(c) Synthesis of (1-acetyl-7-methyl-1H-indazol-5-yl) acetate

Acetic anhydride (2.20 ml, 23.3 mmol), tetrabutylammonium bromide (124 mg, 0.383 mmol), potassium acetate (1.50 g, 15.3 mmol) and isoamyl nitrite (1.34 ml, 9.97 mmol) were added in that order to a solution of [4-(acetylamino)-3,5-dimethylphenyl]acetate (1.69 g, 7.64 mmol) in ethyl acetate (26 ml), and the resulting mixture was heated under reflux for 4 hours. The reaction mixture was cooled to room temperature, poured into water, and then extracted with ethyl acetate. The extract solution was washed with a saturated aqueous sodium chloride solution, dried over sodium sulfate, and then distilled under reduced pressure to remove the solvent. The residue was purified by a silica gel column chromatography (eluent: hexane/ethyl acetate=7:1–5:1) and then washed with diethyl ether to obtain (1-acetyl-7-methyl-1H-indazol-5-yl)acetate (875 mg, 49%).

(d) Synthesis of 7-methyl-1H-indazol-5-ol

A 2N-aqueous lithium hydroxide solution (3.7 ml, 7.4 mmol) was added to a solution of (1-acetyl-7-methyl-1H-indazol-5-yl)acetate (850 mg, 3.66 mmol) in methanol-tetrahydrofuran (1:1, 7.4 ml), and the resulting mixture was stirred at room temperature for 30 minutes. A saturated aqueous ammonium chloride solution was poured into the reaction solution, followed by extraction with ethyl acetate, and the extract solution was washed with a saturated aqueous sodium chloride solution, dried over sodium sulfate and then distilled under reduced pressure to remove the solvent. The residue was purified by a silica gel column chromatography (eluent: chloroform/methanol=100:3) to obtain 7-methyl-1H-indazol-5-ol (505 mg, 93%).

(e) Synthesis of cis-4-[(7-methyl-1H-indazol-5-yl)oxy]cyclohexanamine

To a toluene solution (3 ml) of the 2-(trans-4-hydroxycyclohexyl)-1H-isoindazole-1,3(2H)-dione (123 mg, 0.502 mmol) obtained in Example 323, (a) were added 7-methyl-1H-indazol-5-ol (111 mg, 0.749 mmol) and cyanomethylenetri-n-butylphosphorane (226 μl), and the resulting mixture was stirred at 100° C. for 3 hours. After the solvent was distilled off under reduced pressure, the residue was diluted with chloroform and then washed with a 1N-aqueous sodium hydroxide solution, and the solvent was distilled off under reduced pressure. A 30% methylamine-ethanol solution (4 ml) was added to the residue and the resulting mixture was heated under reflux for 3 hours. The reaction product thus obtained was purified by a silica gel column chromatography (eluent: chloroform/methanol/aqueous ammonia=7:1:0.1) to obtain cis-4-[(7-methyl-1H-indazol-5-yl)oxy]cyclohexanamine (70 mg, 57%).

IR (neat) cm$^{-1}$; 1508, 1163, 1016, 953, 941, 924.

The following compound of Example 657 was synthesized by carrying out reaction according to the method described in Example 656, except for using 3-ethylphenol as a starting material.

EXAMPLE 657 cis-4-[(3-Methyl-1H-indazol-5-yl)oxy]cyclohexanamine

IR (neat) cm$^{-1}$; 1504, 1448, 1348, 1213, 1205, 1066, 810.

EXAMPLE 658

Synthesis of cis-4-[(4,7-dimethyl-1H-indazol-5-yl)oxy]cyclohexanamine (a) Synthesis of (1-acetyl-4,7-dimethyl-1H-indazol-5-yl) acetate Acetic anhydride (49.8 ml, 0.528 mol), tetrabutylammonium bromide (2.85 g, 0.0088 mol), potassium acetate (34.5 g, 0.352 mol) and isoamyl nitrite (30.7 ml, 0.229 mol) were added in that order to a solution in ethyl acetate (600 ml) of [4-(acetylamino)-2,3,5-trimethylphenyl]acetate (41.4 g, 0.176 mol) synthesized by carrying out reactions according to the methods described in Example 2, a) and b), except for using 2,3,5-trimethylphenol as a starting material. The resulting mixture was heated under reflux for 4 hours. The reaction mixture was cooled to room temperature, poured into water, and then extracted with ethyl acetate. The extract solution was washed with a saturated aqueous sodium chloride solution, dried over sodium sulfate, and then distilled under reduced pressure to remove the solvent. The residue was washed successively with toluene, diethyl ether and methanol to obtain (1-acetyl-4,7-dimethyl-1H-indazol-5-yl)acetate (20.4 g, 47%). As to the filtrate, the solvent was distilled off under reduced pressure, and a mixture of (4,7-dimethyl-1H-indazol-5-yl)acetate and (6,7-dimethyl-1H-indazol-5-yl)acetate (approximately 1:1, 7.1 g, 20%) was also obtained from a fraction of hexane-ethyl acetate=1:1 by a silica gel column chromatography.

(b) Synthesis of 4,7-dimethyl-1H-indazol-5-ol

A 2N-aqueous lithium hydroxide solution (85 ml, 170 mmol) was added to a solution of (1-acetyl-4,7-dimethyl-1H-indazol-5-yl)acetate (20.3 g, 82.4 mmol) in methanol-tetrahydrofuran (1:1, 170 ml) under ice-cooling, and the resulting mixture was stirred at room temperature for 30 minutes. A saturated aqueous ammonium chloride solution was poured into the reaction solution, followed by extraction with ethyl acetate, and the extract solution was washed with a saturated aqueous sodium chloride solution, dried over sodium sulfate and then distilled under reduced pressure to remove the solvent. The residue was washed with acetonitrile by repulping to obtain 4,7-dimethyl-1H-indazol-5-ol (13.0 g, 97%).

(c) Synthesis of cis-4-[(4,7-dimethyl-1H-indazol-5-yl)oxy]cyclohexanamine

To a toluene solution (3 ml) of the 2-(trans-4-hydroxycyclohexyl)-1H-isoindazole-1,3(2H)-dione (123 mg, 0.502 mmol) obtained in Example 323, (a) were added 4,7-dimethyl-1H-indazol-5-ol (122 mg, 0.752 mmol) and cyanomethylenetri-n-butylphosphorane (201 mg, 0.750 mmol), and the resulting mixture was stirred at 100° C. for 5 hours. After the solvent was distilled off under reduced pressure, the residue was diluted with chloroform and then washed with a 1N-aqueous sodium hydroxide solution, and the solvent was distilled off under reduced pressure. A 30% methylamine-ethanol solution (10 ml) was added to the residue and the resulting mixture was heated under reflux for 3 hours. After the solvent was distilled off, a 30% methylamine-ethanol solution (10 ml) was added to the residue again, and the resulting mixture was heated under reflux for 7 hours. The solvent was distilled off and then the residue was purified by a silica gel column chromatography (chloroform/methanol/aqueous ammonia=10:1:0.1) to obtain cis-4-[(4,7-dimethyl-1H-indazol-5-yl)oxy]cyclohexanamine (54 mg, 42%).

IR (neat) cm$^{-1}$; 2927, 1676, 1201, 1136, 1001, 949.

EXAMPLE 659

Synthesis of cis-3-[(4-chloro-6,7-dimethyl-1H-indazol-5-yl)oxy]cyclohexanamine (a) Synthesis of 4-chloro-6,7-dimethyl-1H-indazol-5-ol A 2N-aqueous lithium hydroxide solution (28.6 ml, 57.2 mmol) was added to a solution of a mixture of (4,7-dimethyl-1H-indazol-5-yl)acetate and (6,7-dimethyl-1H-indazol-5-yl)acetate (approximately 1:1, 5.30 g, 26.0 mmol) in methanol (30 ml) under ice-cooling, and the resulting mixture was stirred at room temperature for 1.5 hours. A saturated aqueous ammonium chloride solution was poured into the reaction solution, followed by extraction with ethyl acetate, whereby a mixture of 4,7-dimethyl-1H-indazol-5-ol and 6,7-dimethyl-1H-indazol-5-ol (4.31 g, 100%) was obtained. To this mixture were added tetrahydrofuran (200 ml) and N-chlorosuccinimide (1.74 g, 13.0 mmol), and the resulting mixture was stirred at 50° C. for 3 hours. The reaction solution was poured into water to terminate the reaction, and was extracted with ethyl acetate. The extract solution was washed with a saturated aqueous sodium chloride solution, dried over sodium sulfate, and then distilled under reduced pressure to remove the solvent, whereby a crude product was obtained. The crude product was washed three times with methanol to obtain 4-chloro-6,7-dimethyl-1H-indazol-5-ol (440 mg). On the other hand, the solvent of the filtrate was distilled off under reduced pressure and then the residue was purified by a silica gel column chromatography (hexane/ethyl acetate=2:1) to obtain 4-chloro-6,7-dimethyl-1H-indazol-5-ol (980 mg, 1.42 g in total, 56%).

(b) Synthesis of cis-3-[(4-chloro-6,7-dimethyl-1H-indazol-5-yl)oxy]cyclohexanamine To a toluene solution (4 ml) of the 2-(trans-3-hydroxycyclohexyl)-1H-isoindazole-1,3(2H)-dione (246 mg, 1.00 mmol) obtained in Example 385, (b) were added 4-chloro-6,7-dimethyl-1H-indazol-5-ol (197 mg, 1.00 mmol) and cyanomethylenetri-n-butylphosphorane (349 mg, 1.30 mmol), and the resulting mixture was stirred at 100° C. for 3.5 hours. After the solvent was distilled off under reduced pressure, the residue was diluted with chloroform and then washed with a 1N-aqueous sodium hydroxide solution, and the solvent was distilled off under reduced pressure. A 30% methylamine-ethanol solution (5 ml) was added to the residue and the resulting mixture was heated under reflux for 2 hours. After the solvent was distilled off, the residue was purified by a preparative thin-layer silica gel chromatography (eluent: chloroform/methanol/aqueous ammonia=7:1:0.1) to obtain cis-3-[(4-chloro-6,7-dimethyl-1H-indazol-5-yl)oxy]cyclohexanamine (19 mg, 7%).

IR (neat) cm$^{-1}$; 2937, 1473, 1352, 1296, 1074, 995, 933.

The following compounds of Examples 660 and 661 were synthesized by carrying out reaction according to the method described in Example 658.

EXAMPLE 660 cis-3-[(4,7-Dimethyl-1H-indazol-5-yl)oxy]cyclohexanamine

IR (neat) cm$^{-1}$; 2931, 1523, 1450, 1356, 1323, 1099, 1001, 937.

EXAMPLE 661 trans-4-[(4,7-Dimethyl-1H-indazol-5-yl)oxy]cyclohexanamine

IR (neat) cm$^{-1}$; 1525, 1227, 1109, 1086, 941, 937, 850.

EXAMPLE 662

Synthesis of cis-N-{4-[(4,7-dimethyl-1H-indazol-5-yl)oxy]cyclohexyl}-N,N-dimethylamine A 36% aqueous formalin solution (161 μl, 1.93 mmol) was added to a methanolic solution (2 ml) of the cis-4-[(4,7-dimethyl-1H-indazol-5-yl)oxy]cyclohexanamine (100 mg, 0.386 mmol) obtained in Example 658, and the resulting mixture was stirred at room temperature for 1 hour. Sodium cyanoborohydride (51 mg, 0.771 mmol) and acetic acid (110 μl, 1.92 mmol) were added thereto, and the resulting mixture was stirred at room temperature for 18 hours. The methanol was removed by the use of nitrogen gas and chloroform-1N-aqueous sodium hydroxide solution was added to the residue, followed by extraction with chloroform. The extract solution was washed with a saturated aqueous sodium chloride solution, dried over sodium sulfate, and then distilled under reduced pressure to remove the solvent, whereby a crude product was obtained. The crude product was purified by a preparative thin-layer silica gel chromatography (chloroform/methanol/aqueous ammonia=7:1:0.1) to obtain cis-N-{4-[(4,7-dimethyl-1H-indazol-5-yl)oxy]cyclohexyl}-N,N-dimethylamine (77 mg, 69%).

IR (neat) cm$^{-1}$; 1525, 1327, 1227, 1109, 1032, 935.

The following compounds of Examples 663 and 664 were synthesized by carrying out reaction according to the method described in Example 662, except for using the cis-3-[(4,7-dimethyl-1H-indazol-5-yl)oxy]cyclohexanamine obtained in Example 660, as a starting material.

EXAMPLE 663 cis-N-{3-[(4,7-dimethyl-1H-indazol-5-yl)oxy]cyclohexyl}-N,N-dimethylamine

IR (neat) cm$^{-1}$; 2935, 1522, 1323, 1099, 1007, 949.

EXAMPLE 664 cis-N-benzyl-N-{3-[(4,7-dimethyl-1H-indazol-5-yl)oxy]cyclohexyl}amine

IR (neat) cm$^{-1}$; 2935, 1525, 1452, 1356, 1323, 1196, 1097, 1007, 953.

The following compound of Example 665 was synthesized by carrying out reaction according to the method described in Example 662.

EXAMPLE 665 cis-N-benzyl-N-{4-[(4,7-dimethyl-1H-indazol-5-yl)oxy]cyclohexyl}amine

IR (neat) cm$^{-1}$; 2931, 1523, 1450, 1442, 1323, 1101, 937.

The following compounds of Examples 666 and 667 were synthesized by carrying out reaction according to the method described in Example 662, except for using the trans-4-[(4,7-dimethyl-1H-indazol-5-yl)oxy]cyclohexanamine obtained in Example 661, as a starting material.

EXAMPLE 666 trans-N-{4-[(4,7-Dimethyl-1H-indazol-5-yl)oxy]cyclohexyl}-N,N-dimethylamine

IR (neat) cm$^{-1}$; 1520, 1450, 1093, 1055, 1036, 953, 928.

EXAMPLE 667 trans-N-benzyl-N-{4-[(4,7-dimethyl-1H-indazol-5-yl)oxy]cyclohexyl}amine

IR (neat) cm$^{-1}$; 1525, 1452, 1325, 1201, 1103, 944.

EXAMPLE 668

Synthesis of cis-N-{4-[(4,7-dimethyl-1H-indazol-5-yl)oxy]cyclohexyl}propanamide

Triethylamine (108 μl, 0.775 mmol), propionic acid (32 μl, 0.429 mmol), 1-ethyl-3-(3-dimethylaminopropyl)-carbodiimide hydrochloride (83 mg, 0.433 mmol) and 1-hydroxybenzotriazole (58 mg, 0.429 mmol) were added in that order to a dimethylformamide solution (2 ml) of the cis-4-[(4,7-dimethyl-1H-indazol-5-yl)oxy]cyclohexanamine (100 mg, 0.386 mmol) obtained in Example 658, and the resulting mixture was stirred at room temperature for 20 hours. The reaction was terminated by the addition of water, followed by extraction with ethyl acetate-toluene (1:1). The extract solution was washed with a saturated aqueous sodium chloride solution, dried over sodium sulfate, and then distilled under reduced pressure to remove the solvent, whereby a crude product was obtained. The crude product was purified by a silica gel chromatography (eluent: chloroform/methanol=100:2) to obtain cis-N-{4-[(4,7-dimethyl-1H-indazol-5-yl)oxy]cyclohexyl}propanamide (134 mg, 100%).

IR (neat) cm$^{-1}$; 1641, 1541, 1524, 1325, 1128, 1103, 943.

The following compound of Example 669 was synthesized by carrying out reaction according to the method described in Example 668, except for using the cis-3-[(4,7-dimethyl-1H-indazol-5-yl)oxy]cyclohexanamine obtained in Example 660, as a starting material.

EXAMPLE 669 cis-N-{3-[(4,7-dimethyl-1H-indazol-5-yl)oxy]cyclohexyl}propanamide

IR (neat) cm$^{-1}$; 1639, 1541, 1522, 1323, 1101, 1003, 949.

The following compound of Example 670 was synthesized by carrying out reaction according to the method described in Example 668, except for using the trans-4-[(4,7-dimethyl-1H-indazol-5-yl)oxy]cyclohexanamine obtained in Example 661, as a starting material.

EXAMPLE 670 trans-N-{4-[(4,7-dimethyl-1H-indazol-5-yl)oxy]cyclohexyl}propanamide

IR (neat) cm$^{-1}$; 1632, 1537, 1525, 1325, 1200, 1111, 1082, 943.

EXAMPLE 671

Synthesis of cis-N-{4-[(4,7-dimethyl-1H-indazol-5-yl)oxy]cyclohexyl}-N-propylamine Lithium aluminum hydride (70 mg, 1.84 mmol) was added to a tetrahydrofuran solution (5 ml) of the cis-N-{4-[(4,7-dimethyl-1H-indazol-5-yl)oxy]cyclohexyl}propanamide (116 mg, 0.368 mmol) obtained in Example 668, and the resulting mixture was heated under reflux for 5 hours. After the reaction solution was diluted with 10 ml of tetrahydrofuran, the reaction was terminated by careful addition of water (76 μl), a 4N-aqueous sodium hydroxide solution (76 μl) and water (230 μl) in that order under ice-cooling. The reaction solution thus treated was filtered by the use of Celite and the solvent was distilled off under reduced pressure to obtain a crude product. The crude product was purified by a preparative thin-layer silica gel chromatography (chloroform/methanol/aqueous ammonia=7:1:0.1) to obtain cis-N-{4-[(4,7-dimethyl-1H-indazol-5-yl)oxy]cyclohexyl}-N-propylamine (64 mg, 58%).

IR (neat) cm$^{-1}$; 1522, 1325, 1232, 1213, 1105, 939, 920.

The following compound of Example 672 was synthesized by carrying out reaction according to the method described in Example 671, except for using the cis-N-{3-[(4,7-dimethyl-1H-indazol-5-yl)oxy]cyclohexyl}propanamide obtained in Example 669, as a starting material.

EXAMPLE 672 cis-N-{3-[(4,7-dimethyl-1H-indazol-5-yl)oxy]cyclohexyl}-N-propylamine

IR (neat) cm$^{-1}$; 1524, 1454, 1356, 1323, 1099, 1003, 951.

The following compound of Example 673 was synthesized by carrying out reaction according to the method described in Example 671, except for using the trans-N-{4-[(4,7-dimethyl-1H-indazol-5-yl)oxy]cyclohexyl}propanamide obtained in Example 670, as a starting material.

EXAMPLE 673 trans-N-{4-[(4,7-dimethyl-1H-indazol-5-yl)oxy]cyclohexyl}-N-propylamine

IR (neat) cm$^{-1}$; 1525, 1327, 1200, 1107, 941.

EXAMPLE 674

Synthesis of 2-{cis-4-[(4-methyl-1H-indazol-5-yl)oxy]cyclohexyl}-1H-isoindole-1,3(2H)-dione Diisopropyl dicarboxylate (4.85 g, 24.0 mmol) was added dropwise to a mixture of the 5-hydroxy-4-methyl-1H-indazole (2.96 g, 20.0 mmol) obtained in Example 402, the 2-(trans-4-hydroxycyclohexyl)-1H-isoinzole-1,3(2H)-dione (4.90 g, 20.0 mmol) obtained in Example 323, (a), triphenylphosphine (5.77 g, 22.0 mmol) and tetrahydrofuran (120 ml) under ice-cooling. After 30 minutes, the mixture thus obtained was warmed up to room temperature and stirred overnight. After the reaction solution was concentrated, a 1N-aqueous sodium hydroxide solution (200 ml) was added to the residue, followed by extraction with chloroform (120 ml) (three times). The organic layer was washed with a saturated aqueous sodium chloride solution and dried over magnesium sulfate. The solvent was distilled off and the residue oil was purified by a silica gel column chromatography (hexane/ethyl acetate=2:1 to 1:1) to obtain 2-{cis-4-[(4-methyl-1H-indazol-5-yl)oxy]cyclohexyl}-1H-isoindole-1,3(2H)-dione (1.76 g, 23%).

NMR (DMSO-d$_6$) δ; 1.45–1.72 (4H, m), 2.03 (2H, d, J=14.1 Hz), 2.55–2.67 (5H, m), 4.05–4.17 (1H, m), 4.59 (1H, s), 7.16 (1H, d, J=9.0 Hz), 7.19 (1H, d, J=9.2 Hz), 7.75–7.88 (4H, m), 8.03 (1H, s), 12.85 (1H, s).

EXAMPLE 675

Synthesis of cis-4-[(1,4-dimethyl-1H-indazol-5-yl)oxy]cyclohexanamine (a) Synthesis of 2-{cis-4-[(1,4-dimethyl-1H-indazol-5-yl)oxy]cyclohexyl}-1H-isoindazole-1,3(2H)-dione and 2-{cis-4-[(2,4-dimethyl-2H-indazol-5-yl)oxy]cyclohexyl}-1H-isoindazole-1,3(2H)-dione Potassium carbonate (55 mg, 0.398 mmol) and then methyl iodide (15 μl, 0.241 mmol) were added to a suspension of the cis-2-[4-(4-methyl-1H-indazol-5-yloxy)cyclohexyl]-1H-isoindole-1,3(2H)-dione (75 mg, 0.200 mmol) obtained in Example 674 in dimethylformamide (1 ml), and the resulting mixture was stirred at 60° C. for 24 hours. A saturated aqueous ammonium chloride solution was added thereto, followed by extraction with ethyl acetate. The extract solution was washed with a saturated aqueous sodium chloride solution, dried over sodium sulfate, and then distilled under reduced pressure to remove the solvent. By a silica gel column chromatography, 2-{cis-4-[(1,4-dimethyl-1H-indazol-5-yl)oxy]cyclohexyl}-1H-isoindazole-1,3(2H)-dione (31 mg, 40%) was obtained from a fraction of hexane-ethyl acetate=2:1, and 2-{cis-4-[(2,4-dimethyl-2H-indazol-5-yl)oxy]cyclohexyl}-1H-isoindazole-1,3(2H)-dione (13 mg, 17%) was obtained from a fraction of hexane-ethyl acetate=1:1.

(b) Synthesis of cis-4-[(1,4-dimethyl-1H-indazol-5-yl)oxy]cyclohexanamine

A 30% methylamine-ethanol solution (3 ml) was added to 2-{cis-4-[(1,4-dimethyl-1H-indazol-5-yl)oxy]cyclohexyl}-1H-isoindazole-1,3(2H)-dione (30 mg, 0.077 mmol), and the resulting mixture was heated under reflux for 2 hours. The solvent was distilled off under reduced pressure and the residue was purified by a silica gel column chromatography (chloroform/methanol/aqueous ammonia=100:10:1) to obtain cis-4-[(1,4-dimethyl-1H-indazol-5-yl)oxy]cyclohexanamine (16 mg, 80%).

$^1$H-NMR (CD$_3$OD) δ; 1.68 (6H, m), 2.05 (2H, m), 2.48 (3H, s), 2.82 (1H, m), 4.00 (3H, s), 4.43 (1H, m), 7.20 (1H, m), 7.29 (1H, m), 7.94 (1H, s).

EXAMPLE 676

Synthesis of cis-4-[(2,4-dimethyl-2H-indazol-5-yl)oxy]cyclohexanamine

A 30% methylamine-ethanol solution (2 ml) was added to the 2-{cis-4-[(2,4-dimethyl-2H-indazol-5-yl)oxy]cyclohexyl}-1H-isoindazole-1,3(2H)-dione (12 mg, 0.031 mmol) obtained in Example 675, (a), and the resulting mixture was heated under reflux for 2 hours. The solvent was distilled off under reduced pressure and the residue was purified by a silica gel column chromatography (chloroform/methanol/aqueous ammonia=100:10:1) to obtain cis-4-[(2,4-dimethyl-2H-indazol-5-yl)oxy]cyclo-hexanamine (8 mg, 100%).

$^1$H-NMR (CD$_3$OD) δ; 1.71 (6H, m), 2.04 (2H, m), 2.42 (3H, s), 2.86 (1H, m), 4.16 (3H, s), 4.16 (1H, m), 7.14 (1H, m), 7.35 (1H, m), 8.09 (1H, s).

The following compounds of Examples 677 to 680 were synthesized by carrying out reactions according to the methods described in Examples 675 and 676.

EXAMPLE 677 cis-4-[(1-Butyl-4-methyl-1H-indazol-5-yl)oxy]cyclohexanamine $^1$H-NMR (CD$_3$OD) δ; 0.91 (3H, t, J=7.3 Hz), 1.27 (2H, sex, J=7.4 Hz), 1.66 (6H, m), 1.83 (2H, qu, J=7.4 Hz), 2.02 (2H, m), 2.48 (3H, s), 2.78 (1H, m), 4.34 (2H, t, J=7.0 Hz), 4.41 (1H, m), 7.16 (1H, d, J=9.0 Hz), 7.30 (1H, d, J=9.2 Hz), 7.94 (1H, s).

EXAMPLE 678 cis-4-[(2-Butyl-4-methyl-2H-indazol-5-yl)oxy]cyclohexanamine $^1$H-NMR (CD$_3$OD) δ; 0.95 (3H, t, J=7.4 Hz), 1.31 (2H, six, J=7.5 Hz), 1.67 (6H, m), 1.95 (2H, qu, J=7.3 Hz), 2.02 (2H, m), 2.43 (3H, s), 2.8 (1H, m), 4.39 (2H, t, J=7.2 Hz), 4.40 (1H, m), 7.12 (1H, d, J=9.2 Hz), 7.37 (1H, d, J=9.3 Hz), 8.12 (1H, s).

EXAMPLE 679 cis-4-{[4-Methyl-1-(2,2,2-trifluoromethyl)-1H-indazol-5-yl]oxy}cyclohexanamine $^1$H-NMR (CD$_3$OD) δ; 1.67 (6H, m), 2.05 (2H, m), 2.50 (3H, s), 2.79 (1H, m), 4.46 (1H, m), 5.12 (2H, q, J=8.8 Hz), 7.23 (1H, d, J=9.0 Hz), 7.38 (1H, d, J=9.2 Hz), 8.07 (1H, s).

EXAMPLE 680 cis-4-{[4-Methyl-2-(2,2,2-trifluoromethyl)-2H-indazol-5-yl]oxy}cyclohexanamine $^1$H-NMR (CD$_3$OD) δ; 1.66 (6H, m), 2.03 (2H, m), 2.44 (3H, s), 2.77 (1H, m), 4.44 (1H, m), 5.20 (2H, q, J=8.6 Hz), 7.20 (1H, d, J=9.3 Hz), 7.43 (1H, d, J=9.4 Hz), 8.26 (1H, s).

EXAMPLE 681

Synthesis of cis-4-[(3-bromo-4-methyl-1H-indazol-5-yl)oxy]cyclohexanamine (a) Synthesis of 2-{cis-4-[(3-bromo-4-methyl-1-tetrahydro-2H-pyran-2-yl-1H-indazol-5-yl)oxy]cyclohexyl}-1H-isoindazole-1,3(2H)-dione A 2N-aqueous sodium hydroxide solution (1.5 ml) was added to a suspension of the cis-2-[4-(4-methyl-1H-indazol-5-yloxy)cyclohexyl]-1H-isoindole-1,3(2H)-dione (375 mg, 0.999 mmol) obtained in Example 674 in dioxane (3 ml). A solution of bromine (36 μl, 0.699 mmol) in a 2N-aqueous sodium hydroxide solution (1.5 ml) was added thereto under ice-cooling, and the resulting mixture was stirred at the same temperature for 2 hours. A saturated aqueous sodium hydrogesulfite solution (5 ml) was added thereto, and the water was removed as an azeotrope with ethanol. Ethanol (30 ml) and p-toluenesulfonic acid monohydrate (38 mg, 0.200 mmol) were added to the residue, and the resulting mixture was heated under reflux. After 2 hours, p-toluenesulfonic acid monohydrate (152 mg, 0.80 mmol) was added thereto, followed by heating under reflux for another 2 hours. The solvent was distilled off under reduced pressure and ethyl acetate was added to the residue, followed by washing with 1N-hydrochloric acid. The residue thus treated was washed with water, dried over sodium sulfate, and then distilled under reduced pressure to remove the solvent. To the resulting residue was added 1,2-dichloroethane (5 ml), followed by adding thereto 2H-3,4-dihydropyran (140 μl, 1.53 mmol) and p-toluenesulfonic acid monohydrate (38 mg, 0.200 mmol), and the resulting mixture was stirred for 1 week. The solvent was distilled off under reduced pressure and the residue was purified by a silica gel column chromatography (hexane/ethyl acetate=4:1) to obtain 2-{cis-4-[(3-bromo-4-methyl-1-tetrahydro-2H-pyran-2-yl-1H-indazol-5-yl)oxy]cyclohexyl}-1H-isoindazole-1,3(2H)-dione (162 mg, 30%).

(b) Synthesis of cis-4-[(3-bromo-4-methyl-1H-indazol-5-yl)oxy]cyclohexanamine

Trifluoroacetic acid (1.8 ml) was added to a dichloromethane solution (7.2 ml) of 2-{cis-4-[(3-bromo-4-methyl-1-tetrahydro-2H-pyran-2-yl-1H-indazol-5-yl)oxy]cyclohexyl}-1H-isoindazole-1,3(2H)-dione (154 mg, 0.286 mmol), and the resulting mixture was stirred at room temperature for 1 hour. The reaction was terminated by the use of a saturated aqueous sodium hydrogencarbonate solution, followed by extraction with ethyl acetate. The extract solution was washed with a saturated aqueous sodium chloride solution, dried over sodium sulfate, and then distilled under reduced pressure to remove the solvent. A 30% methylamine-ethanol solution (10 ml) was added to the residue and the resulting mixture was heated under reflux for 3 hours. The solvent was distilled off and the residue was purified by a silica gel column chromatography (chloroform/ methanol/aqueous ammonia=10:1:0.1) to obtain cis-4-[(3-bromo-4-methyl-1H-indazol-5-yl)oxy]cyclohexanamine (70 mg, 75%).

¹H-NMR (CD₃OD) δ; 1.71 (6H, m), 2.06 (2H, m), 2.69 (3H, s), 2.93 (1H, m), 4.44 (1H, m), 7.19 (1H, d, J=9.0 Hz), 7.29 (1H, d, J=9.0 Hz).

EXAMPLE 682

Synthesis of 4-ethyl-1H-indazol-5-ol (a) Synthesis of 1-tetrahydro-2H-pyran-2-yl-5-(tetrahydro-2H-pyran-2-yloxy)-4-vinyl-1H-indazole A mixture of the 4-bromo-1-tetrahydro-2H-pyran-2-yl-5-(tetrahydro-2H-pyran-2-yloxy)-1H-indazole (2.00 g, 5.25 mmol) obtained in Example 607, (a), tributylvinyltin (1.83 g, 5.77 mmol) and tetrakis(triphenylphosphine)palladium (606 mg, 0.524 mmol) was stirred in toluene (26.0 ml) for 5 hours with heating under reflux while maintaining the temperature. Tetrakis(triphenylphosphine)palladium (202 mg, 0.171 mmol) was further added thereto and the resulting mixture was stirred for another 3 hours with heating under reflux while maintaining the temperature. After cooling, the reaction mixture was diluted with ethyl acetate and 10% aqueous ammonia was added thereto and stirred. The resulting mixture was filtered by the use of Celite and the filtrate was partitioned by using water and ethyl acetate. The organic layer was washed with a saturated aqueous sodium chloride solution, dried over anhydrous magnesium sulfate, and then filtered, and the filtrate was concentrated under reduced pressure to obtain a crude product. The crude product was purified by a silica gel column chromatography (eluent: hexane/ethyl acetate) to obtain 1-tetrahydro-2H-pyran-2-yl-5-(tetrahydro-2H-pyran-2-yloxy)-4-vinyl-1H-indazole (1.35 g, 78%).

(b) Synthesis of 4-ethyl-1-tetrahydro-2H-pyran-2-yl-5-(tetrahydro-2H-pyran-2-yloxy)-1H-indazole To a solution of 1-tetrahydro-2H-pyran-2-yl-5-(tetrahydro-2H-pyran-2-yloxy)-4-vinyl-1H-indazole (1.35 g, 4.11 mmol) in ethyl acetate (40 ml) was added 10%-palladium/carbon (containing 50% water, 50 mg), and the resulting mixture was stirred for 6 hours at ordinary temperature and atmospheric pressure under a hydrogen atmosphere. To the mixture was further added 10%-palladium/carbon (containing 50% water, 670 mg), and stirred for another 1.5 hours. The reaction mixture was filtered by the use of Celite and washed with methanol, and then the filtrate was concentrated under reduced pressure to obtain 4-ethyl-1-tetrahydro-2H-pyran-2-yl-5-(tetrahydro-2H-pyran-2-yloxy)-1H-indazole (1.41 g).

(c) Synthesis of 4-ethyl-1H-indazol-5-ol

In a mixed solvent of tetrahydrofuran (5.0 ml) and water (2.5 ml) was suspended 4-ethyl-1-tetrahydro-2H-pyran-2-yl-5-(tetrahydro-2H-pyran-2-yloxy)-1H-indazole (1.40 g), followed by adding thereto trifluoroacetic acid (10.0 ml), and the resulting mixture was stirred for 2.5 hours while being maintained at room temperature. The reaction mixture was neutralized with a 2N-aqueous sodium hydroxide solution and extracted with ethyl acetate, and the extract solution was dried over anhydrous magnesium sulfate and filtered. The filtrate was concentrated under reduced pressure to obtain a crude product. The crude product was purified by a silica gel column chromatography (eluent: chloroform/ethyl acetate) to obtain 4-ethyl-1H-indazol-5-ol (314 mg, 47%) as a white solid.

¹H-NMR (DMSO-d₆) δ; 1.15 (3H, t, J=7.4 Hz), 2.80 (2H, q, J=7.4 Hz), 6.92 (1H, d, J=8.8 Hz), 7.15 (1H, d, J=8.8 Hz), 7.92 (1H, s), 8.72 (1H, s), 12.69 (1H, brs).

The following compounds of Examples 683 and 684 were synthesized by carrying out reaction according to the method described in Example 407, except for using the 4-ethyl-1H-indazol-5-ol obtained in Example 682, as a starting material.

EXAMPLE 683

4-Ethyl-5-(piperidin-4-yloxy)-1H-indazole

¹H-NMR (CDCl₃) δ; 1.30 (3H, t, J=7.5 Hz), 1.65–1.77 (2H, m), 2.00–2.07 (2H, m), 2.66–2.75 (2H, m), 2.98 (2H, q, J=7.5 Hz), 3.14–3.21 (2H, m), 4.23 (1H, m), 7.12 (1H, d, J=8.8 Hz), 7.26 (1H, dd, J=8.8, 0.92 Hz), 8.06 (1H, d, J=0.92 Hz).

EXAMPLE 684

5-(Azepan-4-yloxy)-4-ethyl-1H-indazole

¹H-NMR (CDCl₃) δ; 1.28 (3H, t, J=7.5 Hz), 1.54–1.67 (1H, m), 1.82–2.20 (5H, m), 2.82–3.12 (6H, m), 4.45 (1H, m), 7.07 (1H, d, J=9.0 Hz), 7.24 (1H, dd, J=9.0, 1.0 Hz), 8.05 (1H, d, J=1.0 Hz).

EXAMPLE 685

Synthesis of 4-isopropyl-1H-indazol-5-ol (a) Synthesis of 2-[1-tetrahydro-2H-pyran-2-yl-5-(tetrahydro-2H-pyran-2-yloxy)-1H-indazol-4-yl]propan-2-ol A solution of the 4-bromo-1-tetrahydro-2H-pyran-2-yl-5-(tetrahydro-2H-pyran-2-yloxy)-1H-indazole (3.81 g, 10.0 mmol) obtained in Example 607, (a) in tetrahydrofuran (50 ml) was cooled to −78° C., and 1.57M n-butyllithium (7.64 ml, 12.0 mmol) was added dropwise thereto. After the resulting mixture was kept cold at −78° C. for 30 minutes, acetone (1.10 ml, 15.0 mmol) was added dropwise thereto and the resulting mixture was stirred for 1 hour while being kept cold at −78° C. The mixture was warmed up to room temperature and stirred for another 1 hour while maintaining the temperature. After cooling, a saturated aqueous ammonium chloride solution was added thereto and stirred, followed by partition and extraction with ethyl acetate. The organic layer was washed with a saturated aqueous sodium chloride solution, dried over anhydrous magnesium sulfate, and then filtered, and the filtrate was concentrated under reduced pressure to obtain a crude product. The crude product was purified by a silica gel column chromatography (eluent: hexane/ethyl acetate) to obtain 2-[1-tetrahydro-2H-pyran-2-yl-5-(tetrahydro-2H-pyran-2-yloxy)-1H-indazol-4-yl]propan-2-ol (2.46 g, 68%).

(b) Synthesis of 4-isopropyl-1-tetrahydro-2H-pyran-2-yl-5-(tetrahydro-2H-pyran-2-yloxy)-1H-indazole and 4-isopropyl-1-tetrahydro-2H-pyran-2-yl-1H-indazol-5-ol In an autoclave, 10%-palladium/carbon (containing 50% water, 1.0 g) was added to a solution of 2-[1-tetrahydro-2H-pyran-2-yl-5-(tetrahydro-2H-pyran-2-yloxy)-1H-indazol-4-yl]propan-2-ol (1.92 g, 5.33 mmol) in ethanol (26 ml), and the resulting mixture was stirred at 60° C. for 5 hours under a hydrogen atmosphere of 30 atmospheric pressure. The reaction mixture was filtered by the use of Celite and washed with methanol, and then the filtrate was concentrated under reduced pressure to obtain a crude product. The crude product was purified by a silica gel column chromatography (eluent: hexane/ethyl acetate) to obtain 4-isopropyl-1-tetrahydro-2H-pyran-2-yl-5-(tetrahydro-2H-pyran-2-yloxy)-1H-indazole (301 mg, 16%) and 4-isopropyl-1-tetrahydro-2H-pyran-2-yl-1H-indazol-5-ol (586 mg, 42%).

(c) Synthesis of 4-isopropyl-1H-indazol-5-ol

A mixture of 4-isopropyl-1-tetrahydro-2H-pyran-2-yl-5-(tetrahydro-2H-pyran-2-yloxy)-1H-indazole (301 mg, 0.871 mmol) and 4-isopropyl-1-tetrahydro-2H-pyran-2-yl-1H-indazol-5-ol (586 mg, 2.25 mmol) was made into a solution of the mixture in dichloromethane (26 ml), followed by adding thereto trifluoroacetic acid (6.5 ml), and the resulting mixture was stirred for 4 hours while being maintained at room temperature. The reaction solution was diluted with ethyl acetate, neutralized with a saturated aqueous sodium hydrogencarbonate solution and extracted with ethyl acetate, and the extract solution was dried over anhydrous magnesium sulfate and filtered. The filtrate was concentrated under reduced pressure to obtain a crude product. The crude product was purified by a silica gel column chromatography (eluent: chloroform/ethyl acetate) to obtain 4-isopropyl-1H-indazol-5-ol (430 mg, 78%).

$^1$H-NMR (DMSO-$d_6$) δ; 1.48 (6H, d, J=7.2 Hz), 3.59 (1H, sep, J=7.2 Hz), 6.95 (1H, d, J=8.8 Hz), 7.20 (1H, d, J=8.8 Hz), 8.16 (1H, s).

The following compounds of Examples 686 to 689 were synthesized by carrying out reaction according to the method described in Example 640, (a), except for using the 4-isopropyl-1H-indazol-5-ol obtained in Example 685, as a starting material.

EXAMPLE 686 trans-3-[(4-Isopropyl-1H-indazol-5-yl)oxy]cyclohexanamine

IR (neat) cm$^{-1}$; 2933, 2866, 1230, 943, 914.

EXAMPLE 687 cis-3-[(4-Isopropyl-1H-indazol-5-yl)oxy]cyclohexanamine

IR (neat) cm$^{-1}$; 2931, 2862, 1221, 1030, 941, 908.

EXAMPLE 688 trans-4-[(4-Isopropyl-1H-indazol-5-yl)oxy]cyclohexanamine

IR (neat) cm$^{-1}$; 2933, 2864, 1225, 1045, 943, 908.

EXAMPLE 689 cis-4-[(4-Isopropyl-1H-indazol-5-yl)oxy]cyclohexanamine

IR (neat) cm$^{-1}$; 2931, 2866, 1223, 1036, 939, 906.

EXAMPLE 690

Synthesis of 5-hydroxy-1H-indazole-4-carbonitrile (a) 1-Tetrahydro-2H-pyran-2-yl-5-(tetrahydro-2H-pyran-2-yloxy)-1H-indazole-4-carbonitrile A mixture of the 4-bromo-1-tetrahydro-2H-pyran-2-yl-5-(tetrahydro-2H-pyran-2-yloxy)-1H-indazole (763 mg, 2.00 mmol) obtained in Example 607, (a), copper(I) iodide (76 mg, 0.40 mmol), sodium cyanide (412 mg, 8.40 mmol) and tetrakis(triphenylphosphine)palladium (240 mg, 0.208 mmol) was stirred in propionitrile (10.0 ml) for 16 hours with heating under reflux while maintaining the temperature. After cooling, the reaction mixture was diluted with ethyl acetate and filtered by the use of Celite, and the filtrate was partitioned by the use of water and ethyl acetate. The organic layer was washed with a saturated aqueous sodium chloride solution, dried over anhydrous magnesium sulfate, and then filtered, and the filtrate was concentrated under reduced pressure to obtain a crude product. The crude product was purified by a silica gel column chromatography (eluent: hexane/ethyl acetate) to obtain 1-tetrahydro-2H-pyran-2-yl-5-(tetrahydro-2H-pyran-2-yloxy)-1H-indazole-4-carbonitrile (254 mg, 39%).

(b) 5-Hydroxy-1H-indazole-4-carbonitrile

Trifluoroacetic acid (1.5 ml) was added dropwise to a solution of 1-tetrahydro-2H-pyran-2-yl-5-(tetrahydro-2H-pyran-2-yloxy)-1H-indazole-4-carbonitrile (227 mg, 0.693 mmol) in dichloromethane (6.5 ml) at room temperature, and the resulting mixture was stirred for 1.5 hours while being maintained at room temperature. The reaction solution was diluted with ethyl acetate and adjusted to pH 7 with a saturated aqueous sodium hydrogencarbonate solution, followed by partition and extraction. The organic layer was washed with a saturated aqueous sodium chloride solution, dried over anhydrous magnesium sulfate, and then filtered, and the filtrate was concentrated under reduced pressure to obtain a crude product. The crude product was purified by a silica gel column chromatography (eluent: hexane/ethyl acetate) to obtain 5-hydroxy-1H-indazole-4-carbonitrile (108 mg, 98%).

IR (neat) cm$^{-1}$; 3404, 2224, 1147, 937, 928.

The following compound of Example 691 was synthesized by carrying out reaction according to the method described in Example 407, except for using the 5-hydroxy-1H-indazole-4-carbonitrile obtained in Example 690, as a starting material.

EXAMPLE 691

5-(Azepan-4-yloxy)-1H-indazole-4-carbonitrile

IR (neat) cm$^{-1}$; 2933, 2211, 1495, 1313, 1246, 931.

The following compounds of Examples 692 to 695 were synthesized by carrying out reaction according to Example 640, (a), except for using the 5-hydroxy-1H-indazole-4-carbonitrile obtained in Example 690, as a starting material.

EXAMPLE 692 trans-5-[(3-Aminocyclohexyl)oxy]-1H-indazole-4-carbonitrile

IR (neat) cm$^{-1}$; 2933, 2218, 1497, 1308, 1240, 941.

EXAMPLE 693 cis-5-[(3-Aminocyclohexyl)oxy]-1H-indazole-4-carbonitrile

IR (neat) cm$^{-1}$; 2935, 2216, 1497, 1311, 1242, 945.

EXAMPLE 694 trans-5-[(4-Aminocyclohexyl)oxy]-1H-indazole-4-carbonitrile

IR (neat) cm$^{-1}$; 2922, 2208, 1489, 1313, 1248, 935.

EXAMPLE 695 cis-5-[(4-Aminocyclohexyl)oxy]-1H-indazole-4-carbonitrile

IR (neat) cm$^{-1}$; 2925, 2213, 1487, 1053, 1011, 930.

EXAMPLE 696

Synthesis of 5-(azepan-4-yloxy)-1H-indazole-4-carboxamide

Potassium hydroxide (powder, 100 mg) was added to a solution of the 5-(azepan-4-yloxy)-1H-indazole-4-carbonitrile (9.2 mg, 0.036 mmol) obtained in Example 691 in t-butanol (2 ml) at room temperature, and the resulting mixture was stirred for 30 hours with heating under reflux while maintaining the temperature. The reaction mixture was diluted with ethanol and filtered, and the filtrate was concentrated under reduced pressure to obtain a crude product. The crude product was purified by a silica gel column chromatography (eluent: chloroform/methanol/28% aqueous ammonia) to obtain 5-(azepan-4-yloxy)-1H-indazole-4-carboxamide (2.5 mg, 25%).

MS: m/z=275 (M+1)

The following compound of Example 697 was synthesized by carrying out reaction according to the method described in Example 696.

EXAMPLE 697 cis-5-[(3-Aminocyclohexyl)oxy]-1H-indazole-4-carboxamide

MS: m/z=275 (M+1)

EXAMPLE 698

Synthesis of 2-[4-[(4-methoxy-1H-indazol-5-yl)oxy]cyclohexyl]-1H-isoindole-1,3(2H)-dione Under nitrogen, the 2-(4-hydroxycyclohexyl)-1H-isoindole-1,3(2H)-dione (1.23 g, 5.01 mmol) obtained in Example 385, (b), the 4-methoxy-1H-indazol-5-ol (0.906 g, 5.52 mmol) obtained in Example 469 and 90%-cyanomethylenetri-n-butylphosphorane (161 g, 6.02 mmol) were dissolved in toluene (20 ml), and the resulting solution was heated under reflux for 5 hours. The reaction solution was cooled to room temperature and water and a 1N-aqueous sodium hydroxide solution were added thereto. The resulting solution was separated by the addition of toluene and the desired compound was extracted from the aqueous layer with toluene. The combined toluene layer was washed with a saturated aqueous sodium chloride solution, dried by the addition of anhydrous magnesium sulfate, and then filtered. The solvent was distilled off under reduced pressure and the concentration residue thus obtained was purified by a silica gel column chromatography (eluent: n-hexane/ethyl acetate=2/1, 1/1) to obtain 2-[4-[(4-methoxy-1H-indazol-5-yl)oxy]cyclohexyl]-1H-isoindole-1,3(2H)-dione (1.29 g, yield 66%).

IR (neat) cm$^{-1}$; 3373, 2949, 2360, 1697, 1508, 1375, 1350, 1238, 1219, 1076, 1035, 1018.

The compound of Example 699 was synthesized by carrying out reaction according to the method described in Example 698, except for using the trans-2-(3-hydroxycyclohexyl)-1H-isoindole-1,3(2H)-dione obtained in Example 385, (b), as a starting material.

EXAMPLE 699

2-[cis-3-[(4-methoxy-1H-indazol-5-yl)oxy]cyclohexyl]-1H-isoindole-1,3(2H)-dione

IR (neat) cm$^{-1}$; 2358, 2343, 1701, 1508, 1373, 1349, 1228, 1087, 1033.

EXAMPLE 700

Synthesis of N-[cis-3-[(4-methoxy-1H-indazol-5-yl)oxy]cyclohexyl]-N,N-dimethylamine monohydrochloride Under nitrogen, the cis-3-[(4-methoxy-1H-indazol-5-yl)oxy]cyclohexanamine (100 mg, 0.383 mmol) obtained in Example 583 and 36%-formaldehyde (160 mg, 1.91 mmol) were suspended in a mixture of acetonitrile (2 ml) and methanol (2 ml), and the resulting suspension was stirred at room temperature for 20 minutes. Then, sodium cyanoborohydride (48 mg, 0.765 mmol) and acetic acid (0.2 ml) were added thereto, and the resulting mixture was stirred at room temperature for 5 hours. The reaction mixture was diluted with chloroform, washed successively with a 1N-aqueous sodium hydroxide solution, water and a saturated aqueous sodium chloride solution, dried by the addition of anhydrous magnesium sulfate, and then filtered. The solvent was distilled off under reduced pressure and the resulting concentration residue was purified by a silica gel column chromatography (eluent: chloroform/methanol=20/1, chloroform/methanol/aqueous ammonia=20/1/0.1). The residue purified was dissolved in isopropyl alcohol and a 4N-hydrochloric acid/dioxane solution was added thereto and stirred. Then, the solvent was distilled off under reduced pressure to obtain N-[cis-3-[(4-methoxy-1H-indazol-5-yl)oxy]cyclohexyl]-N,N-dimethylamine monohydrochloride (43 mg, yield 34%).

IR (neat) cm$^{-1}$; 3600–2100, 1508, 1380, 1352, 1230, 1089, 1035, 962.

EXAMPLE 701

Synthesis of N-ethyl-N-[cis-3-[(4-methoxy-1H-indazol-5-yl)oxy]cyclohexyl]amine monohydrochloride (a) Synthesis of N-[cis-3-[(4-methoxy-1H-indazol-5-yl)oxy]cyclohexyl]acetamide Under nitrogen, the cis-3-[(4-methoxy-1H-indazol-5-yl)oxy]cyclohexanamine (100 mg, 0.383 mmol) obtained in Example 583 was suspended in N,N-dimethylformamide (3 ml), and acetic acid (25 µl, 0.421 mmol) and triethylamine (107 µl, 0.765 mmol) were added thereto, followed by adding thereto 1-ethyl-3-(3'-dimethylaminopropyl)carbodiimide mono-hydrochloride (81 mg, 0.421 mmol) and 1-hydroxybenzotriazole (57 mg, 0.421 mmol). The resulting mixture was stirred at room temperature for 21 hours.

A 1N-aqueous sodium hydroxide solution was added thereto and stirred for 30 minutes, followed by extraction with ethyl acetate (three times). The combined ethyl acetate layer was washed with a saturated aqueous sodium chloride solution, dried by the addition of anhydrous magnesium sulfate, and then filtered. The solvent was distilled off under reduced pressure and the concentration residue thus obtained was purified by a silica gel column chromatography (eluents: n-hexane/ethyl acetate=1/4 and chloroform/methanol=10/1) to obtain N-[cis-3-[(4-methoxy-1H-indazol-5-yl)oxy]cyclohexyl]acetamide (106 mg, yield 91%).

(b) Synthesis of N-ethyl-N-[cis-3-[(4-methoxy-1H-indazol-5-yl)oxy]cyclohexyl]amine monohydrochloride Under nitrogen, N-[cis-3-[(4-methoxy-1H-indazol-5-yl)oxy]cyclohexyl]acetamide (106 mg, 0.349 mmol) was dissolved in tetrahydrofuran (5 ml), followed by adding thereto lithium aluminum hydride (27 mg, 0.699 mmol), and the resulting mixture was stirred with heating under reflux for about 4 hours.

Under ice-cooling, the reaction solution was diluted with tetrahydrofuran, and water (68 µl) was added thereto and stirred, and then a 4N-aqueous sodium hydroxide solution (68 µl) and water (200 µl) were added thereto and stirred. The solid was filtered off and the solvent was distilled off under reduced pressure. The resulting concentration residue was purified by a silica gel column chromatography (eluent: acetonitrile/aqueous ammonia=100/0, 100/2, 100/5). The residue purified was dissolved in isopropyl alcohol, followed by adding thereto a 4N-hydrochloric acid/dioxane solution, and the resulting mixture was concentrated to dryness to obtain N-ethyl-N-[cis-3-[(4-methoxy-1H-indazol-5-yl)oxy]cyclohexyl]amine monohydrochloride (40 mg, yield 35%).

IR (neat) cm$^{-1}$; 3600–2300, 1583, 1508, 1452, 1382, 1350, 1228, 1091, 1036.

EXAMPLE 702

Synthesis of N-[cis-3-[(4-methoxy-1H-indazol-5-yl)oxy]cyclohexyl]-N-propylamine (a) Synthesis of N-[cis-3-[(4-methoxy-1H-indazol-5-yl)oxy]cyclohexyl]propanamide Under nitrogen, the cis-3-[(4-methoxy-1H-indazol-5-yl)oxy]cyclohexanamine (100 mg, 0.383 mmol) obtained in Example 583 was suspended in N,N-dimethylformamide (2 ml), and propionic acid (31 µl, 0.421 mmol) and triethylamine (107 µl, 0.765 mmol) were added thereto, followed by adding thereto 1-ethyl-3-(3'-dimethylaminopropyl)carbodiimide mono-hydrochloride (81 mg, 0.421 mmol) and 1-hydroxybenzotriazole (57 mg, 0.421 mmol). The resulting mixture was stirred at room temperature for 24 hours. Water was added to the reaction mixture, followed by extraction with ethyl acetate (three times). The combined ethyl acetate layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluent: chloroform/methanol=100/0, 100/2) to obtain N-[cis-3-[(4-methoxy-1H-indazol-5-yl)oxy]cyclohexyl]propanamide (141 mg, yield 116%) as light-yellow tar.

(b) Synthesis of N-[cis-3-[(4-methoxy-1H-indazol-5-yl)oxy]cyclohexyl]-N-propylamine Under nitrogen, N-[cis-3-[(4-methoxy-1H-indazol-5-yl)oxy]cyclohexyl]propanamide (141 mg, 0.444 mmol) was dissolved in tetrahydrofuran (7 ml), followed by adding thereto lithium aluminum hydride (84 mg, 2.22 mmol), and the resulting mixture was stirred with heating under reflux for about 2 hours. Under ice-cooling, the reaction solution was diluted with tetrahydrofuran, and water (84 µl) was added thereto and stirred, and then a 4N-aqueous sodium hydroxide solution (84 µl) and water (250 µl) were added thereto and stirred. The solid was filtered off and the solvent was distilled off under reduced pressure. The resulting concentration residue was purified by a silica gel column chromatography (eluent: acetonitrile/aqueous ammonia=100/0, 100/2, 100/5) to obtain N-[cis-3-[(4-methoxy-1H-indazol-5-yl)oxy]cyclohexyl]-N-propylamine (57 mg, yield 42.3%) as colorless tar.

IR (neat) cm$^{-1}$; 2933, 2856, 2360, 1508, 1388, 1348, 1218, 1095, 1034, 920.

The following compounds of Examples 703 and 704 were synthesized by carrying out reaction according to the method described in Example 702, (a).

EXAMPLE 703

N-[cis-4-[(4-methoxy-1H-indazol-5-yl)oxy]cyclohexyl]acetamide

IR (neat) cm$^{-1}$; 3241, 2944, 2358, 1616, 1560, 1506, 1400, 1336, 1325, 1257, 1225, 1124, 1101, 1039, 941, 908.

EXAMPLE 704

N-[cis-4-[(4-methoxy-1H-indazol-5-yl)oxy]cyclohexyl]propanamide

IR (neat) cm$^{-1}$; 3300–270, 2360, 1637, 1506, 1340, 1252, 1227, 1120, 1095, 929.

The following compound of Example 705 was synthesized by carrying out reaction according to the method described in Example 702, (b), except for using the N-[cis-4-[(4-methoxy-1H-indazol-5-yl)oxy]cyclohexyl]acetamide obtained in Example 703, as a starting material.

EXAMPLE 705

N-ethyl-N-[4-[(4-methoxy-1H-indazol-5-yl)oxy]
cyclohexyl]amine

IR (neat) cm$^{-1}$; 2950–2300, 1495, 1350, 1290, 1225, 1209, 1021, 970, 923.

The following compound of Example 706 was synthesized by carrying out reaction according to the method described in Example 702, (b), except for using the N-[cis-4-[(4-methoxy-1H-indazol-5-yl)oxy]cyclohexyl]propanamide obtained in Example 704, as a starting material.

EXAMPLE 706

N-[4-[(4-methoxy-1H-indazol-5-yl)oxy]cyclohexyl]-
N-propylamine

IR (neat) cm$^{-1}$; 3153, 2931, 1506, 1348, 1221, 1091, 939.

The following compound of Example 707 was synthesized by carrying out reaction according to the method described in Example 700, except for using a free form of the cis-4-[(4-methoxy-1H-indazol-5-yl)oxy]cyclohexanamine monohydrochloride obtained in Example 585, as a starting material.

EXAMPLE 707

N-[4-[(4-methoxy-1H-indazol-5-yl)oxy]cyclohexyl]-
N,N-dimethylamine

IR (neat) cm$^{-1}$; 2940, 2651, 2360, 1498, 1387, 1351, 1232, 1033, 1018, 933.

The following compounds of Examples 708 to 712 were synthesized by carrying out reaction according to the method described in Example 391, except for using the cis-3-[(4-methyl-1H-indazol-5-yl)oxy]cyclohexanamine obtained in Example 411, as a starting material.

EXAMPLE 708

N-{cis-3-[(4-methyl-1H-indazol-5-yl)oxy]
cyclohexyl}butanamide

IR (neat) cm$^{-1}$; 3278, 3178, 2948, 2865, 1633, 1542, 1513, 1214, 1085, 954.

EXAMPLE 709

N-{cis-3-[(4-methyl-1H-indazol-5-yl)oxy]
cyclohexyl}pentanamide

Melting point: 190–193° C.

EXAMPLE 710

N-{cis-3-[(4-methyl-1H-indazol-5-yl)oxy]
cyclohexyl}cyclopentanecarboxamide

Melting point: 242–244° C. (decomp.)

EXAMPLE 711

N-{cis-3-[(4-methyl-1H-indazol-5-yl)oxy]
cyclohexyl}benzamide

IR (neat) cm$^{-1}$; 3297, 3172, 2940, 2865, 1627, 1540, 1083, 950, 694.

EXAMPLE 712

N~2~, N~2~-dimethyl-N~1~-{cis-3-[(4-methyl-1H-
indazol-5-yl)oxy]cyclohexyl}glycinamide IR (neat) cm$^{-1}$; 3286, 2950, 2815, 2765, 1646, 1525, 1513, 1216, 1085, 952.

The following compound of Example 713 was synthesized by carrying out reaction according to the method described in Example 399, except for using the N-{cis-3-[(4-methyl-1H-indazol-5-yl)oxy]cyclohexyl}butanamide obtained in Example 708, as a starting material.

EXAMPLE 713 cis-N-butyl-3-[(4-methyl-1H-indazol-5-yl)oxy]cy-
clohexanamine

IR (neat) cm$^{-1}$; 3270, 2937, 2858, 1517, 1209, 939, 792.

The following compound of Example 714 was synthesized by carrying out reaction according to the method described in Example 399, except for using the N-{cis-3-[(4-methyl-1H-indazol-5-yl)oxy]cyclohexyl}pentanamide obtained in Example 709, as a starting material.

EXAMPLE 714 cis-3-[(4-Methyl-1H-indazol-5-yl)oxy]-N-pentylcy-
clohexanamine

IR (neat) cm$^{-1}$; 3249, 2929, 2863, 2761, 1517, 1220, 1091, 937 cm$^{-1}$.

The following compound of Example 715 was synthesized by carrying out reaction according to the method described in Example 399, except for using the N-{cis-3-[(4-methyl-1H-indazol-5-yl)oxy]
cyclohexyl}cyclopentanecarboxamide obtained in Example 710, as a starting material.

EXAMPLE 715 cis-N-(cyclopentylmethyl)-3-[(4-methyl-1H-indazol-
5-yl)oxy]cyclohexanamine

Melting point: 140–142° C.

The following compound of Example 716 was synthesized by carrying out reaction according to the method described in Example 399, except for using the N-{cis-3-[(4-methyl-1H-indazol-5-yl)oxy]cyclohexyl}benzamide obtained in Example 711, as a starting material.

EXAMPLE 716 cis-N-benzyl-3-[(4-methyl-1H-indazol-5-yl)oxy]cyclohexanamine

IR (neat) cm$^{-1}$; 3255, 2929, 2854, 1521, 941, 746, 700.

EXAMPLE 717

Synthesis of cis-N-(2-chlorobenzyl)-3-[(4-methyl-1H-indazol-5-yl)oxy]cyclohexanamine To a solution of the cis-3-[(4-methyl-1H-indazol-5-yl)oxy]cyclohexanamine (100 mg, 0.407 mmol) obtained in Example 411 in methanol (5 ml) were added 2-chlorobenzaldehyde (46 μl, 0.407 mmol) and acetic acid (23 μl, 0.407 mmol), and the resulting mixture was stirred at room temperature for 30 minutes. Then, acetic acid (46 μl, 0.814 mmol) and sodium cyanoborohydride (28 mg, 0.447 mmol) were added thereto and stirred for 2 hours and a half. Subsequently, the reaction solution was poured into a saturated aqueous sodium hydrogencarbonate solution and extracted with ethyl acetate. The organic layer was washed with a saturated aqueous sodium chloride solution and dried over anhydrous sodium sulfate. The solvent was distilled off under reduced pressure and the resulting residue was purified by a silica gel column chromatography (eluent: chloroform/methanol=30/1) to obtain cis-N-(2-chlorobenzyl)-3-[(4-methyl-1H-indazol-5-yl)oxy]cyclohexanamine (100 mg, 66%).

$^1$H-NMR (DMSO-d$_6$) δ; 0.93–1.02 (1H, m), 1.15–1.31 (3H, m), 1.69–1.73 (1H, m), 1.86–1.89 (1H, m), 1.96–2.00 (1H, m), 2.26–2.30 (1H, m), 2.36 (3H, s), 2.40–2.48 (1H, m), 3.72–3.82 (2H, m), 3.97–4.03 (1H, m), 7.10 (1H, d, J=8.9 Hz), 7.20–7.30 (3H, m), 7.36 (1H, dd, J=7.8, 1.4 Hz), 7.52 (1H, dd, J=7.6, 1.7 Hz), 8.00 (1H, s), 12.86 (1H, s).

The following compounds of Examples 718 to 722 were synthesized by carrying out reaction according to the method described in Example 717, except for using the cis-3-[(4-methyl-1H-indazol-5-yl)oxy]cyclohexanamine obtained in Example 411, as a starting material.

EXAMPLE 718 cis-N-(3-chlorobenzyl)-3-[(4-methyl-1H-indazol-5-yl)oxy]cyclohexanamine

IR (neat) cm$^{-1}$; 3253, 2931, 2854, 1575, 1213, 941, 786.

EXAMPLE 719 cis-N-(4-chlorobenzyl)-3-[(4-methyl-1H-indazol-5-yl)oxy]cyclohexanamine $^1$H-NMR (DMSO-d$_6$) δ; 0.90–1.00 (1H, m), 1.12–1.31 (3H, m), 1.68–1.71 (1H, m), 1.84–1.87 (1H, m), 1.95–1.99 (1H, m), 2.13 (1H, brs), 2.23–2.26 (1H, m), 2.35–2.42 (4H, m), 3.64–3.72 (2H, m), 3.94–4.00 (1H, m), 7.08 (1H, d, J=8.9 Hz), 7.26 (1H, d, J=8.9 Hz), 7.32 (4H, s), 7.99 (1H, s), 12.86 (1H, s).

EXAMPLE 720 cis-N-(2-methoxybenzyl)-3-[(4-methyl-1H-indazol-5-yl)oxy]cyclohexanamine $^1$H-NMR (DMSO-d$_6$) δ; 0.92–1.03 (1H, m), 1.14–1.32 (3H, m), 1.69–1.72 (1H, m), 1.84–1.87 (1H, m), 1.96–1.99 (1H, m), 2.25–2.28 (1H, m), 2.36–2.45 (4H, m), 3.62–3.71 (2H, m), 3.72 (3H, s), 3.96–4.01 (1H, m), 6.84–6.91 (2H, m), 7.15–7.19 (1H, m), 7.09 (1H, d, J=8.9 Hz), 7.25–7.29 (2H, m), 8.00 (1H, s), 12.86 (1H, s).

EXAMPLE 721 cis-N-(3-methoxybenzyl)-3-[(4-methyl-1H-indazol-5-yl)oxy]cyclohexanamine

IR (neat) cm$^{-1}$; 3261, 2931, 2856, 1612, 1514, 1265, 941, 781.

EXAMPLE 722 cis-N-(4-methoxybenzyl)-3-[(4-methyl-1H-indazol-5-yl)oxy]cyclohexanamine

Melting point: 164–166° C.

EXAMPLE 723

Synthesis of 4-methyl-5-[(cis-3-piperidin-1-ylcyclohexyl)oxy]-1H-indazole

Under nitrogen, the cis-3-[(4-methyl-1H-indazol-5-yl)oxy]cyclohexanamine (100 mg, 0.403 mmol) obtained in Example 411 and 25%-glutaraldehyde (187 mg, 0.448 mmol) were dissolved in methanol (10 ml), and the resulting solution was stirred at room temperature for 40 minutes. Then, sodium cyanoborohydride (51 mg, 0.815 mmol) and acetic acid (0.2 ml) were added thereto, and the resulting mixture was stirred at room temperature for 16 hours. The reaction solution was diluted with chloroform and separated by the addition of a 1N-aqueous sodium hydroxide solution, and the desired compound was further extracted from the aqueous layer with chloroform. The combined chloroform layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: acetonitrile/aqueous ammonia=100/0, 100/2, 100/4) to obtain 4-methyl-5-[(cis-3-piperidin-1-ylcyclohexyl)oxy]-1H-indazole (91 mg, yield 71.2%) as a white amorphous substance.

IR (neat) cm$^{-1}$; 3167, 2933, 2358, 2343, 1508, 1221, 1155, 1095, 985, 941.

EXAMPLE 724

Synthesis of cis-3-[(4-methyl-1-tetrahydro-2H-pyran-2-yl-1H-indazol-5-yl)oxy]cyclohexanamine Under nitrogen, the cis-3-[(4-methyl-1H-indazol-5-yl)oxy]cyclohexanamine (500 mg, 2.04 mmol) obtained in Example 411 was suspended in dichloromethane (10 ml), and 3,4-dihydro-2H-pyran (205 μl, 2.24 mmol) and pyridinium p-toluenesulfonate (51 mg, 0.204 mmol) were added thereto, followed by adding thereto p-toluenesulfonic acid monohydrate (387 mg, 2.04 mmol). N-methyl-2-pyrrolidinone (10 ml) was added thereto to effect dissolution, and the resulting solution was stirred as follows: at room temperature for 17 hours; at 60° C. for 3.5 hours; and then at 80° C. for 10 hours. The reaction solution was cooled to room temperature and a 1N-aqueous sodium hydroxide solution was added thereto, followed by extraction with chloroform (twice). The combined chloroform layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluents: chloroform/methanol=20/1 and chloroform/methanol/aqueous ammonia=10/0.8/0.1) to obtain cis-3-[(4-methyl-1-tetrahydro-2H-pyran-2-yl-1H-indazol-5-yl)oxy]cyclohexanamine (602 mg, yield 89.6%) as colorless tar.

IR (neat) $cm^{-1}$; 2933, 1504, 1222, 1079, 1039, 980, 912.

EXAMPLE 725

Synthesis of 4-methyl-5-[(cis-3-pyrrolidin-1-ylcyclohexyl)oxy]-1-tetrahydro-2H-pyran-2-yl-1H-indazole Under nitrogen, the cis-3-[(4-methyl-1-tetrahydro-2H-pyran-2-yl-1H-indazol-5-yl)oxy]cyclohexanamine (100 mg, 0.304 mmol) obtained in Example 724 was dissolved in N,N-dimethylacetamide (3 ml), followed by adding thereto 1,4-dibromobutane (36 μl, 0.304 mmol) and potassium carbonate (105 mg, 0.759 mmol), and the resulting mixture was stirred at 80° C. for 1.5 hours. The reaction solution was cooled to room temperature and water was added thereto, followed by extraction with chloroform (twice). The combined chloroform layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluent: acetonitrile/aqueous ammonia=100/0, 100/2) to obtain 4-methyl-5-[(cis-3-pyrrolidin-1-ylcyclohexyl)oxy]-1-tetrahydro-2H-pyran-2-yl-1H-indazole (64 mg, yield 55.0%) as light-yellow tar.

$^1$H-NMR (CDCl$_3$) δ; 7.97 (s, 1H), 7.34 (d, 1H, J=9.0 Hz), 7.10 (d, 1H, J=9.0 Hz), 5.66 (dd, 1H, J=9.5, 2.6 Hz), 4.04–3.93 (m, 2H), 2.66 (m, 4H), 2.61–2.39 (m, 2H), 2.46 (s, 3H), 2.22–1.98 (m, 5H), 1.86–1.65 (m, 8H), 1.54 (m, 1H), 1.48–1.21 (m, 3H).

LC/MS; M+1=384.

EXAMPLE 726

Synthesis of 4-methyl-5-[(cis-3-pyrrolidin-1-ylcyclohexyl)oxy]-1H-indazole Monohydrochloride Under nitrogen, the 4-methyl-5-[(cis-3-pyrrolidin-1-ylcyclohexyl)oxy]-1-tetrahydro-2H-pyran-2-yl-1H-indazole (60 mg, 0.156 mmol) obtained in Example 725 was dissolved in isopropyl alcohol (2 ml), followed by adding thereto a 4N-hydrochloric acid/1,4-dioxane solution (2 ml), and the resulting mixture was stirred at room temperature for 3 hours. The solvent was distilled off under reduced pressure and the resulting concentration residue was purified by a silica gel column chromatography (eluent: acetonitrile/aqueous ammonia=100/0, 100/2, 100/4). Then, a 4N-hydrochloric acid/1,4-dioxane solution was added thereto and the solvent was distilled off under reduced pressure to obtain 4-methyl-5-[(cis-3-pyrrolidin-1-ylcyclohexyl)oxy]-1H-indazole monohydrochloride (55 mg, yield 100%) as a hygroscopic light-yellow solid.

IR (neat) $cm^{-1}$; 3600–2300, 1635, 1508, 1456, 1380, 1221, 1089, 997, 943.

EXAMPLE 727

Synthesis of 4-methyl-5-[(cis-3-morpholin-4-ylcyclohexyl)oxy]-1-tetrahydro-2H-pyran-2-yl-1H-indazole Under nitrogen, the cis-3-[(4-methyl-1-tetrahydro-2H-pyran-2-yl-1H-indazol-5-yl)oxy]cyclohexanamine (90 mg, 0.273 mmol) obtained in Example 724 was dissolved in N,N-dimethylacetamide (2 ml), followed by adding thereto bis(2-bromoethyl) ether (34 μl, 0.273 mmol) and potassium carbonate (94 mg, 0.683 mmol), and the resulting mixture was stirred at 80° C. for 6 hours. The reaction solution was cooled to room temperature and a 1N-aqueous sodium hydroxide solution was added thereto, followed by extraction with chloroform (three times). The combined chloroform layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluent: acetonitrile/aqueous ammonia=100/0, 100/1) to obtain 4-methyl-5-[(cis-3-morpholin-4-ylcyclohexyl)oxy]-1-tetrahydro-2H-pyran-2-yl-1H-indazole (83 mg, yield 76.0%) as light-yellow tar.

$^1$H-NMR (CDCl$_3$) δ; 7.97 (s, 1H), 7.34 (d, 1H, J=8.8 Hz), 7.10 (d, 1H, J=8.8 Hz), 5.66 (dd, 1H, J=9.4, 2.6 Hz), 4.04–3.93 (m, 2H), 3.71 (m, 5H), 2.55 (m, 5H), 2.46 (s, 3H), 2.35 (m, 2H), 2.17–2.01 (m, 3H), 1.89–1.65 (m, 5H), 1.49–1.30 (m, 2H), 1.21 (m, 2H).

LC/MS; M+1=400.

EXAMPLE 728

Synthesis of 4-methyl-5-[(cis-3-morpholin-4-ylcyclohexyl)oxy]-1H-indazole

Under nitrogen, the 4-methyl-5-[(cis-3-morpholin-4-ylcyclohexyl)oxy]-1-tetrahydro-2H-pyran-2-yl-1H-indazole (80 mg, 0.200 mmol) obtained in Example 727 was dissolved in isopropyl alcohol (3 ml), followed by adding thereto 4N-hydrochloric acid/1,4-dioxane (3 ml), and the resulting mixture was stirred at room temperature for 19 hours. The solvent was distilled off under reduced pressure and the resulting concentration residue was purified by a silica gel column chromatography (eluent: acetonitrile/aqueous ammonia=100/0, 100/1, 100/2) to obtain 4-methyl-5-[(cis-3-morpholin-4-ylcyclohexyl)oxy]-1H-indazole (55 mg, yield 87.1%) as a white amorphous substance.

IR (neat) $cm^{-1}$; 3197, 2935, 2858, 1508, 1223, 1113, 1031, 993, 941.

EXAMPLE 729

Synthesis of N-benzyl-N-methyl-N-[cis-3-[(4-methyl-1H-indazol-5-yl)oxy]cyclohexyl]amine Under nitrogen, the N-benzyl-N-[cis-3-[(4-methyl-1H-indazol-5-yl)oxy]cyclohexyl]amine (150 mg, 0.447 mmol) obtained in Example 716 and 36%-formaldehyde (56 mg, 0.671 mmol) were suspended in methanol (5 ml), followed by adding thereto acetic acid (0.2 ml), and the resulting mixture was stirred at room temperature for 30 minutes. Then, sodium cyanoborohydride (56 mg, 0.894 mmol) was added thereto and the resulting mixture was stirred at room temperature for 17 hours. The reaction mixture was diluted with chloroform and then separated by the addition of a 1N-aqueous sodium hydroxide solution, and the desired compound was further extracted from the aqueous layer with chloroform. The combined chloroform layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluent: acetonitrile/aqueous ammonia=100/0, 100/1) to obtain N-benzyl-N-methyl-N-[cis-3-[(4-methyl-1H-indazol-5-yl)oxy]cyclohexyl]amine (136 mg, yield 87.0%) as a white amorphous substance.

IR (neat) cm$^{-1}$; 3172, 2935, 2858, 1508, 1221, 1093, 1001, 941.

EXAMPLE 730

Synthesis of N-methyl-N-[cis-3-[(4-methyl-1H-indazol-5-yl)oxy]cyclohexyl]amine

Under nitrogen, the N-benzyl-N-methyl-N-[cis-3-[(4-methyl-1H-indazol-5-yl)oxy]cyclohexyl]amine (80 mg, 0.229 mmol) obtained in Example 729 was dissolved in ethanol (4 ml), followed by adding thereto ammonium formate (144 mg, 2.29 mmol) and then 10%-Pd/C (containing 50% water) (20 mg), and the resulting mixture was stirred with heating under reflux for 2 hours. The reaction mixture was cooled to room temperature and the Pd/C was filtered off. Then, the solvent was distilled off under reduced pressure and the resulting concentration residue was purified by a silica gel column chromatography (eluent: acetonitrile/aqueous ammonia=100/0, 100/1, 100/2, 100/4) to obtain N-methyl-N-[cis-3-[(4-methyl-1H-indazol-5-yl)oxy]cyclohexyl]amine (50 mg, yield 84.2%) as a white amorphous substance.

IR (neat) cm$^{-1}$; 3500–1495, 1373, 1218, 1203, 1093, 1025, 943.

EXAMPLE 731

Synthesis of N-[cis-3-[(4-methyl-1H-indazol-5-yl)oxy]cyclohexyl]-N-phenylamine monohydrochloride (a) Synthesis of N-[cis-3-[(4-methyl-1-tetrahydro-2H-pyran-2-yl-1H-indazol-5-yl)oxy]cyclohexyl]-N-phenylamine and N-[cis-3-[(4-methyl-1-tetrahydro-2H-pyran-2-yl-1H-indazol-5-yl)oxy]cyclohexyl]-N,N-diphenylamine Under nitrogen, tris(dibenzylideneacetone)(chloroform)dipalladium(0) (57 mg, 0.0554 mmol) and rac-2,2'-bis(diphenylphosphino)-1,1'-binaphthyl (69 mg, 0.111 mmol) were dissolved in toluene (2 ml), and the resulting solution was stirred at room temperature for 1 hour. A solution prepared by dissolving bromobenzene (117 µl, 1.108 mmol) and the cis-3-[(4-methyl-1-tetrahydro-2H-pyran-2-yl-1H-indazol-5-yl)oxy]cyclohexanamine (365 mg, 1.108 mmol) obtained in Example 724 in toluene (8 ml), and sodium tert-butoxide (213 mg, 2.22 mmol) were added thereto, and the resulting mixture was stirred at 80° C. for 4 hours. The reaction solution was cooled to room temperature and water was added thereto, followed by extraction with ethyl acetate. The ethyl acetate layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=5/1, 4/1) to obtain N-[cis-3-[(4-methyl-1-tetrahydro-2H-pyran-2-yl-1H-indazol-5-yl)oxy]cyclohexyl]-N-phenylamine (174 mg, yield 38.7%) as a yellow amorphous substance and N-[cis-3-[(4-methyl-1-tetrahydro-2H-pyran-2-yl-1H-indazol-5-yl)oxy]cyclohexyl]-N,N-diphenylamine (83 mg, yield 15.6%) as a white amorphous substance.

(b) Synthesis of N-[cis-3-[(4-methyl-1H-indazol-5-yl)oxy]cyclohexyl]-N-phenylamine monohydrochloride Under nitrogen, N-[cis-3-[(4-methyl-1-tetrahydro-2H-pyran-2-yl-1H-indazol-5-yl)oxy]cyclohexyl]-N-phenylamine (100 mg, 0.247 mmol) was dissolved in isopropyl alcohol (4 ml), followed by adding thereto a 4N-hydrochloric acid/1,4-dioxane solution (4 ml), and the resulting mixture was stirred at room temperature for 20 hours. The solvent was distilled off under reduced pressure and the resulting concentration residue was thoroughly dispersed and suspended in isopropyl alcohol. Thereafter, the solid was collected by filtration, washed with a small volume of isopropyl alcohol and then dried under reduced pressure to obtain N-[cis-3-[(4-methyl-1H-indazol-5-yl)oxy]cyclohexyl]-N-phenylamine (71 mg, yield 80.5%) as a whitely yellow solid.

IR (neat) cm$^{-1}$; 3100–2300, 1531, 1492, 1388, 1375, 1268, 1213, 1200, 978.

EXAMPLE 732

Synthesis of N-[cis-3-[(4-methyl-1H-indazol-5-yl)oxy]cyclohexyl]-N,N-diphenylamine Under nitrogen, the N-[cis-3-[(4-methyl-1-tetrahydro-2H-pyran-2-yl-1H-indazol-5-yl)oxy]cyclohexyl]-N,N-diphenylamine (82 mg, 0.172 mmol) obtained in Example 731, (a) was dissolved in isopropyl alcohol (4 ml), followed by adding thereto a 4N-hydrochloric acid/1,4-dioxane solution (4 ml), and the resulting mixture was stirred at room temperature for 20 hours. The solvent was distilled off under reduced pressure and a saturated aqueous sodium hydrogencarbonate solution was added to the residue, followed by extraction with ethyl acetate. The ethyl acetate layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=3/1) to obtain N-[cis-3-[(4-methyl-1H-indazol-5-yl)oxy]cyclohexyl]-N,N-diphenylamine (52 mg, yield 76.8%) as a whitely yellow amorphous substance.

IR (neat) cm$^{-1}$; 3172, 2937, 2358, 2343, 1587, 1492, 1294, 1223, 1093, 1010, 945.

EXAMPLE 733

Synthesis of N-methyl-N-[cis-3-[(4-methyl-1H-indazol-5-yl)oxy]cyclohexyl]-N-phenylamine (a) Synthesis of N-methyl-N-[cis-3-[(4-methyl-1-tetrahydro-2H-pyran-2-yl-1H-indazol-5-yl)oxy]cyclohexyl]-N-phenylamine Under nitrogen, the N-[cis-3-[(4-methyl-1-tetrahydro-2H-pyran-2-yl-1H-indazol-5-yl)oxy]cyclohexyl]-N-phenylamine (100 mg, 0.247 mmol) obtained in Example 731, (a) and 36%-formaldehyde (31 mg, 0.370 mmol) were dissolved in methanol (4 ml), followed by adding thereto acetic acid (0.2 ml), and the resulting mixture was stirred at room temperature for 1 hour. Then, sodium cyanoborohydride (31 mg, 0.493 mmol) was added thereto and the resulting mixture was stirred at room temperature for 1 hour. The reaction solution was diluted with chloroform and separated by the addition of a 1N-aqueous sodium hydroxide solution, and the aqueous layer was further extracted with chloroform. The combined chloroform layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=5/1) to obtain N-methyl-N-[cis-3-[(4-methyl-1-tetrahydro-2H-pyran-2-yl-1H-indazol-5-yl)oxy]cyclohexyl]-N-phenylamine (89 mg, yield 86.0%) as colorless tar.

(b) Synthesis of N-methyl-N-[cis-3-[(4-methyl-1H-indazol-5-yl)oxy]cyclohexyl]-N-phenylamine Under nitrogen, N-methyl-N-[cis-3-[(4-methyl-1-tetrahydro-2H-pyran-2-yl-1H-indazol-5-yl)oxy]cyclohexyl]-N-phenylamine (89 mg, 0.212 mmol) was dissolved in isopropyl alcohol (4 ml), followed by adding thereto a 4N-hydrochloric acid/1,4-dioxane solution (4 ml), and the resulting mixture was stirred at room temperature for 22 hours. The solvent was distilled off under reduced pressure, and the residue was neutralized with aqueous ammonia and concentrated to dryness under reduced pressure. The resulting concentration residue was purified by a silica gel column chromatography (eluent: n-hexane/ethyl acetate=3/1) to obtain N-methyl-N-[cis-3-[(4-methyl-1H-indazol-5-yl)oxy]cyclohexyl]-N-phenylamine (62 mg, yield 87.1%) as a white amorphous substance.

IR (neat) cm$^{-1}$; 3172, 2937, 2859, 1594, 1504, 1223, 1200, 1093, 943.

EXAMPLE 734

Synthesis of 4-methyl-5-(4-nitrophenoxy)-1H-indazole (a) Synthesis of 4-methyl-1-tetrahydro-2H-pyran-2-yl-1H-indazol-5-ol Under nitrogen, the 4-methyl-1H-indazol-5-ol (500 mg, 3.37 mmol) obtained in Example 402 was suspended in dichloromethane (20 ml), followed by adding thereto 3,4-dihydro-2H-pyran (239 μl, 3.71 mmol) and p-toluenesulfonic acid monohydrate (64 mg, 0.337 mmol). Tetrahydrofuran (25 ml) was added thereto to effect dissolution, and the reaction was carried out at room temperature for 2 days. The solvent was distilled off under reduced pressure and water was added to the residue, followed by extraction with ethyl acetate. The ethyl acetate layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=3/1) to obtain 4-methyl-1-tetrahydro-2H-pyran-2-yl-1H-indazol-5-ol (477 mg, yield 60.9%).

(b) Synthesis of 4-methyl-5-(4-nitrophenoxy)-1H-indazole

Under nitrogen, 4-methyl-1-tetrahydro-2H-pyran-2-yl-1H-indazol-5-ol (200 mg, 0.861 mmol) was dissolved in N,N-dimethylformamide (5 ml), followed by adding thereto 4-fluoronitrobenzene (100 μl, 0.947 mmol) and potassium carbonate (179 mg, 1.29 mmol), and the resulting mixture was stirred at 50° C. for 1 hour. After the reaction solution was cooled to room temperature, a 1N-aqueous hydrochloric acid solution (6 ml) and methanol (3 ml) were added thereto and the resulting mixture was stirred at room temperature for 2 hours. The mixture was adjusted to pH 9 with a saturated aqueous sodium hydrogencarbonate solution and extracted twice with ethyl acetate/toluene=3/1. The combined extract layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=3/1) to obtain 4-methyl-5-(4-nitrophenoxy)-1H-indazole (192 mg, yield 82.8%) as a yellow solid.

IR (neat) cm$^{-1}$; 3180, 2359, 2343, 1589, 1506, 1487, 1348, 1348, 1111.

EXAMPLE 735

Synthesis of 4-[(4-methyl-1H-indazol-5-yl)oxy]aniline monohydrochloride

Under nitrogen, the 4-methyl-5-(4-nitrophenoxy)-1H-indazole (139 mg, 0.516 mmol) obtained in Example 734 was dissolved in methanol (20 ml), followed by adding thereto 10%-Pd/C (containing 50% water) (20 mg), and the resulting mixture was stirred under a hydrogen atmosphere for 1.5 hours at ordinary temperature and atmospheric pressure. After the replacement on the nitrogen, the Pd/C was filtered off and then the solvent was distilled off under reduced pressure. A portion (50 mg, 0.186 mmol) of the resulting concentration residue was dissolved in isopropyl alcohol (3 ml), followed by adding thereto a 4N-hydrochloric acid/1,4-dioxane solution (2 ml), and the resulting mixture was stirred at room temperature for 1.5 hours. The solid precipitated was collected by filtration, washed with the filtrate and then a small volume of isopropyl alcohol, and dried under reduced pressure to obtain 4-[(4-methyl-1H-indazol-5-yl)oxy]aniline monohydrochloride (39 mg, yield 78%) as a white solid.

IR (neat) cm$^{-1}$; 3200–2200, 1504, 1241, 1201, 1103.

EXAMPLE 736

Synthesis of 4-methyl-5-(3-nitrophenoxy)-1H-indazole (a) Synthesis of 4-methyl-5-(3-nitrophenoxy)-1-tetrahydro-2H-pyran-2-yl-1H-indazole Under nitrogen, the 4-methyl-1-tetrahydro-2H-pyran-2-yl-1H-indazol-5-ol (130 mg, 0.560 mmol) obtained in Example 734, (a) and m-dinitrobenzene (103 mg, 0.615 mmol) were dissolved in N-methyl-2-pyrrolidinone (4 ml), followed by adding thereto potassium carbonate (193 mg, 1.39 mmol), and the resulting mixture was stirred at 120° C. for 2 hours and then at 150° C. for 2 hours. Water was added to the reaction solution, followed by extraction with toluene/ethyl acetate=1/3 (twice). The combined extract layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=5/1) to obtain 4-methyl-5-(3-nitrophenoxy)-1-tetrahydro-2H-pyran-2-yl-1H-indazole (136 mg, yield 69%) as a yellow solid.

(b) Synthesis of 4-methyl-5-(3-nitrophenoxy)-1H-indazole

Under nitrogen, 4-methyl-S-(3-nitrophenoxy)-1-tetrahydro-2H-pyran-2-yl-1H-indazole (136 mg, 0.385 mmol) was dissolved in methanol (5 ml), followed by adding thereto a 4N-hydrochloric acid/1,4-dioxane solution (5 ml), and the resulting mixture was stirred at room temperature for 2 hours. After the solvent was distilled off under reduced pressure, a saturated aqueous sodium hydrogencarbonate solution was added to the residue, followed by extraction with ethyl acetate. The ethyl acetate layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=3/1) to obtain 4-methyl-5-(3-nitrophenoxy)-1H-indazole (94 mg, yield 91%).

IR (neat) cm$^{-1}$; 3500–2700, 1531, 1513, 1473, 1346, 1276, 1232, 939.

EXAMPLE 737

Synthesis of 3-[(4-methyl-1H-indazol-5-yl)oxy]aniline monohydrochloride

Under nitrogen, the 4-methyl-5-(3-nitrophenoxy)-1H-indazole (60 mg, 0.223 mmol) obtained in Example 736 was dissolved in methanol (10 ml), followed by adding thereto 10%-Pd/C (containing water) (20 mg), and the resulting mixture was stirred at room temperature for 2 hours while adding hydrogen thereto. After the replacement on the nitrogen (theoretical amount of hydrogen: 15 ml), the Pd/C was filtered off by the use of Celite and then the solvent was distilled off under reduced pressure. The resulting concentration residue was dissolved in isopropyl alcohol (1 ml), followed by adding thereto a 4N-hydrochloric acid/1,4-dioxane solution (2 ml), and the resulting mixture was stirred at room temperature for 1 hour and then under ice-cooling for 1 hour. The white solid precipitated was collected by filtration, washed with diethyl ether, and dried under reduced pressure to obtain 3-[(4-methyl-1H-indazol-5-yl)oxy]aniline monohydrochloride (50 mg, yield 81%) as a white solid.

IR (neat) cm$^{-1}$; 3300–2200, 1531, 1485, 1387, 1270, 1254, 1203, 1141, 1082, 953.

EXAMPLE 738

Synthesis of 5-(2-chloro-4-nitrophenoxy)-4-methyl-1H-indazole

Under nitrogen, the 4-methyl-1-tetrahydro-2H-pyran-2-yl-1H-indazol-5-ol (150 mg, 0.646 mmol) obtained in Example 734, (a) and 3-chloro-4-fluoronitrobenzene (125 mg, 0.710 mmol) were dissolved in N,N-dimethylformamide (2 ml), followed by adding thereto potassium carbonate (134 mg, 0.969 mmol), and the resulting mixture was stirred at 70° C. for 1.5 hours. After the reaction solution was cooled to room temperature, water was added thereto, followed by extraction with toluene/ethyl acetate=1/3. The extract layer was washed with water and then a saturated aqueous sodium chloride solution, dried by the addition of anhydrous magnesium sulfate, and then filtered. The solvent was distilled off under reduced pressure and the resulting concentration residue was suspended in methanol (10 ml), followed by adding thereto a 4N-hydrochloric acid/1,4-dioxane solution (5 ml), and the resulting mixture was stirred at room temperature for 14 hours. (The residue was once dissolved and then gave a white suspension again). The resulting mixture was made basic by adding triethylamine slowly under ice-cooling, and the solvent was distilled off under reduced pressure. Then, water was added to the residue, followed by extraction with ethyl acetate. The extract layer was washed with a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=3/1, 2/1) to obtain 5-(2-chloro-4-nitrophenoxy)-4-methyl-1H-indazole (168 mg, yield 86%).

IR (neat) cm$^{-1}$; 3313, 1583, 1516, 1471, 1338, 1265, 1209, 1120, 1080, 1055, 906, 895.

EXAMPLE 739

Synthesis of 3-chloro-4-[(4-methyl-1H-indazol-5-yl)oxy]aniline monohydrochloride Under nitrogen, the 5-(2-chloro-4-nitrophenoxy)-4-methyl-1H-indazole (120 mg, 0.395 mmol) obtained in Example 738 was dissolved in ethanol (6 ml), followed by adding thereto tin(II) chloride dihydrate (446 mg, 1.98 mmol), and the resulting mixture was stirred at 80° C. for 1 hour. The reaction solution was cooled to room temperature and then poured into water, and the resulting mixture was adjusted to pH>8 with a 1N aqueous sodium hydroxide solution and extracted twice with ethyl acetate/tetrahydrofuran=5/1. The combined extract layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=2/1, 1/1, 1/2) to obtain a yellow solid. The solid obtained was dissolved in 1,4-dioxane (2 ml), followed by adding thereto a 4N-hydrochloric acid/1,4-dioxane solution (2 ml), and the resulting mixture was stirred at room temperature. Thereafter, diethyl ether (about 15 ml) was added thereto and stirred, and the yellow solid precipitated was collected by filtration, washed with diethyl ether and then dried under reduced pressure to obtain 3-chloro-4-[(4-methyl-1H-indazol-5-yl)oxy]aniline monohydrochloride (45 mg, yield 42%).

IR (neat) cm$^{-1}$; 3300–2150, 1489, 1389, 1255, 1205, 1061, 806.

EXAMPLE 740

Synthesis of 3-[(4-methyl-1H-indazol-5-yl)oxy]benzonitrile Monohydrochloride (a) Synthesis of 3-[(4-methyl-1-tetrahydro-2H-pyran-2-yl-1H-indazol-5-yl)oxy]benzonitrile Under nitrogen, the 4-methyl-1-tetrahydro-2H-pyran-2-yl-1H-indazol-5-ol (300 mg, 1.29 mmol) obtained in Example 734, (a) and 3-nitrobenzonitrile (210 mg, 1.42 mmol) were dissolved in N-methyl-2-pyrrolidinone (6 ml), followed by adding thereto potassium carbonate (446 mg, 3.23 mmol), and the resulting mixture was stirred at 150° C. for 16 hours. After the reaction solution was cooled to room temperature, water was added thereto and the resulting mixture was adjusted to pH 6 with a 1N-aqueous hydrochloric acid solution and extracted with toluene/ethyl acetate=1/3. The extract layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=6/1, 3/1, 2/1) to obtain 3-[(4-methyl-1-tetrahydro-2H-pyran-2-yl-1H-indazol-5-yl)oxy]benzonitrile (299 mg, yield 69%).

(b) Synthesis of 3-[(4-methyl-1H-indazol-5-yl)oxy]benzonitrile Monohydrochloride Under nitrogen, 3-[(4-methyl-1-tetrahydro-2H-pyran-2-yl-1H-indazol-5-yl)oxy]benzonitrile (299 mg, 0.897 mmol) was dissolved in a mixture of isopropyl alcohol (6 ml) and 1,4-dioxane (6 ml), followed by adding thereto a 4N-hydrochloric acid/1,4-dioxane solution (6 ml), and the resulting mixture was stirred at room temperature for 23 hours. After diethyl ether (30 ml) was added thereto and stirred, the precipitate was collected by filtration, washed with diethyl ether and then dried under reduced pressure to obtain 3-[(4-methyl-1H-indazol-5-yl)oxy]benzonitrile hydrochloride (176 mg, yield 69%).

IR (neat) cm$^{-1}$; 3100–2050, 1581, 1529, 1479, 1429, 1388, 1246, 1157, 939.

EXAMPLE 741

Synthesis of 4-[(4-methyl-1H-indazol-5-yl)oxy]benzonitrile Monohydrochloride (a) Synthesis of 4-[(4-methyl-1-tetrahydro-2H-pyran-2-yl-1H-indazol-5-yl)oxy]benzonitrile Under nitrogen, the 4-methyl-1-tetrahydro-2H-pyran-2-yl-1H-indazol-5-ol (300 mg, 1.29 mmol) obtained in Example 734, (a) and 4-fluorobenzonitrile (172 mg, 1.42 mmol) were dissolved in N,N-dimethylformamide (6 ml), followed by adding thereto potassium carbonate (268 mg, 1.94 mmol), and the resulting mixture was stirred at 50° C. for 2 hours and then at 70° C. for 22 hours. After the reaction solution was cooled to room temperature, water was added thereto, followed by extraction with toluene/ethyl acetate=1/2 (twice). The combined extract layer was washed with water and then a saturated aqueous sodium chloride solution, dried by the addition of anhydrous magnesium sulfate, and then filtered. The solvent was distilled off under reduced pressure and the resulting concentration residue was purified by a silica gel column chromatography (eluent: n-hexane/ethyl acetate=5/1, 4/1) to obtain 4-[(4-methyl-1-tetrahydro-2H-pyran-2-yl-1H-indazol-5-yl)oxy]benzonitrile (342 mg, yield 79%).

(b) Synthesis of 4-[(4-methyl-1H-indazol-5-yl)oxy]benzonitrile monohydrochloride Under nitrogen, 4-[(4-methyl-1-tetrahydro-2H-pyran-2-yl-1H-indazol-5-yl)oxy]benzonitrile (338 mg, 1.01 mmol) was dissolved in 1,4-dioxane (6 ml), followed by adding thereto a 4N-hydrochloric acid/1,4-dioxane solution (6 ml), and the resulting mixture was stirred at room temperature for 23 hours. After diethyl ether (30 ml) was added thereto and stirred, the precipitate was collected by filtration, washed with diethyl ether and then dried under reduced pressure to obtain 4-[(4-methyl-1H-indazol-5-yl)oxy]benzonitrile monohydrochloride (239 mg, yield 83%).

IR (neat) cm$^{-1}$; 3100–2040, 1604, 1527, 1500, 1388, 1261, 1238, 1167, 1155.

EXAMPLE 742

Synthesis of 1-[4-[(4-methyl-1H-indazol-5-yl)oxy]phenyl]methylamine monohydrochloride Under nitrogen, the 4-[(4-methyl-1H-indazol-5-yl)oxy]benzonitrile monohydrochloride (70 mg, 0.245 mmol) obtained in Example 741 was suspended in tetrahydrofuran (2 ml), and lithium aluminum hydride (46 mg, 1.22 mmol) was added thereto under ice-cooling. The resulting mixture was cooled to room temperature and stirred for 4 hours. Under ice-cooling, water (46 μl) was slowly added thereto, followed by adding thereto a 4N-aqueous sodium hydroxide solution (46 μl), water (140 μl) and tetrahydrofuran (5 ml), and the resulting mixture was stirred at room temperature. The precipitate was filtered off, and the residue was washed with tetrahydrofuran and then distilled under reduced pressure to remove the solvent. The resulting concentration residue was purified by a silica gel column chromatography (eluent: acetonitrile/aqueous ammonia=100/0, 50/1, 25/1) to obtain a white solid (41 mg). The solid obtained was dissolved in 1,4-dioxane (2 ml), followed by adding thereto a 4N-hydrochloric acid/1,4-dioxane solution (2 ml), and the resulting mixture was stirred at room temperature for 1 hour. Then, diethyl ether (about 15 ml) was added thereto and stirred, and the resulting white solid was collected by filtration, washed with diethyl ether and then dried under reduced pressure to obtain 1-[4-[(4-methyl-1H-indazol-5-yl)oxy]phenyl]methylamine monohydrochloride (46 mg, yield 65%).

IR (neat) cm$^{-1}$; 3060–2060, 1508, 1230, 835.

EXAMPLE 743

Synthesis of 1-[3-[(4-methyl-1H-indazol-5-yl)oxy]phenyl]methylamine monohydrochloride Under nitrogen, the 3-[(4-methyl-1H-indazol-5-yl)oxy]benzonitrile monohydrochloride (60 mg, 0.210 mmol) obtained in Example 740 was suspended in tetrahydrofuran (2 ml), and lithium aluminum hydride (40 mg, 1.05 mmol) was added thereto under ice-cooling. The resulting mixture was cooled to room temperature and stirred for 4 hours. Under ice-cooling, water (40 µl) was slowly added thereto, followed by adding thereto a 4N-aqueous sodium hydroxide solution (40 µl), water (120 µl) and tetrahydrofuran (5 ml), and the resulting mixture was stirred at room temperature. The precipitate was filtered off, and the residue was washed with tetrahydrofuran and then distilled under reduced pressure to remove the solvent. The resulting concentration residue was purified by a silica gel column chromatography (eluent: acetonitrile/aqueous ammonia=100/0, 50/1, 25/1) to obtain a white solid (31 mg). The solid obtained was dissolved in 1,4-dioxane (2 ml), followed by adding thereto a 4N-hydrochloric acid/1,4-dioxane solution (2 ml), and the resulting mixture was stirred at room temperature for 1 hour. Then, diethyl ether (about 15 ml) was added thereto and stirred, and the resulting white solid was collected by filtration, washed with diethyl ether and then dried under reduced pressure to obtain 1-[3-[(4-methyl-1H-indazol-5-yl)oxy]phenyl]methylamine monohydrochloride (39 mg, yield 64%).

IR (neat) cm$^{-1}$; 3200–2100, 1589, 1527, 1489, 1446, 1385, 1251, 1207, 1161, 1101, 937.

EXAMPLE 744

Synthesis of trans-4-((4-ethyl-1H-indazol-5-yl)oxy)cyclohexanamine (a) Synthesis of trans-2-{4-[(4-ethyl-1H-indazol-5-yl)oxy]cyclohexyl}-1H-isoindole-1,3(2H)-dione A cyanomethylenetributylphosphorane/toluene solution (1.2 g, 4.53 mmol) was added to a solution prepared by dissolving the 4-ethyl-1H-indazol-5-ol (359 mg, 1.46 mmol) obtained in Example 682 and the cis-2-(4-hydroxycyclohexyl)-1H-isoinzole-1,3(2H)-dione (854 mg, 3.48 mmol) obtained in Example 323, (c) in toluene (15 ml), and the resulting mixture was stirred at 120° C. for 3 hours. The reaction solution was concentrated, and to the resulting residue were added chloroform and a 1N-aqueous sodium hydroxide solution to effect partition, followed by extraction with chloroform (twice). The extract solution was dried over anhydrous magnesium sulfate. The residue was purified by a silica gel chromatography (hexane/ethyl acetate=2/1) to obtain trans-2-{4-[(4-ethyl-1H-indazol-5-yl)oxy]cyclohexyl}-1H-isoindole-1,3(2H)-dione (681.1 mg, 50%).

(b) 4-((4-Ethyl-1H-indazol-5-yl)oxy)cyclohexanamine hydrochloride was obtained by carrying out reaction according to the method described in Example 14, except for using trans-2-{4-[(4-ethyl-1H-indazol-5-yl)oxy]cyclohexyl}-1H-isoindole-1,3(2H)-dione.

IR (neat) cm$^{-1}$; 800, 1072, 1122, 1257, 1508.

EXAMPLE 745

Synthesis of cis-3-((4-ethyl-1H-indazol-5-yl)oxy)cyclohexanamine cis-3-((4-Ethyl-1H-indazol-5-yl)oxy)cyclohexanamine was obtained by carrying out reaction according to the method described in Example 744, except for using the trans-2-(3-hydroxycyclohexyl)-1H-isoindole-1,3(2H)-dione obtained in Example 385, (b).

LC/MS: M+1=288.0

EXAMPLE 746

Synthesis of cis-4-((4-ethyl-1H-indazol-5-yl)oxy)cyclohexanamine cis-4-((4-Ethyl-1H-indazol-5-yl)oxy)cyclohexanamine was obtained by carrying out reaction according to the method described in Example 744, except for using the trans-2-(4-hydroxycyclohexyl)-1H-isoindole-1,3(2H)-dione obtained in Example 323, (a).

LC/MS: M+1=260.3

EXAMPLE 747

Synthesis of trans-3-((4-ethyl-1H-indazol-5-yl)oxy)cyclohexanamine trans-3-((4-Ethyl-1H-indazol-5-yl)oxy)cyclo-hexanamine was obtained by carrying out reaction according to the method described in Example 744, except for using the cis-2-(3-hydroxycyclohexyl)-1H-isoindole-1,3(2H)-dione obtained in Example 326, (d).

IR (neat) cm$^{-1}$; 906, 945, 1107, 1223, 1506.

The following compounds of Examples 748 and 749 were synthesized by carrying out reaction according to the method described in Example 389, except for using the trans-3-[(4-methyl-1H-indazol-5-yl)oxy]cyclohexanamine obtained in Example 409, as a starting material.

EXAMPLE 748 trans-N,N-dimethyl-3-[(4-methyl-1H-indazol-5-yl)oxy]cyclohexanamine monohydrochloride IR (neat) cm$^{-1}$; 2643, 1220, 1151, 964.

EXAMPLE 749 trans-N,N-dipropyl-3-[(4-methyl-1H-indazol-5-yl)oxy]cyclohexanamine monohydrochloride

LC/MS: M+1=330

The following compound of Example 750 was synthesized by carrying out reaction according to the method described in Example 140, except for using the trans-3-[(4- methyl-1H-indazol-5-yl)oxy]cyclohexanamine obtained in Example 409, as a starting material.

EXAMPLE 750 trans-N-cyclopentyl-3-[(4-methyl-1H-indazol-5-yl)oxy]cyclohexanamine

Melting point: 110–112° C.

EXAMPLE 751

Synthesis of trans-N-ethyl-3-[(4-methyl-1H-indazol-5-yl)oxy]cyclohexanamine (a) Synthesis of N-{trans-3-[(4-methyl-1H-indazol-5-yl)oxy]cyclohexyl}acetamide The title compound was synthesized by carrying out reaction according to the method described in Example 391, except for using the trans-3-[(4-methyl-1H-indazol-5-yl)oxy]cyclohexanamine obtained in Example 409, as a starting material.

(b) Synthesis of trans-N-ethyl-3-[(4-methyl-1H-indazol-5-yl)oxy]cyclohexanamine

The title compound was synthesized by carrying out reaction according to the method described in Example 399, except for using N-{trans-3-[(4-methyl-1H-indazol-5-yl)oxy]cyclohexyl}acetamide as a starting material.
Melting point: 95–97° C.

EXAMPLE 752

Synthesis of trans-N-propyl-3-[(4-methyl-1H-indazol-5-yl)oxy]cyclohexanamine monohydrochloride (a) Synthesis of N-{trans-3-[(4-methyl-1H-indazol-5-yl)oxy]cyclohexyl}propanamide The title compound was synthesized by carrying out reaction according to the method described in Example 391, except for using the trans-3-[(4-methyl-1H-indazol-5-yl)oxy]cyclohexanamine obtained in Example 409, as a starting material.

(b) Synthesis of trans-N-propyl-3-[(4-methyl-1H-indazol-5-yl)oxy]cyclohexanamine monohydrochloride The title compound was synthesized by carrying out reaction according to the method described in Example 392, except for using N-{trans-3-[(4-methyl-1H-indazol-5-yl)oxy]cyclohexyl}propanamide as a starting material.
IR (neat) cm$^{-1}$; 2782, 1222, 1091, 970, 941.

EXAMPLE 753

Synthesis of N,N-dimethyl-N-cis-3-[(4-methyl-1H-indazol-5-yl)oxy]cyclohexylamine Acetic acid (0.060 ml) was added to a methanolic solution (1.0 ml) of the cis-3-[(4-methyl-1H-indazol-5-yl)oxy]cyclohexylamine (46 mg, 0.20 mmol) obtained in Example 411, followed by adding thereto paraformaldehyde (30 mg, 1.0 mmol), and the resulting mixture was stirred at room temperature for 2 hours. Then, a methanolic solution (0.5 ml) of sodium cyanoborohydride (63 mg, 1.0 mmol) was added thereto and the resulting mixture was stirred overnight at room temperature. A 1N-aqueous sodium hydroxide solution (0.8 ml) was added to the reaction solution and the solvent was distilled off. The residue oil was purified by elution by a silica gel column chromatography (hexane/ethyl acetate/triethylamine=5:15:1) to obtain N,N-dimethyl-N-cis-3-[(4-methyl-1H-indazol-5-yl)oxy]cyclohexylamine (29.8 mg, 54%).
MS: m/z=274 (M+1)

The following compounds of Examples 754 to 757 were synthesized by carrying out reaction according to the method described in Example 753.

EXAMPLE 754

N,N-dipropyl-N-cis-3-[(4-methyl-1H-indazol-5-yl)oxy]cyclohexylamine

MS: m/z=330 (M+1)

EXAMPLE 755

N,N-dibutyl-N-cis-3-[(4-methyl-1H-indazol-5-yl)oxy]cyclohexylamine

MS: m/z=358 (M+1)

EXAMPLE 756

N-isopropyl-N-cis-3-[(4-methyl-1H-indazol-5-yl)oxy]cyclohexylamine

Melting point: 152–156° C.

EXAMPLE 757

N-cyclopentyl-N-cis-3-[(4-methyl-1H-indazol-5-yl)oxy]cyclohexylamine

Melting point: 166–168° C.

EXAMPLE 758

Synthesis of N-ethyl-N-cis-3-[(4-methyl-1H-indazol-5-yl)oxy]cyclohexylamine (a) Synthesis of N-cis-3-[(4-methyl-1H-indazol-5-yl)oxy]cyclohexylacetamide Acetic acid (0.036 g, 0.60 mmol), triethylamine (0.21 ml, 1.5 mmol), 1-hydroxybenztriazole (0.081 g, 0.60 mmol) and 1-ethyl-3-(3'-dimethylaminopropyl)carbodiimide monohydrochloride (0.115 g, 0.60 mmol) were added to a solution of the cis-3-[(4-methyl-1H-indazol-5-yl)oxy]cyclohexylamine (147 mg, 0.60 mmol) obtained in Example 411 in N,N-dimethylformamide (2 ml) and stirred overnight. A 2N-aqueous lithium hydroxide solution (2 ml) was added thereto, and the resulting mixture was stirred for some time, added to water, and then extracted three times with toluene/ethyl acetate=1/1. The organic layer was washed with water and a saturated aqueous sodium chloride solution and dried over anhydrous sodium sulfate. The solvent was distilled off under reduced pressure, and the solid precipitated was suspended in a hexane/ethyl acetate mixed solvent and stirred to be washed. The solid was collected by filtration and dried under reduced pressure to obtain N-cis-3-[(4-methyl-1H-indazol-5-yl)oxy]cyclohexylacetamide (163 mg, 95%).

$^1$H-NMR (DMSO-d$_6$) δ; 1.20–1.30 (3H, m), 1.65–1.97 (5H, m), 1.92–2.14 (2H, m), 2.29 (1H, s), 2.37 (3H, s), 3.46–3.63 (1H, m), 3.99–4.10 (1H, m), 7.07–7.18 (1H, m), 7.18–7.32 (1H, m), 8.00 (1H, s), 12.87 (1H, s).

(b) Synthesis of N-ethyl-N-cis-3-[(4-methyl-1H-indazol-5-yl)oxy]cyclohexylamine

N-cis-3-[(4-methyl-1H-indazol-5-yl)oxy]cyclohexylacetamide (0.153 g, 0.53 mmol) was added to a suspension of lithium aluminum hydride (0.057 g, 1.5 mmol) in tetrahydrofuran (10 ml), and the resulting mixture was stirred with heating under reflux for 2 hours. The resulting solution was cooled on an ice bath, and water (0.02 ml), a 2N-aqueous sodium hydroxide solution (0.04 ml) and water (0.04 ml) were added dropwise thereto in that order. Then, the insoluble material was removed by filtration using Celite. The filtrate was purified by elution by a silica gel column chromatography (hexane/ethyl acetate/triethylamine=5:15:1) to obtain N-ethyl-N-cis-3-[(4-methyl-1H-indazol-5-yl)oxy]cyclo-hexylamine (91.5 mg, 63%).

MS: m/z=274 (M+1)

The following compound of Example 759 was synthesized by carrying out reaction according to the method described in Example 758.

EXAMPLE 759

EXAMPLE 9

N-propyl-N-cis-3-[(4-methyl-1H-indazol-5-yl)oxy]cyclohexylamine

MS: m/z=288 (M+1)

EXAMPLE 760

Synthesis of N,N-diethyl-N-cis-3-[(4-methyl-1H-indazol-5-yl)oxy]cyclohexylamine (a) Synthesis of N-ethyl-N-cis-3-[(4-methyl-1H-indazol-5-yl)oxy]cyclohexylacetamide Acetic acid (0.013 g, 0.22 mmol), triethylamine (0.070 ml, 0.50 mmol), 1-hydroxybenztriazole (0.029 g, 0.22 mmol) and 1-ethyl-3-(3'-dimethylaminopropyl)carbodiimide monohydrochloride (0.042 g, 0.22 mmol) were added to a solution of the N-ethyl-N-cis-3-[(4-methyl-1H-indazol-5-yl)oxy]cyclohexylamine (59.4 mg, 0.217 mmol) obtained in Example 758 in N,N-dimethylformamide (1 ml) and stirred overnight. A 2N-aqueous lithium hydroxide solution (2 ml) was added thereto, and the resulting mixture was stirred for some time, added to water, and then extracted three times with toluene/ethyl acetate=1/1. The organic layer was washed with water and a saturated aqueous sodium chloride solution and dried over anhydrous sodium sulfate. The solvent was distilled off under reduced pressure, and the solid precipitated was suspended in a hexane/ethyl acetate mixed solvent and stirred to be washed. The solid was collected by filtration and dried under reduced pressure to obtain N-ethyl-N-cis-3-[(4-methyl-1H-indazol-5-yl)oxy]cyclohexylacetamide (63.4 mg, 93%).

$^1$H-NMR (DMSO-d$_6$) δ; 0.92–1.15 (3H, m), 1.15–1.52 (4H, m), 1.52–1.84 (4H, m), 1.84–2.20 (4H, m), 2.29 (1H, s), 2.38 (3H, s), 3.16–3.29 (1H, m), 3.96–4.14 (1H, m), 7.07–7.18 (1H, m), 7.18–7.32 (1H, m), 8.00 (1H, s), 12.87 (1H, s).

(b) Synthesis of N,N-diethyl-N-cis-3-[(4-methyl-1H-indazol-5-yl)oxy]cyclohexylamine N-ethyl-N-cis-3-[(4-methyl-1H-indazol-5-yl)oxy]cyclohexylacetamide (0.057 g, 0.18 mmol) was added to a suspension of lithium aluminum hydride (0.020 g, 0.053 mmol) in tetrahydrofuran (5 ml), and the resulting mixture was stirred with heating under reflux for 2 hours. The resulting solution was cooled on an ice bath, and water (0.04 ml), a 2N-aqueous sodium hydroxide solution (0.08 ml) and water (0.12 ml) were added dropwise thereto in that order. Then, the insoluble material was removed by filtration using Celite. The filtrate was purified by elution by a silica gel column chromatography (hexane/ethyl acetate/triethylamine=5:15:1) to obtain N,N-diethyl-N-cis-3-[(4-methyl-1H-indazol-5-yl)oxy]cyclohexylamine (29.2 mg, 53%).

MS: m/z=302 (M+1)

The following compound of Example 761 was synthesized by carrying out reaction according to the method described in Example 760, except for using the cis-N-ethyl-4-[(4-methyl-1H-indazol-5-yl)oxy]cyclohexanamine obtained in Example 466, as a starting material.

EXAMPLE 761

N,N-diethyl-N-cis-4-[(4-methyl-1H-indazol-5-yl)oxy]cyclohexylamine

MS: m/z=302 (M+1)

EXAMPLE 762

Synthesis of trans-3-[(4-trifluoromethyl-1H-indazol-5-yl)oxy]cyclohexylamine (a) Synthesis of 2-{trans-3-[(4-trifluoromethyl-1H-indazol-5-yl)oxy]cyclohexyl}-1H-isoindole-1,3(2H)-dione Diisopropyl dicarboxylate (0.364 g, 1.80 mmol) was added dropwise to a mixture of the 5-hydroxy-4-trifluoromethyl-1H-indazole (0.303 g, 1.50 mmol) obtained in Example 474, the cis-2-(3-hydroxycyclohexyl)-1H-isoindole-1,3(2H)-dione (0.368 g, 1.50 mmol) obtained in Example 326, (d), triphenylphosphine (433 mg, 1.65 mmol) and tetrahydrofuran (10 ml) under ice-cooling. After 30 minutes, the mixture thus obtained was warmed up to room temperature and stirred overnight. The reaction mixture was concentrated and then the residue oil was purified by elution by a silica gel column chromatography (hexane/ethyl acetate=3:1 to 2:1) to obtain 0.324 g of a crude product 2-{trans-3-[(4-trifluoromethyl-1H-indazol-5-yl)oxy]cyclohexyl}-1H-isoindole-1,3(2H)-dione (a mixture with cis-2-(3-hydroxycyclohexyl)-1H-isoindole-1,3(2H)-dione).

(b) Synthesis of trans-3-[(4-trifluoromethyl-1H-indazol-5-yl)oxy]cyclohexylamine A mixture of the crude product 2-{trans-3-[(4-trifluoromethyl-1H-indazol-5-yl)oxy]cyclohexyl}-1H-isoindole-1,3 (2H)-dione (0.324 g) and a 30% methylamine/methanol solution (15 ml) was stirred at 90° C. for 3 hours. The solvent was distilled off and the residue solid was purified by elution by a silica gel column chromatography (chloroform/methanol=20:1→chloroform/methanol/triethylamine=10:1:1) to obtain trans-3-[(4-trifluoromethyl-1H-indazol-5-yl)oxy]cyclohexylamine (70.4 mg, 16%, two steps).

NMR (DMSO-$d_6$) δ; 0.80–1.30 (2H m), 1.35–1.97 (4H, m), 1.90–2.11 (1H, m), 2.67–2.80 (1H, m), 2.95–3.10 (1H, m), 3.29–3.41 (1H, m), 4.97 (1H, s), 7.40 (2H, d, J=9.2 Hz), 7.81 (1H, d, J=9.0 Hz), 8.01 (1H, s).

EXAMPLE 763

Synthesis of N-cis-3-[(4-trifluoromethyl-1H-indazol-5-yl)oxy]cyclohexylacetamide Acetic acid (0.014 g, 0.22 mmol), triethylamine (0.075 ml, 0.54 mmol), 1-hydroxybenztriazole (0.030 g, 0.22 mmol) and 1-ethyl-3-(3'-dimethylaminopropyl)carbodiimide monohydrochloride (0.043 g, 0.22 mmol) were added to a solution of the cis-3-[(4-trifluoromethyl-1H-indazol-5-yl)oxy]cyclohexylamine (0.066 g, 0.22 mmol) obtained in Example 587 in N,N-dimethylformamide (1 ml) and stirred overnight. A 2N-aqueous lithium hydroxide solution (0.4 ml) was added thereto, and the resulting mixture was stirred for some time, added to water, and then extracted three times with toluene/ethyl acetate=1/1. The organic layer was washed with water and a saturated aqueous sodium chloride solution and dried over anhydrous sodium sulfate. The solvent was distilled off under reduced pressure, and the solid precipitated was suspended in a hexane/ethyl acetate mixed solvent and stirred to be washed. The solid was collected by filtration and dried under reduced pressure to obtain N-cis-3-[(4-trifluoromethyl-1H-indazol-5-yl)oxy]cyclohexylacetamide (0.067 g, 89%).

$^1$H-NMR (DMSO-$d_6$) δ; 0.93–1.40 (4H, m), 1.65–1.85 (5H, m), 1.94–2.20 (2H, m), 3.52–3.73 (1H, m), 4.45–4.62 (1H, m), 7.47 (1H, d, J=9.1 Hz), 7.80 (1H, d, J=9.4 Hz), 8.00 (1H, s), 13.42 (1H, s).

The following compound of Example 764 was synthesized by carrying out reaction according to the method described in Example 763.

EXAMPLE 764

N-cis-3-[(4-trifluoromethyl-1H-indazol-5-yl)oxy]cyclohexylpropanamide $^1$H-NMR (DMSO-$d_6$) δ; 0.94 (1H, d, J=7.6 Hz), 1.02–1.38 (4H, m), 1.67–1.80 (2H, m), 1.95–2.15 (4H, m), 3.57–3.75 (1H, m), 4.45–4.60 (1H m), 7.47 (1H, d, J=9.1 Hz), 7.80 (1H, d, J=9.4 Hz), 8.00 (1H, s), 13.42 (1H, s).

EXAMPLE 765

Synthesis of N-ethyl-N-cis-3-[(4-trifluoromethyl-1H-indazol-5-yl)oxy]cyclohexylamine The N-cis-3-[(4-trifluoromethyl-1H-indazol-5-yl)oxy]cyclohexylacetamide (0.062 g, 0.18 mmol) obtained in Example 16 was added to a suspension of lithium aluminum hydride (0.020 g, 0.54 mmol) in tetrahydrofuran (3 ml), and the resulting mixture was stirred with heating under reflux for 7 hours. The resulting solution was cooled on an ice bath, and water (0.02 ml), a 2N-aqueous sodium hydroxide solution (0.04 ml) and water (0.08 ml) were added dropwise thereto in that order. Then, the insoluble material was removed by filtration using Celite. The filtrate was purified by elution by a silica gel column chromatography (ethyl acetate/triethylamine=20:1) to obtain N-ethyl-N-cis-3-[(4-trifluoromethyl-1H-indazol-5-yl)oxy]cyclohexylamine (27.8 mg, 47%).

Melting point: 158–163° C.

The following compound of Example 766 was synthesized by carrying out reaction according to the method described in Example 765, except for using the N-cis-3-[(4-trifluoromethyl-1H-indazol-5-yl)oxy]cyclohexylpropanamide obtained in Example 764, as a starting material.

EXAMPLE 766

N-propyl-N-cis-3-[(4-trifluoromethyl-1H-indazol-5-yl)oxy]cyclohexylamine

IR (neat) cm$^{-1}$; 1504, 1329, 1234, 1119, 1037, 903.

EXAMPLE 767

Synthesis of N,N-dimethyl-N-cis-3-[(4-trifluoromethyl-1H-indazol-5-yl)oxy]cyclohexylamine Acetic acid (0.065 ml) was added to a methanolic solution (1.0 ml) of the cis-3-[(4-trifluoromethyl-1H-indazol-5-yl)oxy]cyclohexylamine (70 mg, 0.24 mmol) obtained in Example 587, followed by adding thereto a 37% aqueous formaldehyde solution (35 mg, 1.2 mmol), and the resulting mixture was stirred at room temperature for 2 hours. Then, a methanolic solution (0.5 ml) of sodium cyanoborohydride (70 mg, 1.1 mmol) was added thereto and the resulting mixture was stirred overnight at room temperature. A 1N-aqueous sodium hydroxide solution (0.8 ml) was added to the reaction solution and the solvent was distilled off. The residue oil was purified by elution by a silica gel column chromatography (ethyl acetate/triethylamine/ethanol=20:1:1) to obtain N,N-dimethyl-N-cis-3-[(4-trifluoromethyl-1H-indazol-5-yl)oxy]cyclohexylamine (48.3 mg, 63%).

IR (neat) cm$^{-1}$; 1508, 1329, 1236, 1115, 901.

The following compound of Example 768 was synthesized by carrying out reaction according to the method described in Example 767, except for using the trans-4-{[4-(trifluoromethyl)-1H-indazol-5-yl]oxy}cyclohexanamine obtained in Example 586, as a starting material.

EXAMPLE 768

N,N-dimethyl-N-trans-4-[(4-trifluoromethyl-1H-indazol-5-yl)oxy]cyclohexylamine

IR (neat) cm$^{-1}$; 1506, 1327, 1236, 1188, 1120, 1052, 941, 902.

EXAMPLE 769

Synthesis of N-benzyl-N-trans-4-[(4-methyl-1H-indazol-5-yl)oxy]cyclohexylamine

Acetic acid (0.060 ml) was added to a methanolic solution (2.0 ml) of the trans-4-[(4-methyl-1H-indazol-5-yl)oxy]cyclohexylamine (98 mg, 0.40 mmol) obtained in Example 408, followed by adding thereto benzaldehyde (85 mg, 0.80 mmol), and the resulting mixture was stirred at room temperature for 2 hours. Then, a methanolic solution (0.5 ml) of sodium cyanoborohydride (30 mg, 0.48 mmol) was added thereto and the resulting mixture was stirred overnight at room temperature. A 1N-aqueous sodium hydroxide solution (0.8 ml) was added to the reaction solution and the solvent was distilled off. The residue oil was purified by elution by a silica gel column chromatography (hexane/ethyl acetate=1:2→ethyl acetate/triethylamine=20:1) to obtain N-benzyl-N-trans-4-[(4-methyl-1H-indazol-5-yl)oxy]cyclohexylamine (45.6 mg, 31%).

IR (neat) cm$^{-1}$; 1452, 1232, 1099, 935, 804, 744, 696.

The following compounds of Examples 770 to 781 were synthesized by carrying out reaction according to the method described in Example 769.

EXAMPLE 770

N-(2-chlorobenzyl)-N-trans-4-[(4-methyl-1H-indazol-5-yl)oxy]cyclohexylamine

IR (neat) cm$^{-1}$; 1232, 1101, 943, 800, 754.

EXAMPLE 771

N-(3-chlorobenzyl)-N-trans-4-[(4-methyl-1H-indazol-5-yl)oxy]cyclohexylamine

Melting point: 134–137° C.

EXAMPLE 772

N-(4-chlorobenzyl)-N-trans-4-[(4-methyl-1H-indazol-5-yl)oxy]cyclohexylamine

Melting point: 148–150° C.

EXAMPLE 773

N-(3-methoxybenzyl)-N-trans-4-[(4-methyl-1H-indazol-5-yl)oxy]cyclohexylamine

Melting point: 150–153° C.

EXAMPLE 774

N-(4-methoxybenzyl)-N-trans-4-[(4-methyl-1H-indazol-5-yl)oxy]cyclohexylamine

Melting point: 176–178° C.

EXAMPLE 775

N-(3-trifluoromethylbenzyl)-N-trans-4-[(4-methyl-1H-indazol-5-yl)oxy]cyclohexylamine IR (neat) cm$^{-1}$; 1508, 1327, 1120, 943, 804, 702.

EXAMPLE 776

N-(1,3-benzodioxol-5-ylmethyl)-N-trans-4-[(4-methyl-1H-indazol-5-yl)oxy]cyclohexylamine IR (neat) cm$^{-1}$; 1247, 1034, 928, 796.

EXAMPLE 777

N-trans-4-[(4-methyl-1H-indazol-5-yl)oxy]cyclohexyl-N-(pyridin-2-ylmethyl)amine

IR (neat) cm$^{-1}$; 1508, 1221, 1091, 941, 756.

EXAMPLE 778

N-trans-4-[(4-methyl-1H-indazol-5-yl)oxy]cyclohexyl-N-(pyridin-3-ylmethyl)amine

IR (neat) cm$^{-1}$; 1508, 1222, 1091, 941, 755.

EXAMPLE 779

N-trans-4-[(4-methyl-1H-indazol-5-yl)oxy]cyclohexyl-N-(pyridin-4-ylmethyl)amine

IR (neat) cm$^{-1}$; 1558, 1222, 1095, 941, 796.

EXAMPLE 780

N-isobutyl-N-trans-4-[(4-methyl-1H-indazol-5-yl)oxy]cyclohexylamine

IR (neat) cm$^{-1}$; 1236, 1101, 935, 873, 790.

EXAMPLE 781

N-phenethyl-N-trans-4-[(4-methyl-1H-indazol-5-yl)oxy]cyclohexylamine

IR (neat) cm$^{-1}$; 1508, 1220, 1093, 940.

EXAMPLE 782

Synthesis of N-trans-{4-[(4-methyl-1H-indazol-5-yl)oxy]cyclohexyl}cyclopropanecarboxamide Cyclopropanecarboxylic acid (0.034 g, 0.40 mmol), triethylamine (0.14 ml, 1.0 mmol), 1-hydroxybenztriazole (0.054 g, 0.40 mmol) and 1-ethyl-3-(3'-dimethylamino-propyl)carbodiimide monohydrochloride (0.077 g, 0.40 mmol) were added to a solution of the trans-4-[(4-methyl-1H-indazol-5-yl)oxy]cyclohexylamine (98 mg, 0.40 mmol) obtained in Example 408 in N,N-dimethylformamide (2 ml) and stirred overnight. A 2N-aqueous lithium hydroxide solution (2 ml) was added thereto, and the resulting mixture was stirred for a while, then added to water, and extracted three times with toluene/ethyl acetate=1/1. The organic layer was washed with water and a saturated aqueous sodium chloride solution and dried over anhydrous sodium sulfate. The solvent was distilled off under reduced pressure, and the solid precipitated was suspended in a hexane/ethyl acetate mixed solvent and stirred to be washed. The solid was collected by filtration and dried under reduced pressure to obtain N-trans-{4-[(4-methyl-1H-indazol-5-yl)oxy]cyclohexyl}cyclopropanecarboxamide (115 mg, 92%).

$^1$H-NMR (DMSO-d$_6$) δ; 0.55–0.67 (4H, m), 1.15–1.32 (2H, m), 1.38–1.53 (3H, m), 1.75–1.86 (2H, m), 1.95–2.06 (2H m), 2.36 (3H, s), 3.50–3.65 (1H, m), 3.97–4.09 (1H m), 7.12 (1H, d, J=9.0 Hz), 7.27 (1H, d, J=9.0 Hz), 8.00 (1H, s), 12.84 (1H, s).

The following compounds of Examples 783 to 787 were synthesized by carrying out reaction according to the method described in Example 782.

EXAMPLE 783

N-trans-{4-[(4-methyl-1H-indazol-5-yl)oxy]cyclohexyl}cyclopentanecarboxamide $^1$H-NMR (DMSO-d$_6$) δ; 1.13–1.30 (2H, m), 1.36–1.73 (11H, m), 1.74–1.85 (2H, m), 1.95–2.06 (2H, m), 2.36 (3H, s), 3.46–3.65 (1H, m), 3.95–4.07 (1H, m), 7.12 (1H, d, J=9.0 Hz), 7.27 (1H, d, J=9.0 Hz), 7.61 (1H, d, J=7.7 Hz), 8.00 (1H, s), 12.85 (1H, s).

EXAMPLE 784

2-Methoxy-N-trans-{4-[(4-methyl-1H-indazol-5-yl)oxy]cyclohexyl}acetamide $^1$H-NMR (DMSO-d$_6$) δ; 1.26–1.53 (4H, m), 1.70–1.81 (2H, m), 1.90–2.06 (2H, m), 2.37 (3H, s), 3.27 (3H, s), 3.58–3.70 (1H, m), 3.75 (2H, s), 3.95–4.03 (1H, m), 7.11 (1H, d, J=8.8 Hz), 7.27 (1H, d, J=8.6 Hz), 7.56 (1H, d, J=8.0 Hz), 8.00 (1H, s), 12.86 (1H, s).

EXAMPLE 785

N-trans-{4-[(4-methyl-1H-indazol-5-yl)oxy]cyclohexyl}tetrahydrofurane-2-carboxamide $^1$H-NMR (DMSO-d$_6$) δ; 1.17–1.55 (4H, m), 1.69–1.86 (5H, m), 1.96–2.16 (3H, m), 2.37 (3H, s), 3.52–3.68 (1H, m), 3.68–3.80 (1H, m), 3.80–3.90 (1H, m), 3.90–4.02 (1H, m), 4.11–4.18 (1H, m), 7.11 (1H, d, J=8.8 Hz), 7.27 (1H, d, J=8.8 Hz), 7.50 (1H, d, J=8.3 Hz), 8.00 (1H, s), 12.86 (1H, s).

EXAMPLE 786

N-trans-{4-[(4-methyl-1H-indazol-5-yl)oxy]cyclohexyl}tetrahydrofurane-3-carboxamide $^1$H-NMR (DMSO-d$_6$) δ; 1.14–1.31 (2H, m), 1.39–1.55 (2H, m), 1.75–1.87 (2H, m), 1.87–2.06 (4H, m), 2.37 (3H, s), 2.80–2.92 (1H, m), 3.50–3.73 (4H, m), 3.81 (1H, t, J=8.1 Hz), 3.95–4.06 (1H, m), 4.11–4.18 (1H, m), 7.12 (1H, d, J=8.8 Hz), 7.27 (1H, d, J=8.8 Hz), 7.82 (1H, d, J=8.3 Hz), 8.00 (1H, s), 12.85 (1H, s).

EXAMPLE 787

2-Dimethylamino-N-trans-{4-[(4-methyl-1H-indazol-5-yl)oxy]cyclohexyl}acetamide $^1$H-NMR (DMSO-d$_6$) δ; 1.22–1.55 (4H, m), 1.70–1.82 (2H, m), 1.91–2.04 (2H, m), 2.14 (6H, s), 2.37 (3H, s), 2.80 (2H, s), 3.55–3.70 (1H, m), 3.95–4.06 (1H, m), 7.11 (1H, d, J=9.0 Hz), 7.27 (1H, d, J=8.8 Hz), 8.00 (1H, s), 12.86 (1H, s).

EXAMPLE 788

Synthesis of N-cyclopropylmethyl-N-trans-4-[(4-methyl-1H-indazol-5-yl)oxy]cyclohexylamine The N-trans-{4-[(4-methyl-1H-indazol-5-yl)oxy]cyclohexyl}cyclopropanecarboxamide (0.108 g, 0.35 mmol) obtained in Example 35 was added to a suspension of lithium aluminum hydride (0.040 g, 1.1 mmol) in tetrahydrofuran (2 ml), and the resulting mixture was stirred with heating under reflux for 7 hours. The resulting solution was cooled on an ice bath, and water (0.02 ml), a 2N-aqueous sodium hydroxide solution (0.04 ml) and water (0.08 ml) were added dropwise thereto in that order. Then, the insoluble material was removed by filtration using Celite. The filtrate was purified by elution by a silica gel chromatography (hexane/ethyl acetate/triethylamine=5:15:1) to obtain N-cyclopropylmethyl-N-trans-4-[(4-methyl-1H-indazol-5-yl)oxy]cyclohexylamine (82.3 mg, 80%).

Melting point: 132–134° C.

The following compound of Example 789 was synthesized by carrying out reaction according to the method described in Example 788, except for using the N-trans-{4-[(4-methyl-1H-indazol-5-yl)oxy]cyclohexyl}cyclopentanecarboxamide obtained in Example 783, as a starting material.

EXAMPLE 789

N-cyclopentylmethyl-N-trans-4-[(4-methyl-1H-indazol-5-yl)oxy]cyclohexylamine

Melting point: 180° C.

The following compound of Example 790 was synthesized by carrying out reaction according to the method described in Example 788, except for using the 2-methoxy-N-trans-{4-[(4-methyl-1H-indazol-5-yl)oxy]cyclohexyl}acetamide obtained in Example 784, as a starting material.

EXAMPLE 790

N-(2-methoxyethyl)-N-trans-4-[(4-methyl-1H-indazol-5-yl)oxy]cyclohexylamine

IR (neat) cm$^{-1}$; 1508, 1220, 1093, 941.

The following compound of Example 791 was synthesized by carrying out reaction according to the method described in Example 788, except for using the N-trans-{4-[(4-methyl-1H-indazol-5-yl)oxy]cyclohexyl}tetrahydrofurane-2-carboxamide obtained in Example 785, as a starting material.

EXAMPLE 791

N-trans-{4-[(4-methyl-1H-indazol-5-yl)oxy]cyclohexyl}-N-(tetrahydrofuran-2-ylmethyl)amine IR (neat) cm$^{-1}$; 1508, 1220, 1072, 941.

The following compound of Example 792 was synthesized by carrying out reaction according to the method described in Example 788, except for using the N-trans-{4-[(4-methyl-1H-indazol-5-yl)oxy]cyclohexyl}tetrahydrofurane-3-carboxamide obtained in Example 786, as a starting material.

EXAMPLE 792

N-trans-{4-[(4-methyl-1H-indazol-5-yl)oxy]cyclohexyl}-N-(tetrahydrofuran-3-ylmethyl)amine IR (neat) cm$^{-1}$; 1508, 1223, 1092, 943.

EXAMPLE 793

Methyl 3-({trans-4-[(4-methyl-1H-indazol-5-yl)oxy] cyclohexyl}amino)propanoate

A mixture of the trans-4-[(4-methyl-1H-indazol-5-yl)oxy] cyclohexylamine (98.1 mg, 0.40 mmol) obtained in Example 408, methyl methacrylate (43 mg, 0.50 mmol) and methanol (2.0 ml) was stirred at 50° C. for 6 hours. The solvent was distilled off and the residue oil was subjected to elution by a silica gel column chromatography (ethyl acetate→ethyl acetate/triethylamine=20:1) to obtain methyl 3-({trans-4-[(4-methyl-1H-indazol-5-yl)oxy]cyclohexyl}-amino}propanoate (121 mg, 91%).

$^1$H-NMR (DMSO-$d_6$) δ; 0.95–1.13 (2H, m), 1.32–1.60 (3H, m), 1.90–2.02 (4H, m), 2.30–2.45 (5H, m), 2.58–2.67 (2H, s), 3.57 (3H, s), 3.96–4.07 (1H, m), 7.10 (1H, d, J=9.0 Hz), 7.26 (1H, d, J=8.8 Hz), 7.99 (1H, s), 12.84 (1H, s).

EXAMPLE 794

Synthesis of 4-methyl-5-[(trans-4-pyrrolidin-1-ylcyclohexyl)oxy]-1H-indazole (a) Synthesis of trans-4-[(4-methyl-1-tetrahydro-2H-pyran-2-yl-1H-indazol-5-yl)oxy]cyclohexylamine A mixture of the trans-4-[(4-methyl-1H-indazol-5-yl)oxy] cyclohexylamine (245 mg, 1.00 mmol) obtained in Example 408, pyridinium p-toluenesulfonate (50 mg, 0.20 mmol), p-toluenesulfonic acid monohydrate (380 mg, 2.00 mmol) and N-methylpyrrolidone (5.0 ml) was stirred at 90° C. for 13 hours. A 1N-aqueous sodium hydroxide solution (30 ml) was added to the reaction solution, followed by extraction with chloroform (20 ml) (twice). The extract solution was dried over magnesium sulfate and then concentrated to dryness, and the residue oil was purified by elution by a silica gel column chromatography (chloroform/methanol=50:1→chloroform/methanol/triethylamine=20:1:1) to obtain trans-4-[(4-methyl-1-tetrahydro-2H-pyran-2-yl-1H-indazol-5-yl)oxy]cyclohexylamine (215 mg, 65%).

$^1$H-NMR (CDCl$_3$) δ; 1.08–2.20 (12H, m), 2.40–2.62 (5H, m), 2.71–2.85 (1H, m), 3.68–3.80 (1H, m), 3.92–4.07 (2H, m), 5.66 (1H, dd, J=9.4 Hz, 2.6 Hz), 7.10 (1H, d, J=9.0 Hz), 7.34 (1H, d, J=9.2 Hz), 7.97 (1H, s).

(b) Synthesis of 4-methyl-5-[(trans-4-pyrrolidin-1-ylcyclohexyl)oxy]-1-tetrahydro-2H-pyran-2-yl-1H-indazole A mixture of trans-4-[(4-methyl-1-tetrahydro-2H-pyran-2-yl-1H-indazol-5-yl)oxy]cyclohexylamine (106 mg, 0.321 mmol), 1,4-dibromobutane (69.3 mg, 0.321 mmol), potassium carbonate (110 mg, 0.80 mmol) and N,N-dimethylacetamide (2.0 ml) was stirred at 80° C. for 2 hours. A 1N-aqueous sodium hydroxide solution (20 ml) was added to the reaction solution, followed by extraction with chloroform (20 ml) (twice). The extract solution was dried over magnesium sulfate and then concentrated to dryness, and the residue oil was purified by elution by a silica gel column chromatography (hexane/ethyl acetate=1:2→hexane/ethyl acetate/triethylamine=20:40:3) to obtain 4-methyl-5-[(trans-4-pyrrolidin-1-ylcyclohexyl)oxy]-1-tetrahydro-2H-pyran-2-yl-1H-indazole (67.1 mg, 55%).

$^1$H-NMR (CDCl$_3$) δ; 0.75–2.20 (16H, m), 2.43–2.65 (9H, m), 3.68–3.80 (1H, m), 3.92–4.07 (2H, m), 5.62–5.68 (1H, m), 7.10 (1H, d, J=9.0 Hz), 7.34 (1H, d, J=9.2 Hz), 7.96 (1H, s)

(c) Synthesis of 4-methyl-5-[(trans-4-pyrrolidin-1-ylcyclohexyl)oxy]-1H-indazole A mixture of 4-methyl-5-[(trans-4-pyrrolidin-1-ylcyclohexyl)oxy]-1-tetrahydro-2H-pyran-2-yl-1H-indazole (62.1 mg, 0.162 mmol), a 4N-hydrochloric acid/dioxane solution (2.0 ml) and isopropanol (2.0 ml) was stirred at room temperature for 4 hours. The solvent was distilled off and a 1N-aqueous sodium hydroxide solution (20 ml) was added to the residue, followed by extraction with ethyl acetate (20 ml) (twice). The extract solution was dried over magnesium sulfate and then concentrated to dryness, and the residue oil was purified by elution by a silica gel column chromatography (hexane/ethyl acetate/triethylamine=20:40:3) to obtain 4-methyl-5-[(trans-4-pyrrolidin-1-ylcyclohexyl)oxy]-1H-indazole (28.3 mg, 58%).

IR (neat) cm$^{-1}$; 1506, 1217, 1097, 941.

The following compounds of Example 795 to Example 802 were synthesized according to the processes described in Example 455 and Example 461, except for using the cis-4-[(4-methyl-1H-indazol-5-yl)oxy]cyclohexanamine obtained in Example 410, as a starting material.

EXAMPLE 795

Synthesis of N-{cis-4-[(4-methyl-1H-indazol-5-yl) oxy]cyclohexyl}-N-pentylamine (a) N-{cis-4-[(4-methyl-1H-indazol-5-yl)oxy] cyclohexyl}pentanamide MS: m/z=330 (M+1)

(b) N-{cis-4-[(4-methyl-1H-indazol-5-yl)oxy]cyclohexyl}-N-pentylamine

IR (neat) cm$^{-1}$; 2933, 2852, 1225, 1095, 939, 787.

EXAMPLE 796

Synthesis of N-isobutyl-N-{cis-4-[(4-methyl-1H-indazol-5-yl)oxy]cyclohexyl}amine (a) 2-methyl-N-{cis-4-[(4-methyl-1H-indazol-5-yl) oxy]cyclohexyl}propanamide MS: m/z=316 (M+1)

(b) N-isobutyl-N-{cis-4-[(4-methyl-1H-indazol-5-yl) oxy]cyclohexyl}amine

IR (neat) cm$^{-1}$; 2935, 2864, 1228, 1103, 953, 943, 796.

EXAMPLE 797

Synthesis of N-(2-methoxyethyl)-N-{cis-4-[(4-methyl-1H-indazol-5-yl)oxy]cyclohexyl}amine (a) 2-methoxy-N-{cis-4-[(4-methyl-1H-indazol-5-yl) oxy]cyclohexyl}acetamide MS: m/z=318 (M+1)

(b) N-(2-methoxyethyl)-N-{cis-4-[(4-methyl-1H-indazol-5-yl)oxy]cyclohexyl}amine

¹H-NMR (CDCl₃) δ; 1.54–1.78 (8H, m), 2.03–2.07 (2H, m), 2.49 (3H, s), 2.60 (1H, m), 2.86 (2H, t, J=5.2 Hz), 3.38 (3H, s), 3.55 (2H, t, J=5.2 Hz), 3.70 (1H, m), 4.36 (1H, m), 7.08 (1H, d, J=8.8 Hz), 7.24 (1H, d, J=8.8 Hz), 8.01 (1H, d, J=0.92 Hz)

EXAMPLE 798

Synthesis of N-(cyclopropylmethyl)-N-{cis-4-[(4-methyl-1H-indazol-5-yl)oxy]cyclohexyl}amine (a) N-{cis-4-[(4-methyl-1H-indazol-5-yl)oxy]cyclohexyl}cyclopropanecarboxamide MS: m/z=314 (M+1)

(b) N-(cyclopropylmethyl)-N-{cis-4-[(4-methyl-1H-indazol-5-yl)oxy]cyclohexyl}amine ¹H-NMR (CDCl₃) δ; 0.11–0.16 (2H, m), 0.44–0.52 (2H, m), 1.01 (1H, m), 1.53–1.78 (6H, m), 2.02–2.07 (2H, m), 2.46 (3H, s), 2.55 (2H, d, J=7.0 Hz), 2.61–2.68 (1H, m), 4.34 (1H, m), 7.05 (1H, d, J=8.9 Hz), 7.24 (1H, d, J=8.9 Hz), 8.02 (1H, d, J=0.92 Hz).

EXAMPLE 799

Synthesis of N-(cyclopentylmethyl)-N-{cis-4-[(4-methyl-1H-indazol-5-yl)oxy]cyclohexyl}amine (a) N-{cis-4-[(4-methyl-1H-indazol-5-yl)oxy]cyclohexyl}cyclopentanecarboxamide MS: m/z=342 (M+1)

(b) N-(cyclopentylmethyl)-N-{cis-4-[(4-methyl-1H-indazol-5-yl)oxy]cyclohexyl}amine IR (neat) cm⁻¹; 2929, 2862, 1223, 1090, 939, 914, 795.

EXAMPLE 800

Synthesis of N-{cis-4-[(4-methyl-1H-indazol-5-yl)oxy]cyclohexyl}-N-(tetrahydrofuran-2-ylmethyl)amine (a) N-{cis-4-[(4-methyl-1H-indazol-5-yl)oxy]cyclohexyl}tetrahydrofuran-2-carboxamide MS: m/z=344 (M+1)

(b) N-{cis-4-[(4-methyl-1H-indazol-5-yl)oxy]cyclohexyl}-N-(tetrahydrofuran-2-ylmethyl)amine ¹H-NMR (CDCl₃) δ; 1.50–1.80 (7H, m), 1.83–2.07 (5H, m), 2.48 (3H, s), 2.56–2.63 (1H, m), 2.68 (1H, dd, J=12, 8.0 Hz), 2.79 (1H, dd, J=12, 3.8 Hz), 3.73–3.80 (1H, m), 3.84–3.91 (1H, m), 4.00–4.08 (1H, m), 4.34 (1H, m), 7.07 (1H, d, J=8.9 Hz), 7.24 (1H, d, J=8.9 Hz), 8.02 (1H, d, J=0.92 Hz).

EXAMPLE 801

Synthesis of N-{cis-4-[(4-methyl-1H-indazol-5-yl)oxy]cyclohexyl}-N-(tetrahydrofuran-3-ylmethyl)amine (a) N-{cis-4-[(4-methyl-1H-indazol-5-yl)oxy]cyclohexyl}tetrahydrofuran-3-carboxamide MS: m/z=344 (M+1)

(b) N-{cis-4-[(4-methyl-1H-indazol-5-yl)oxy]cyclohexyl}-N-(tetrahydrofuran-3-ylmethyl)amine ¹H-NMR (CDCl₃) δ; 1.55–1.75 (7H, m), 2.02–2.13 (3H, m), 2.33–2.45 (1H, m), 2.49 (3H, s), 2.53–2.63 (1H, m), 2.68 (2H, d, J=7.7 Hz), 3.52 (1H, dd, J=8.4, 6.1 Hz), 3.72–3.79 (1H, m), 3.84–3.95 (1H, m), 4.32 (1H, m), 7.07 (1H, d, J=8.9 Hz), 7.24 (1H, d, J=8.9 Hz), 8.02 (1H, d, J=0.92 Hz).

EXAMPLE 802

Synthesis of N-benzyl-N-{cis-4-[(4-methyl-1H-indazol-5-yl)oxy]cyclohexyl}amine (a) N-{cis-4-[(4-methyl-1H-indazol-5-yl)oxy]cyclohexyl}benzamide MS: m/z=350 (M+1)

(b) N-benzyl-N-{cis-4-[(4-methyl-1H-indazol-5-yl)oxy]cyclohexyl}amine

¹H-NMR (CDCl₃) δ; 1.54–1.83 (6H, m), 2.02–2.08 (2H, m), 2.50 (3H, s), 2.66 (1H, m), 3.69 (1H, m), 3.87 (2H, s), 4.33 (1H, m), 7.08 (1H, d, J=9.0 Hz), 7.22 (1H, d, J=9.0 Hz), 7.22–7.39 (5H, m), 8.02 (1H, d, J=0.92 Hz).

The following compounds of Example 803 to Example 807 were synthesized according to the process described in Example 423, except for using the cis-4-[(4-methyl-1H-indazol-5-yl)oxy]cyclohexanamine obtained in Example 410, as a starting material.

EXAMPLE 803

N-(2-chlorobenzyl)-N-{cis-4-[(4-methyl-1H-indazol-5-yl)oxy]cyclohexyl}amine

¹H-NMR (CDCl₃) δ; 1.56–1.65 (2H, m), 1.73–1.83 (4H, m), 2.01–2.10 (2H, m), 2.47 (3H, s), 2.72 (1H, m), 4.00 (2H, s), 4.35 (1H, m), 7.07 (1H, d, J=9.0 Hz), 7.17–7.50 (5H, m), 8.00 (1H, s).

EXAMPLE 804

N-(3-chlorobenzyl)-N-{cis-4-[(4-methyl-1H-indazol-5-yl)oxy]cyclohexyl}amine

¹H-NMR (CDCl₃) δ; 1.54–1.77 (6H, m), 2.02–2.07 (2H, m), 2.48 (3H, s), 2.65 (1H, m), 3.84 (2H, s), 4.32 (1H, m), 7.06 (1H, d, J=9.0 Hz), 7.19–7.25 (4H, m), 7.35 (1H, s), 8.02 (1H, d, J=0.92 Hz).

EXAMPLE 805

N-(4-chlorobenzyl)-N-{cis-4-[(4-methyl-1H-indazol-5-yl)oxy]cyclohexyl}amine $^1$H-NMR (CDCl$_3$) δ; 1.55–1.75 (6H, m), 2.02–2.08 (2H, m), 2.51 (3H, s), 2.62 (1H, m), 3.82 (2H, s), 4.33 (1H, m), 7.09 (1H, d, J=8.9 Hz), 7.24 (1H, d, J=8.9 Hz), 7.29 (4H, s), 8.03 (1H, d, J=0.55 Hz).

EXAMPLE 806

N-(2-furylmethyl)-N-{cis-4-[(4-methyl-1H-indazol-5-yl)oxy]cyclohexyl}amine $^1$H-NMR (CDCl$_3$) δ; 1.59–1.77 (6H, m), 2.03–2.08 (2H, m), 2.48 (3H, s), 2.66 (1H, m), 3.89 (2H, s), 4.36 (1H, m), 6.21 (1H, d, J=3.1 Hz), 6.32 (1H, m), 7.08 (1H, d, J=9.0 Hz), 7.24 (1H, d, J=9.0 Hz), 7.37 (1H, m), 8.01 (1H, s).

EXAMPLE 807

N-{cis-4-[(4-methyl-1H-indazol-5-yl)oxy]cyclohexyl}-N-(thien-2-ylmethyl)amine $^1$H-NMR (CDCl$_3$) δ; 1.54–1.77 (6H, m), 2.02–2.08 (2H, m), 2.49 (3H, s), 2.72 (1H, m), 4.08 (2H, s), 4.34 (1H, m), 6.95–6.97 (2H, m), 7.08 (1H, d, J=9.0 Hz), 7.20–7.25 (2H, m), 8.02 (1H, d, J=1.1 Hz).

EXAMPLE 808

N-(2-fluorobenzyl)-N-{cis-4-[(4-methyl-1H-indazol-5-yl)oxy]cyclohexyl}amine $^1$H-NMR (CDCl$_3$) δ; 1.54–1.78 (6H, m), 2.02–2.08 (2H, m), 2.50 (3H, s), 2.63 (1H, m), 3.92 (2H, s), 4.33 (1H, m), 7.00–7.13 (3H, m), 7.20–7.27 (2H, m), 7.37 (1H, dt-like, J=7.5, 1.8 Hz), 8.02 (1H, d, J=0.92 Hz).

EXAMPLE 809

N-(3-fluorobenzyl)-N-{cis-4-[(4-methyl-1H-indazol-5-yl)oxy]cyclohexyl}amine $^1$H-NMR (CDCl$_3$) δ; 1.54–1.76 (6H, m), 2.01–2.08 (2H, m), 2.49 (3H, s), 2.64 (1H, m), 3.86 (2H, s), 4.32 (1H, m), 6.93 (1H, m), 7.05–7.12 (3H, m), 7.20–7.31 (2H, m), 8.03 (1H, d, J=0.92 Hz).

EXAMPLE 810

N-(4-fluorobenzyl)-N-{cis-4-[(4-methyl-1H-indazol-5-yl)oxy]cyclohexyl}amine $^1$H-NMR (CDCl$_3$) δ; 1.53–1.80 (6H, m), 2.02–2.07 (2H, m), 2.47 (3H, s), 2.68 (1H, m), 3.87 (2H, s), 4.33 (1H, m), 6.96–7.06 (3H, m), 7.22 (1H, d, J=8.8 Hz), 7.31–7.35 (2H, m), 8.00 (1H, d, J=0.92 Hz).

EXAMPLE 811

N-(2-methoxybenzyl)-N-{cis-4-[(4-methyl-1H-indazol-5-yl)oxy]cyclohexyl}amine

IR (neat) cm$^{-1}$; 2943, 1497, 1250, 1227, 1126, 941, 752.

EXAMPLE 812

N-(3-methoxybenzyl)-N-{cis-4-[(4-methyl-1H-indazol-5-yl)oxy]cyclohexyl}amine

IR (neat) cm$^{-1}$; 2939, 1265, 1221, 1039, 941, 785.

EXAMPLE 813

N-(4-methoxybenzyl)-N-{cis-4-[(4-methyl-1H-indazol-5-yl)oxy]cyclohexyl}amine

IR (neat) cm$^{-1}$; 2945, 1508, 1250, 941, 750.

The following compounds of Examples 814 and 815 were synthesized according to the process described in Example 455, except for using the cis-4-[(4-methyl-1H-indazol-5-yl)oxy]cyclohexanamine obtained in Example 410, as a starting material.

EXAMPLE 814

3,3,3-Trifluoro-N-{cis-4-[(4-methyl-1H-indazol-5-yl)oxy]cyclohexyl}propanamide

MS: m/z=356 (M+1)

EXAMPLE 815

2-(Benzyloxy)-N-{cis-4-[(4-methyl-1H-indazol-5-yl)oxy]cyclohexyl}acetamide

MS: m/z=394 (M+1)

EXAMPLE 816

Synthesis of 4-methyl-5-[(4-morpholin-cis-4-ylcyclohexyl)oxy]-1H-indazole hydrochloride (a) Synthesis of 2-{cis-4-[(4-methyl-1-tetrahydro-2H-pyran-2-yl-1H-indazol-5-yl)oxy]cyclohexyl}-1H-isoindole-1,3(2H)-dione To a solution of 2-{cis-4-[(4-methyl-1H-indazol-5-yl)oxy]cyclohexyl}-1H-isoindole-1,3(2H)-dione (100 mg, 0.266 mmol) in tetrahydrofuran (2.7 ml) were added 3,4-dihydro-2H-pyran (36 μl, 0.399 mmol) and p-toluenesulfonic acid monohydrate (15 mg, 0.069 mmol), and the resulting mixture was stirred for 4 hours while being maintained at 70° C. The reaction solution was allowed to cool, and then was concentrated under reduced pressure to obtain a crude product. The crude product was purified by a silica gel column chromatography (eluent: hexane/ethyl acetate) to obtain 2-{cis-4-[(4-methyl-1-tetrahydro-2H-pyran-2-yl-1H-indazol-5-yl)oxy]cyclohexyl}-1H-isoindole-1,3(2H)-dione (99.6 mg, 82%).

(b) Synthesis of cis-4-[(4-methyl-1-tetrahydro-2H-pyran-2-yl-1H-indazol-5-yl)oxy]cyclohexanamine A mixture of 2-{cis-4-[(4-methyl-1-tetrahydro-2H-pyran-2-yl-1H-indazol-5-yl)oxy]cyclohexyl}-1H-isoindole-1,3 (2H)-dione (95.5 mg, 0.208 mmol) and a 30% methylamine-ethanol solution (5.0 ml) was stirred with heating under reflux for 2 hours. The reaction solution was allowed to cool, and then was concentrated under reduced pressure to obtain a crude product. The crude product was purified by a silica gel column chromatography (eluent: chloroform/methanol/

28% aqueous ammonia) to obtain cis-4-[(4-methyl-1-tetrahydro-2H-pyran-2-yl-1H-indazol-5-yl)oxy]cyclohexanamine (60.4 mg, 88%).

(c) Synthesis of 4-methyl-5-[(4-morpholin-cis-4-ylcyclohexyl)oxy]-1-tetrahydro-2H-pyran-2-yl-1H-indazole To a solution of cis-4-[(4-methyl-1-tetrahydro-2H-pyran-2-yl-1H-indazol-5-yl)oxy]cyclohexanamine (200 mg, 0.607 mmol) in N,N-dimethylformamide (4.0 ml) were added bis-2-bromoethyl ether (76.4 μl, 0.607 mmol) and potassium carbonate (252 mg, 1.82 mmol), and the resulting mixture was stirred for 6 hours while being maintained at 80° C. The reaction solution was allowed to cool, and then was filtered, and the filtrate was concentrated under reduced pressure to obtain a crude product. The crude product was purified by a silica gel column chromatography (eluent: chloroform/methanol) to obtain 4-methyl-5-[(4-morpholin-cis-4-ylcyclohexyl)oxy]-1-tetrahydro-2H-pyran-2-yl-1H-indazole (186 mg, 77%).

(d) Synthesis of 4-methyl-5-[(4-morpholin-cis-4-ylcyclohexyl)oxy]-1H-indazole Hydrochloride To a solution of 4-methyl-5-[(4-morpholin-cis-4-ylcyclohexyl)oxy]-1-tetrahydro-2H-pyran-2-yl-1H-indazole (186 mg, 0.465 mmol) in 2-propanol (4.0 ml) was added 4N-hydrochloric acid-dioxane (4.0 ml, 16 mmol), and the resulting mixture was stirred for 24 hours while being maintaining at room temperature. The white precipitate formed was collected by filtration and dried under reduced pressure to obtain 4-methyl-5-[(4-morpholin-cis-4-ylcyclohexyl)oxy]-1H-indazole hydrochloride (149 mg, 91%).

$^1$H-NMR (DMSO-$d_6$) δ; 1.56 (2H, m), 1.80–2.08 (6H, m), 2.45 (3H, s), 3.08–3.15 (2H, m), 3.24 (1H, m), 3.42 (2H, d-like, J=12.1 Hz), 3.85–3.98 (4H, m), 4.48 (1H, m), 7.12 (1H, d, J=8.9 Hz), 7.29 (1H, d, J=8.9 Hz), 8.02 (1H, d, J=0.92 Hz), 10.97 (1H, brs).

The following compounds of Examples 817 and 818 were synthesized according to the process described in Example 423, except for using the cis-5-[(3-aminocyclohexyl)oxy]-1H-indazole-4-carbonitrile obtained in Example 693, as a starting material.

EXAMPLE 817 cis-5-{[3-(Benzylamino)cyclohexyl]oxy}-1H-indazole-4-carbonitrile

IR (neat) cm$^{-1}$; 2939, 2222, 1495, 1313, 1236, 1028, 945, 750.

EXAMPLE 818 cis-5-{[3-(Dimethylamino)cyclohexyl]oxy}-1H-indazole-4-carbonitrile

IR (neat) cm$^{-1}$; 2937, 2218, 1498, 1311, 1242, 1022, 947, 795.

EXAMPLE 819

Synthesis of 2-methyl-N-{cis-3-[(4-methyl-1H-indazol-5-yl)oxy]cyclohexyl}propanamide Isobutyric acid (36.2 μL, 0.39 mmol), 1-ethyl-3-(3'-dimethylaminopropyl)carbodiimide monohydrochloride (74.8 mg, 0.39 mmol), hydroxybenzotriazole (52.8 mg, 0.39 mmol) and triethylamine (0.18 ml, 1.28 mmol) were added to a solution of monohydrochloride (100 mg, 0.35 mmol) of the cis-3-[(4-methyl-1H-indazol-5-yl)oxy]cyclohexanamine obtained in Example 411 in N,N-dimethylformamide (5 ml), and the resulting mixture was stirred overnight at room temperature. The reaction solution was partitioned by the addition of ethyl acetate, toluene and water, and then extracted twice with ethyl acetate-toluene (1/1). The extract solution was washed with a saturated aqueous sodium hydrogencarbonate solution and then dried over anhydrous magnesium sulfate. The solvent was distilled off under reduced pressure and the resulting residue was purified by a silica gel column chromatography (eluent: hexane/ethyl acetate=1/1 to 0/1) to obtain 2-methyl-N-{cis-3-[(4-methyl-1H-indazol-5-yl)oxy]cyclohexyl}propanamide (86.3 mg, 77%).

IR (neat) cm$^{-1}$; 953, 1086, 1215, 1543, 1635.

The following compounds of Examples 820 to 826 were synthesized by carrying out reaction according to the method described in Example 819.

EXAMPLE 820

N-{cis-3-[(4-methyl-1H-indazol-5-yl)oxy]cyclohexyl}tetrahydrofuran-3-carboxamide IR (neat) cm$^{-1}$; 954, 1031, 1215, 1514, 1543, 1633.

EXAMPLE 821

2-Methoxy-N-{cis-3-[(4-methyl-1H-indazol-5-yl)oxy]cyclohexyl}acetamide

IR (neat) cm$^{-1}$; 953, 1112, 1232, 1512, 1647.

EXAMPLE 822

3,3,3-Trifluoro-N-{cis-3-[(4-methyl-1H-indazol-5-yl)oxy]cyclohexyl}propanamide

IR (neat) cm$^{-1}$; 1013, 1084, 1146, 1552, 1655.

EXAMPLE 823

N-{cis-3-[(4-methyl-1H-indazol-5-yl)oxy]cyclohexyl}cyclopropanecarboxamide

IR (neat) cm$^{-1}$; 955, 1086, 1217, 1551, 1633.

EXAMPLE 824

2,2-Dimethyl-N-{cis-3-[(4-methyl-1H-indazol-5-yl)oxy]cyclohexyl}propanamide

IR (neat) cm$^{-1}$; 951, 1200, 1535, 1628, 2945.

EXAMPLE 825

2-(1,3-Dioxo-1,3-dihydro-2H-isoindol-2-yl)-N-{cis-3-[(4-methyl-1H-indazol-5-yl)oxy]cyclohexyl}acetamide

LC/MS: M+1=433.4

EXAMPLE 826

N-{cis-3-[(4-methyl-1H-indazol-5-yl)oxy]cyclohexyl}isonicotinamide

IR (neat) cm$^{-1}$; 650, 945, 1009, 1537, 1633.

EXAMPLE 827

Synthesis of N-isobutyl-N-{cis-3-[(4-methyl-1H-indazol-5-yl)oxy]cyclohexyl}amine Monohydrochloride Lithium aluminum hydride (45.6 mg, 1.20 mmol) was added to a THF solution (5 ml) of the 2-methyl-N-{cis-3-[(4-methyl-1H-indazol-5-yl)oxy]cyclohexyl}propanamide (76 mg, 0.24 mmol) obtained in Example 819, and the resulting mixture was stirred with heating at 85° C. for 12 hours. The reaction solution was cooled, and water (46 μl), a 2N-aqueous sodium hydroxide solution (92 μl) and then water (138 μl) were added thereto and stirred for 30 minutes, followed by filtration using Celite. The residue was purified by a silica gel chromatography (ethyl acetate, methanol (5% aqueous ammonia):chloroform=1/10). To a solution of the purified residue in 2-propanol was added a 1N-hydrochloric acid-diethyl ether solution (0.25 mL), and stirred for 30 minutes, and the solvent was distilled off under reduced pressure. Then, the residue was crystallized from 2-propanol-diisopropyl ether-diethyl ether to obtain N-isobutyl-N-{cis-3-[(4-methyl-1H-indazol-5-yl)oxy]cyclohexyl}amine monohydrochloride (42.0 mg, 49%).

LC/MS: M+1=302.3

EXAMPLE 828

Synthesis of N-{cis-3-[(4-methyl-1H-indazol-5-yl)oxy]cyclohexyl}-N-(tetrahydrofuran-3-ylmethyl)amine Monohydrochloride N-{cis-3-[(4-methyl-1H-indazol-5-yl)oxy]cyclohexyl}-N-(tetrahydrofuran-3-ylmethyl)amine monohydrochloride was obtained according to the process described in Example 827, except for using the N-{cis-3-[(4-methyl-1H-indazol-5-yl)oxy]cyclohexyl}tetrahydrofuran-3-carboxamide obtained in Example 820.

IR (neat) cm$^{-1}$; 1041, 1090, 1223, 1510, 2943.

EXAMPLE 829

Synthesis of N-(2-methoxyethyl)-N-{cis-3-[(4-methyl-1H-indazol-5-yl)oxy]cyclohexyl}amine Monohydrochloride N-(2-methoxyethyl)-N-{cis-3-[(4-methyl-1H-indazol-5-yl)oxy]cyclohexyl}amine monohydrochloride was obtained according to the process described in Example 827, except for using the 2-methoxy-N-{cis-3-[(4-methyl-1H-indazol-5-yl)oxy]cyclohexyl}acetamide obtained in Example 821.

LC/MS: M+1=304.2

EXAMPLE 830

Synthesis of N-(cyclopropylmethyl)-N-{cis-3-[(4-methyl-1H-indazol-5-yl)oxy]cyclohexyl}amine Monohydrochloride N-(cyclopropylmethyl)-N-{cis-3-[(4-methyl-1H-indazol-5-yl)oxy]cyclohexyl}amine monohydrochloride was obtained according to the process described in Example 827, except for using the N-{cis-3-[(4-methyl-1H-indazol-5-yl)oxy]cyclohexyl}cyclopropanecarboxamide obtained in Example 823.

IR (neat) cm$^{-1}$; 800, 1211, 1267, 1529, 2611.

EXAMPLE 831

Synthesis of N-{cis-3-[(4-methyl-1H-indazol-5-yl)oxy]cyclohexyl}-N-neopentylamine Monohydrochloride N-(3,3-dimethylbutyl)-N-{cis-3-[(4-methyl-1H-indazol-5-yl)oxy]cyclohexyl}amine monohydrochloride was obtained according to the process described in Example 827, except for using the 2,2-dimethyl-N-{cis-3-[(4-methyl-1H-indazol-5-yl)oxy]cyclohexyl}propanamide obtained in Example 824.

IR (neat) cm$^{-1}$; 1115, 1227, 1375, 1518, 2953.

EXAMPLE 832

Synthesis of N~1~-{cis-3-[(4-methyl-1H-indazol-5-yl)oxy]cyclohexyl}glycinamide monohydrochloride A 40% methylamine methanolic solution (5 mL) was added to the 2-(1,3-dioxo-1,3-dihydro-2H-isoindol-2-yl)-N-{cis-3-[(4-methyl-1H-indazol-5-yl)oxy]cyclohexyl}acetamide (70 mg, 0.16 mmol) obtained in Example 825, and the resulting mixture was stirred overnight. The reaction solution was distilled under reduced pressure to remove the solvent and then the residue was purified by a silica gel chromatography. To a solution of the purified residue in 2-propanol was added a hydrochloric acid-diethyl ether solution, and stirred for 30 minutes. After the solvent was distilled off under reduced pressure, the residue was crystallized from 2-propanol-diisopropyl ether-diethyl ether to obtain N~1~(identification is required)-{cis-3-[(4-methyl-1H-indazol-5-yl)oxy]cyclohexyl}glycinamide monohydrochloride (39 mg, 79%).

IR (neat) cm$^{-1}$; 1201, 1267, 1556, 1662, 2943.

EXAMPLE 833

Synthesis of N-{cis-3-[(4-methyl-1H-indazol-5-yl)oxy]cyclohexyl}-N-(pyridin-4-ylmethyl)amine Isonicotinaldehyde (42.8 μl, 0.45 mmol) and acetic acid (0.23 mL, 4.08 mmol) were added to a methanolic solution (5 ml) of the cis-3-[(4-methyl-1H-indazol-5-yl)oxy]cyclohexanamine (100 mg, 0.41 mmol) obtained in Example 411, and the resulting mixture was stirred for 10 minutes. Then, sodium cyanoborohydride (28.2 mg, 0.45 mmol) was added thereto and stirred for 2 hours. An aqueous sodium hydroxide solution was added to the reaction solution, followed by extraction with chloroform (three times), and the extract solution was dried over anhydrous magnesium sulfate. The residue was purified by a silica gel chromatography (ethyl acetate, methanol (5% aqueous ammonia): chloroform=10/

100) to obtain N-{cis-3-[(4-methyl-1H-indazol-5-yl)oxy]cyclohexyl}-N-(pyridin-4-ylmethyl)amine (58.7 mg, 43%).

IR (neat) cm$^{-1}$; 941, 1092, 1221, 1508, 1603, 2933.

The following compounds of Example 834 to Example 836 were synthesized by carrying out reaction according to the method described in Example 833.

EXAMPLE 834

N-{cis-3-[(4-methyl-1H-indazol-5-yl)oxy]cyclohexyl}-N-(pyridin-3-ylmethyl)amine monohydrochloride

LC/MS: M+1=337.3

EXAMPLE 835

N-{cis-3-[(4-methyl-1H-indazol-5-yl)oxy]cyclohexyl}-N-(pyridin-2-ylmethyl)amine

IR (neat) cm$^{-1}$; 939, 1092, 1221, 1732, 2935.

EXAMPLE 836

Ethyl N-{cis-3-[(4-methyl-1H-indazol-5-yl)oxy]cyclohexyl}glycinate

LC/MS: M+1=332.5

EXAMPLE 837

Synthesis of 2-({cis-3-[(4-methyl-1H-indazol-5-yl)oxy]cyclohexyl}amino)ethanol

The ethyl N-{cis-3-[(4-methyl-1H-indazol-5-yl)oxy]cyclohexyl}glycinate obtained in Example 836 was added to a tetrahydrofuran suspension of lithium aluminum hydride, and the resulting mixture was stirred at room temperature for 3 hours. Water, a 2N-aqueous sodium hydroxide solution and then water were added to the reaction mixture and stirred for 1 hour, followed by filtration using Celite. The filtrate was concentrated and then purified by a preparative thin-layer chromatography (methanol (containing aqueous ammonia)/chloroform=1/10) to obtain 2-({cis-3-[(4-methyl-1H-indazol-5-yl)oxy]cyclohexyl}amino)ethanol (17.6 mg, 40%).

IR (neat) cm$^{-1}$; 943, 1057, 1093, 1223, 3188.

EXAMPLE 838

Synthesis of methyl N-{cis-3-[(4-methyl-1H-indazol-5-yl)oxy]cyclohexyl}-β-alaniate Methyl acrylate (0.04 mL, 0.49 mmol) was added to a methanolic solution (5 mL) of the cis-3-[(4-methyl-1H-indazol-5-yl)oxy]cyclohexanamine (100 mg, 0.41 mmol) obtained in Example 411, and the resulting mixture was stirred with heating at 50° C. for 2 hours. The reaction solution was concentrated under reduced pressure and then purified by a silica gel chromatography (ethyl acetate, methanol/chloroform=1/10) to obtain methyl N-{cis-3-[(4-methyl-1H-indazol-5-yl)oxy]cyclohexyl}-β-alaniate (88.0 mg, 65%).

LC/MS: M+1=332.2

The compound of Example 839 was synthesized by carrying out reaction according to the method described in Example 838.

EXAMPLE 839 tert-Butyl N-{cis-3-[(4-methyl-1H-indazol-5-yl)oxy]cyclohexyl}-β-alaniate

LC/MS: M+1=374.3

EXAMPLE 840

Synthesis of N-{cis-3-[(4-methyl-1H-indazol-5-yl)oxy]cyclohexyl}-β-alanine bis(trifluoroacetate)

A dichloromethane solution (5 mL) of the tert-butyl N-{cis-3-[(4-methyl-1H-indazol-5-yl)oxy]cyclohexyl}-β-alaniate (106 mg, 0.28 mmol) obtained in Example 839 was added to a solution of trifluoroacetic acid (5 mL) in dichloromethane (5 mL) at 0° C. and stirred at room temperature for 2 hours. The reaction solution was distilled under reduced pressure to remove the solvent, followed by azeotropic distillation with toluene, whereby N-{cis-3-[(4-methyl-1H-indazol-5-yl)oxy]cyclohexyl}-β-alanine bis(trifluoroacetate) (196.2 mg, quant.) was obtained.

LC/MS: M+1=318.2

EXAMPLE 841

Synthesis of trans-N-{4-[(4-ethyl-1H-indazol-5-yl)oxy]cyclohexyl}-N,N-dimethylamine Acetic acid (0.14 mL, 2.5 mmol) and an aqueous formaldehyde solution (209.3 mg, 2.5 mmol) were added to a methanolic solution (3 mL) of the trans-4-((4-ethyl-1H-indazol-5-yl)oxy)cyclohexanamine (130 mg, 0.5 mmol) obtained in Example 744, and then sodium cyanoborohydride (157.7 mg, 2.5 mmol) was added thereto and stirred overnight. A 1N-aqueous sodium hydroxide solution was added to the reaction solution, followed by extraction with chloroform (three times), and the extract solution was dried over anhydrous magnesium sulfate. The residue was purified by a silica gel chromatography (methanol:chloroform=0/100 to 10/100) to obtain trans-N-{4-[(4-ethyl-1H-indazol-5-yl)oxy]cyclohexyl}-N,N-dimethylamine (82.3 mg, 57%).

IR (neat) cm$^{-1}$; 798, 895, 947, 1057, 1498.

EXAMPLE 842

Synthesis of N-{cis-3-[(4-ethyl-1H-indazol-5-yl)oxy]cyclohexyl}-N,N-dimethylamine monohydrochloride Reaction was carried out according to the method described in Example 841, except for using the cis-3-((4-ethyl-1H-indazol-5-yl)oxy)cyclohexanamine obtained in Example 745. To a 2-propanol solution (5 ml) of the resulting purified product (125 mg) was added a 1N-hydrochloric acid/diethyl ether solution (0.88 mL), and stirred for 30 minutes. The solvent was distilled off under reduced pressure and then the residue was crystallized from 2-propanol-diisopropyl ether-diethyl ether to obtain N-{cis-3-[(4-ethyl-1H-indazol-5-yl)oxy]cyclohexyl}-N,N-dimethylamine monohydrochloride (85.2 mg, 46%).

IR (neat) cm$^{-1}$; 982, 1036, 1211, 1257, 1525.

EXAMPLE 843

Synthesis of cis-N-{4-[(4-ethyl-1H-indazol-5-yl)oxy]cyclohexyl}-N,N-dimethylamine monohydrochloride Except for using the cis-4-((4-ethyl-1H-indazol-5-yl)oxy)cyclohexanamine obtained in Example 746, cis-N-{4-[(4-ethyl-1H-indazol-5-yl)oxy]cyclohexyl}-N,N-dimethylamine monohydrochloride was obtained according to the process described in Example 842.

IR (neat) cm$^{-1}$; 843, 943, 997, 1242, 1446.

EXAMPLE 844

Synthesis of N-{trans-3-[(4-ethyl-1H-indazol-5-yl)oxy]cyclohexyl}-N,N-dimethylamine monohydrochloride N-{trans-3-[(4-ethyl-1H-indazol-5-yl)oxy]cyclohexyl}-N,N-dimethylamine monohydrochloride was obtained according to the process described in Example 842, except for using trans-3-((4-methyl-1H-indazol-5-yl)oxy)cyclohexanamine.

IR (neat) cm$^{-1}$; 804, 841, 1211, 1259, 1527.

EXAMPLE 845

Synthesis of trans-N-{4-[(4-ethyl-1H-indazol-5-yl)oxy]cyclohexyl}acetamide

Except for using the trans-4-((4-ethyl-1H-indazol-5-yl)oxy)cyclohexanamine obtained in Example 744, trans-N-{4-[(4-ethyl-1H-indazol-5-yl)oxy]cyclohexyl}acetamide was obtained according to the process described in Example 819.

IR (neat) cm$^{-1}$; 1111, 1321, 1551, 1624, 2937.

EXAMPLE 846

Synthesis of trans-N-{4-[(4-ethyl-1H-indazol-5-yl)oxy]cyclohexyl}propanamide

Except for using the trans-4-((4-ethyl-1H-indazol-5-yl)oxy)cyclohexanamine obtained in Example 744, trans-N-{4-[(4-ethyl-1H-indazol-5-yl)oxy]cyclohexyl}propanamide was obtained according to the process described in Example 819.

IR (neat) cm$^{-1}$; 1119, 1231, 1545, 1633, 2933.

EXAMPLE 847

Synthesis of N-{cis-3-[(4-ethyl-1H-indazol-5-yl)oxy]cyclohexyl}acetamide

N-{cis-3-[(4-ethyl-1H-indazol-5-yl)oxy]cyclohexyl}acetamide was obtained according to the process described in Example 819, except for using the cis-3-((4-ethyl-1H-indazol-5-yl)oxy)cyclohexanamine obtained in Example 745.

IR (neat) cm$^{-1}$; 957, 1111, 1232, 1545, 1632.

EXAMPLE 848

Synthesis of cis-N-{4-[(4-ethyl-1H-indazol-5-yl)oxy]cyclohexyl}acetamide

Except for using the cis-4-((4-ethyl-1H-indazol-5-yl)oxy)cyclohexanamine obtained in Example 746, cis-N-{4-[(4-ethyl-1H-indazol-5-yl)oxy]cyclohexyl}acetamide was obtained according to the process described in Example 819.

LC/MS: M+1=302.3

EXAMPLE 849

Synthesis of N-{trans-3-[(4-methyl-1H-indazol-5-yl)oxy]cyclohexyl}acetamide

N-{trans-3-[(4-methyl-1H-indazol-5-yl)oxy]cyclohexyl}acetamide was obtained according to the process described in Example 819, except for using the trans-3-((4-ethyl-1H-indazol-5-yl)oxy)cyclohexanamine obtained in Example 747.

LC/MS: M+1=302.3

EXAMPLE 850

Synthesis of trans-N-ethyl-4-[(4-ethyl-1H-indazol-5-yl)oxy]cyclohexanamine monohydrochloride Except for using the trans-N-{4-[(4-ethyl-1H-indazol-5-yl)oxy]cyclohexyl}acetamide obtained in Example 845, trans-N-ethyl-4-[(4-ethyl-1H-indazol-5-yl)oxy]cyclohexanamine monohydrochloride was obtained according to the process described in Example 827.

IR (neat) cm$^{-1}$; 791, 845, 1059, 1213, 1524.

EXAMPLE 851

Synthesis of trans-4-[(4-ethyl-1H-indazol-5-yl)oxy]-N-propylcyclohexanamine monohydrochloride (a) Synthesis of trans-N-{4-[(4-ethyl-1H-indazol-5-yl)oxy]cyclohexyl}propanamide Except for using the trans-4-((4-ethyl-1H-indazol-5-yl)oxy)cyclohexanamine obtained in Example 744, trans-N-{4-[(4-ethyl-1H-indazol-5-yl)oxy]cyclohexyl}propanamide was obtained according to the process described in Example 819.

(b) Synthesis of trans-4-[(4-ethyl-1H-indazol-5-yl)oxy]-N-propylcyclohexanamine monohydrochloride Except for using trans-N-{4-[(4-ethyl-1H-indazol-5-yl)oxy]cyclohexyl}propanamide, trans-4-[(4-ethyl-1H-indazol-5-yl)oxy]-N-propylcyclohexanamine monohydrochloride was obtained according to the process described in Example 827.

$^1$H-NMR (DMSO-d$_6$) δ; 0.90 (t, 3H), 1.17 (t, 3H), 1.45 (q, 4H), 1.63 (m, 2H), 2.09 (m, 4H), 2.84 (m, 4H), 3.03 (m, 1H), 4.06 (m, 1H), 7.16 (d, 1H, J=8.89 Hz), 7.29 (d, 1H, J=8.89 Hz), 8.03 (s, 1H), 8.77 (br, 1H), 8.89 (br, 1H).

EXAMPLE 852

Synthesis of N-ethyl-N-{cis-3-[(4-ethyl-1H-indazol-5-yl)oxy]cyclohexyl}amine monohydrochloride N-ethyl-N-{cis-3-[(4-ethyl-1H-indazol-5-yl)oxy]cyclohexyl}amine monohydrochloride was obtained according to the process described in Example 827, except for using the N-{cis-3-[(4-ethyl-1H-indazol-5-yl)oxy]cyclohexyl}acetamide obtained in Example 847.

IR (neat) cm$^{-1}$; 799, 1036, 1211, 1257, 1527.

EXAMPLE 853

Synthesis of N-{cis-3-[(4-ethyl-1H-indazol-5-yl)oxy]cyclohexyl}-N-propylamine monohydrochloride (a) Synthesis of N-{cis-3-[(4-ethyl-1H-indazol-5-yl)oxy]cyclohexyl}propanamide N-{cis-3-[(4-ethyl-1H-indazol-5-yl)oxy]cyclohexyl}propanamide was obtained by carrying out reaction according to the method described in Example 819, except for using the cis-3-((4-ethyl-1H-indazol-5-yl)oxy)cyclohexanamine obtained in Example 745.

(b) Synthesis of N-{cis-3-[(4-ethyl-1H-indazol-5-yl)oxy]cyclohexyl}-N-propylamine monohydrochloride N-{cis-3-[(4-ethyl-1H-indazol-5-yl)oxy]cyclohexyl}-N-propylamine monohydrochloride was obtained by carrying out reaction according to the method described in Example 827, except for using N-{cis-3-[(4-ethyl-1H-indazol-5-yl)oxy]cyclohexyl}propanamide.

IR (neat) cm$^{-1}$; 1012, 1207, 1257, 1456, 1527.

EXAMPLE 854

Synthesis of cis-N-ethyl-N-{4-[(4-ethyl-1H-indazol-5-yl)oxy]cyclohexyl}amine monohydrochloride Except for using the cis-N-{4-[(4-ethyl-1H-indazol-5-yl)oxy]cyclohexyl}acetamide obtained in Example 848, cis-N-ethyl-N-{4-[(4-ethyl-1H-indazol-5-yl)oxy]cyclohexyl}amine monohydrochloride was obtained according to the process described in Example 827.

IR (neat) cm$^{-1}$; 812, 1045, 1217, 1261, 1525.

EXAMPLE 855

Synthesis of cis-N-{4-[(4-ethyl-1H-indazol-5-yl)oxy]cyclohexyl}-N-propylamine monohydrochloride Except for using the cis-4-((4-ethyl-1H-indazol-5-yl)oxy)cyclohexanamine obtained in Example 746, cis-N-{4-[(4-ethyl-1H-indazol-5-yl)oxy]cyclohexyl}-N-propylamine monohydrochloride was obtained according to the process described in Example 853.

IR (neat) cm$^{-1}$; 800, 1217, 1261, 1525, 2939.

EXAMPLE 856

Synthesis of N-ethyl-N-{trans-3-[(4-ethyl-1H-indazol-5-yl)oxy]cyclohexyl}amine monohydrochloride N-ethyl-N-{trans-3-[(4-ethyl-1H-indazol-5-yl)oxy]cyclohexyl}amine monohydrochloride was obtained according to the process described in Example 827, except for using the N-{trans-3-[(4-methyl-1H-indazol-5-yl)oxy]cyclohexyl}acetamide obtained in Example 849.

IR (neat) cm$^{-1}$; 800, 1221, 1257, 1458, 1527, 2943.

EXAMPLE 857

Synthesis of N-{trans-3-[(4-ethyl-1H-indazol-5-yl)oxy]cyclohexyl}-N-propylamine monohydrochloride N-{trans-3-[(4-ethyl-1H-indazol-5-yl)oxy]cyclohexyl}-N-propylamine monohydrochloride was obtained according to the process described in Example 853, except for using the trans-3-((4-ethyl-1H-indazol-5-yl)oxy)cyclohexanamine obtained in Example 747.

IR (neat) cm$^{-1}$; 1221, 1257, 1458, 1525, 2939.

EXAMPLE 858

Synthesis of 5-{(2S*4R*6S*)-[(2,6-dimethylpiperidin-4-yl)oxy]}-4-methyl-1H-indazole hydrochloride (a) Synthesis of t-butyl(2S*4R*6S*)-4-hydroxy-2,6-dimethylpiperidine-1-carbonate Triethylamine (1.67 ml, 12.0 mmol) and di-tert-butyl dicarbonate (2.76 ml, 12.0 mmol) were added to a solution of (2S*4S*6S*)-2,6-dimethyl-4-hydroxypiperidine hydrochloride (388 mg, 3.00 mmol) in dimethylformamide (6 ml), and the resulting mixture was stirred at 60° C. for 3 hours. Then, di-tert-butyl dicarbonate (1.38 ml, 6.0 mmol) was added thereto and the resulting mixture was stirred at 60° C. for another 2 hours. The reaction was terminated by the addition of water and 5%-potassium hydrogensulfate, followed by extraction with ethyl acetate-toluene (1:1). The extract solution was washed with a saturated aqueous sodium chloride solution, dried over sodium sulfate, and then distilled under reduced pressure to remove the solvent, whereby t-butyl(2S*4R*6S*)-4-hydroxy-2,6-dimethylpiperidine-1-carbonate (373 mg, 54%) was obtained.

(b) Synthesis of 5-{(2S*4R*6S*)-[(2,6-dimethylpiperidin-4-yl)oxy]}-4-methyl-1H-indazole hydrochloride To a toluene solution (4 ml) of t-butyl (2S*4R*6S*)-4-hydroxy-2,6-dimethylpiperidine-1-carbonate (144 mg, 0.628 mmol) were added 4-methyl-1H-indazol-5-ol (140 mg, 0.945 mol) and cyanomethylenetri-n-butylphosphorane (253 mg, 0.943 mmol), and the resulting mixture was stirred at 100° C. for 5 hours. The solvent was distilled off under reduced pressure, and the residue was diluted with chloroform and then washed with a 1N-aqueous sodium hydroxide solution. Thereafter, the solvent was distilled off under reduced pressure. Methanol (3 ml) and 4N-hydrochloric acid-dioxane (3 ml) were added to the residue, and the resulting mixture was stirred at room temperature for 1 hour. After the solvent was distilled off, the residue was crystallized from methanol-ethyl acetate to obtain 5-{

(2S*4R*6S*)-[(2,6-dimethylpiperidin-4-yl)oxy]}-4-methyl-1H-indazole hydrochloride (30 mg, 16%).

IR (neat) cm$^{-1}$; 1283, 1219, 1209, 1151, 997, 941.

TEST EXAMPLE 1

Assay of the inhibition of phosphorylation by Rho kinase

A bovine brain extract fraction was prepared as follows. That is, gray matter was minced off from bovine brain and suspended in a buffer solution for immunoprecipitation (10 mM tris(hydroxymethyl)aminomethane (Tris) (pH 7.5), 1% Triton X-100, 0.5% NP-40, 150 mM NaCl, 20 mM sodium fluoride, 1 mM ethylenediaminetetraacetic acid (EDTA), 1 mM ethylene glycol bis($\beta$-aminoethyl ether)-N,N,N',N'-tetraacetic acid (EGTA) and 0.2 mM phenylmethylsulfonyl fluoride (PMSF)) in 2 volumes of the gray matter. The tissue was homogenized by the use of a Potter type homogenizer made of polytetrafluoroethylene. After centrifugation at 20,000 g for 15 minutes, the supernatant was collected and then subjected to ultracentrifugation at 100,000 g for 60 minutes. The supernatant was used as a bovine extract fraction.

An anti-Rho kinase antibody immobilized plate was prepared as follows. That is, a secondary antibody (anti-goat IgG (Fc) antibody) was diluted with phosphate-buffered saline: PBS) 300-fold (1 μl antibody/300 μl PBS), and 100 μl of the resulting dilution was added to each well of a 96-well ELISA plate. After coating at room temperature for 2 hours, the supernatant was removed. Thereafter, 100 μl of PBS was added and then the supernatant was removed (this washing operation was carried out twice). After the washing, 100 μl of a blocking buffer solution (0.05% Tween 20 and 0.25% bovine serum albumin (fatty acid free)/PBS) was added, followed by blocking at room temperature for 1 hour. After the blocking, each well was washed twice with 100 μl of the blocking buffer solution, and 100 μl of a primary antibody (anti-ROKII (Rho kinase) peptide antibody) diluted 200-fold (0.5 μl (0.1 μg)/100 μl) with PBS was added, followed by coating at room temperature for 2 hours. After the coating, each well was washed once with 100 μl of the blocking buffer solution. In addition, 100 μl of the blocking buffer solution was added to obtain an anti-Rho kinase antibody immobilized plate.

Using the aforesaid plate, Rho kinase was selectively immobilized from the bovine brain extract fraction, and phosphorylation by Rho kinase was assayed. To each well of the antibody-immobilized plate was added 100 μl of a bovine brain extract solution prepared so as to have a concentration of 1.5 mg/ml, and the reactions were incubated at 4° C. for 1 hour to immobilize Rho kinase on the plate. After completion of the reaction, the supernatant was removed and each well was washed three times with 100 μl of the buffer solution for immunoprecipitation. In addition, each well was washed three times with 100 μl of buffer solution A (50 mM Tris (pH 7.5), 10 mM MgCl$_2$ and 150 mM NaCl). To each well of the plate freed from the supernatant was added 40 μl of the aforesaid buffer solution for reaction (50 mM Tris-HCl (pH 7.5), 2 mM EDTA and 10 mM MgCl$_2$). Further, adenosine 5'-triphosphate (ATP) buffer (0.1 μM ATP (containing 6 nM [γ-$^{32}$P]ATP) and 10 μg histone (HF2A)) containing each compound was prepared, and 10 μl of this solution was added to each well of the plate to initiate the reaction. The reactions were carried out at room temperature for 4 hours. The reactions were terminated by the addition of a phosphoric acid solution of a final concentration of 75 mM and 50 μM ATP. After completion of the reaction, 50 μl of the reaction solutions were spotted onto a phosphocellulose filter for Beta Plate 1205 (Wallac) only. After the spot, the filter was washed with 150 ml of a 75 mM phosphoric acid solution for 10 minutes. This washing operation was repeated three times. After completion of the washing, the filter was dried and then wrapped in a cellophane bag, and 10 ml of a liquid scintillation cocktail was added. The amount of energy ($\beta$-ray radioactivity count) trapped in the filter was measured with Beta Plate 1205.

A count measured for a sample containing no Rho kinase was taken as a background count (=activity 0%), and a count (the phosphorylating-activity of Rho kinase) measured for a sample containing no compound was taken as activity of 100%. A compound concentration at which the phosphorylation reaction was inhibited by 50% was taken as an IC$_{50}$ value for Rho kinase.

In this test, the IC$_{50}$ value for Rho kinase of the compound of Example 1 was 0.4 μl/ml.

TEST EXAMPLE 2

Inhibitory Effect on the Contraction of the Detrusor of Isolated Bladder

Hartley male guinea pigs (aged about 7 weeks) were killed by a blow on the head followed by exsaguination, and the bladders were isolated and then suspended (static tension: 1 g) in a magunus bath with a capacity of 25 ml filled with Krebs-Henseleit solution (118.4 mM NaCl, 25 mM NaHCO$_3$, 1.2 mM KH$_2$PO$_4$, 4.7 mM KCl, 2.5 mM CaCl$_2$, 1.2 mM MgSO$_4$ and 11 mM glucose) maintained at 37° C., aerated with 95% O$_2$-5% CO$_2$. The tension of a specimen of the bladder was measured with an isometric transducer and recorded in a recorder through an amplifier (AP-6416, Nihon Kohden). After 45 minutes stabilization, the bladder specimen was contracted by acetylcholine at concentrations of 0.3 to 300 μM. Thereafter, the bladder specimen was washed with Krebs-Henseleit solution to be stabilized, and then a test material was added in an amount of 100 μg/ml. From 10 minutes after the addition, the bladder specimen was contracted again by acetylcholine at concentrations of 0.3 to 300 μM. The inhibitory effect was evaluated on the basis of the rate of bladder contraction determined by taking the maximum contraction reaction caused by the first acetylcholine addition as 100%. The results are shown in FIG. 1.

INDUSTRIAL APPLICABILITY

The compound of the present invention has inhibitory effect on Rho kinase and is useful as a therapeutic agent for diseases which are such that morbidity due to them is expected to be improved by inhibition of Rho kinase and secondary effects such as inhibition of the Na$^+$/H$^+$ exchange transport system caused by the Rho kinase inhibition, for example, hypertension, peripheral circulatory disorder, angina, cerebral vasospasm, premature birth, and asthma, which are improved by smooth muscle relaxing effect, and diseases (chronic arterial obstruction and cerebrovascular accident) caused by hyperaggregability of platelet; diseases such as arteriosclerosis, fibroid lung, fibroid liver, liver failure, fibroid kidney, renal glomerulosclerosis, kidney failure, organ hypertrophy, prostatic hypertrophy, complications of diabetes, blood vessel restenosis, and cancer, which are improved by inhibitory effect on cell over-proliferation•emigration•fibrosing (e.g. fibroblast proliferation, smooth muscle cell proliferation, mesangial cell proliferation and hemoendothelial cell proliferation); cardiac hypertrophy; heart failure, ischemic diseases; inflammation;

autoimmune diseases; AIDS; fertilization and implantation of fertilized ovum; osteopathias such as osteoporosis; brain functional disorder; infection of digestive tracts with bacteria; sepsis; adult respiratory distress syndrome; retinopathy; glaucoma; and erectile dysfunction.

What is claimed is:

1. A method of treating disease through inhibiting Rho kinase, wherein the disease is selected from the group consisting of hypertension, angina, cerebral vasospasm, asthma, prostatic hypertrophy, blood vessel restinosis, cardiac hypertrophy, glaucoma, erectile dysfunction, and urinary incontinence, said method comprising administering a therapeutically effective amount of a compound represented by the formula (5):

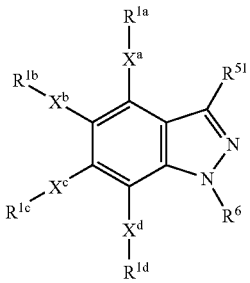

(5)

wherein the groups represented by the formulas $R^{1a}$ and $X^a$ are as follows:
(i) $R^{1a}$ is a substituted or unsubstituted alkyl group and $X^a$ is a single bond, or
(ii) $R^{1a}$ is a carboxyl group, a substituted or unsubstituted alkyl group, a substituted or unsubstituted cycloalkyl group, a substituted or unsubstituted cycloalkenyl group, a substituted or unsubstituted alkoxycarbonyl group, a substituted or unsubstituted alkylsulfonyl group, a substituted or unsubstituted arylsulfonyl group, or a cycloalkyl group substituted by a substituted or unsubstituted alkyl group, and $X^a$ is a group represented by the formula: —O—, —C(=O)N($R^3$)—, —S(O)$_n$—, —S(O)$_2$N($R^3$)— or —C(=O)—

$R^{1b}$ is a substituted or unsubstituted cycloalkyl group, or a substituted or unsubstituted cycloalkenyl group;

$X^b$ is a group represented by the formula: —O—, —N($R^3$)—, —NHC(=O)—, or —C(=O)NH—, both of the groups represented by the formulas $R^{1c}$-$X^c$ and $R^{1d}$-$X^d$ are hydrogen atoms, provided that when $R^{1a}$ is an unsubstituted alkyl group, the corresponding $X^a$ is not the group represented by the formula: —C(=O)—;

$R^3$ is a hydrogen atom, an unsubstituted alkyl group, an unsubstituted cycloalkyl group, or an unsubstituted arylalkyl group, $R^{51}$ is a hydrogen atom, a halogen atom, a nitro group, a carboxyl group, an unsubstituted alkyl group, an unsubstituted cycloalkyl group, an unsubstituted cycloalkenyl group, an unsubstituted alkoxycarbonyl group, or a group represented by the formula: —OR$^8$, —N($R^9$)$R^{10}$, —CON($R^9$)$R^{10}$, —SO$^2$N($R^9$)$R^{10}$ or —S(O)$_m R^{11}$, m is 0, 1 or 2, each of $R^8$, $R^9$ and $R^{10}$, which may be the same or different, is a hydrogen atom, an unsubstituted alkyl group, an unsubstituted cycloalkyl group, an unsubstituted cycloalkenyl group, an unsubstituted alkoxycarbonyl group, or an unsubstituted arylalkyl group, $R^{11}$ is an unsubstituted alkyl group, an unsubstituted cycloalkyl group, an unsubstituted cycloalkenyl group, or an unsubstituted arylalkyl group, and $R^6$ is a hydrogen atom, an unsubstituted alkyl group, an unsubstituted cycloalkyl group, an unsubstituted cycloalkenyl group, an unsubstituted alkoxycarbonyl group, or a group represented by the formula: —CON($R^9$)$R^{10}$, —SO$_2$N($R^9$)$R^{10}$ or —S(O)$_{mR}R^{11}$;

a prodrug of said compound, or a pharmaceutically acceptable salt of said compound or prodrug.

2. A compound represented by the formula (5):

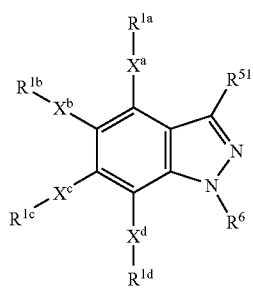

(5)

wherein the groups represented by the formulas $R^{1a}$ and $X^a$ are as follows:
(i) $R^{1a}$ is a substituted or unsubstituted alkyl group and $X^a$ is a single bond, or
(ii) $R^{1a}$ is a carboxyl group, a substituted or unsubstituted alkyl group, a substituted or unsubstituted cycloalkyl group, a substituted or unsubstituted cycloalkenyl group, a substituted or unsubstituted alkoxycarbonyl group, a substituted or unsubstituted alkylsulfonyl group, a substituted or unsubstituted arylsulfonyl group, or a cycloalkyl group substituted by a substituted or unsubstituted alkyl group, and $X^a$ is a group represented by the formula: —O—, —C(=O)N($R^3$)—, —S(O)$_n$—, —S(O)$_2$N($R^3$)— or —C(=O)—

$R^{1b}$ is a substituted or unsubstituted cycloalkyl group, or a substituted or unsubstituted cycloalkenyl group;

$X^b$ is a group represented by the formula: —O—, —N($R^3$)—, —NHC(=O)—, or —C(=O)NH—, both of the groups represented by the formulas $R^{1c}$—$X^c$ and $R^{1d}$—$X^d$ are hydrogen atoms, provided that when Ria is an unsubstituted alkyl group, the corresponding Xa is not the group represented by the formula: —C(=O)—;

$R^3$ is a hydrogen atom, an unsubstituted alkyl group, an unsubstituted cycloalkyl group, or an unsubstituted arylalkyl group, $R^{51}$ is a hydrogen atom, a halogen atom, a nitro group, a carboxyl group, an unsubstituted alkyl group, an unsubstituted cycloalkyl group, an unsubstituted cycloalkenyl group, an unsubstituted alkoxycarbonyl group, or a group represented by the formula: —OR$^8$, —N($R^9$)$R^{10}$, CON($R^9$)$R^{10}$, —SO$_2$N($R^9$)$R^{10}$ or —S(O)$_m$ $R^{11}$, m is 0, 1 or 2, each of $R^8$, $R^9$ and $R^{10}$, which may be the same or different, is a hydrogen atom, an unsubstituted alkyl group, an unsubstituted cycloalkyl group, an unsubstituted cycloalkenyl group, an unsubstituted alkoxycarbonyl group, or an unsubstituted arylalkyl group, $R^{11}$ is an unsubstituted alkyl group, an unsubstituted cycloalkyl group, an unsubstituted cycloalkenyl group, or an unsubstituted arylalkyl group, and $R^6$ is a hydrogen atom, an unsubstituted alkyl group, an unsubstituted cycloalkyl group, an unsubstituted cycloalkenyl group, an unsubstituted alkoxycarbonyl group, or a group represented by the formula: —CON$(R^9)R^{10}$, —SO$_2$N$(R^9)R^{10}$ or —S(O)$_{mR}{}^{11}$;

a prodrug of said compound or a pharmaceutically acceptable salt of said compound or prodrug.

3. A compound, a prodrug thereof or a pharmaceutically acceptable salt of the compound or prodrug according to claim 2, wherein the group represented by $X^a$ is a group represented by the formula: —O—.

4. A pharmaceutical composition comprising a compound, a prodrug thereof or a pharmaceutically acceptable salt of the compound or prodrug according to any one of claims 2 to 3.

5. A compound according to claim 2, wherein $R^{51}$ and $R^6$ are hydrogen atoms;

a prodrug of said compound or a pharmaceutically acceptable salt of said compound or prodrug.

6. A compound according to claim 2, wherein $R^{1b}$ is a substituted cycloalkyl group and $X^b$ is a group represented by the formula: —O—;

a prodrug of said compound or a pharmaceutically acceptable salt of said compound or prodrug.

7. A compound according to claim 2, wherein $R^{1a}$ is a substituted or unsubstituted alkyl group and $X^a$ is a single bond or a group represented by the formula: —O— or —S—;

a prodrug of said compound or a pharmaceutically acceptable salt of said compound or prodrug.

8. A compound according to claim 2, wherein $R^{51}$ and $R^6$ are hydrogen atoms;

$R^{1b}$ is a substituted cycloalkyl group;

and $X^b$ is a group represented by the formula: —O—;

a prodrug of said compound or a pharmaceutically acceptable salt of said compound or prodrug.

9. A compound according to claim 2, wherein $R^{51}$ and $R^6$ are hydrogen atoms;

$R^{1a}$ is a substituted or unsubstituted alkyl group;

and $X^a$ is a single bond or a group represented by the formula: —O— or —S—;

a prodrug of said compound or a pharmaceutically acceptable salt of said compound or prodrug.

10. A compound according to claim 2, wherein $R^{1b}$ is a substituted cycloalkyl group;

$X^b$ is a group represented by the formula: —O—;

$R^{1a}$ is a substituted or unsubstituted alkyl group;

and $X^a$ is a single bond or a group represented by the formula: —O— or —S—;

a prodrug of said compound or a pharmaceutically acceptable salt of said compound or prodrug.

11. A compound according to claim 2, wherein $R^{1b}$ is a substituted cycloalkyl group;

$R^{1b}$ is a substituted cycloalkyl group;

$X^b$ is a group represented by the formula: —O—;

$R^{1a}$ is a substituted or unsubstituted alkyl group;

and $X^a$ is a single bond or a group represented by the formula: —O— or —S—;

a prodrug of said compound or a pharmaceutically acceptable salt of said compound or prodrug.

12. A method of treating disease through inhibiting Rho kinase according to claim 1, wherein the disease is urinary incontinence.

* * * * *